US012673936B2

(12) United States Patent
Fu et al.

(10) Patent No.: US 12,673,936 B2
(45) Date of Patent: Jul. 7, 2026

(54) ISOINDOLINONE COMPOUNDS, AND USES THEREOF

(71) Applicant: HANGZHOU GLUBIO PHARMACEUTICAL CO., LTD., Hangzhou (CN)

(72) Inventors: Liqiang Fu, Shanghai (CN); Linglong Kong, Shanghai (CN); Yifeng Xia, San Diego, CA (US)

(73) Assignee: HANGZHOU GLUBIO PHARMACEUTICAL CO., LTD., Hangzhou (CN)

( * ) Notice: Subject to any disclaimer, the term of this patent is extended or adjusted under 35 U.S.C. 154(b) by 390 days.

(21) Appl. No.: 18/568,744

(22) PCT Filed: Jun. 6, 2022

(86) PCT No.: PCT/CN2022/097236
§ 371 (c)(1),
(2) Date: Dec. 8, 2023

(87) PCT Pub. No.: WO2022/257897
PCT Pub. Date: Dec. 15, 2022

(65) Prior Publication Data

US 2024/0294500 A1 Sep. 5, 2024

(30) Foreign Application Priority Data

Jun. 8, 2021 (WO) ................ PCT/CN2021/099003
Mar. 29, 2022 (WO) ................ PCT/CN2022/083853

(51) Int. Cl.

| | |
|---|---|
| ***C07D 401/14*** | (2006.01) |
| ***A61K 31/454*** | (2006.01) |
| ***A61K 31/4545*** | (2006.01) |
| ***A61K 31/496*** | (2006.01) |
| ***A61P 35/00*** | (2006.01) |
| ***C07D 401/04*** | (2006.01) |
| ***C07D 405/14*** | (2006.01) |

(52) U.S. Cl.
CPC .......... *C07D 401/14* (2013.01); *A61K 31/454* (2013.01); *A61K 31/4545* (2013.01); *A61K 31/496* (2013.01); *A61P 35/00* (2018.01); *C07D 401/04* (2013.01); *C07D 405/14* (2013.01)

(58) Field of Classification Search
CPC .................................................... C07D 401/14
USPC .......................................................... 514/323
See application file for complete search history.

(56) References Cited

U.S. PATENT DOCUMENTS

| | | | | |
|---|---|---|---|---|
| 8,877,780 | B2 | 11/2014 | Muller et al. | |
| 9,447,070 | B2 | 9/2016 | Muller et al. | |
| 9,694,084 | B2 * | 7/2017 | Bradner | A61K 47/54 |
| 9,801,868 | B2 | 10/2017 | Muller et al. | |

FOREIGN PATENT DOCUMENTS

| | | | |
|---|---|---|---|
| CN | 102112463 | A | 6/2011 |
| WO | 2019241274 | A1 | 12/2019 |
| WO | 2020102195 | A1 | 5/2020 |
| WO | 2020118098 | A1 | 6/2020 |
| WO | 2020242960 | A1 | 12/2020 |
| WO | 2020243379 | A1 | 12/2020 |

OTHER PUBLICATIONS

Behan, Fiona M. et al., “Prioritization of cancer therapeutic targets using CRISPR-Cas9 screens”; Nature; vol. 568; Year: 2019; pp. 511-516 (with nature research report total 27 pages).
Jaras, Marcus et al., “Csnk1a1 inhibition has p53-dependent therapeutic efficacy in acute myeloid leukemia”; J Exp Med.; vol. 211, No. 4; Year: 2014; pp. 605-612.
Kronke, Jan et al., “Lenalidomide induces ubiquitination and degradation of CK1a in del(5q) MDS”; Nature; vol. 523; Year: 2015; pp. 1-20.
Kronke, Jan et al., “Lenalidomide Causes Selective Degradation of IKZF1 and IKZF3 in Multiple Myeloma Cells”; Science; vol. 343(6168), ISSN 1095-9203; Jan. 17, 2014; pp. 301-305.
Lu, Gang et al., “The Myeloma Drug Lenalidomide Promotes the Cereblon-Dependent Destruction of Ikaros Proteins”; Science; vol. 343 (6168); Jan. 17, 2014; pp. 305-309.
Matyskiela, Mary E. et al., “SALL4 mediates teratogenicity as a thalidomidedependent cereblon substrate”; Nature Chemical Biology; vol. 14 (10); Sep. 6, 2018; pp. 981-987.
An, Jian et al., “pSILAC mass spectrometry reveals ZFP91 as IMiD-dependent substrate of the CRL4CRBN ubiquitin ligase”; Nature Communications; vol. 8, ncomms15398; May 22, 2017; pp. 1-11.
Zhouravleva, Galina et al., “Termination of translation in eukaryotes is governed by two interacting polypeptide chain release factors, eRF1 and eRF3”; tHE EMBO Journal; vol. 14, No. 16; Year: 1995; pp. 4065-4072.
Matyskiela, Mary E. et al., “A novel cereblon modulator recruits GSPT1 to the CRL4CRBN ubiquitin ligase”; Nature; vol. 535 (18611); Year: 2016; pp. 252-257.
Surka, Christine et al., “CC-90009, a novel cereblon E3 ligase modulator, targets acute myeloid leukemia blasts and leukemia stem cells”; Blood; vol. 137, No. 5; Feb. 2021; pp. 661-677.
Uy, Geoffrey L. et al., “Clinical Activity of CC-90009, a Cereblon E3 Ligase Modulator and First-in-Class GSPT1 Degrader, As a Single Agent in Patients with Relapsed or Refractory Acute Myeloid Leukemia (R/R AML): First Results from a Phase I Dose-Finding Study”; Blood; vol. 134, (Supplement_1): 232; Nov. 13, 2019; pp. 1-5.

(Continued)

*Primary Examiner* — Niloofar Rahmani
(74) *Attorney, Agent, or Firm* — NKL Law; Bin Lu; Allen Xue

(57) ABSTRACT

Isoindolinone compounds represented by the structural formula (I) or pharmaceutically-acceptable salts thereof can be used for the treatment of a proliferative disorder. Pharmaceutical compositions contain the isoindolinone compound or a salt thereof, and a pharmaceutically acceptable carrier.

19 Claims, No Drawings

(56) References Cited

OTHER PUBLICATIONS

Jiang, Shaojie et al.; "Casein kinase 1α: biological mechanisms and theranostic potential"; Cell Communication and Signaling; vol. 16:23; May 24, 2018, pp. 1-24.
Liu, Chunming et al.; "Control of β-Catenin Phosphorylation/Degradation by a Dual-Kinase Mechanism"; Cell; vol. 108; Mar. 22, 2002; pp. 837-847.
Huart et al., "CK1α Plays a Central Role in Mediating MDM2 Control of p53 and E2F-1 Protein Stability"; The Journal of Biological Chemstry; vol. 284; No. 47, Nov. 20, 2009; pp. 32384-32394.
Wu, Shaofang et al., "Casein Kinase 1α Regulates an MDMX Intramolecular Interaction to Stimulate p53 Binding"; Molecular and Cellular Biology; vol. 32, No. 23; Dec. 2012; pp. 4821-4832.
Richter, Julia et al., "CK1α overexpression correlates with poor survival in colorectal cancer"; BMC Cancer; vol. 18:140; Feb. 6, 2018; pp. 1-11.
Tsherniak, Aviad et al., "Defining a Cancer Dependency Map"; Cell; vol. 170; Jul. 27, 2017; pp. 564-576.

* cited by examiner

ISOINDOLINONE COMPOUNDS, AND USES THEREOF

FIELD OF THE INVENTION

The present application belongs to the field of medicine. The invention provides isoindolinone compounds represented by the structural formula (I) or pharmaceutically-acceptable salts thereof, and use thereof in the treatment of a proliferative disorder. The invention also provides pharmaceutical compositions comprising a compound described herein or a slat thereof, and a pharmaceutically acceptable carrier.

BACKGROUND

Casein kinase 1 alpha (CK1α), encoded by gene CSNK1A1, is a ubiquitously expressed serine/threonine protein kinase in the CK1 kinase family. CK1α is involved in the regulation of multiple physiological and pathological processes of cells, and coordinates the orderly progression of life through different signal transduction pathways (Jiang et al., *Cell Commun Signal* (2018) 16: 23). For example, CK1α, as a key regulator of the Wnt/β-catenin pathway, directly phosphorylates β-catenin at Ser45 and thereby targets it for proteasomal degradation (Liu et al., Cell (2002) 108: 837-847). CK1α was also known to regulate the protein stability of tumor suppressor p53 via modulating the activity of the MDM2/MDMX E3 ligase complex (Huart et al., *J Biol Chem* (2009) 284: 32384-94; Wu et al., *Mol Cell Biol* (2012) 32: 4821-4832). Overexpression of CK1α in many types of human cancers was reported, however, the precise role of CK1α in the development of each respective tumor type has not been clearly elucidated (Richter et al., *BMC Cancer* (2018) 18: 140). The Cancer Dependency Map (DepMap) Project revealed that inactivation of CK1α via clustered regularly interspaced short palindromic repeats (CRISPR)/cas9-mediated gene knockout or short hairpin (shRNA)-mediated gene knockdown significantly reduced the proliferation and/or survival of many cancer cell lines from a variety of cancer types (Tsherniak et al., *Cell* (2017) 170: 564-576; Behan et al., *Nature* (2019) 568: 511-516). Moreover, inhibition of CK1α using shRNA interference or D4476, a CK1α kinase inhibitor, effectively abrogated the development of MLL-AF9 leukemia with much less effect on normal hematopoietic stem and progenitor cells (HSPCs) in mice (Jaras et al, *J Exp Med* (2014) 211(4): 605-612). Collectively, these data suggest that CK1α is a potential therapeutic target for both hematological malignancies and solid tumor indications.

CK1α is a well-known neosubstrate of lenalidomide, a FDA-approved drug for the treatment of human multiple myeloma and lower-risk myelodysplastic syndromes with 5q deletion (del(5q) MDS) (Kronke et al., *Nature* (2015) 523: 183-188). Lenalidomide acts as a molecular glue protein degrader that repurposes the CUL4/DDB1/CRBN/RBX1 E3 ligase complex to target CK1α for poly-ubiquitination and proteasomal degradation. However, in addition to CK1α, lenalidomide also induces the degradation of a number of other neosubstrates including Ikaros, Aiolos, ZFP91 and SALL4 (Kronke et al., *Science* (2014) 343(6168): 301-305; Lu et al., *Science* (2014) 343(6168): 305-309; Matyskiela et al., *Nat Chem Biol* (2018) 14(10): 981-987; An et al., *Nat Commun* (2017) 8: 15398). To date, CK1α-selective molecular glue degraders for the treatment of cancer and other human diseases have not been developed.

GSPT1, also known as eRF3a (eukaryotic release factor 3a), is a key translation termination factor that binds and activates eRF1 to mediate stop codon recognition and nascent protein release from translating ribosomes (Zhouravleva et al., *EMBO J* (1995) 14(16): 4065-4072). A few CRBN-based molecular glue degraders including CC-885 and CC-90009 were reported to degrade GSPT1, resulting in antitumor efficacy in acute myloid leukemia (AIL) (Matyskiela et al., *Nature* (2016) 535: 252-257; Surka et al., *Blood* (2021) 137 (5): 661-677). However, CC-90009-induced GSPT1 degradation triggered severe on-target toxicities including hypocalcemia, hypotension, and hyperbilirubinemia in human AML patients (Uy et al., *Blood* (2019) 134 (Supplement 1): 232). Thus, the off-target degradation of GSPT1 should be avoided when developing a next-generation CK1α-selective molecular glue degrader as a more tolerable and less toxic therapeutic agent. Furthermore, the GSPT1 degrading activity should be carefully assayed and monitored during such development because the GSPT1 activity of all known classes of cereblon-based molecular glue degraders can not be obviously predicted by their chemical structures.

SUMMARY OF THE INVENTION

A first embodiment of the present invention is directed to a compound represented by Structural Formula (I):

(I)

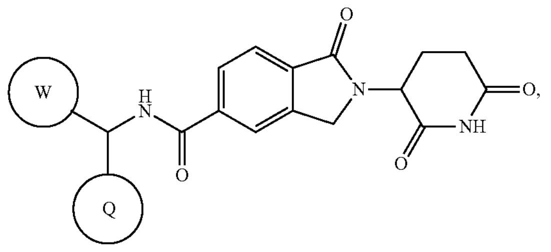

or a pharmaceutically acceptable salt thereof, wherein the variables are as defined and described herein. Another embodiment of the present invention is directed to a compound represented by Structural Formula (II):

(II)

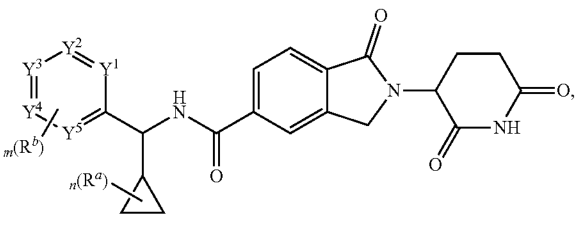

or a pharmaceutically acceptable salt thereof, wherein the variables are as defined and described herein. Another embodiment of the present invention is directed to a compound represented by Structural Formula (III):

(III)

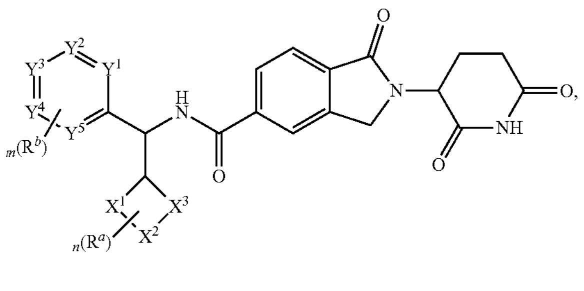

or a pharmaceutically acceptable salt thereof, wherein the variables are as defined and described herein. Another embodiment of the present invention is directed to a compound represented by Structural Formula (IV):

(IV)

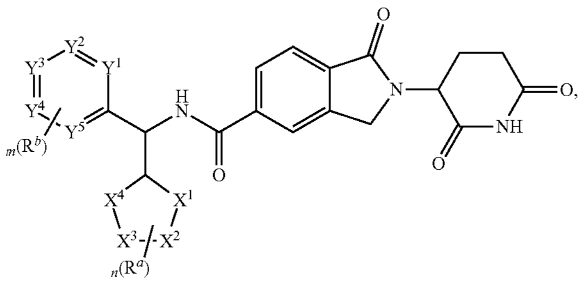

or a pharmaceutically acceptable salt thereof, wherein the variables are as defined and described herein. Another embodiment of the present invention is directed to a compound represented by Structural Formula (V):

(V)

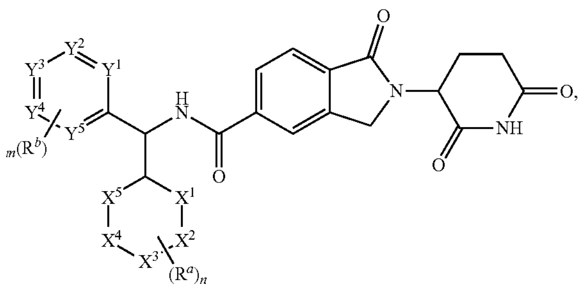

or a pharmaceutically acceptable salt thereof, wherein the variables are as defined and described herein. Another embodiment of the present invention is directed to a compound represented by Structural Formula (VI):

(VI)

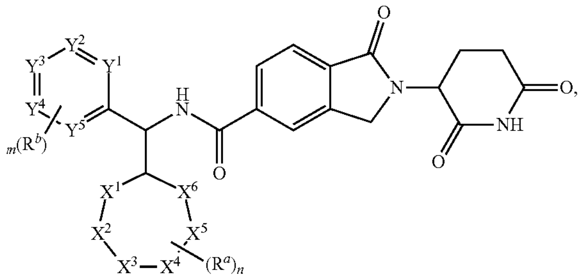

or a pharmaceutically acceptable salt thereof, wherein the variables are as defined and described herein. Another embodiment of the present invention is directed to a compound represented by Structural Formula (VII):

(VII)

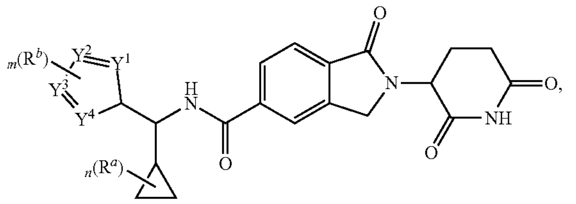

or a pharmaceutically acceptable salt thereof, wherein the variables are as defined and described herein. Another embodiment of the present invention is directed to a compound represented by Structural Formula (VIII):

(IX)

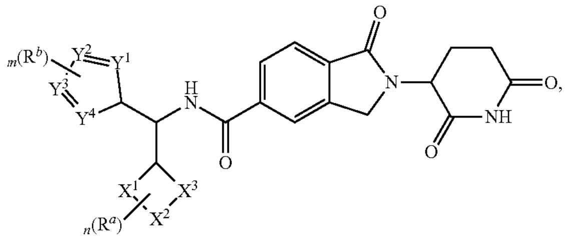

or a pharmaceutically acceptable salt thereof, wherein the variables are as defined and described herein. Another embodiment of the present invention is directed to a compound represented by Structural Formula (IX):

(IX)

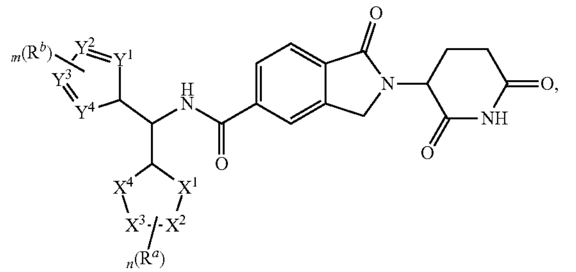

or a pharmaceutically acceptable salt thereof, wherein the variables are as defined and described herein. Another embodiment of the present invention is directed to a compound represented by Structural Formula (X):

(X)

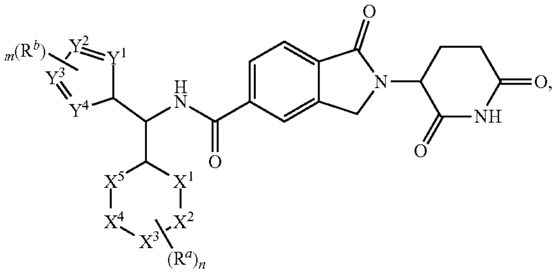

or a pharmaceutically acceptable salt thereof, wherein the variables are as defined and described herein. Another embodiment of the present invention is directed to a compound represented by Structural Formula (XI):

(XI)

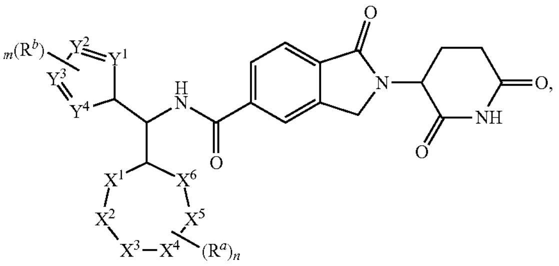

or a pharmaceutically acceptable salt thereof, wherein the variables are as defined and described herein. Another embodiment of the present invention is directed to a compound represented by Structural Formula (XII):

(XII)

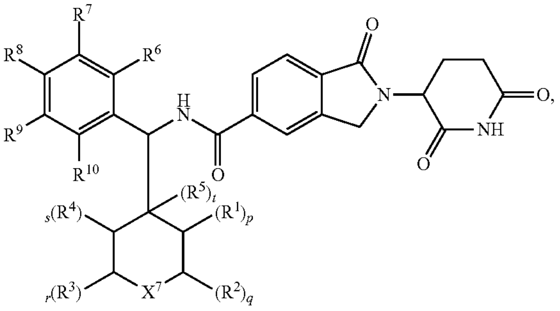

or a pharmaceutically acceptable salt thereof, wherein the variables are as defined and described herein. Another embodiment of the present invention is directed to a compound represented by Structural Formula (XIII):

(XIII)

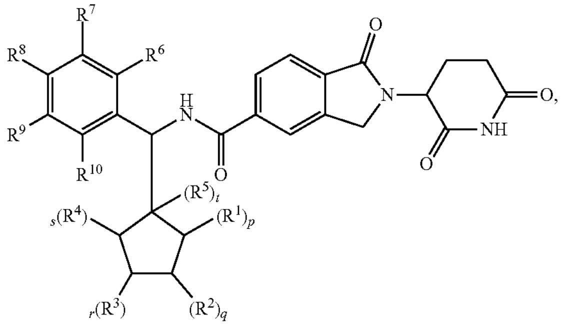

or a pharmaceutically acceptable salt thereof, wherein the variables are as defined and described herein. Another embodiment of the present invention is directed to a compound represented by Structural Formula (XIV):

(XIV)

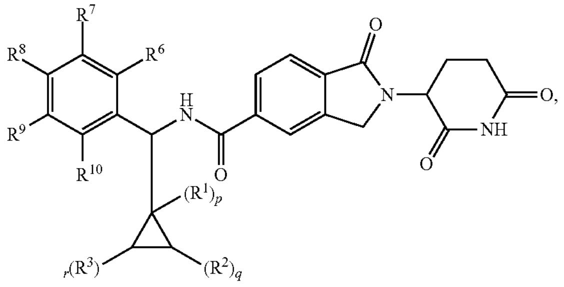

or a pharmaceutically acceptable salt thereof, wherein the variables are as defined and described herein. Another embodiment of the present invention is directed to a compound represented by Structural Formula (XV):

(XV)

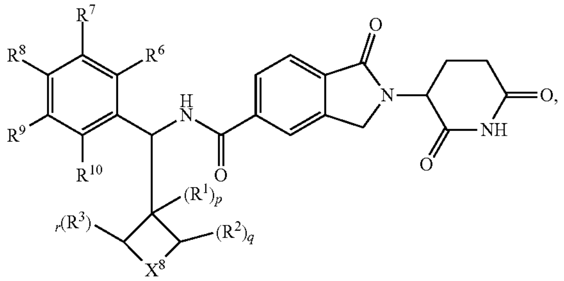

or a pharmaceutically acceptable salt thereof, wherein the variables are as defined and described herein. Another embodiment of the present invention is directed to a pharmaceutical composition comprising a pharmaceutically acceptable carrier or diluent and a compound described herein, or a pharmaceutically acceptable salt thereof. The pharmaceutical composition is used in therapy, such as treating a proliferative disorder in a subject.

DETAILED DESCRIPTION OF THE INVENTION

The present invention is directed to a compound represented by the following structural formulae, or a pharmaceutically acceptable salt thereof. The variables in the following structural formulae are described herein in the following paragraphs. It is understood that the invention encompasses all combinations of the substituent variables (e.g., $R^a$, $R^b$, $R^1$, $R^2$, $R^3$, etc.) defined herein. The compounds described herein or salts thereof are useful in the treatment a proliferative disorder.

A first embodiment of the present invention is directed to a compound represented by structural formula (I):

(I)

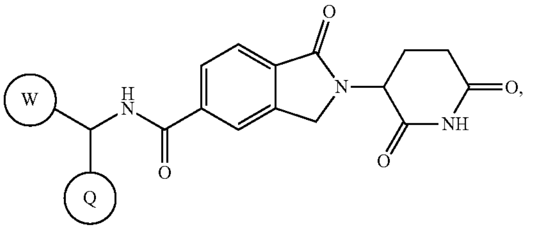

or a pharmaceutically acceptable salt thereof, wherein:

the moiety

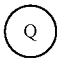

is $C_{3-8}$ cycloalkyl optionally substituted with 1 to 6 $R^a$, 4 to 10 membered monocyclic or bicyclic heterocyclyl optionally substituted with 1 to 6 $R^a$, having 1 to 3 heteroatoms selected from N, O, and S, each $R^a$ is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)$OR^{11}$, —$C_0$-$C_4$alkyl$NR^{11}R^{12}$, —C(O)$NR^{11}R^{12}$, —$SO_2R^{11}$, —$SO_2NR^{11}R^{12}$, —OC(O)$R^{11}$, and —C($NR^{11}$)$NR^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl); and wherein when moiety

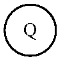

bears greater than or equal to two $R^a$, two $R^a$ are optionally taken together with atoms to which they are bound to form a carbocyclyl or heterocyclyl ring; the moiety

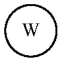

is 6 to 18 membered aryl optionally substituted with 1 to 6 $R^b$, 5 to 18 membered heteroaryl optionally substituted with 1 to 6 $R^b$, having 1 to 3 heteroatoms selected from N, O, and S, each $R^b$ is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)$OR^{11}$, —$C_0$-$C_4$alkyl$NR^{11}R^{12}$, —C(O)$NR^{11}R^{12}$, —$SO_2R^{11}$, —$SO_2NR^{11}R^{12}$, —OC(O)$R^{11}$, and —C($NR^{11}$)$NR^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl); and wherein when moiety

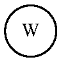

bears greater than or equal to two $R^b$, two $R^b$ are optionally taken together with atoms to which they are bound to form a carbocyclyl or heterocyclyl ring.

In a first aspect of the first embodiment: the moiety

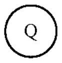

is selected from the group consisting of

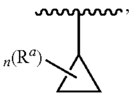
,
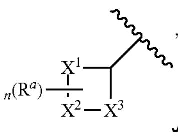
,
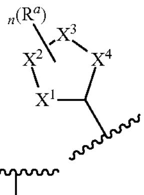
,
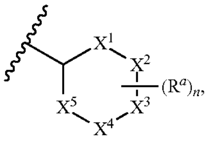
and
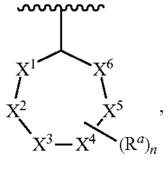
, wherein n, for each occurrence, is independently 0, 1, 2, 3, 4, 5, or 6; $X^1$, for each occurrence, is independently C, N, O, or S; $X^2$, for each occurrence, is independently C, N, O, or S; $X^3$, for each occurrence, is independently C, N, O, or S; $X^4$, for each occurrence, is independently C, N, O, or S; $X^5$, for each occurrence, is independently C, N, O, or S; and, $X^6$, for each occurrence, is independently C, N, O, or S. A wavy line indicates a point of attachment. The remaining variables (e.g., $R^a$) are as described and defined in the first embodiment.

Preferably, the moiety

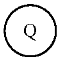

is

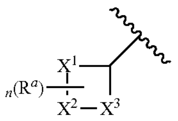

wherein:

n, for each occurrence, is independently 0, 1, 2, 3, 4, 5, or 6;

$X^1$, for each occurrence, is independently C, N, O, or S;

$X^2$, for each occurrence, is independently C, N, O, or S;

$X^3$, for each occurrence, is independently C, N, O, or S; and $R^a$, for each occurrence, is independently selected from H, F, Cl, Br, Me, CN, MeO, Et, $CF_3O$,

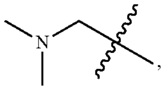, 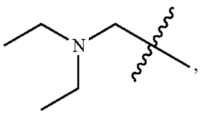,

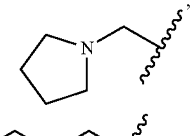, 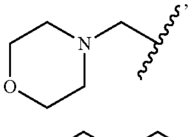,

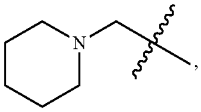, 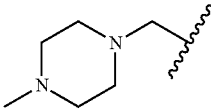,

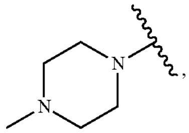, 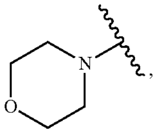,

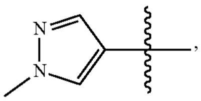, 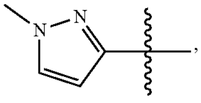, 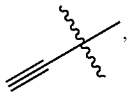,

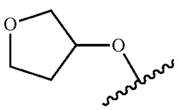, 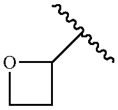, 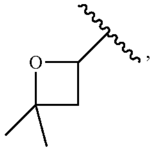, $CF_3$, and EtO—.

In a second aspect of the first embodiment: the moiety

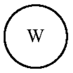

is

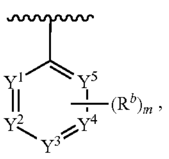 or 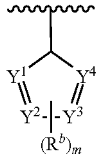, wherein m, for each occurrence, is independently 0, 1, 2, 3, 4, 5, or 6; $Y^1$, for each occurrence, is independently C, N, O, or S; $Y^2$, for each occurrence, is independently C, N, O, or S; $Y^3$, for each occurrence, is independently C, N, O, or S; $Y^4$, for each occurrence, is independently C, N, O, or S; and $Y^5$, for each occurrence, is independently C, N, O, or S. A wavy line indicates a point of attachment. The remaining variables (e.g., $R^b$) are as described and defined in the first embodiment.

Preferably, the moiety

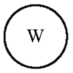

is

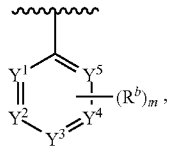, wherein m, for each occurrence, is independently 0, 1, 2, 3, 4, or 5;

$Y^1$, for each occurrence, is independently C, N, O, or S;

$Y^2$, for each occurrence, is independently C, N, O, or S;

$Y^3$, for each occurrence, is independently C, N, O, or S;

$Y^4$, for each occurrence, is independently C, N, O, or S;

$Y^5$, for each occurrence, is independently C, N, O, or S; and $R^b$, for each occurrence, is selected from H, F, Cl, Br, Me, CN, MeO, Et, $CF_3O$,

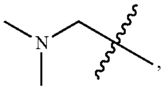, 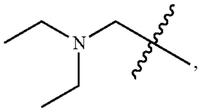,

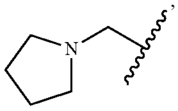, 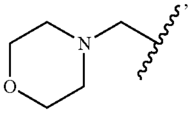,

-continued

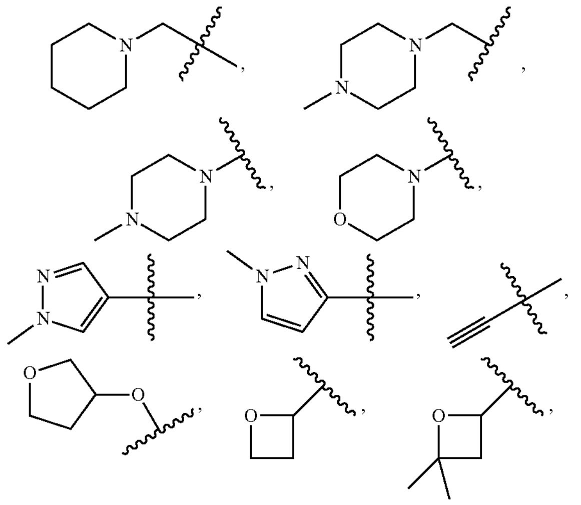

$CF_3$, and EtO—. In a third aspect of the first embodiment, the number of substituents linked to the moiety

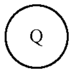

is 0, 1, 2, 3, 4, 5 or 6.

In a fourth aspect of the first embodiment, the number of heteroatoms in the moiety

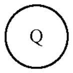

is 0, 1, 2, or 3.

In a fifth aspect of the first embodiment, the number of substituents linked to the moiety

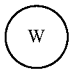

is 0, 1, 2, 3, 4, 5 or 6.

In a sixth aspect of the first embodiment, the number of heteroatoms in the moiety

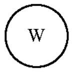

is 0, 1, 2, or 3.

In a seventh aspect of the first embodiment, the moiety

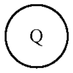

is selected from

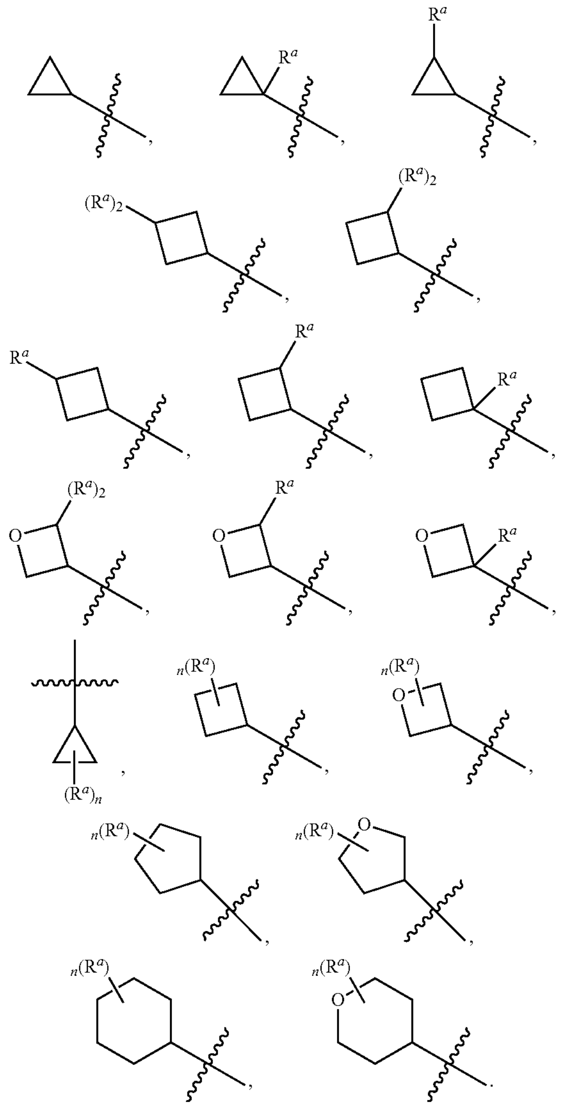

Preferably, the moiety

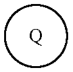

is selected from

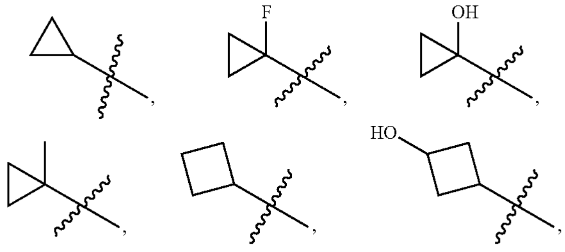

-continued

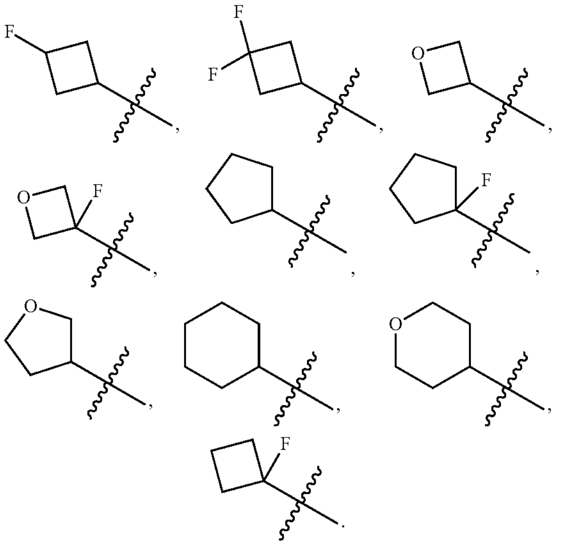

In a eighth aspect of the first embodiment, the moiety

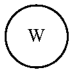

is selected from

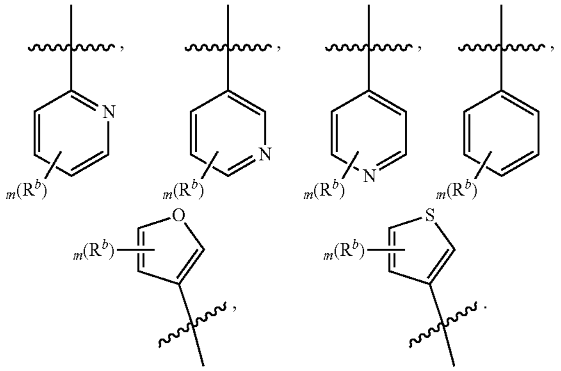

Preferably, the moiety

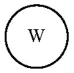

is selected from

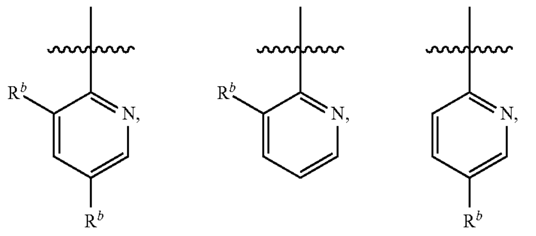

-continued

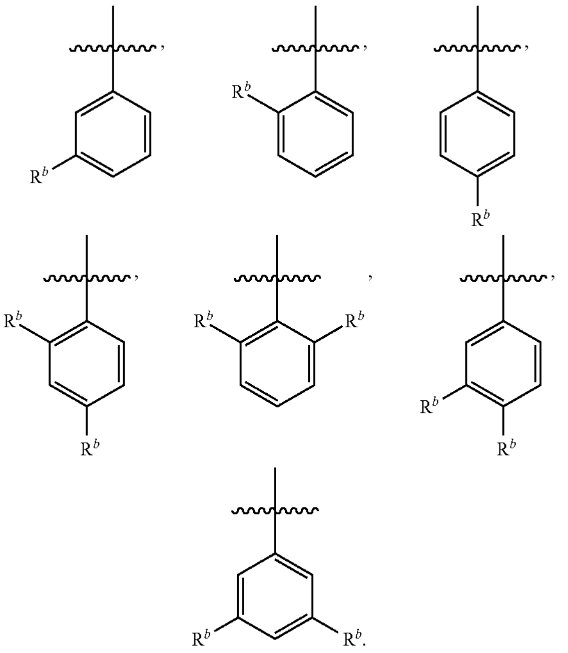

In a ninth aspect of the first embodiment, each $R^a$ is independently selected from H, F, Cl, Br, Me, CN, MeO, Et, $CF_3O$,

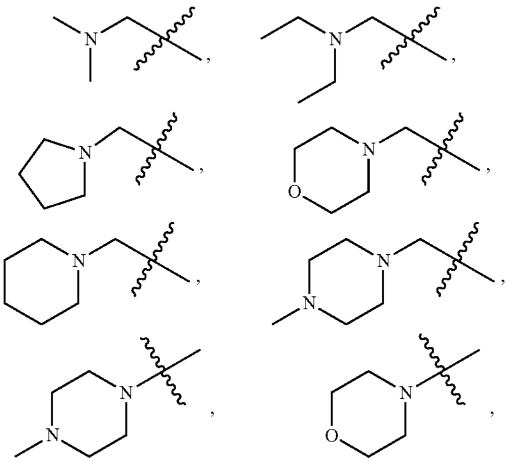

$CF_3$, EtO—.

Preferably, $R^a$ is selected from H, F, Cl, Me, CN, MeO,

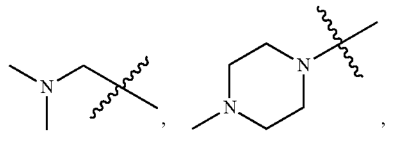

$CF_3$.

In a tenth aspect of the first embodiment, each $R^b$ is independently selected from H, F, Cl, Br, Me, CN, MeO—, Et, $CF_3O$,

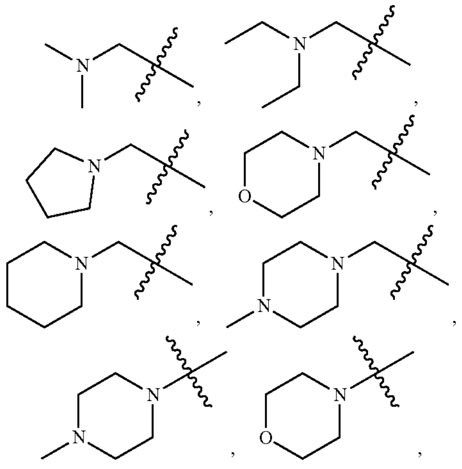

$CF_3$, EtO—.

Preferably, $R^b$ is selected from H, F, Cl, Me, CN, MeO—,

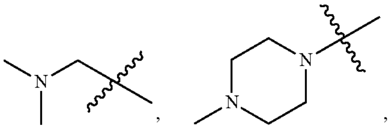

$CF_3$.

In an eleventh aspect of the first embodiment, the structural formula (I) is (I-1)

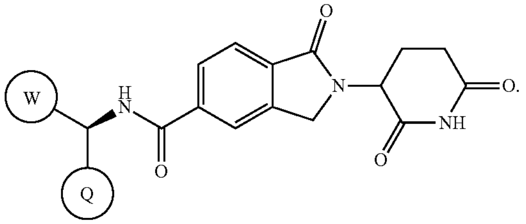

In a twelfth aspect of the first embodiment, the structural formula (I) is (I-2)

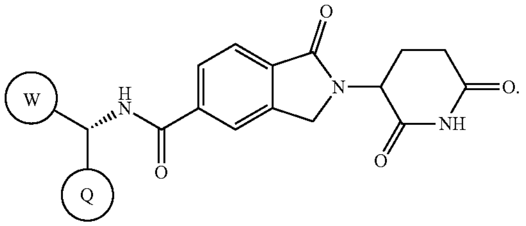

In a thirteenth aspect of the first embodiment, the compound represented by structural formula (I) is a compound represented by (I-3)

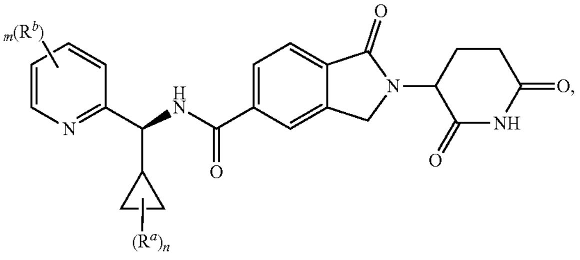

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

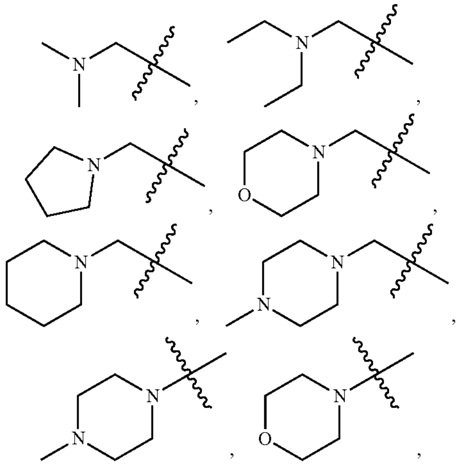

$CF_3$, and EtO—; and each $R^b$ is independently selected from H, F, Cl, Br, Me, CN, MeO, Et, $CF_3O$,

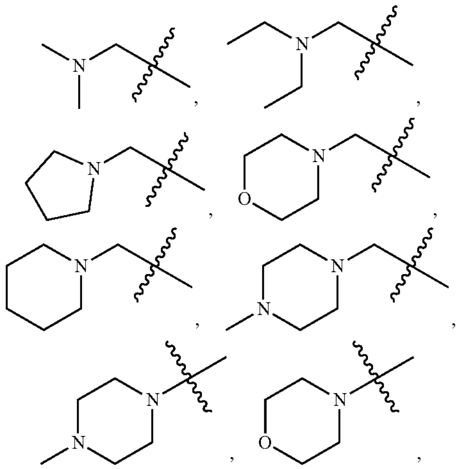

$CF_3$, and EtO—.

In a fourteenth aspect of the first embodiment, the compound represented by structural formula (I) is a compound represented by (I-4)

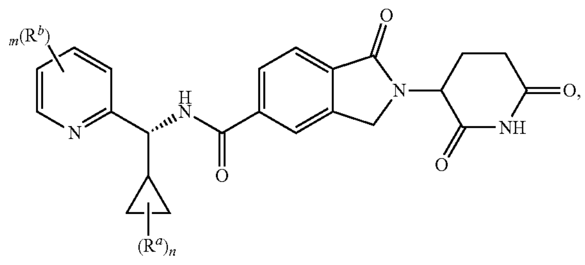

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

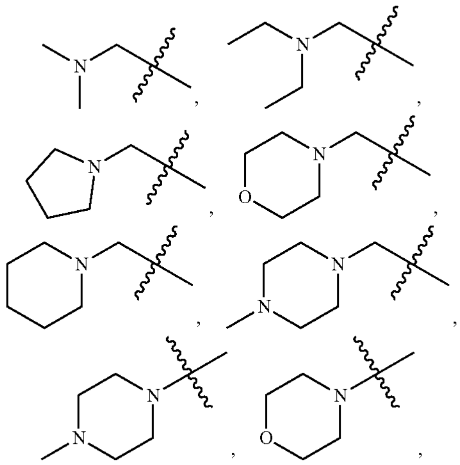

$CF_3$, and EtO—; and each $R^b$ is independently selected from H, F, Cl, Br, Me, CN, MeO Et $CF_3O$,

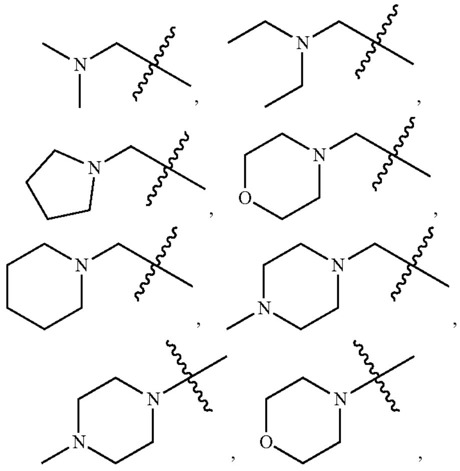

$CF_3$, and EtO—.

In a fifteenth aspect of the first embodiment, the compound represented by structural formula (I) is a compound represented by (I-5)

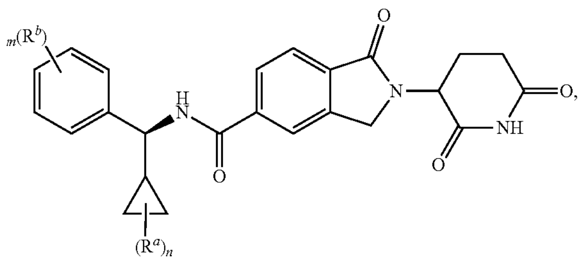

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

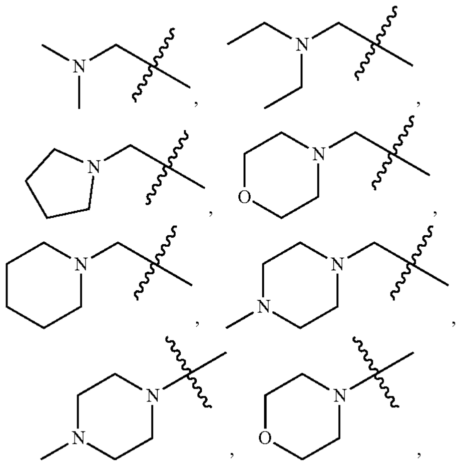

$CF_3$, and EtO—; and each $R^b$ is independently selected from H, F, Cl, Br, Me, CN, MeO, Et, $CF_3O$,

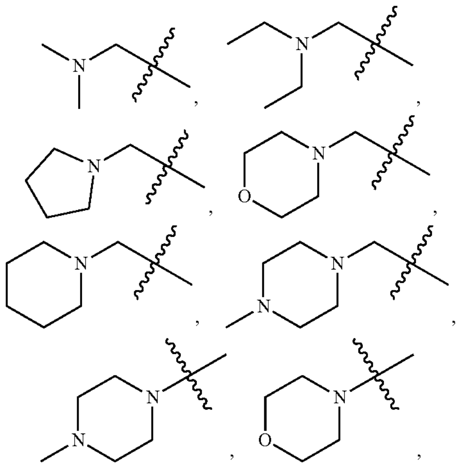

$CF_3$, and EtO—.

In a sixteenth aspect of the first embodiment, the compound represented by structural formula (I) is a compound represented by (I-6)

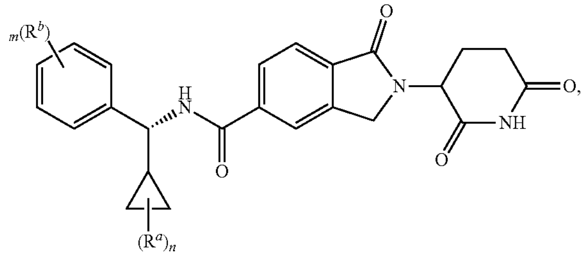

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

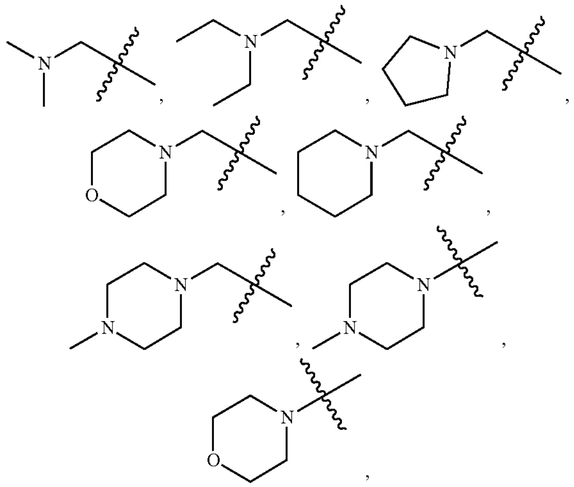

$CF_3$, and EtO—; and each $R^b$ is independently selected from H, F, Cl, Br, Me, CN, MeO, Et, $CF_3O$,

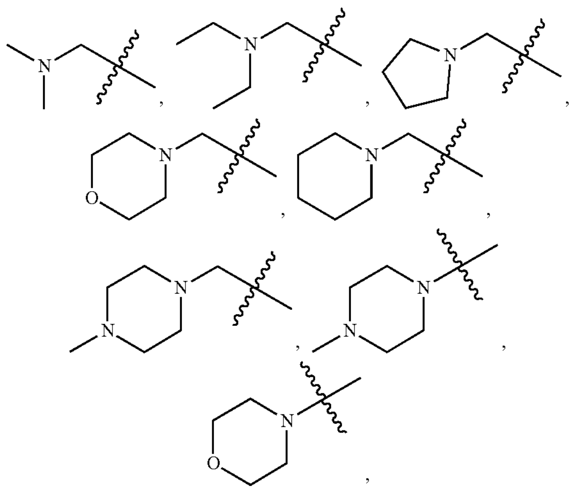

$CF_3$, and EtO—.

In a seventeenth aspect of the first embodiment, the compound represented by structural formula (I) is a compound represented by (I-7)

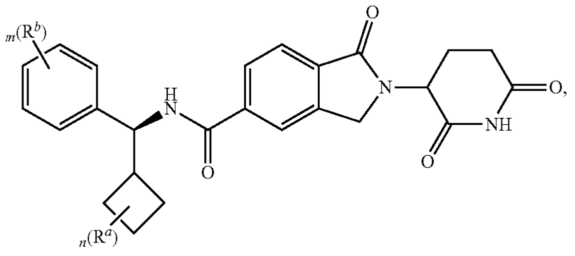

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

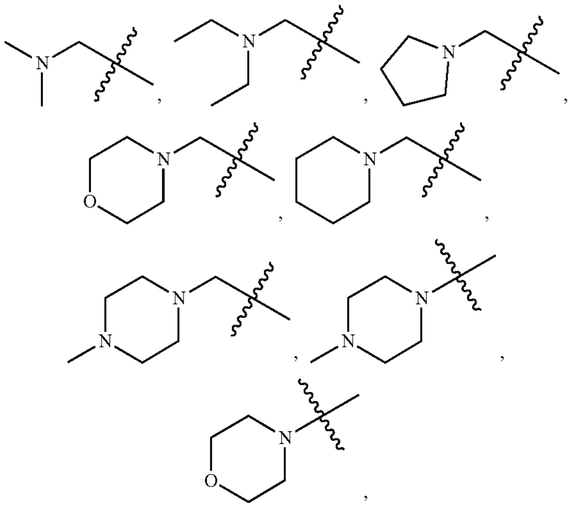

$CF_3$, and EtO—; and each $R^b$ is independently selected from H, F, Cl, Br, Me, CN, MeO, Et, $CF_3O$,

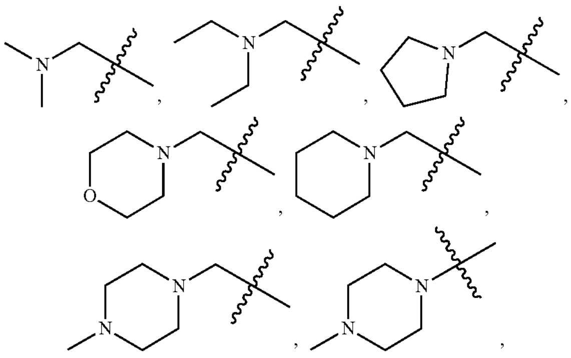

-continued

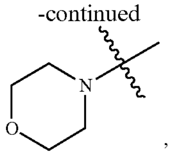
, $CF_3$, and EtO—.

In an eighteenth aspect of the first embodiment, the compound represented by structural formula (I) is a compound represented by (I-8)

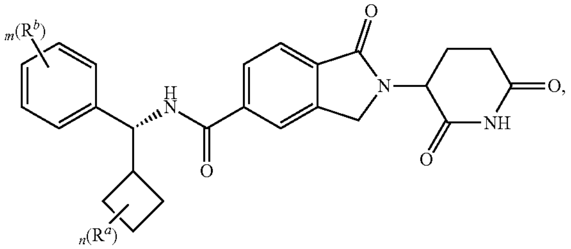

or a pharmaceutically acceptable salt thereof, wherein n is 0, 1, 2, or 3;

m is 0, 1, 2, or 3, each $R^a$ independently is selected from H, F, Cl, Br, Me, CN, MeO, Et, $CF_3O$,

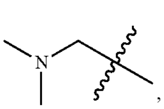
,
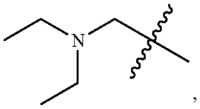
,
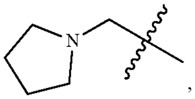
,
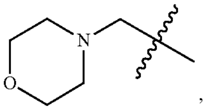
,
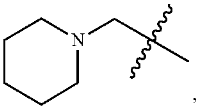
,
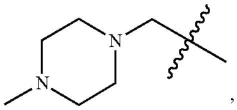
,
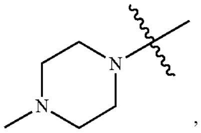
,
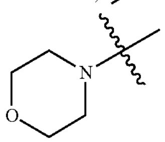
, $CF_3$, and EtO—; and each $R^b$ is independently selected from H, F, Cl, Br, Me, CN, MeO—, Et, $CF_3O$,

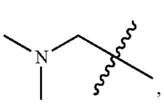
,
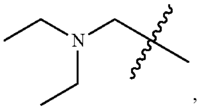
,
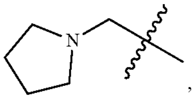
,
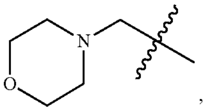
,
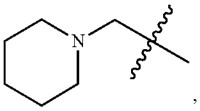
,

-continued

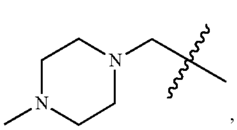
,
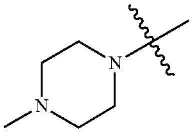
,
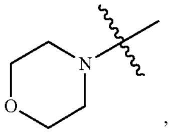
, $CF_3$, and EtO—.

In a nineteenth aspect of the first embodiment, the compound represented by structural formula (I) is a compound represented by (I-9)

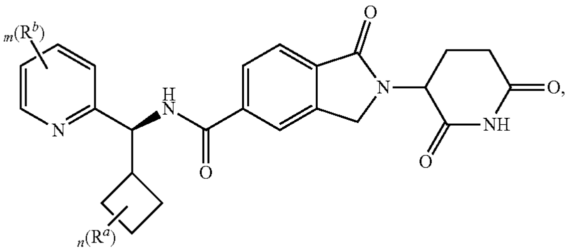

or a pharmaceutically acceptable salt thereof, wherein n is 0, 1, 2, or 3;

m is 0, 1, 2, or 3, each $R^a$ independently is selected from H, F, Cl, Br, Me, CN, MeO, Et, $CF_3O$,

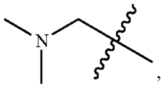
,
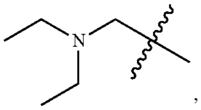
,
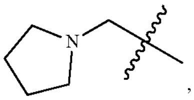
,
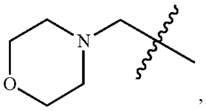
,
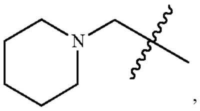
,
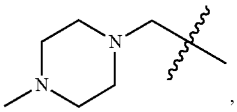
,
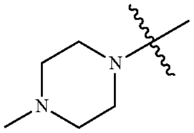
,
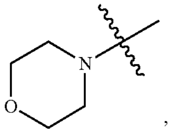
, $CF_3$, and EtO—; and each $R^b$ is independently selected from H, F, Cl, Br, Me, CN, MeO, Et, $CF_3O$,

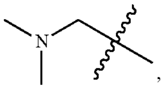
,
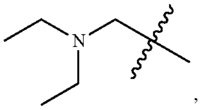
,
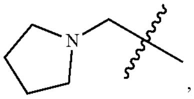
,

-continued

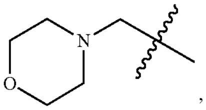,
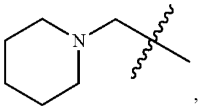,
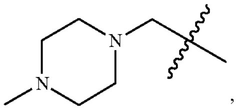,
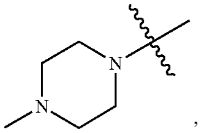,
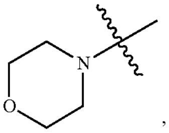, $CF_3$, and EtO—.

In a twentieth aspect of the first embodiment, the compound represented by structural formula (I) is a compound represented by (I-10)

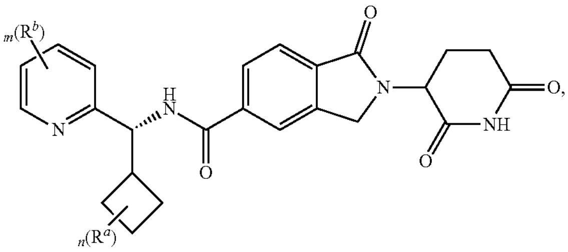

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

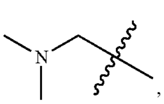,
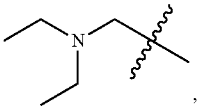,
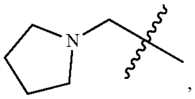,
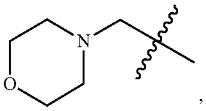,
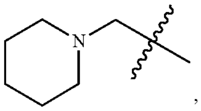,
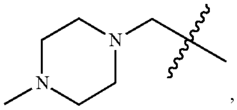,
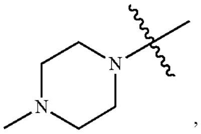,
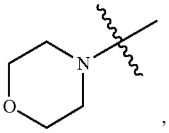, $CF_3$, and EtO—; and each $R^b$ is independently selected from H, F, Cl, Br, Me, CN, MeO, Et, $CF_3O$,

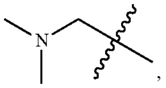,
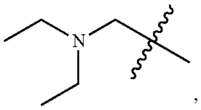,
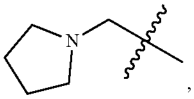,
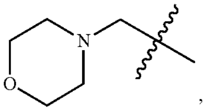,
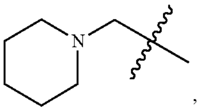,
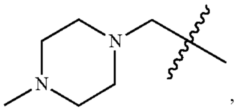,
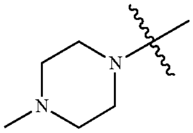,
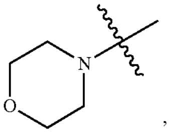, $CF_3$, and EtO—.

In a 21th aspect of the first embodiment, the compound represented by structural formula (I) is a compound represented by (I-11)

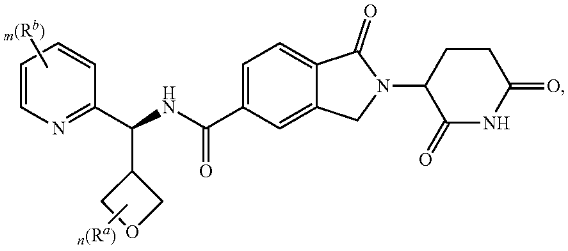

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

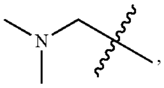,
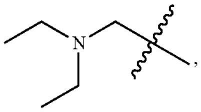,
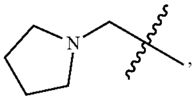,
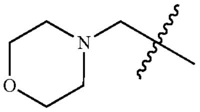,
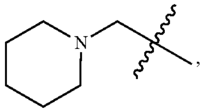,
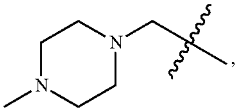,
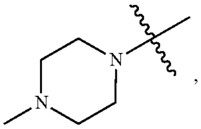,
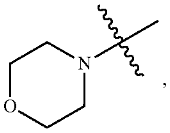, $CF_3$ and EtO—; and each $R^b$ is independently selected from H, F, Cl, Br, Me, CN, MeO, Et, $CF_3O$,

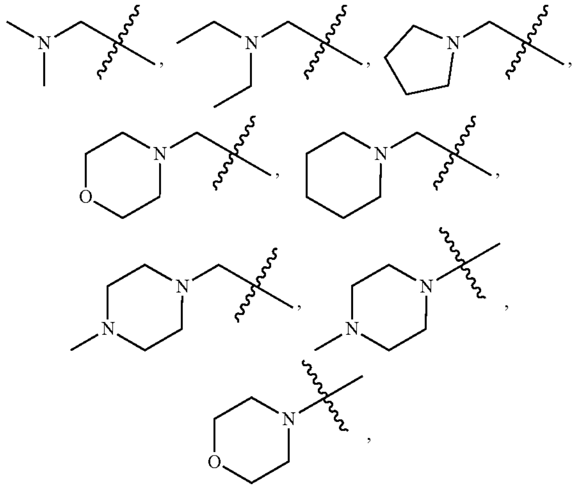

$CF_3$, and EtO—.

In a 22th aspect of the first embodiment, the compound represented by structural formula (I) is a compound represented by (I-12)

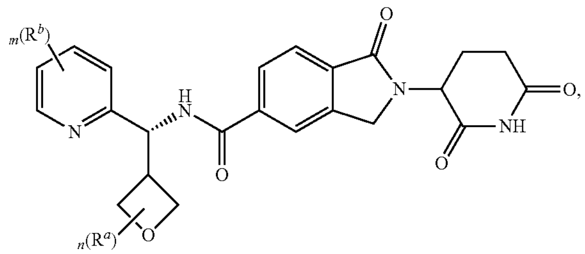

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

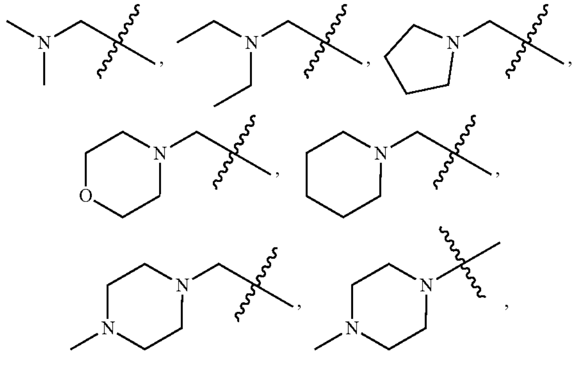

-continued

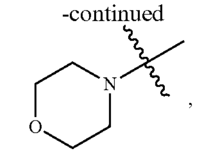

$CF_3$, and EtO—; and each $R^b$ is independently selected from H, F, Cl, Br, Me, CN, MeO, Et, $CF_3O$,

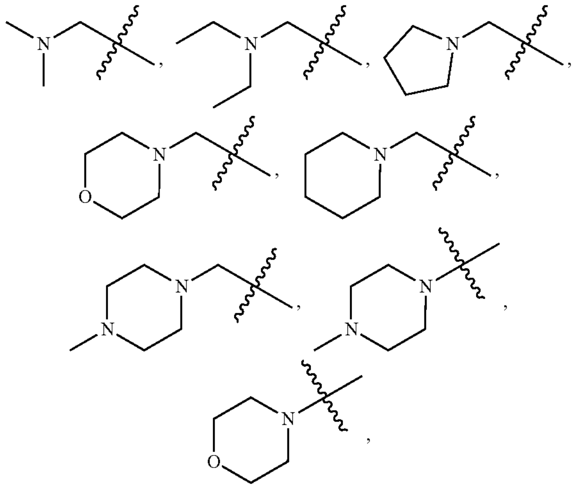

$CF_3$, and EtO—.

In a 23th aspect of the first embodiment, the compound represented by structural formula (I) is a compound represented by (I-13)

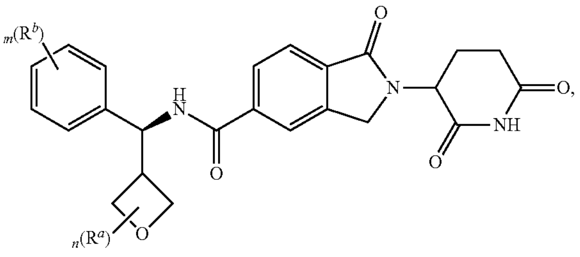

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

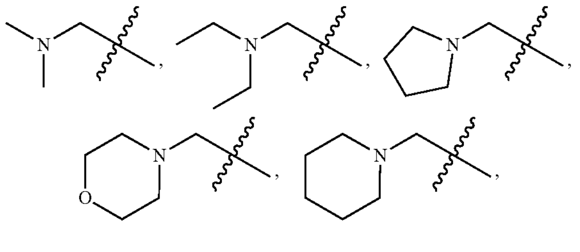

-continued

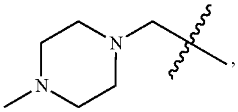, 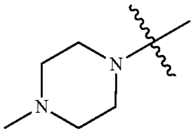, 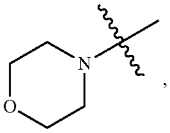, $CF_3$, and EtO—; and each $R^b$ is independently selected from H, F, Cl, Br, Me, CN, MeO, Et, $CF_3O$,

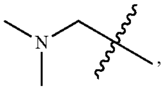, 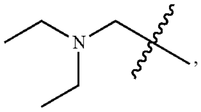, 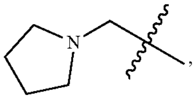, 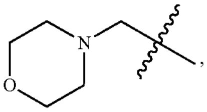, 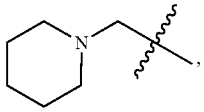, 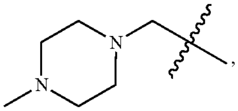, 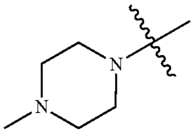, 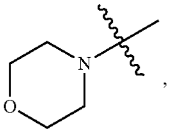, $CF_3$, and EtO—.

In a 24th aspect of the first embodiment, the compound represented by structural formula (I) is a compound represented by (I-14)

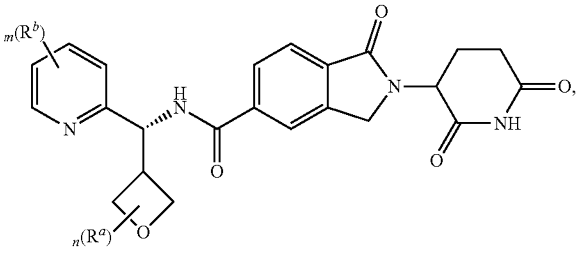

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

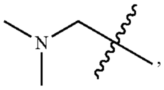, 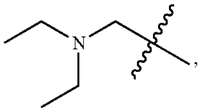, 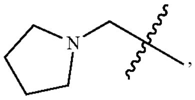, 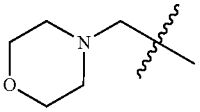, 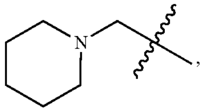, 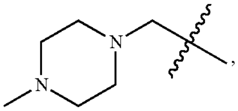, 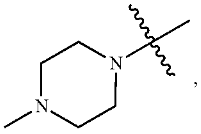, 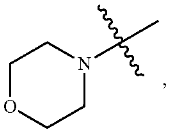, $CF_3$, and EtO—; and each $R^b$ is independently selected from H, F, Cl, Br, Me, CN, MeO, Et, $CF_3O$,

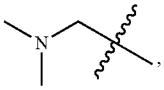, 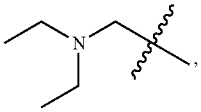, 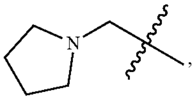, 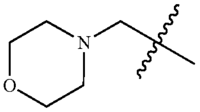, 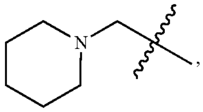, 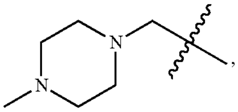, 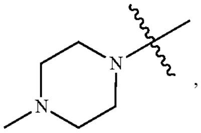, 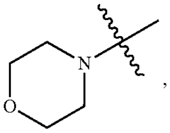, $CF_3$, and EtO—.

In a 25th aspect of the first embodiment, the compound represented by structural formula (I) is a compound represented by (I-15)

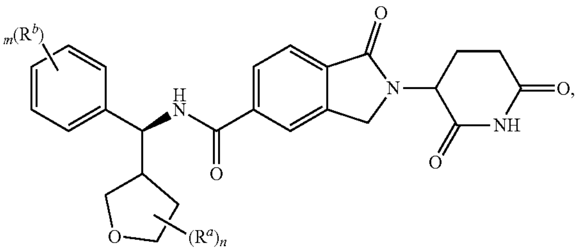

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

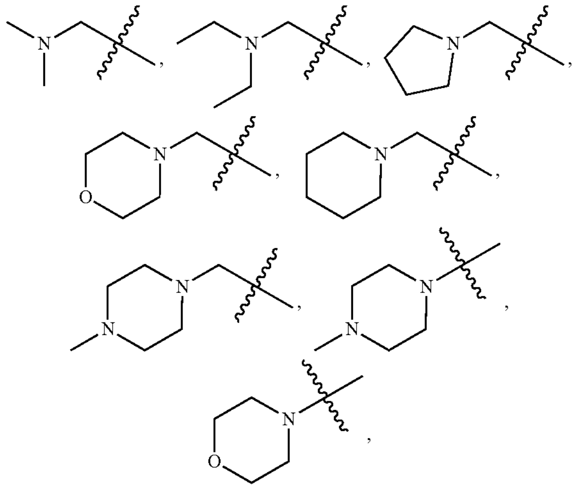

$CF_3$, and EtO—; and each $R^b$ is independently selected from H, F, Cl, Br, Me, CN, MeO, Et, $CF_3O$,

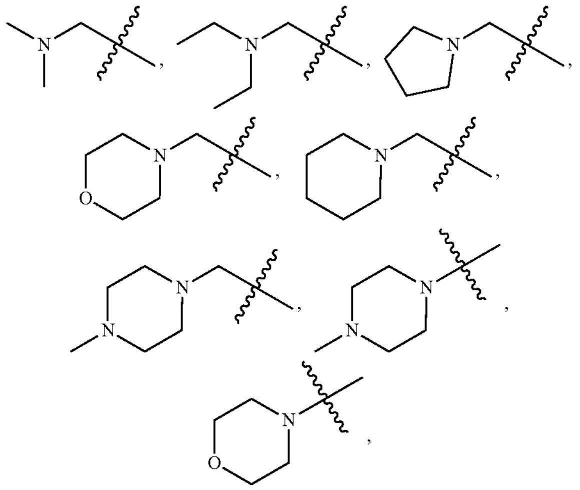

$CF_3$, and EtO—.

In a 26th aspect of the first embodiment, the compound represented by structural formula (I) is a compound represented by (I-16)

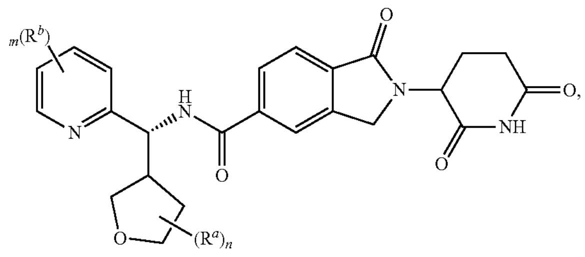

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

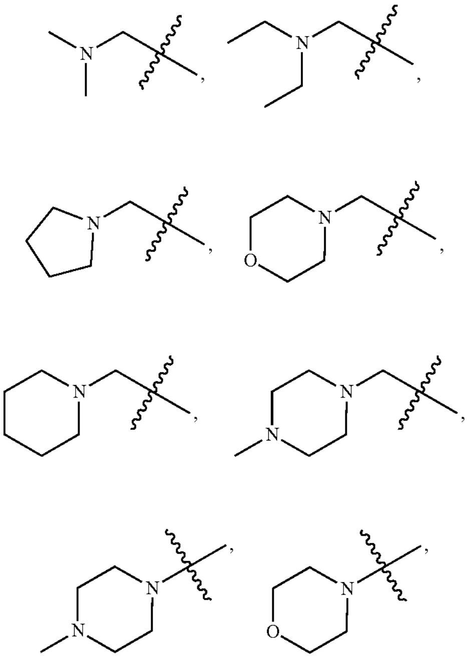

$CF_3$, and EtO—; and each $R^b$ is independently selected from H, F, Cl, Br, Me, CN, MeO, Et, $CF_3O$,

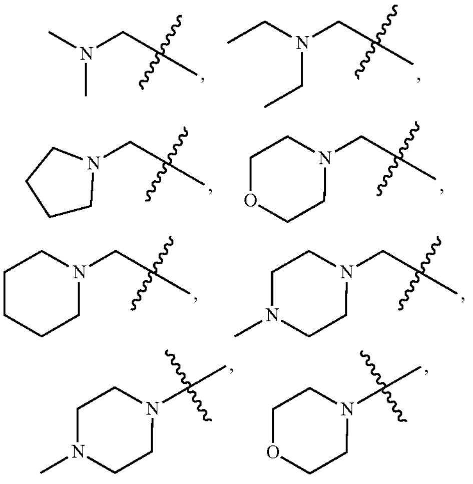

$CF_3$, and EtO—.

In a 27th aspect of the first embodiment, the compound represented by structural formula (I) is a compound represented by (I-17)

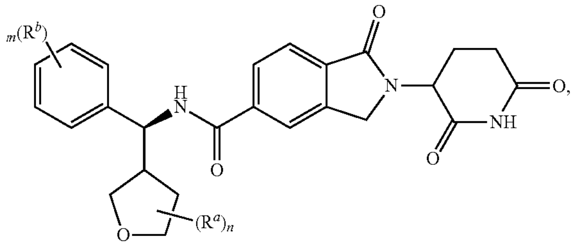

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

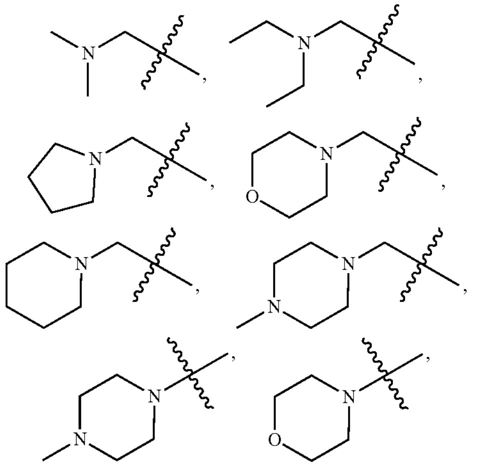

$CF_3$, and EtO—; and each $R^b$ is independently selected from H, F, Cl, Br, Me, CN, MeO, Et, $CF_3O$,

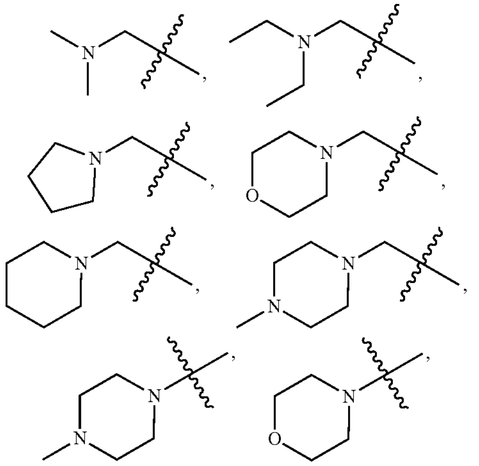

$CF_3$, and EtO—.

In a 28th aspect of the first embodiment, the compound represented by structural formula (I) is a compound represented by (I-18)

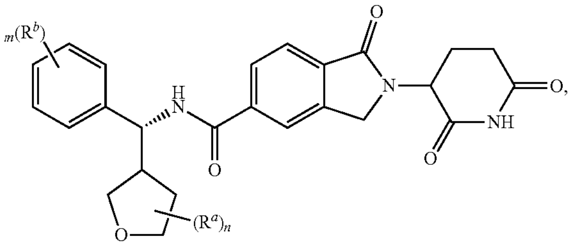

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

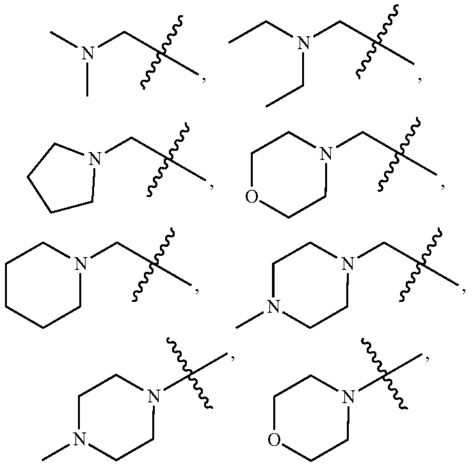

$CF_3$, and EtO—; and each $R^b$ is independently selected from H, F, Cl, Br, Me, CN, MeO, Et, $CF_3O$,

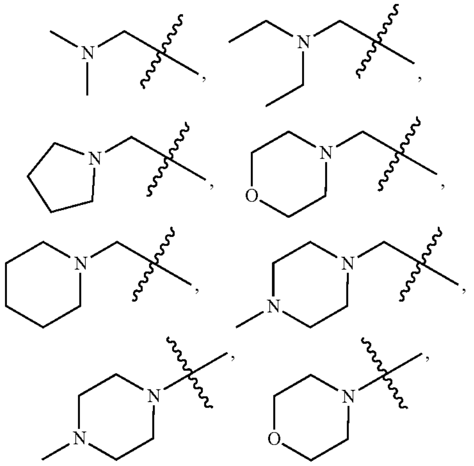

$CF_3$, and EtO—.

In a 29th aspect of the first embodiment, the compound represented by structural formula (I) is a compound represented by (I-19)

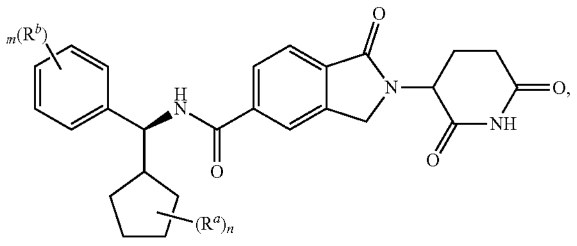

or a pharmaceutically acceptable salt thereof, wherein
n is 0, 1, 2, or 3;
m is 0, 1, 2, or 3,
each $R^a$ is independently selected from H, F, Cl, Br, Me, CN, MeO, Et, $CF_3O$,

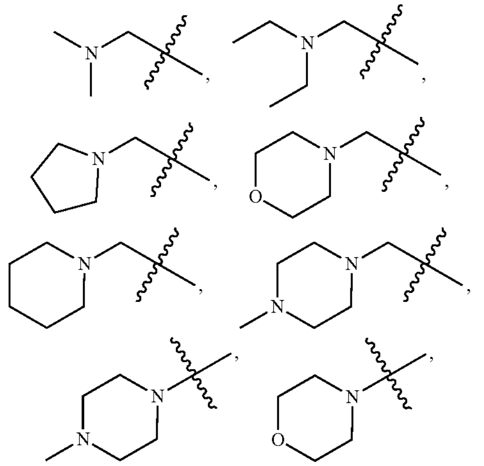

$CF_3$, and EtO—; and
each $R^b$ is independently selected from H, F, Cl, Br, Me, CN, MeO, Et, $CF_3O$,

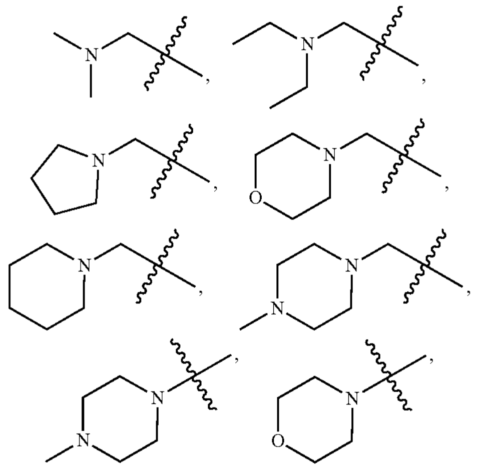

$CF_3$, and EtO—.

In a 30th aspect of the first embodiment, the compound represented by structural formula (I) is a compound represented by (I-20)

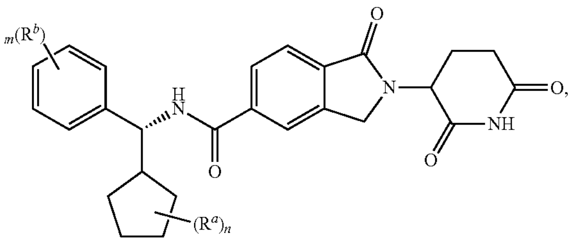

or a pharmaceutically acceptable salt thereof, wherein
n is 0, 1, 2, or 3;
m is 0, 1, 2, or 3,
each $R^a$ is independently selected from H, F, Cl, Br, Me, CN, MeO, Et, $CF_3O$,

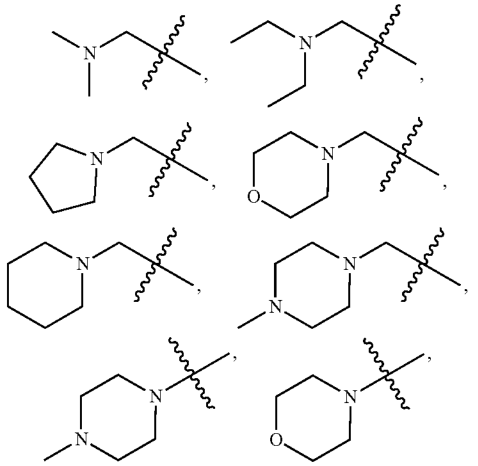

$CF_3$, and EtO—; and
each $R^b$ is independently selected from H, F, Cl, Br, Me, CN, MeO, Et, $CF_3O$,

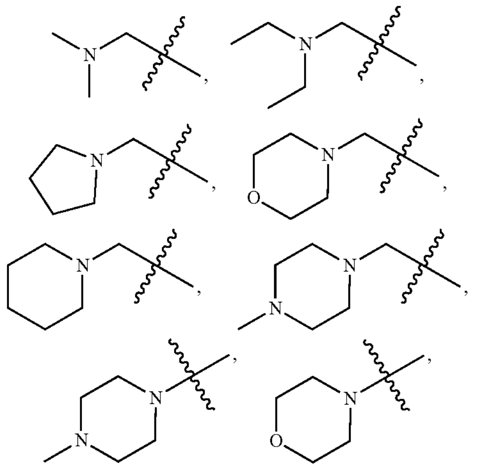

$CF_3$, and EtO—.

In a 31th aspect of the first embodiment, the compound represented by structural formula (I) is a compound represented by (I-21)

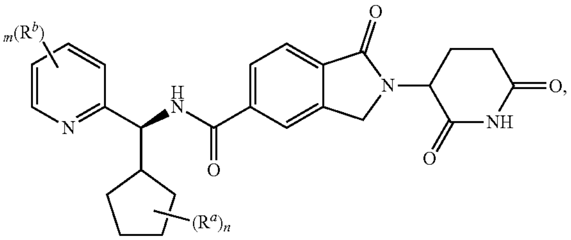

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

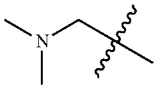, 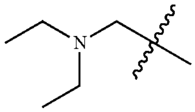, 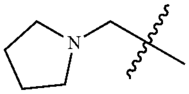, 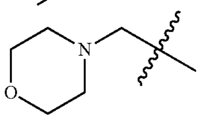, 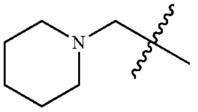, 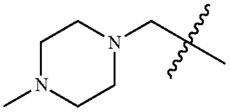, 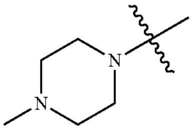, 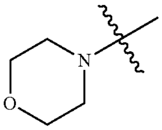, $CF_3$, and EtO—; and each $R^b$ is independently selected from H, F, Cl, Br, Me, CN, MeO, Et, $CF_3O$,

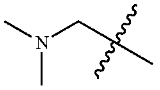, 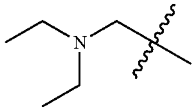, 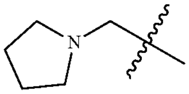, 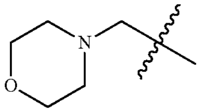, 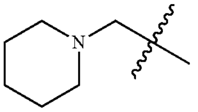, 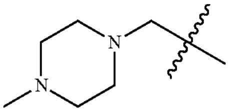, 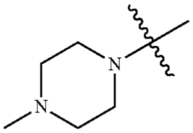, 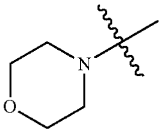, $CF_3$, and EtO—.

In a 32th aspect of the first embodiment, the compound represented by structural formula (I) is a compound represented by (I-22)

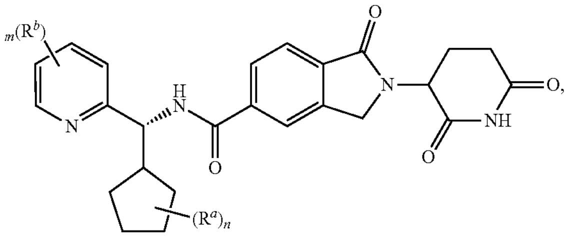

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

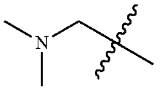, 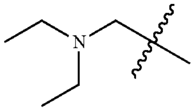, 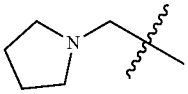, 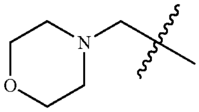, 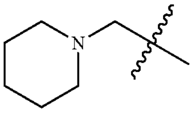, 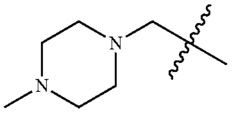, 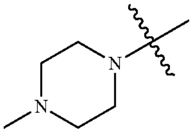, 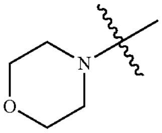, $CF_3$, and EtO—; and each $R^b$ is independently selected from H, F, Cl, Br, Me, CN, MeO, Et, $CF_3O$,

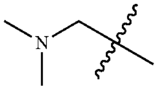, 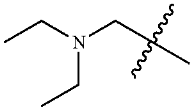, 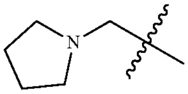, 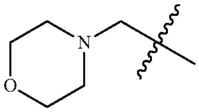, 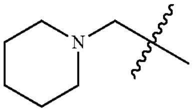, 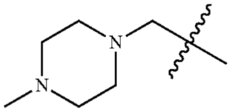, 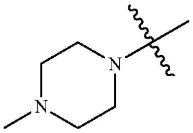, 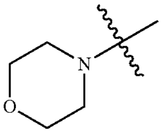, $CF_3$, and EtO—.

In a 33th aspect of the first embodiment, the compound represented by structural formula (I) is a compound represented by (I-23)

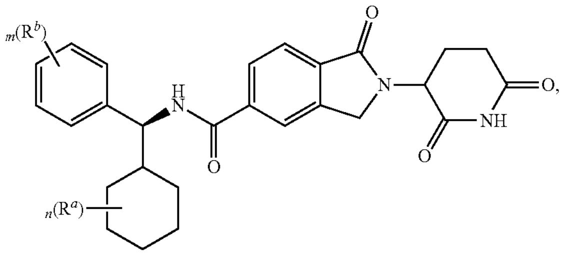

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

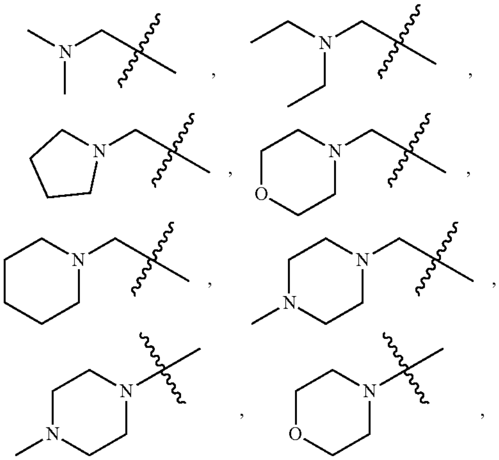

$CF_3$, and EtO—; and each $R^b$ is independently selected from H, F, Cl, Br, Me, CN, MeO, Et, $CF_3O$,

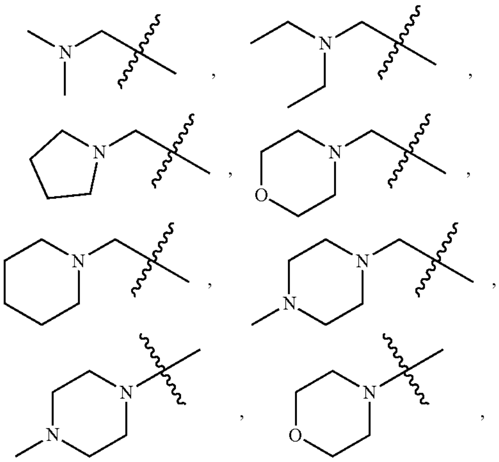

$CF_3$, and EtO—.

In a 34th aspect of the first embodiment, the compound represented by structural formula (I) is a compound represented by (I-24)

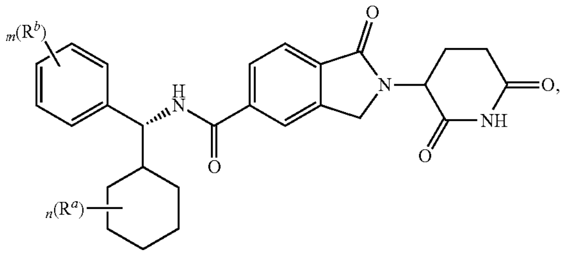

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

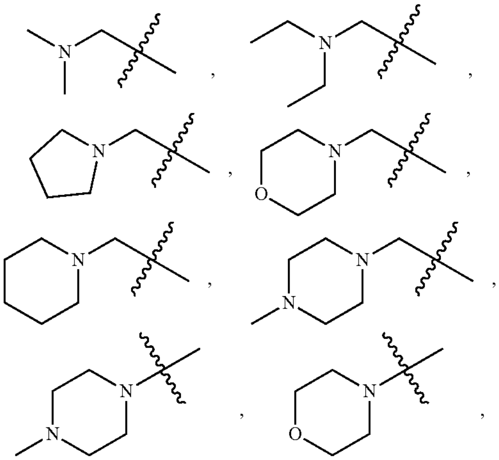

$CF_3$, and EtO—; and each $R^b$ is independently selected from H, F, Cl, Br, Me, CN, MeO, Et, $CF_3O$,

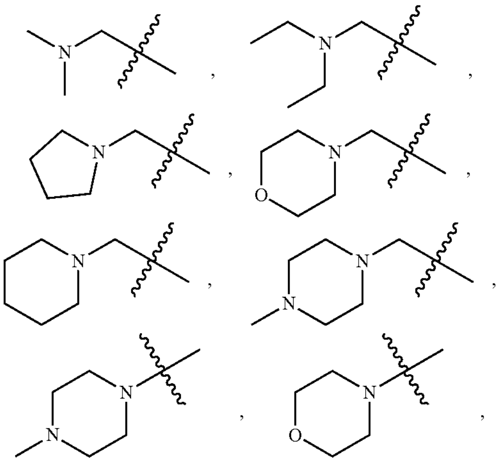

$CF_3$, and EtO—.

In a 35th aspect of the first embodiment, the compound represented by structural formula (I) is a compound represented by (I-25)

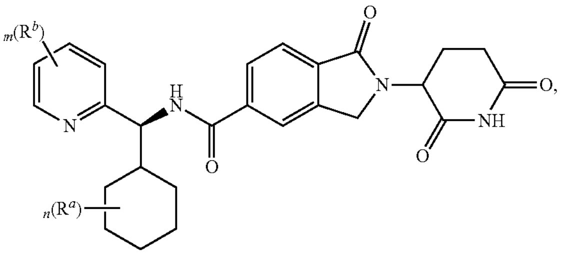

or a pharmaceutically acceptable salt thereof, wherein
n is 0, 1, 2, or 3;
m is 0, 1, 2, or 3,
each $R^a$ is independently selected from H, F, Cl, Br, Me, CN, MeO, Et, $CF_3O$,

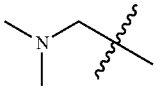, 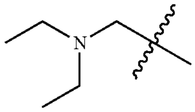, 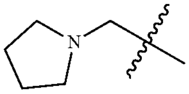, 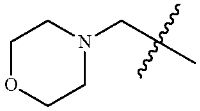, 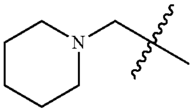, 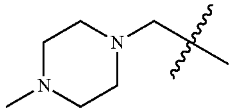, 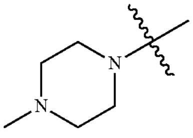, 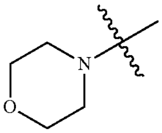, $CF_3$, and EO; and
each $R^b$ is independently selected from H, F, Cl, Br, Me, CN, MeO, Et, $CF_3O$,

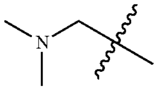, 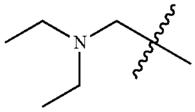, 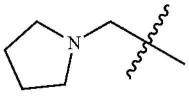, 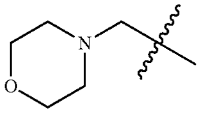, 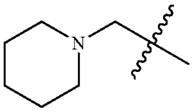, 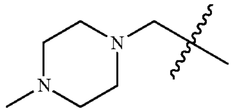, 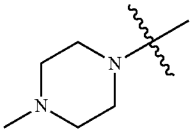, 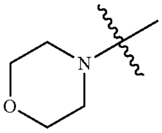, $CF_3$, and EtO—.

In a 36th aspect of the first embodiment, the compound represented by structural formula (I) is a compound represented by (I-26)

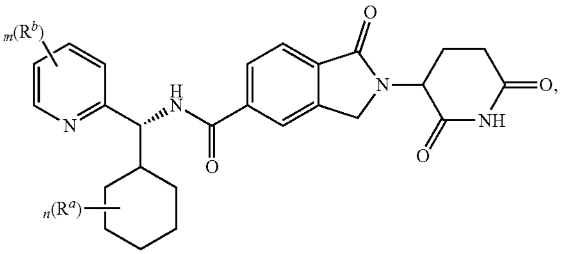

or a pharmaceutically acceptable salt thereof, wherein
n is 0, 1, 2, or 3;
m is 0, 1, 2, or 3,
each $R^a$ is independently selected from H, F, Cl, Br, Me, CN, MeO, Et, $CF_3O$,

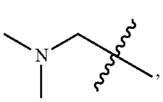, 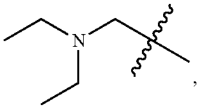, 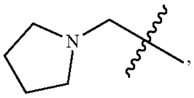, 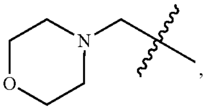, 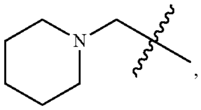, 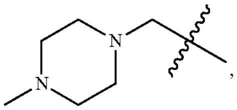, 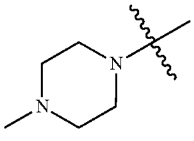, 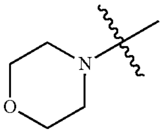, $CF_3$, and EtO—; and
each $R^b$ is independently selected from H, F, Cl, Br, Me, CN, MeO, Et, $CF_3O$,

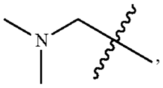, 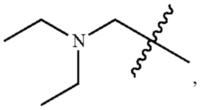, 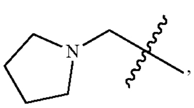, 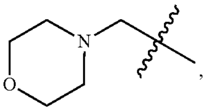, 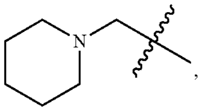, 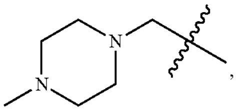, 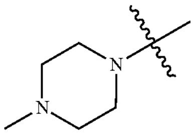, 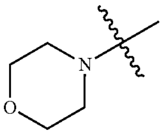, $CF_3$, and EtO—.

In a 37th aspect of the first embodiment, the compound represented by structural formula (I) is a compound represented by (I-27)

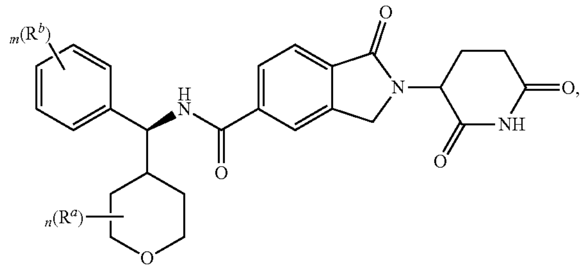

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

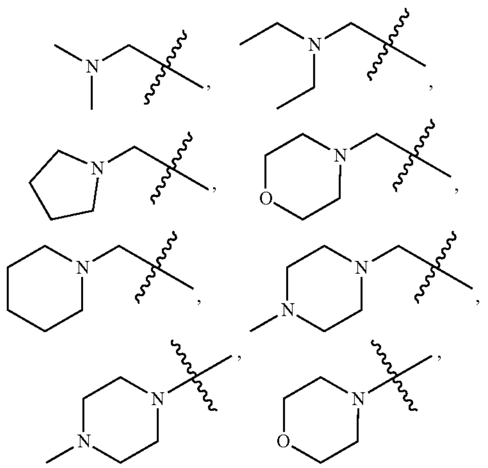

$CF_3$, and EtO—; and each $R^b$ is independently selected from H, F, Cl, Br, Me, CN, MeO, Et, $CF_3O$,

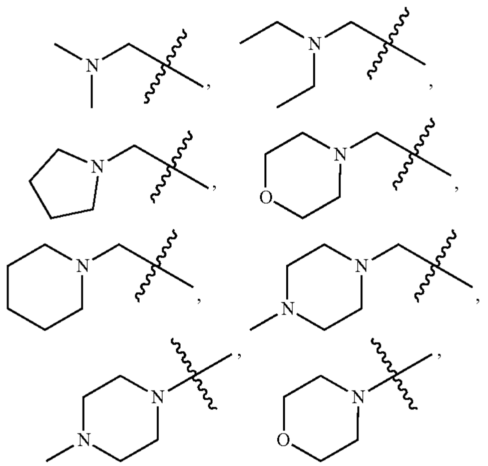

$CF_3$, and EtO—.

In a 38th aspect of the first embodiment, the compound represented by structural formula (I) is a compound represented by (I-28)

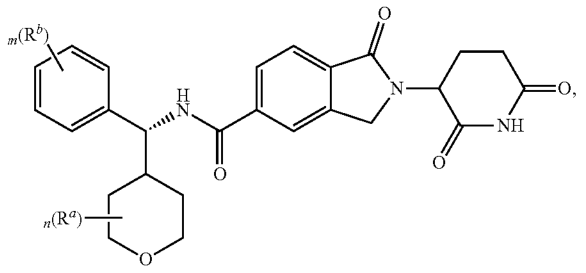

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

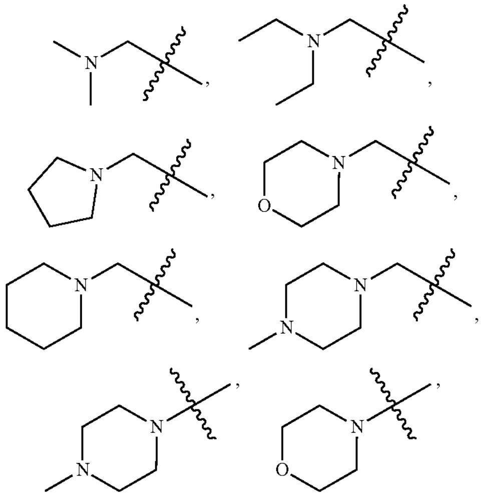

$CF_3$, and EtO—; and each $R^b$ is independently selected from H, F, Cl, Br, Me, CN, MeO, Et, $CF_3O$,

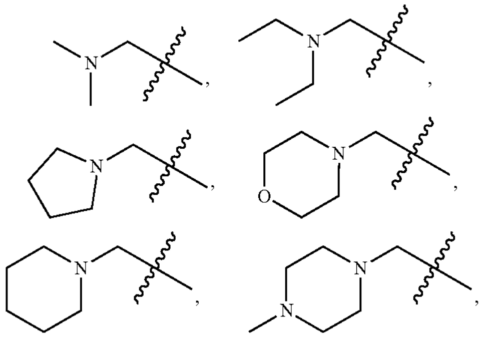

-continued

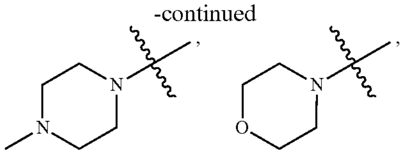

$CF_3$, and EtO—.

In a 39th aspect of the first embodiment, the compound represented by structural formula (I) is a compound represented by (I-29)

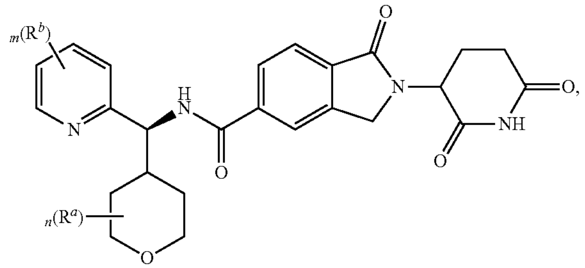

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

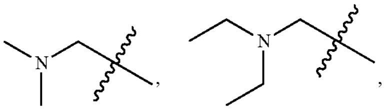

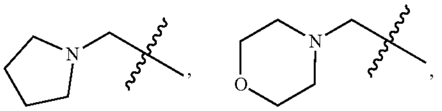

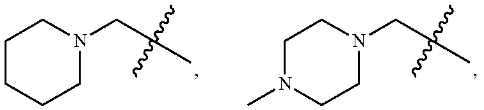

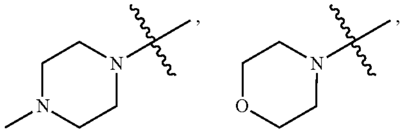

$CF_3$, and EtO—; and each $R^b$ is independently selected from H, F, Cl, Br, Me, CN, MeO, Et, $CF_3O$,

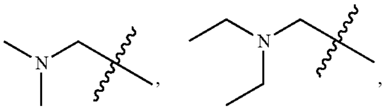

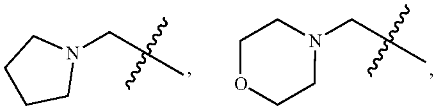

-continued

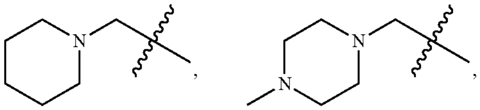

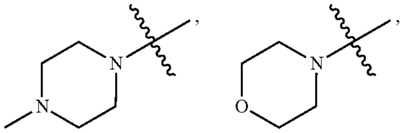

$CF_3$, and EtO—.

In a 40th aspect of the first embodiment, the compound represented by structural formula (I) is a compound represented by (I-30)

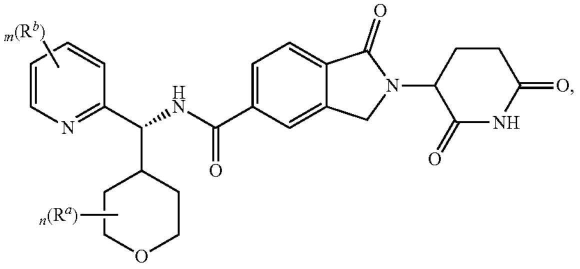

or a pharmaceutically acceptable salt thereof, wherein n is 0, 1, 2, or 3;

m is 0, 1, 2, or 3, each $R^a$ is independently selected from H, F, Cl, Br, Me, CN, MeO, Et, $CF_3O$,

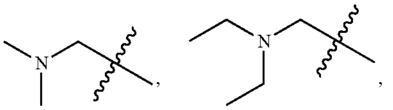

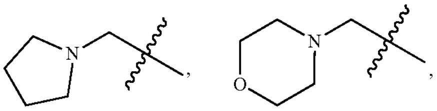

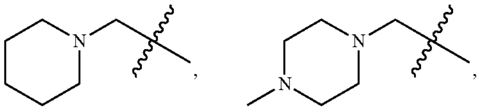

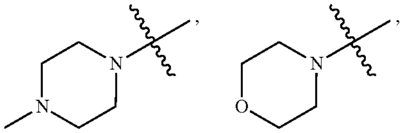

$CF_3$, and EtO—; and each $R^b$ is independently selected from H, F, Cl, Br, Me, CN, MeO, Et, $CF_3O$,

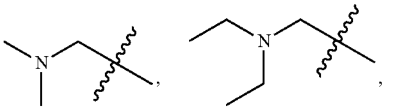

-continued

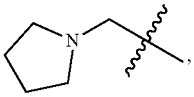, 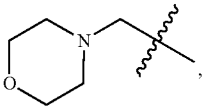, 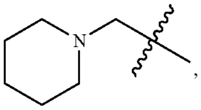, 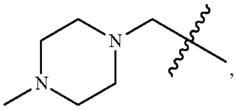, 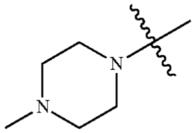, 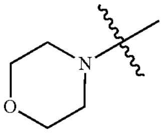, $CF_3$, and EtO—.

A second embodiment of the invention is a compound of structural formula (II)

(II)

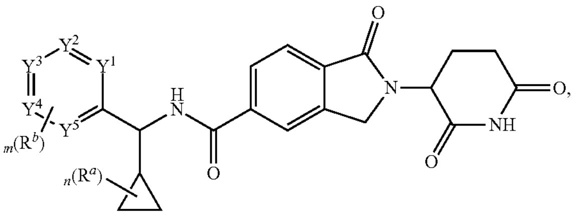

or a pharmaceutically acceptable salt thereof, with the proviso that the total number of heteroatoms in the moiety

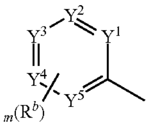

is less than or equal to 3. The remaining variables are as described and defined in the first embodiment, or any aspect thereof.

A third embodiment of the invention is a compound of structural formula (III)

(III)

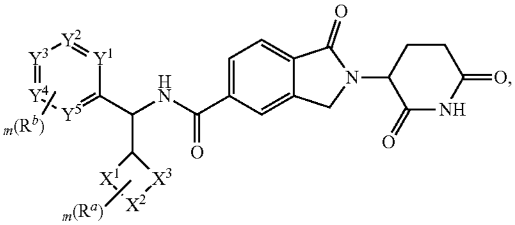

or a pharmaceutically acceptable salt thereof, with the proviso that the total number of heteroatoms in the moiety

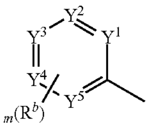

is less than or equal to 3. The remaining variables are as described and defined in the first embodiment, or any aspect thereof.

A fourth embodiment of the invention is a compound of structural formula (IV)

(IV)

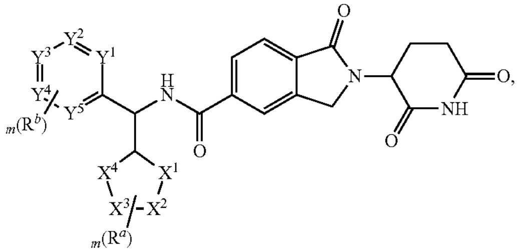

or a pharmaceutically acceptable salt thereof, with the proviso that the total number of heteroatoms in the moiety

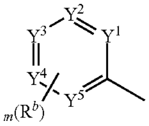

is less than or equal to 3; and the total number of heteroatoms in the moiety

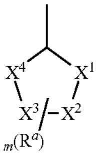

is less than or equal to 3. The remaining variables are as described and defined in the first embodiment, or any aspect thereof.

A fifth embodiment of the invention is a compound of structural formula (V)

(V)

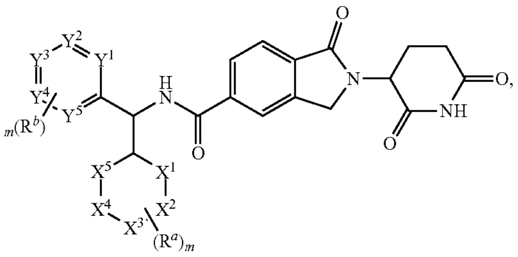

or a pharmaceutically acceptable salt thereof, with the proviso that the total number of heteroatoms in the moiety

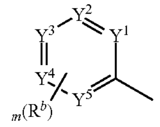

is less than or equal to 3; and the total number of heteroatoms in the moiety

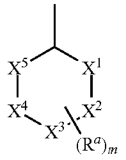

is less than or equal to 3. The remaining variables are as described and defined in the first embodiment, or any aspect thereof.

A sixth embodiment of the invention is a compound of structural formula (VI)

(VI)

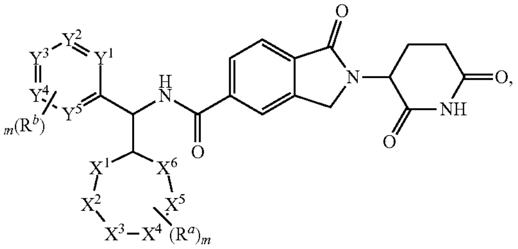

or a pharmaceutically acceptable salt thereof, with the proviso that the total number of heteroatoms in the moiety

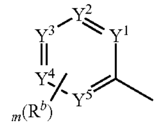

is less than or equal to 3; and the total number of heteroatoms in the moiety

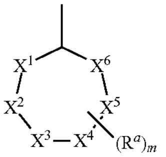

is less than or equal to 3. The remaining variables are as described and defined in the first embodiment, or any aspect thereof.

A seventh embodiment of the invention is a compound of structural formula (VII)

(VII)

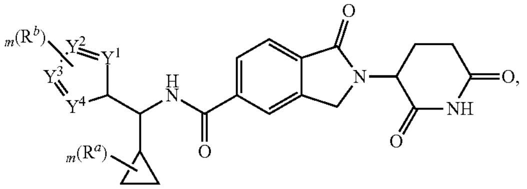

or a pharmaceutically acceptable salt thereof, with the proviso that the total number of heteroatoms in the moiety

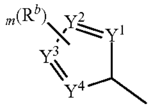

is less than or equal to 3. The remaining variables are as described and defined in the first embodiment, or any aspect thereof.

An eighth embodiment of the invention is a compound of structural formula (VIII)

(VIII)

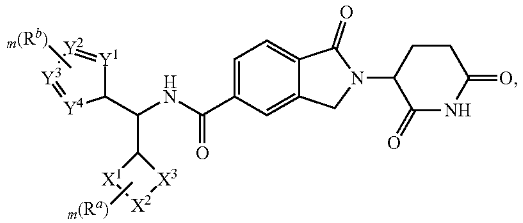

or a pharmaceutically acceptable salt thereof, with the proviso that the total number of heteroatoms in the moiety

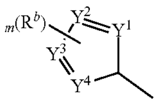

is less than or equal to 3. The remaining variables are as described and defined in the first embodiment, or any aspect thereof.

A ninth embodiment of the invention is a compound of structural formula (IX)

(IX)

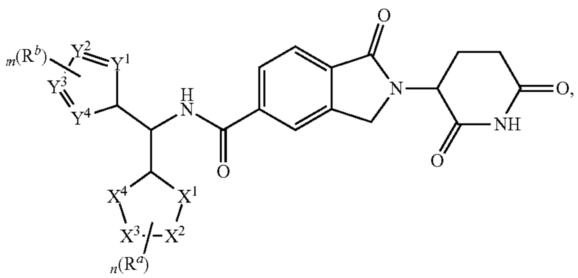

or a pharmaceutically acceptable salt thereof, with the proviso that the total number of heteroatoms in the moiety

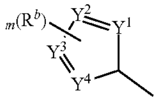

is less than or equal to 3; and the total number of heteroatoms in the moiety

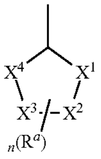

is less than or equal to 3. The remaining variables are as described and defined in the first embodiment, or any aspect thereof.

A tenth embodiment of the invention is a compound of structural formula (X)

(X)

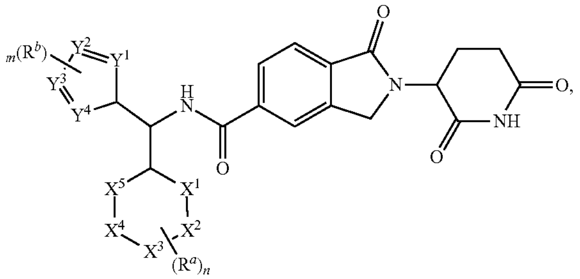

or a pharmaceutically acceptable salt thereof, with the proviso that the total number of heteroatoms in the moiety

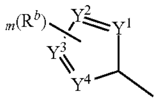

is less than or equal to 3; and the total number of heteroatoms in the moiety

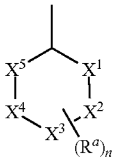

is less than or equal to 3. The remaining variables are as described and defined in the first embodiment, or any aspect thereof.

An eleventh embodiment of the invention is a compound of structural formula (XI)

(XI)

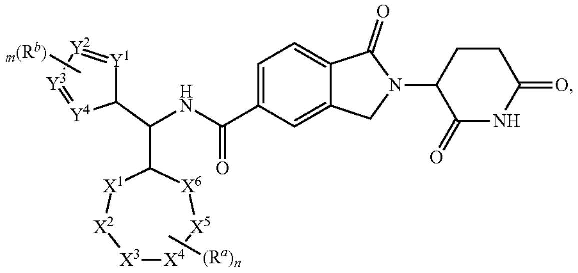

or a pharmaceutically acceptable salt thereof, with the proviso that the total number of heteroatoms in the moiety

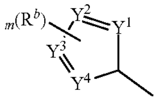

is less than or equal to 3; and the total number of heteroatoms in the moiety

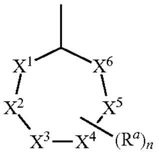

is less than or equal to 3. The remaining variables are as described and defined in the first embodiment, or any aspect thereof.

A twelfth embodiment of the invention is a compound of structural formula (XII)

(XII)

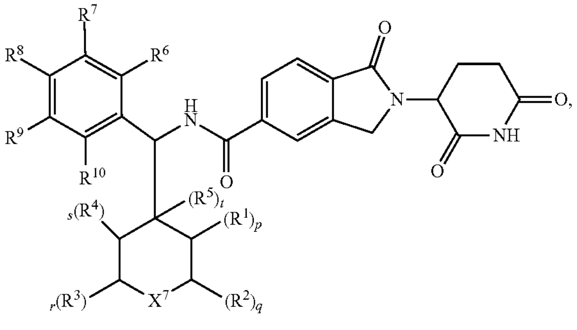

or a pharmaceutically acceptable salt thereof, wherein:

$R^1$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)$OR^{11}$, —$C_0$-$C_4$alkyl$NR^{11}R^{12}$, —C(O)$NR^{11}R^{12}$, —$SO_2R^{11}$, —$SO_2NR^{11}R^{12}$, —OC(O)$R^{11}$, and —C($NR^{11}$)$NR^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl);

$R^2$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)$OR^{11}$, —$C_0$-$C_4$alkyl$NR^{11}R^{12}$, —C(O)$NR^{11}R^{12}$, —$SO_2R^{11}$, —$SO_2NR^{11}R^{12}$, —OC(O)$R^{11}$, and —C($NR^{11}$)$NR^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl);

$R^3$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)$OR^{11}$, —$C_0$-$C_4$alkyl$NR^{11}R^{12}$, —C(O)$NR^{11}R^{12}$, —$SO_2R^{11}$, —$SO_2NR^{11}R^{12}$, —OC(O)$R^{11}$, and —C($NR^{11}$)$NR^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl);

$R^4$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)$OR^{11}$, —$C_0$-$C_4$alkyl$NR^{11}R^{12}$, —C(O)$NR^{11}R^{12}$, —$SO_2R^{11}$, —$SO_2NR^{11}R^{12}$, —OC(O)$R^{11}$, and —C($NR^{11}$)$NR^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl);

$R^5$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)$OR^{11}$, —$C_0$-$C_4$alkyl$NR^{11}R^{12}$, —C(O)$NR^{11}R^{12}$, —$SO_2R^{11}$, —$SO_2NR^{11}R^{12}$, —OC(O)$R^{11}$, and —C($NR^{11}$)$NR^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl);

p, for each occurrence, is independently 0, 1, or 2;

q, for each occurrence, is independently 0, 1, or 2;

r, for each occurrence, is independently 0, 1, or 2;

s, for each occurrence, is independently 0, 1, or 2;

t, for each occurrence, is independently 0, 1, or 2;

$X^7$, for each occurrence, is independently $C(R^{15})_2$, $N(R^{16})$, O, or S;

$R^{15}$ or $R^{16}$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)O$R^{11}$, —$C_0$-$C_4$alkylN$R^{11}R^{12}$, —C(O)N$R^{11}R^{12}$, —S$O_2R^{11}$, —S$O_2$N$R^{11}R^{12}$, —OC(O)$R^{11}$, and —C(N$R^{11}$)N$R^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl);

$R^6$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)O$R^{11}$, —$C_0$-$C_4$alkylN$R^{11}R^{12}$, —C(O)N$R^{11}R^{12}$, —S$O_2R^{11}$, —S$O_2$N$R^{11}R^{12}$, —OC(O)$R^{11}$, and —C(N$R^{11}$)N$R^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl);

$R^7$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)O$R^{11}$, —$C_0$-$C_4$alkylN$R^{11}R^{12}$, —C(O)N$R^{11}R^{12}$, —S$O_2R^{11}$, —S$O_2$N$R^{11}R^{12}$, —OC(O)$R^{11}$, and —C(N$R^{11}$)N$R^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl);

$R^8$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)O$R^{11}$, —$C_0$-$C_4$alkylN$R^{11}R^{12}$, —C(O)N$R^{11}R^{12}$, —S$O_2R^{11}$, —S$O_2$N$R^{11}R^{12}$, —OC(O)$R^{11}$, and —C(N$R^{11}$)N$R^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl);

$R^9$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)O$R^{11}$, —$C_0$-$C_4$alkylN$R^{11}R^{12}$, —C(O)N$R^{11}R^{12}$, —S$O_2R^{11}$, —S$O_2$N$R^{11}R^{12}$, —OC(O)$R^{11}$, and —C(N$R^{11}$)N$R^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl);

$R^{10}$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)O$R^{11}$, —$C_0$-$C_4$alkylN$R^{11}R^{12}$, —C(O)N$R^{11}R^{12}$, —S$O_2R^{11}$, —S$O_2$N$R^{11}R^{12}$, —OC(O)$R^{11}$, and —C(N$R^{11}$)N$R^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl), with the proviso that the total number of substituents in the moiety

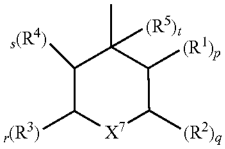

is less than or equal to 6.

In a first aspect of the twelfth embodiment, each of $R^1$, $R^2$, $R^3$, $R^4$, $R^5$, $R^6$, $R^7$, $R^8$, $R^9$, $R^{10}$, $R^{15}$, or $R^{16}$ is independently selected from H, F, Cl, Br, Me, CN, MeO—, Et, $CF_3O$,

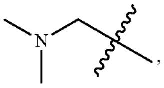
,
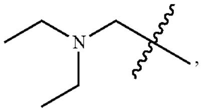
,
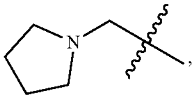
,
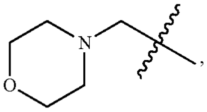
,
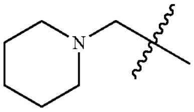
,
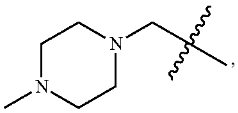
,
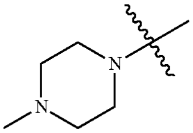
,
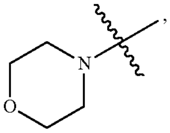
, $CF_3$, EtO—.

A thirteenth embodiment of the invention is a compound of structural formula (XIII)

(XIII)

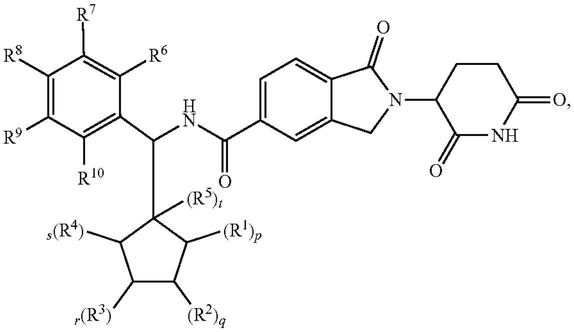

or a pharmaceutically acceptable salt thereof, with the proviso that the total number of substituents in the moiety

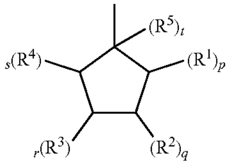

is less than or equal to 6. The variables therein are as described and defined in the twelfth embodiment, or any aspect thereof.

In a first aspect of the thirteenth embodiment, each of $R^1$, $R^2$, $R^3$, $R^4$, $R^5$, $R^6$, $R^7$, $R^8$, $R^9$, or $R^{10}$, is independently selected from H, F, Cl, Br, Me, CN, MeO—, Et, $CF_3O$,

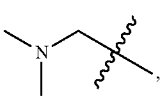
,
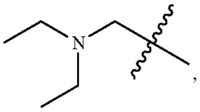
,
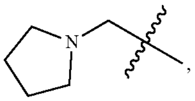
,
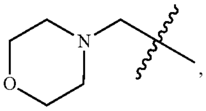
,
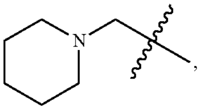
,
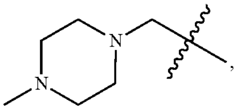
,
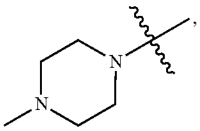
,
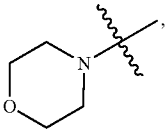
, $CF_3$, EtO—.

A fourteenth embodiment of the invention is a compound of structural formula (XIV)

(XIV)

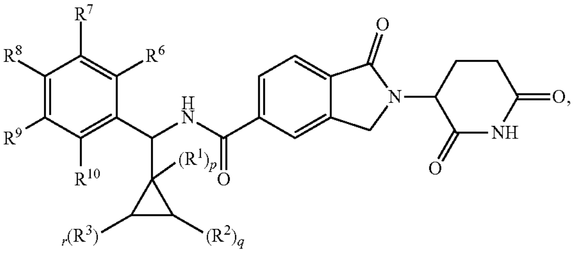

or a pharmaceutically acceptable salt thereof, with the proviso that the total number of substituents in the moiety

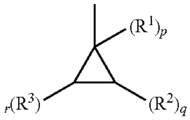

is less than or equal to 5. The variables therein are as described and defined in the twelfth embodiment, or any aspect thereof.

In a first aspect of the fourteenth embodiment, each of $R^1$, $R^2$, $R^3$, $R^6$, $R^7$, $R^8$, $R^9$, or $R^{10}$, is independently selected from H, F, Cl, Br, Me, CN, MeO—, Et, $CF_3O$,

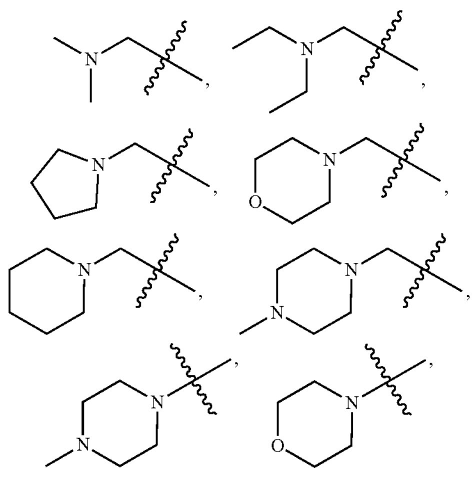

$CF_3$, EtO—.

A fifteenth embodiment of the invention is a compound of structural formula (XV)

(XV)

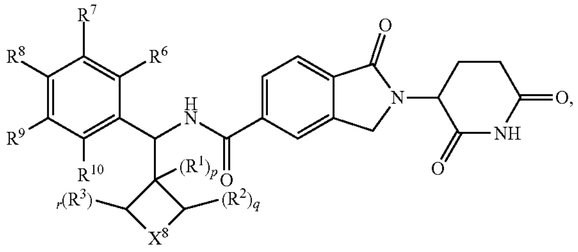

or a pharmaceutically acceptable salt thereof, wherein:

$X^8$, for each occurrence, is independently $C(R^{17})_2$, $N(R^{18})$, O, or S;

$R^{17}$ or $R^{18}$, for each occurrence, is independently selected from hydrogen, halogen, hydroxyl, nitro, cyano, amino, mercapto, —COOH, $C_1$-$C_6$alkyl, $C_2$-$C_6$ alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$ cycloalkyl), —O—$C_0$-$C_4$alkyl($C_3$-$C_7$ cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)$OR^{11}$, —$C_0$-$C_4$alkyl$NR^{11}R^{12}$, —C(O)$NR^{11}R^{12}$, —$SO_2R^{11}$, —$SO_2NR^{11}R^{12}$, —OC(O)$R^{11}$, and —C($NR^1$)$NR^{11}R^{12}$, wherein $R^{11}$ and $R^{12}$ are independently chosen from hydrogen, $C_1$-$C_6$alkyl, —$C_0$-$C_4$alkyl($C_3$-$C_7$ cycloalkyl), and —O—$C_0$-$C_4$alkyl($C_3$-$C_7$ cycloalkyl), with the proviso that the total number of substituents in the moiety

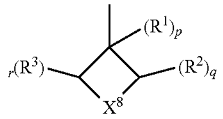

is less than or equal to 6. The remaining variables are as described and defined in the twelfth embodiment, or any aspect thereof.

In a first aspect of the fifteenth embodiment, each of $R^1$, $R^2$, $R^3$, $R^6$, $R^7$, $R^8$, $R^9$, $R^{10}$, $R^{17}$, or $R^{18}$ is independently selected from H, F, Cl, Br, Me, CN, MeO—, Et, $CF_3O$,

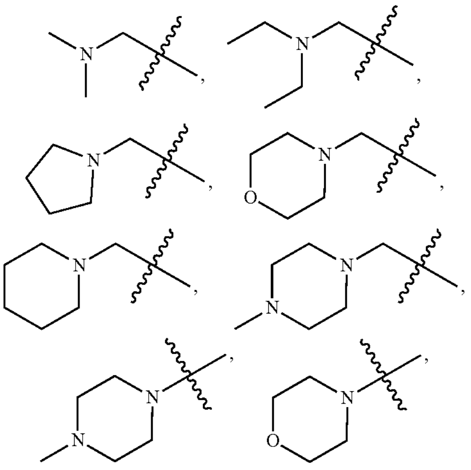

$CF_3$, EtO—. In any embodiment above or any aspect thereof, the number of substituents linked thereon can be 0, 1, 2, 3, 4, 5 or 6.

In any embodiment above or any aspect thereof, m can be 0, 1, 2, 3, 4, 5 or 6.

In any embodiment above or any aspect thereof, n can be 0, 1, 2, 3, 4, 5 or 6.

The present invention also relates to the following compounds:

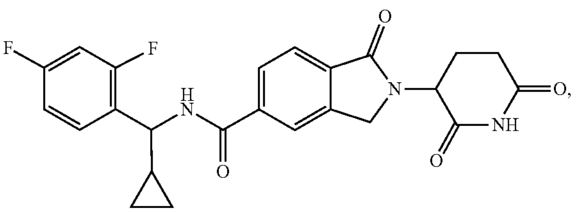

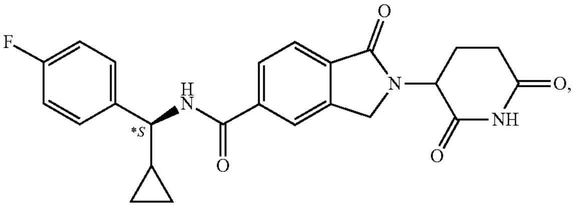

-continued
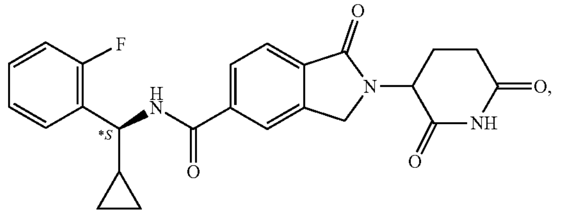
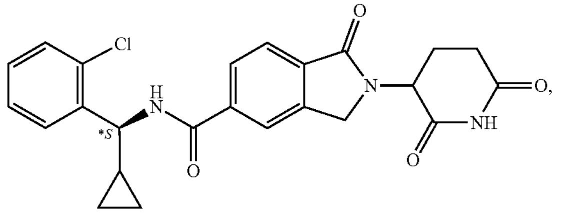
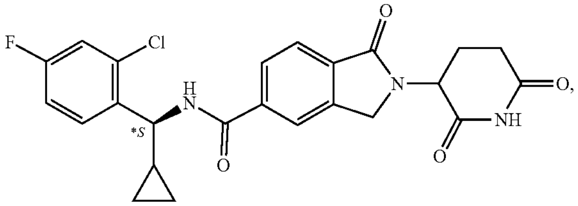
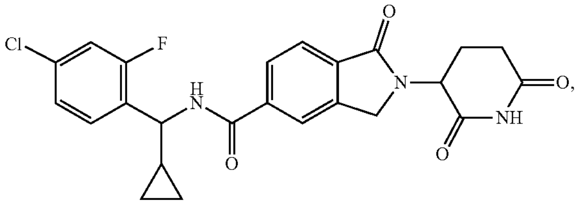
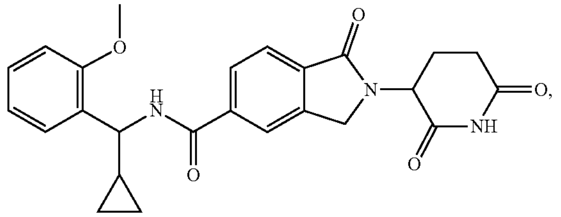
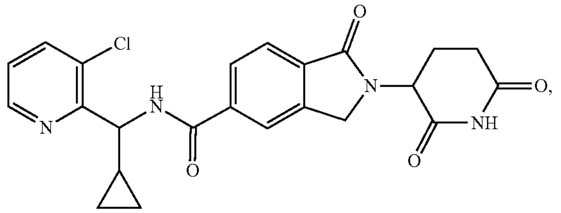
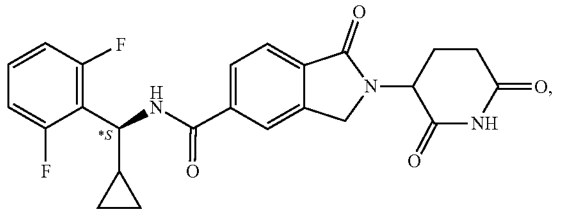
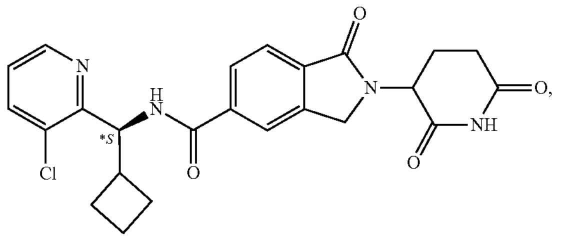
-continued
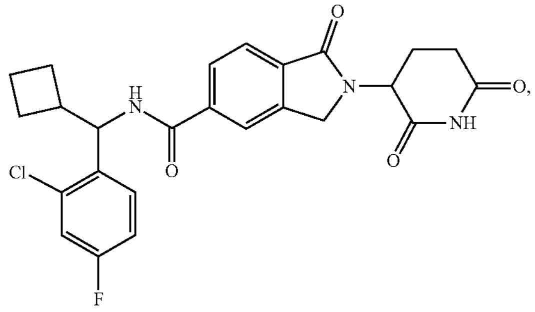
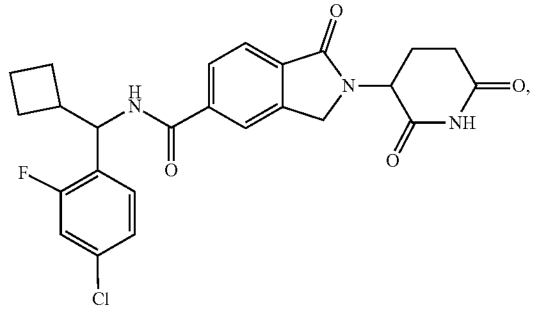
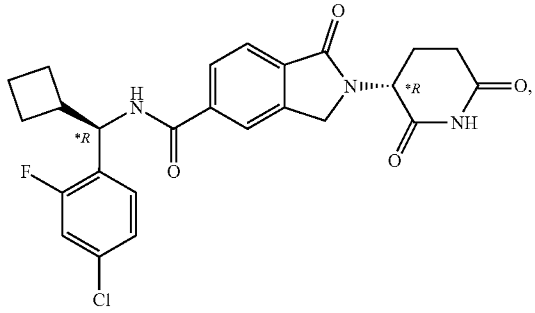
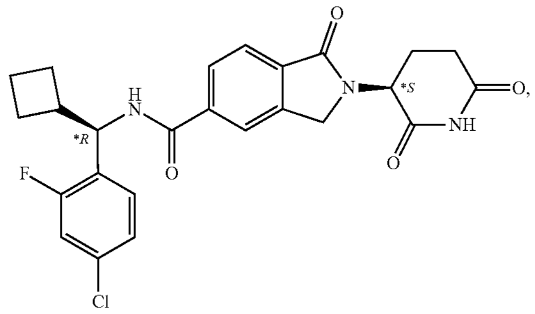
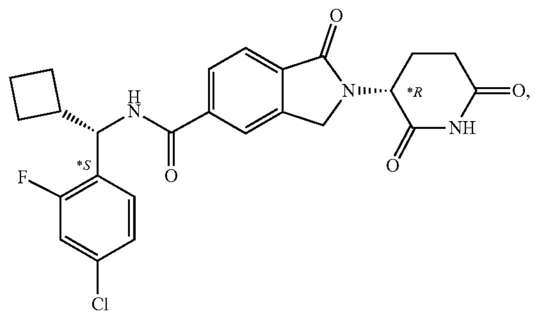

-continued
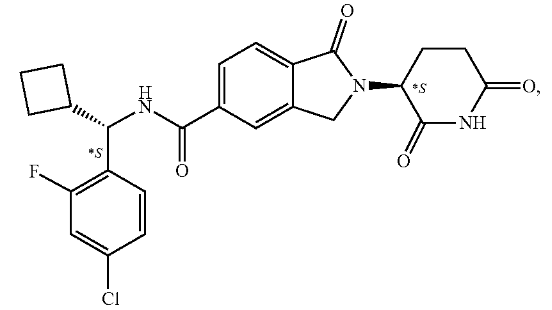
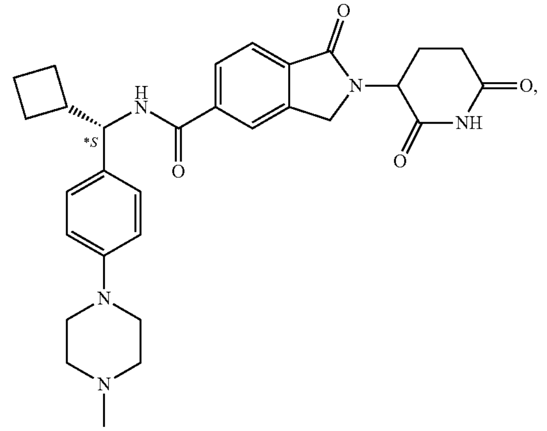
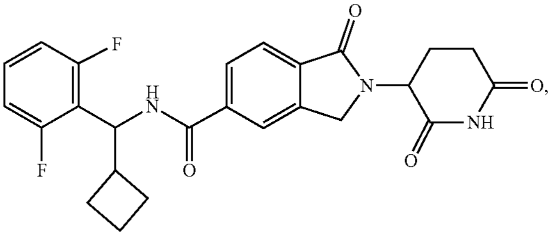
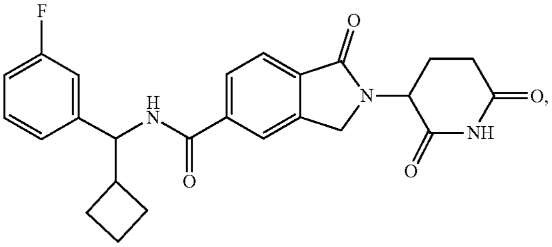
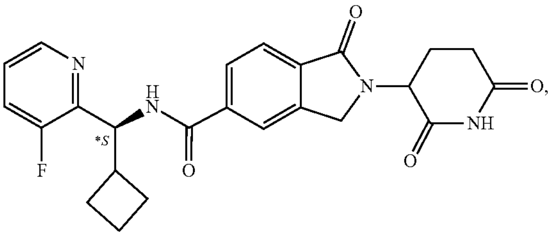
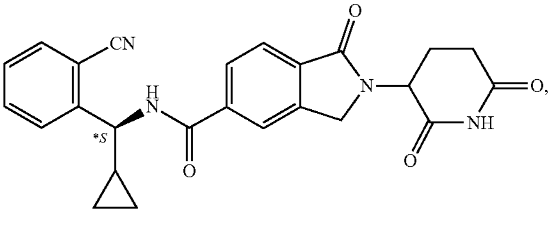
-continued
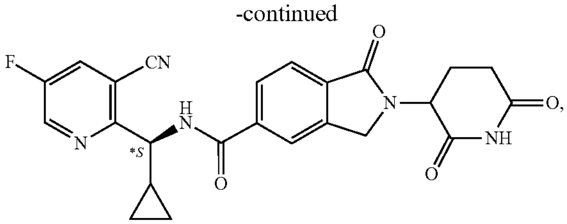
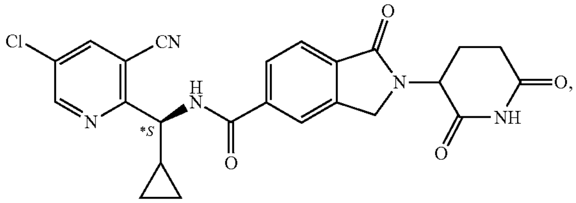
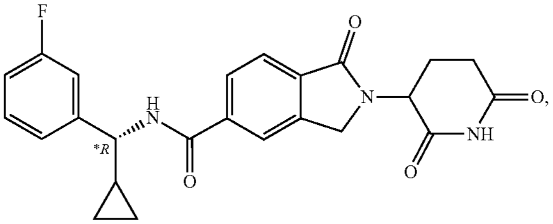
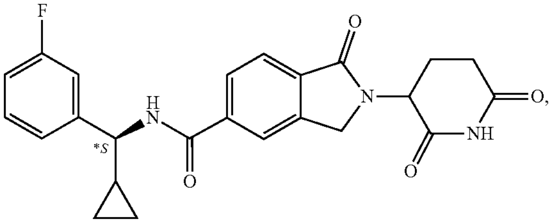
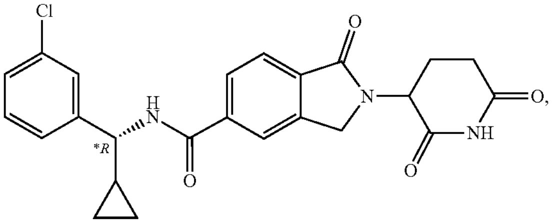
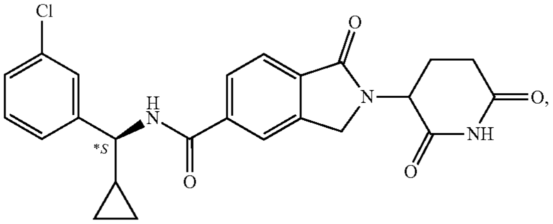
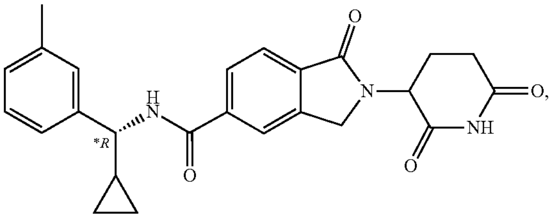
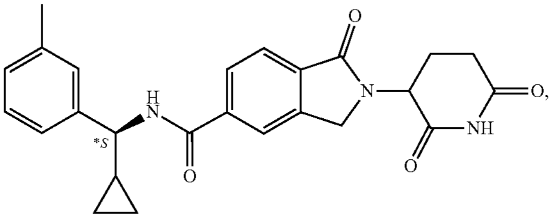

-continued
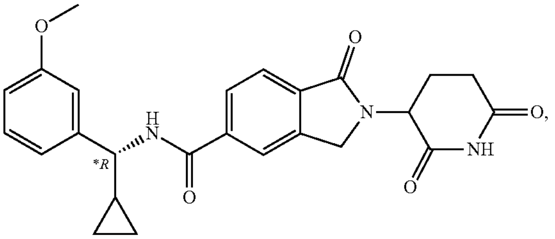
,
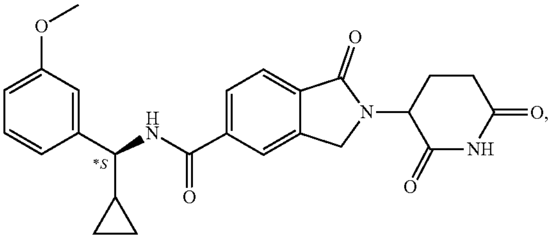
,
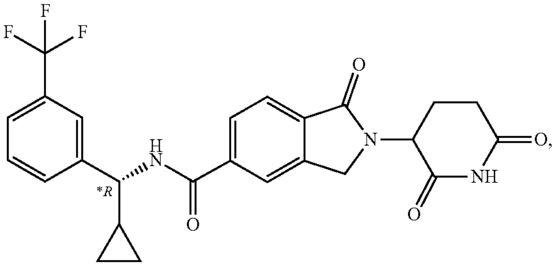
,
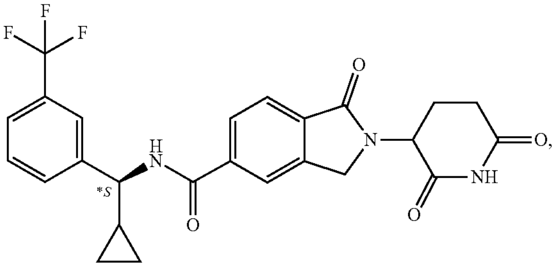
,
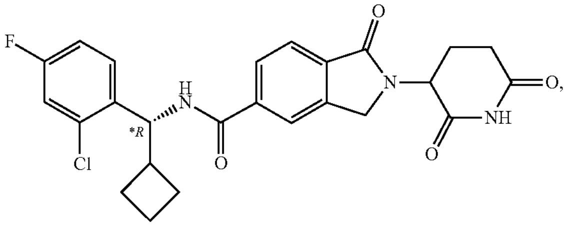
,
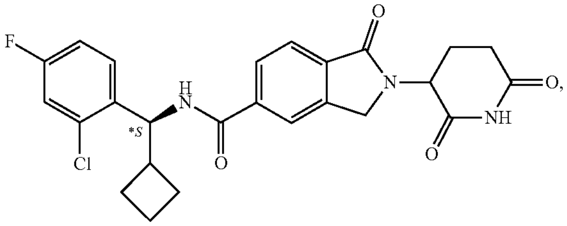
,
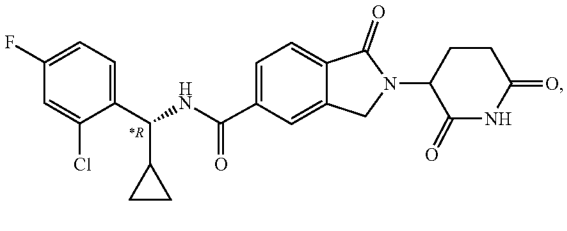
,
-continued
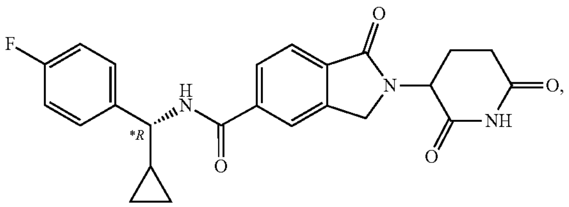
,
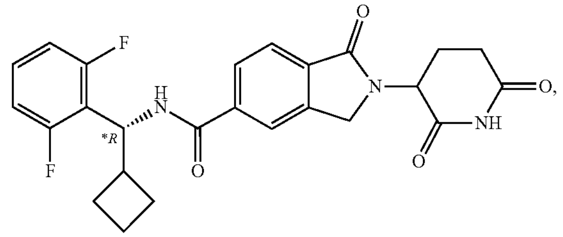
,
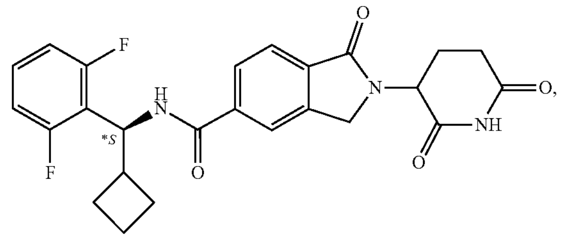
,
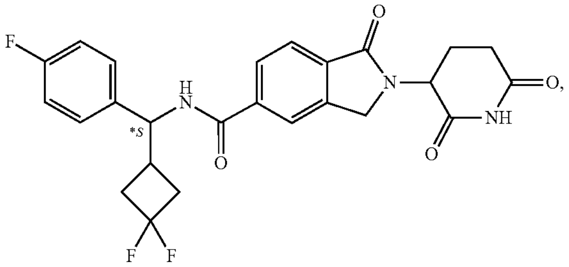
,
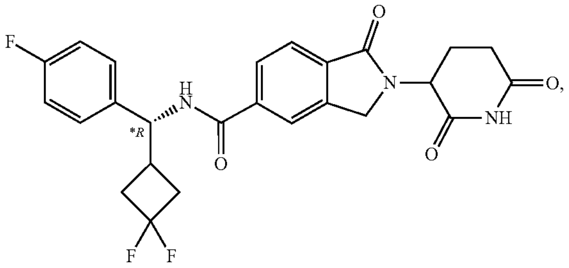
,
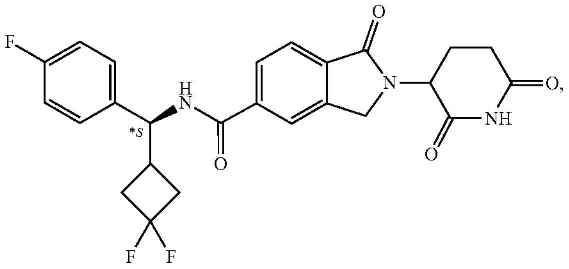
,
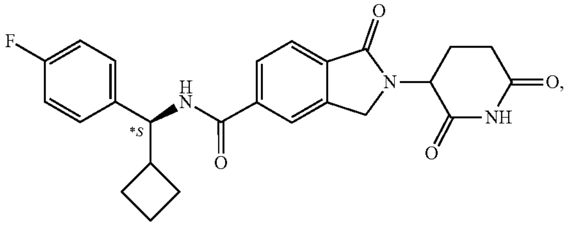
, -continued
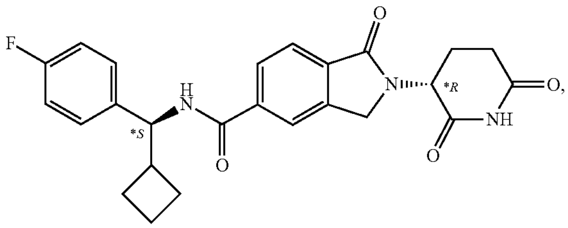
,
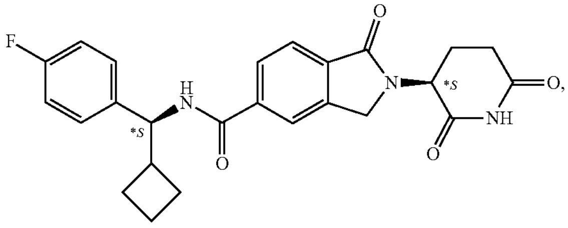
,
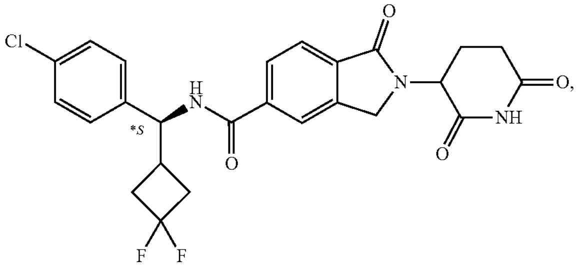
,
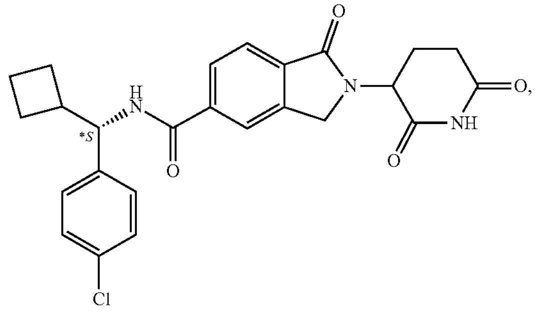
,
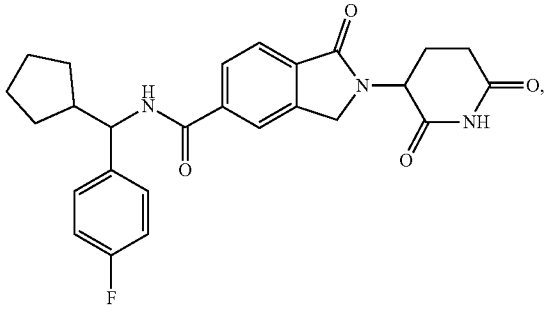
,
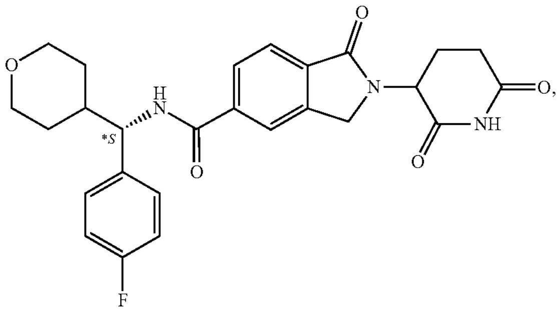
,
-continued
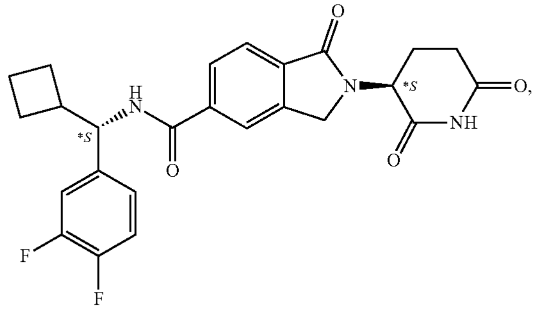
,
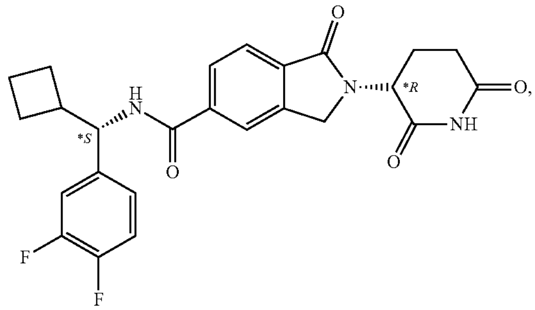
,
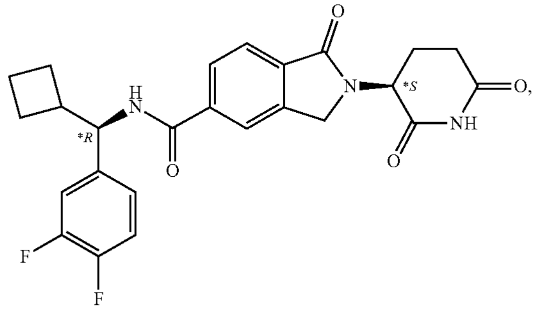
,
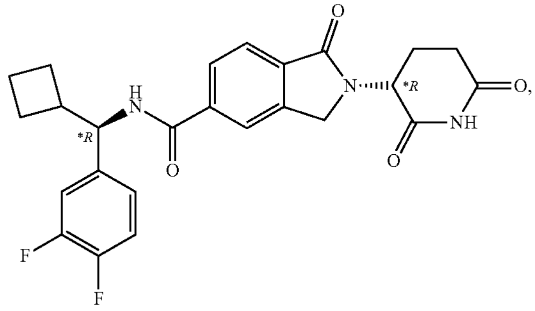
,
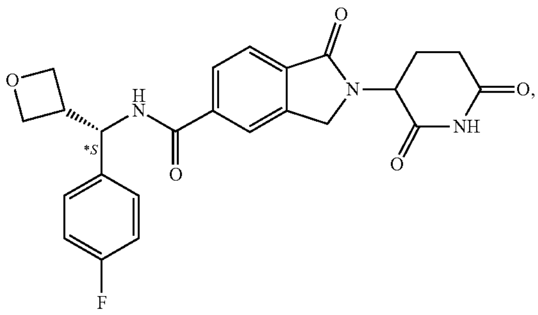
, -continued
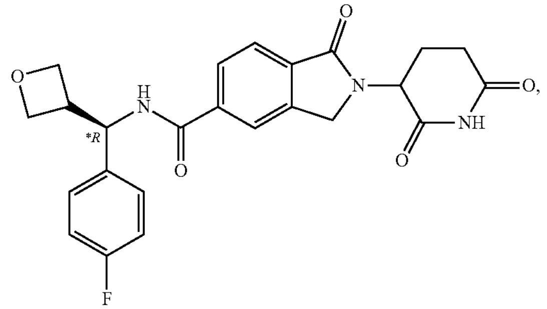,
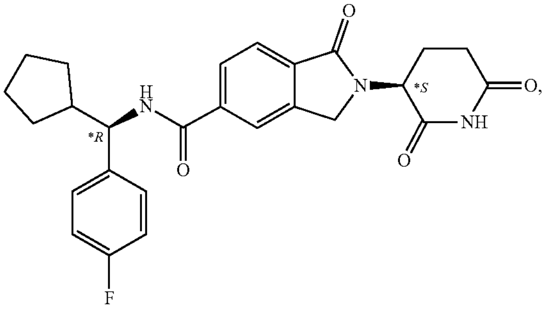,
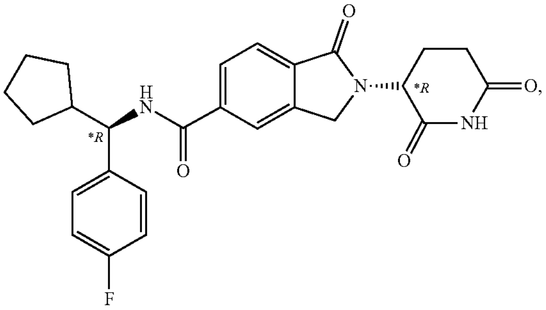,
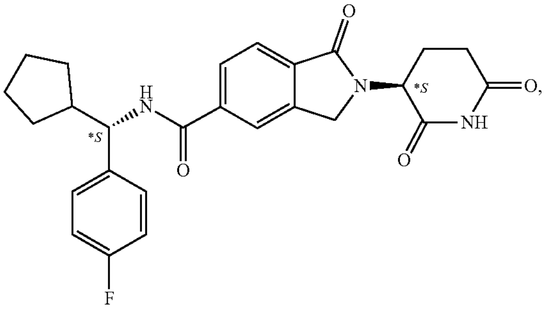,
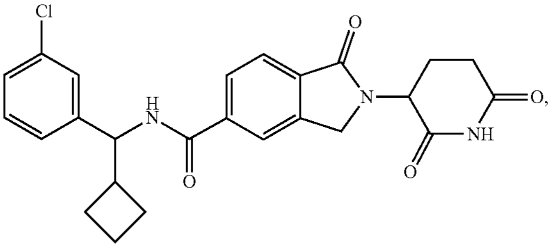,
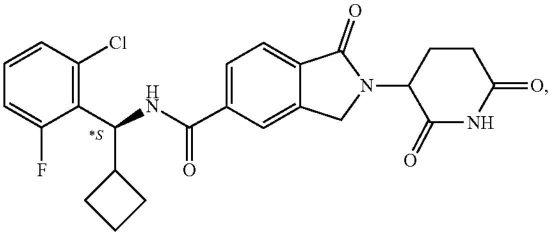,
-continued
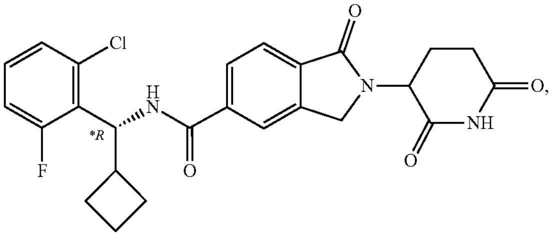,
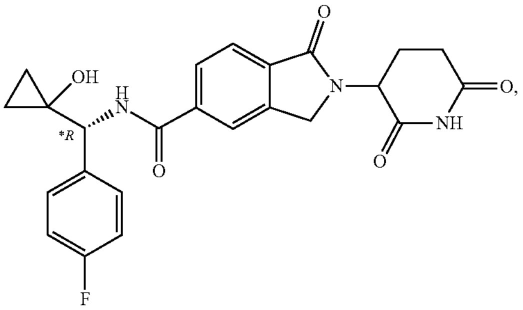,
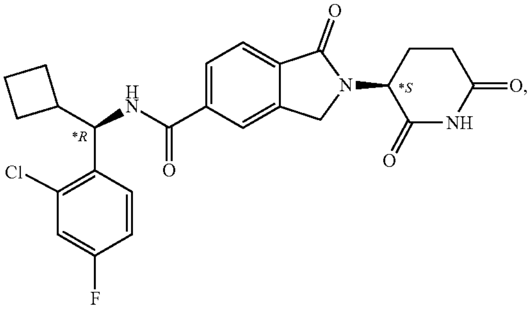,
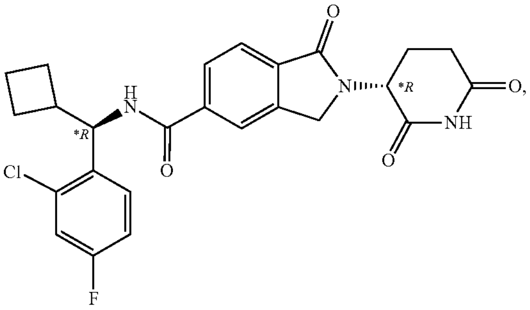,
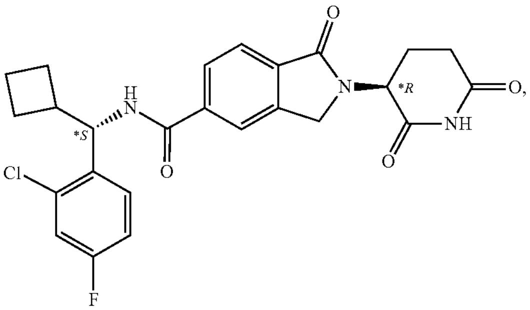, -continued
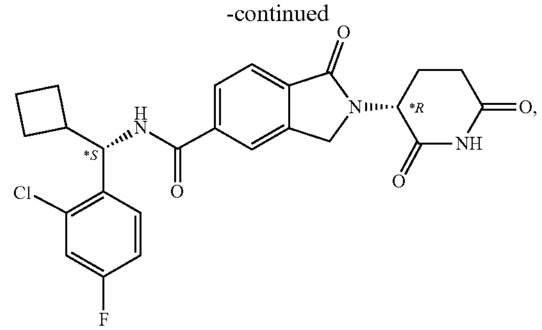
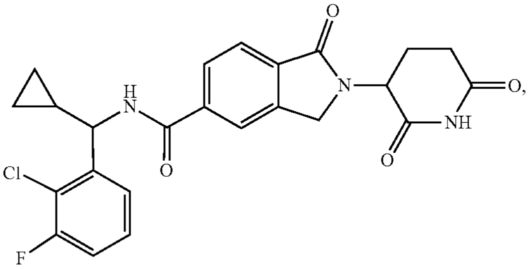
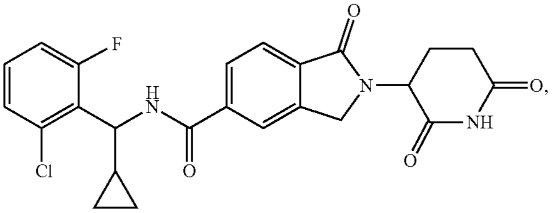
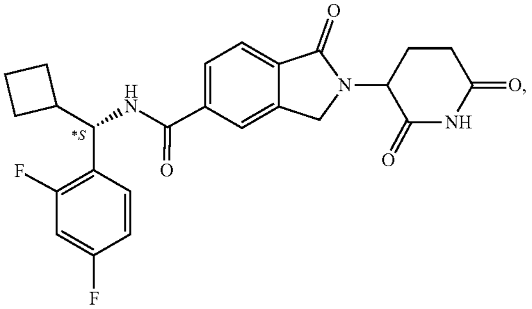
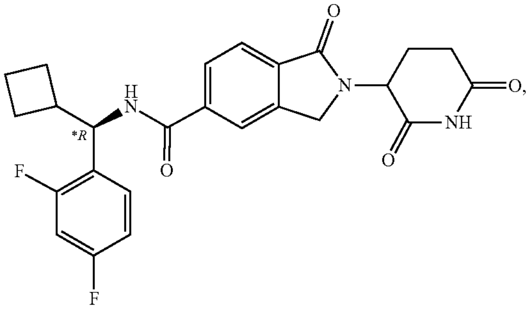
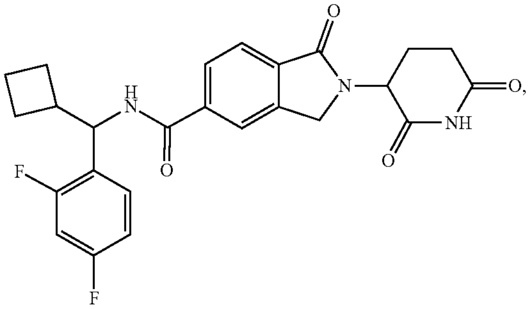
-continued
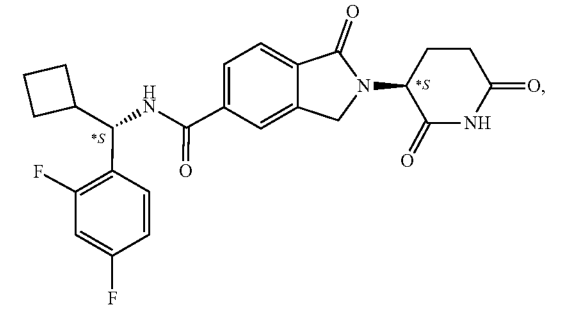
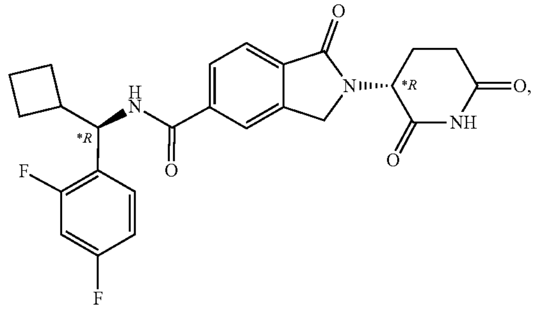
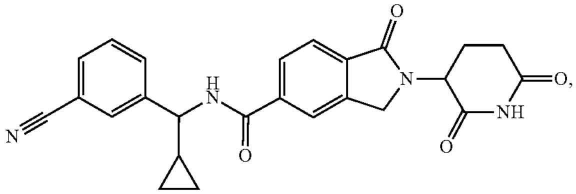
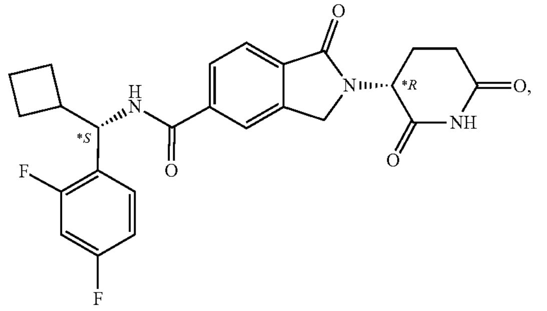
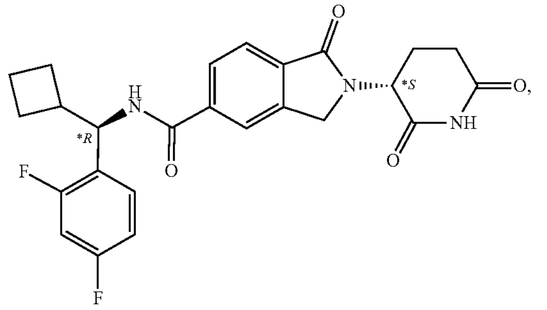
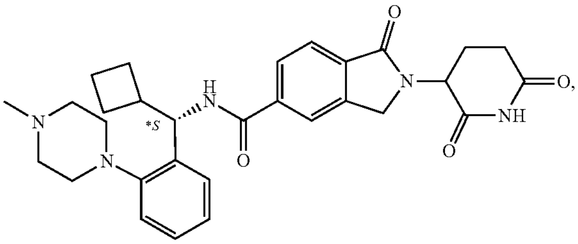

-continued
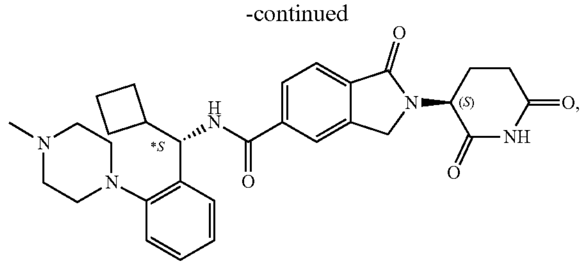
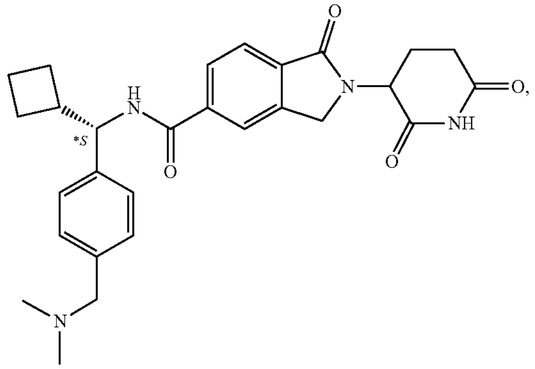
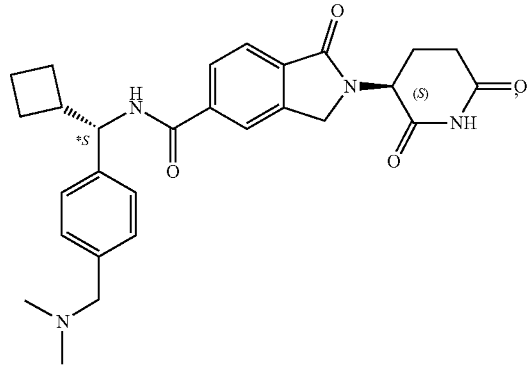
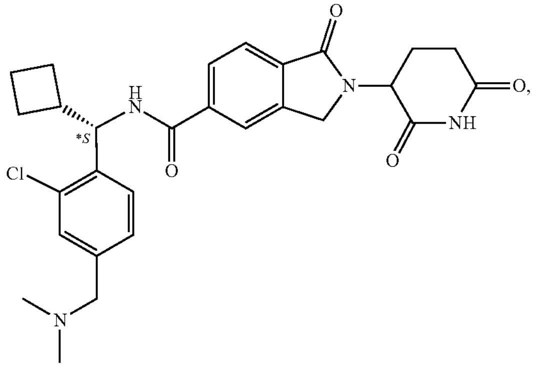
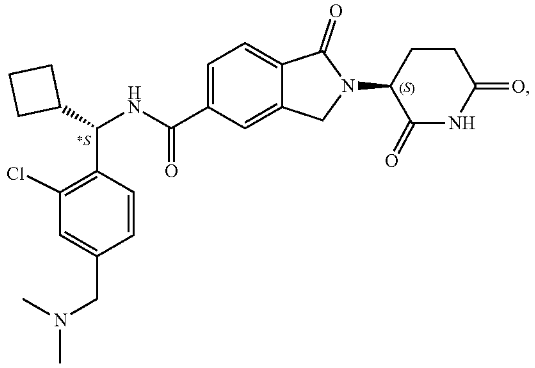
-continued
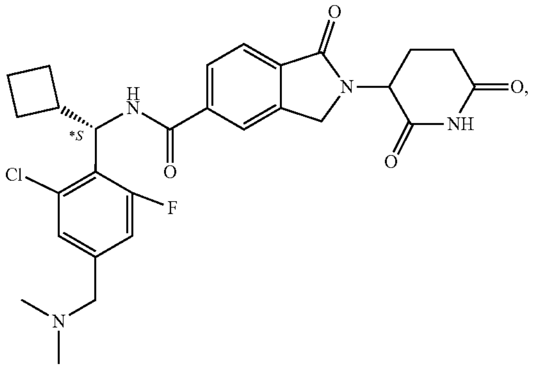
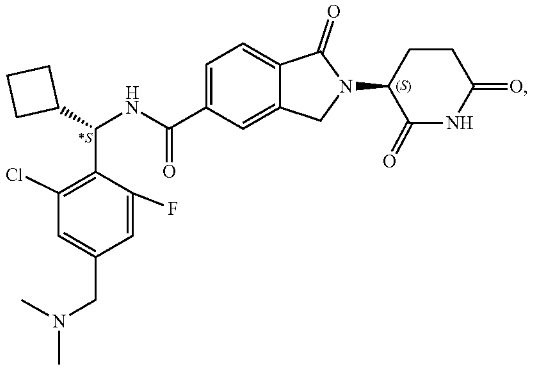
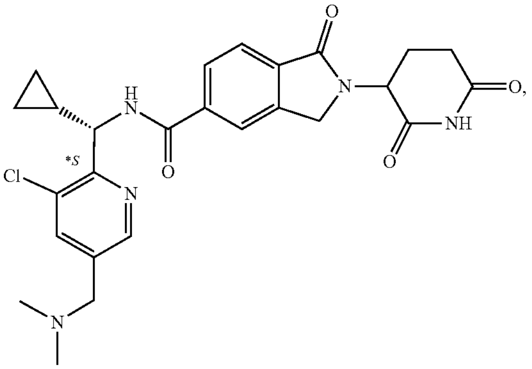
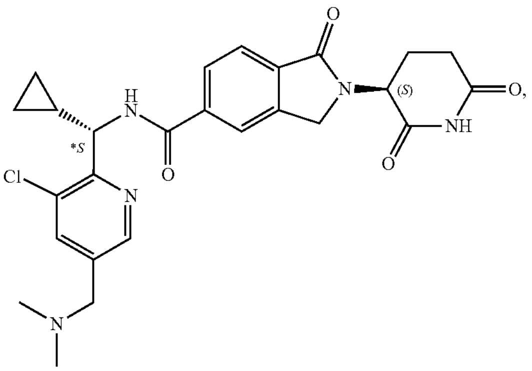

-continued
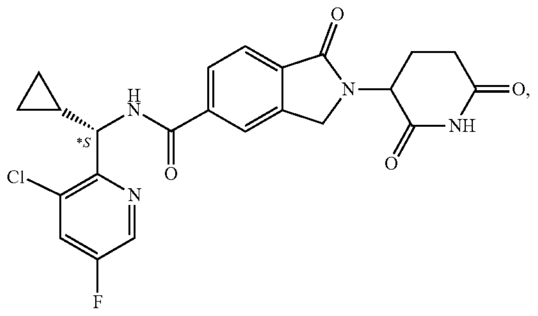
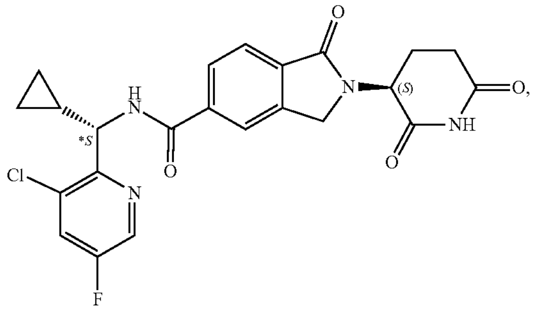
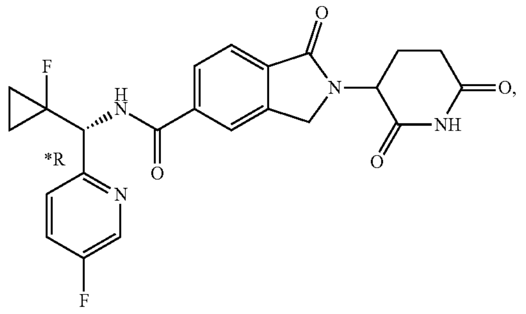
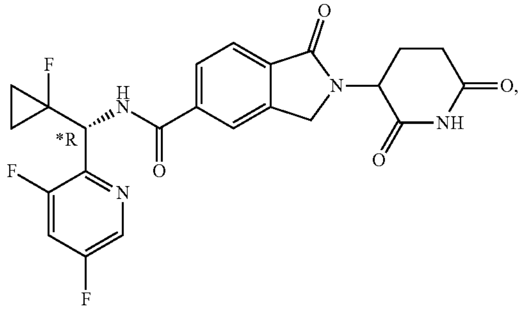
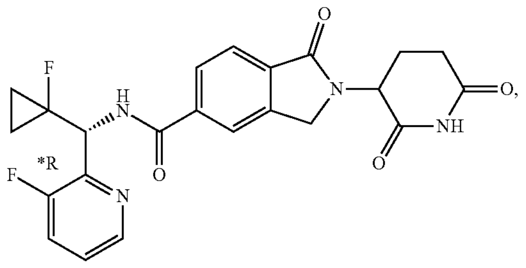
-continued
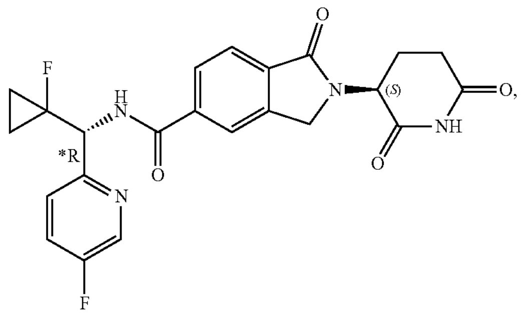
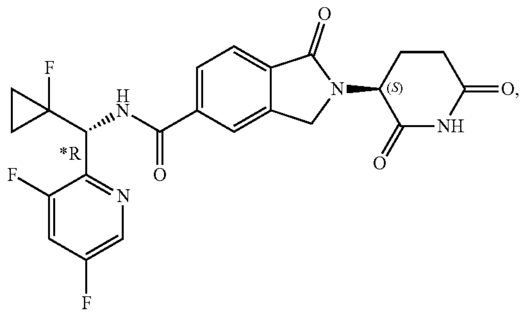
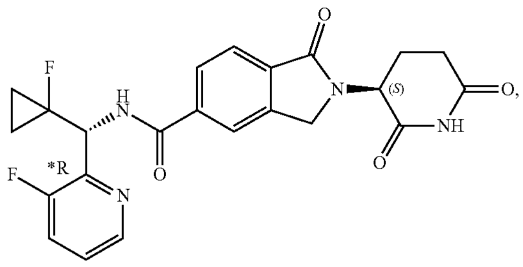
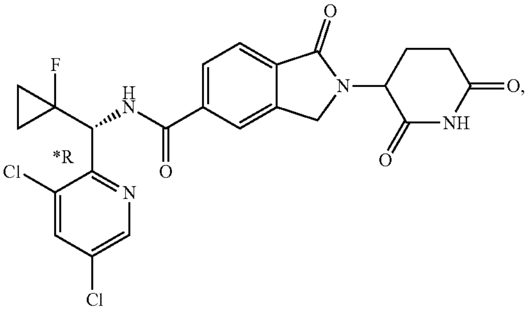
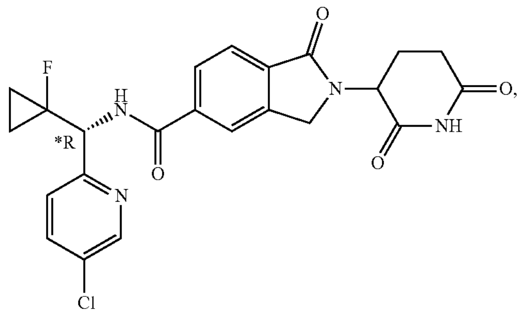

-continued
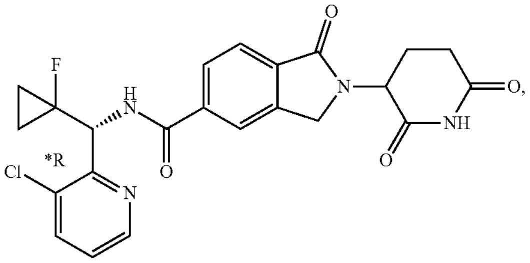
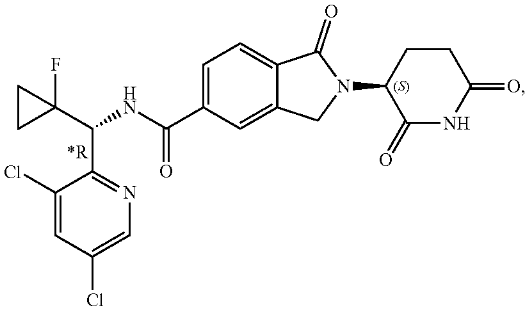
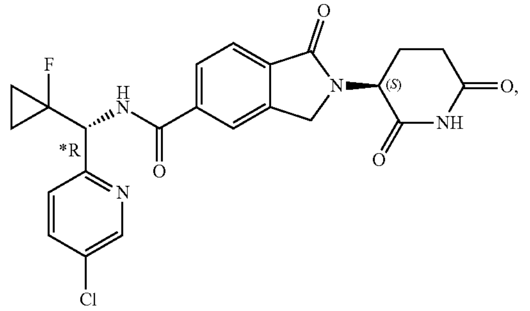
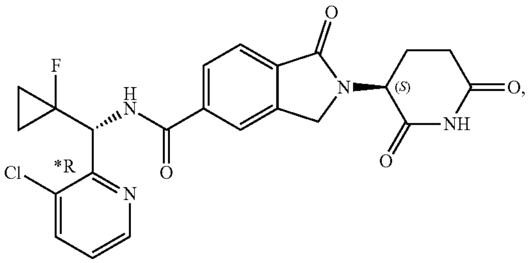
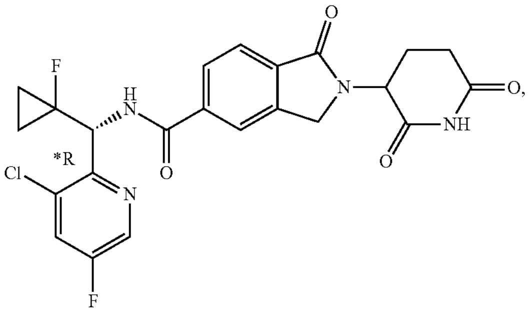
-continued
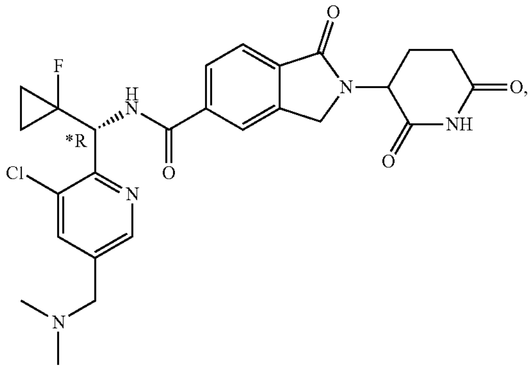
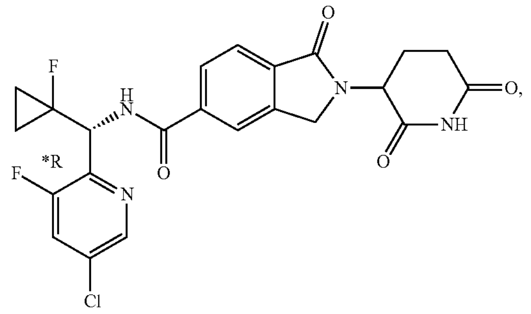
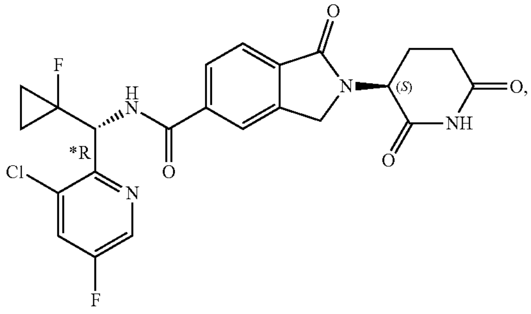
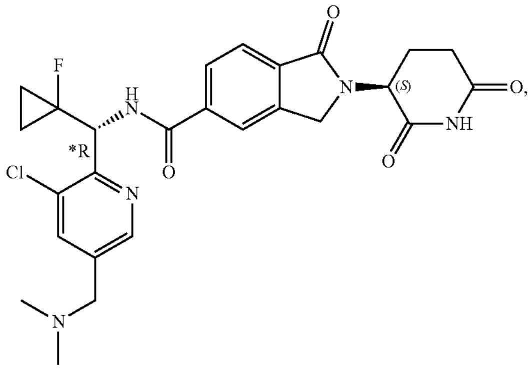
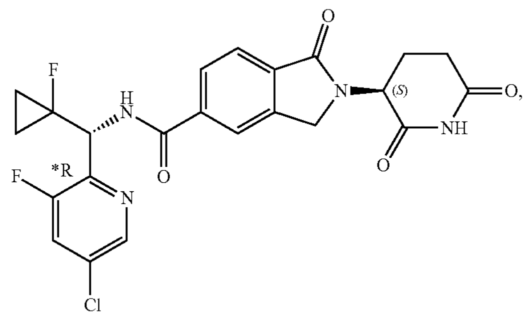

-continued
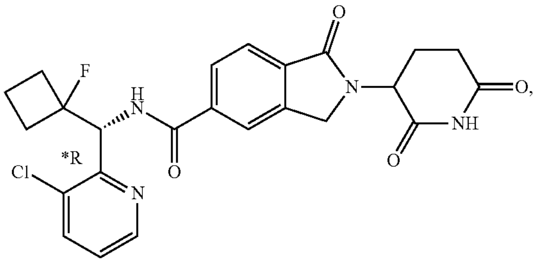
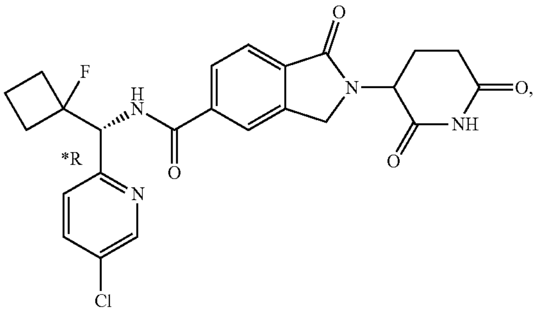
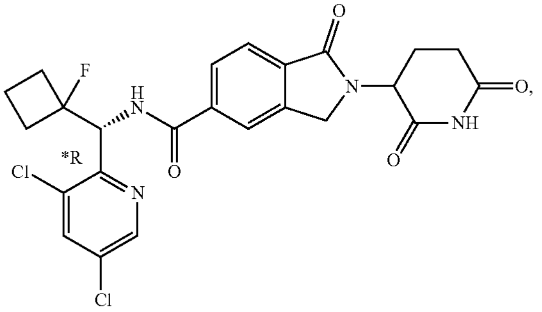
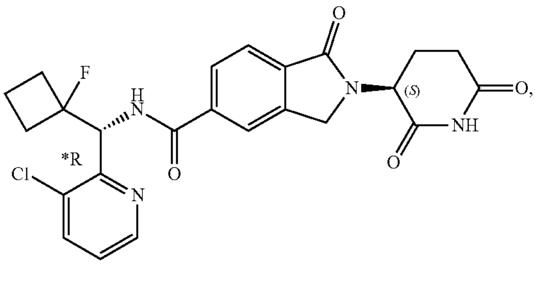
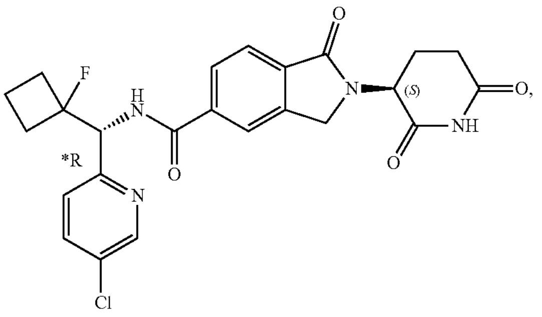
-continued
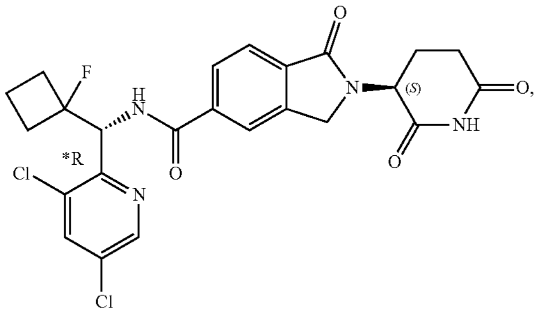
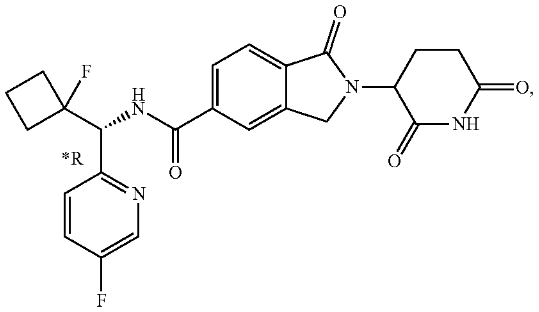
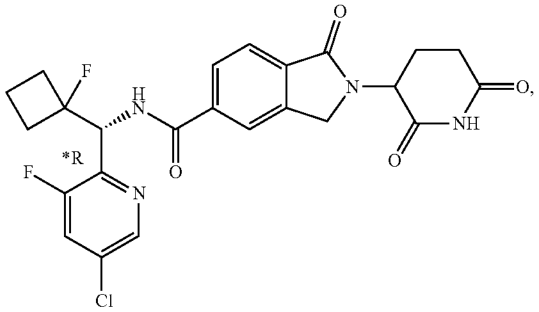
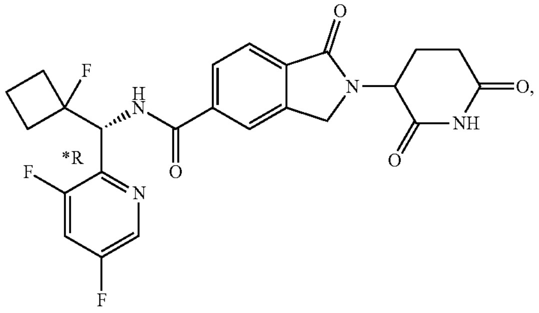
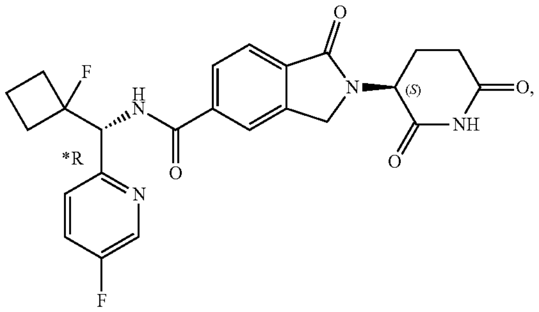

-continued
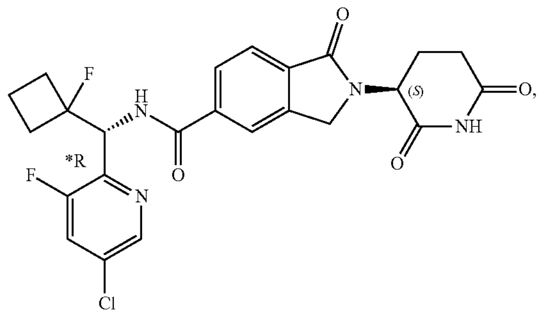,
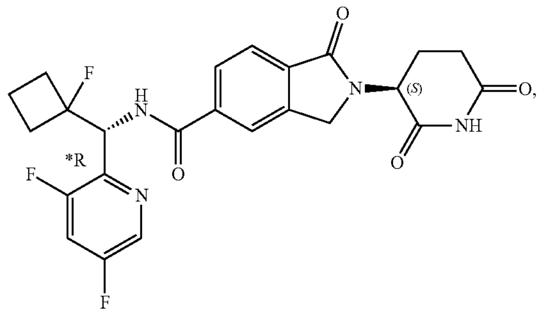,
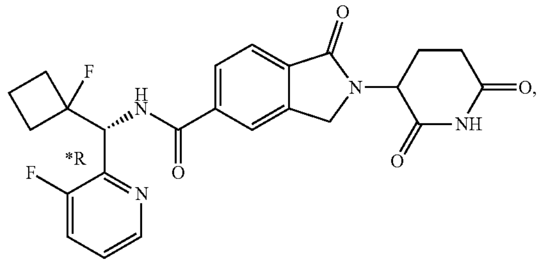,
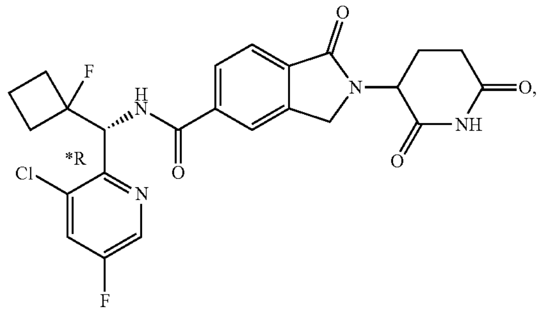,
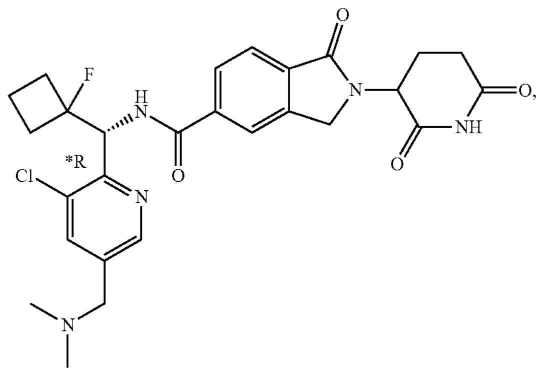,
-continued
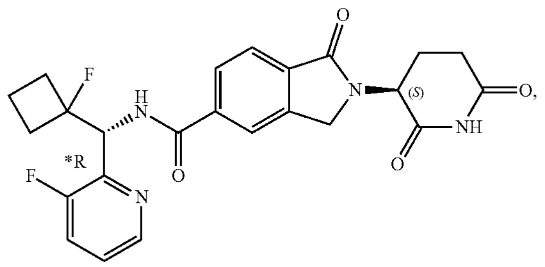,
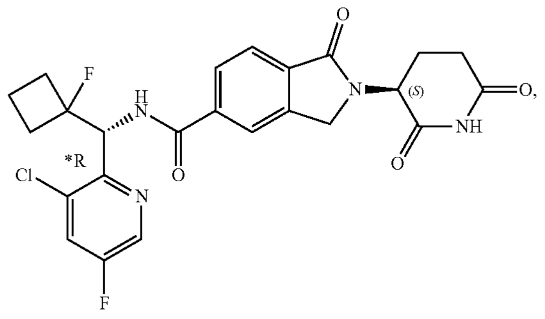,
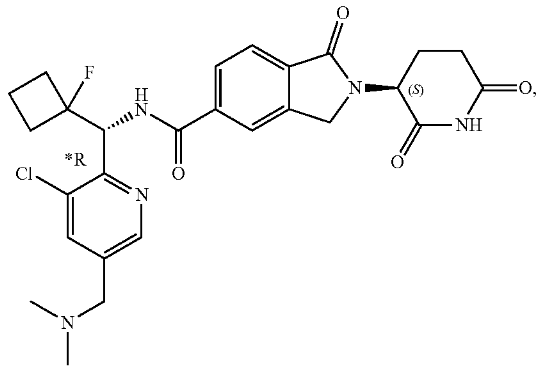,
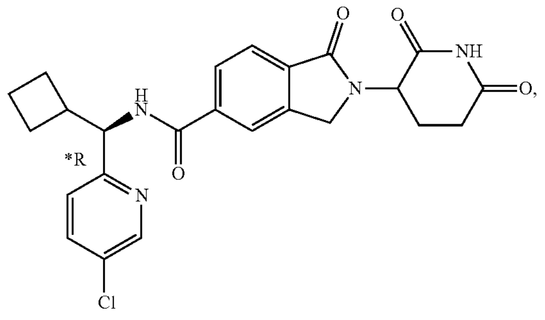,
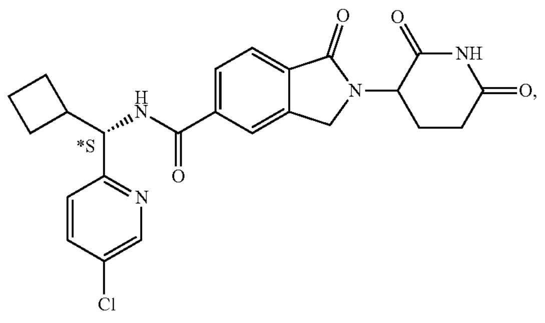, -continued
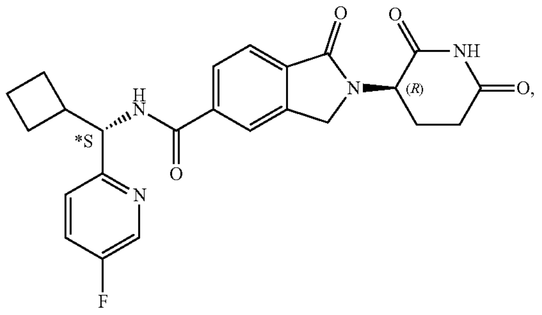
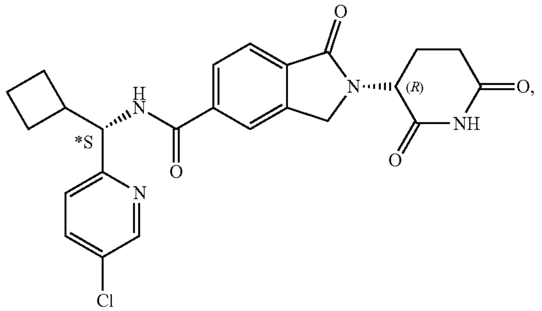
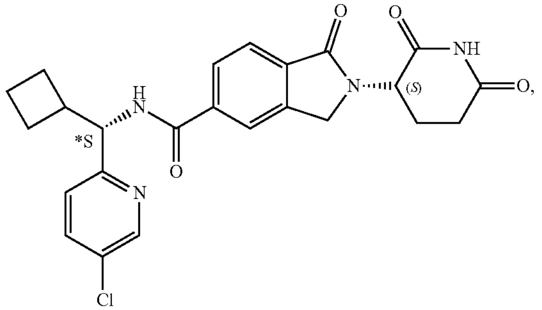
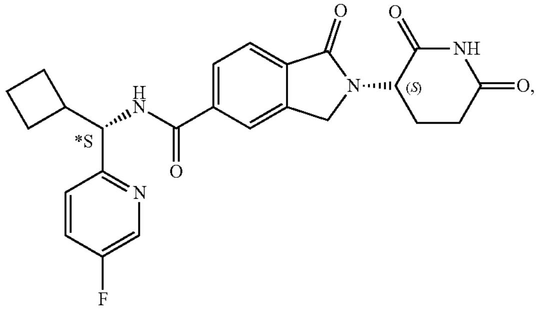
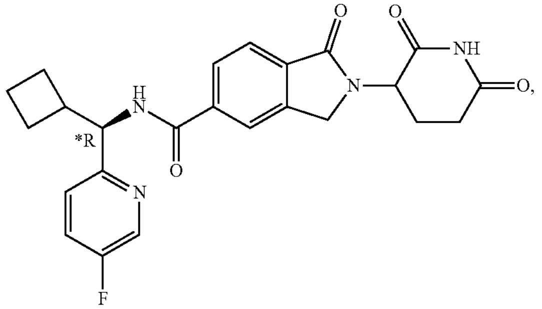
-continued
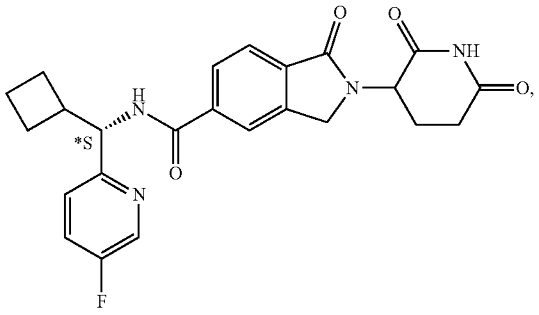
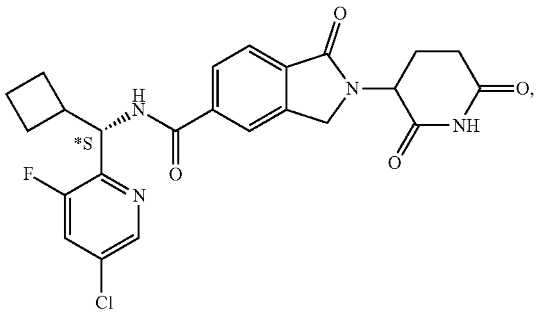
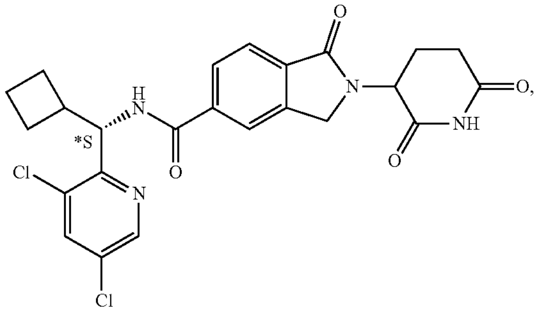
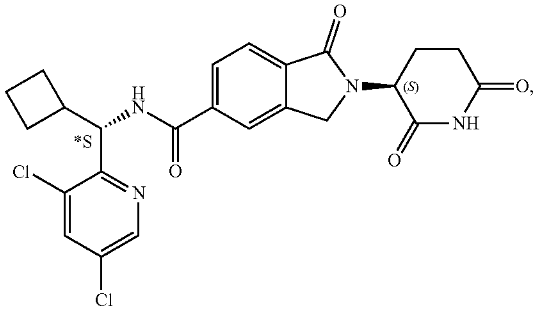
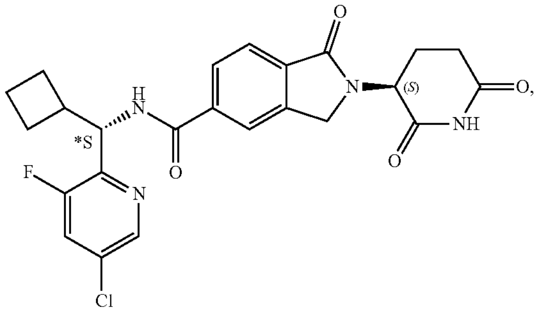

-continued
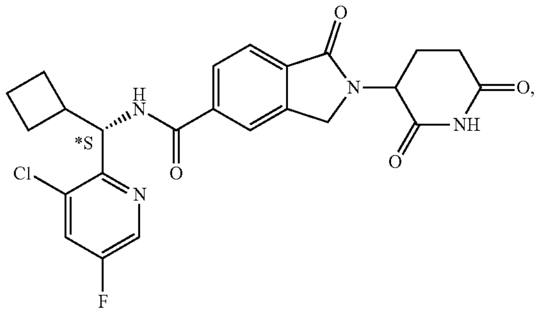
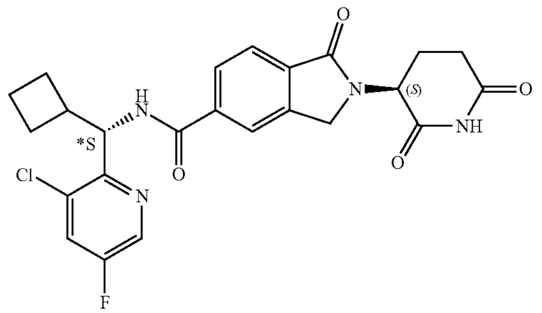
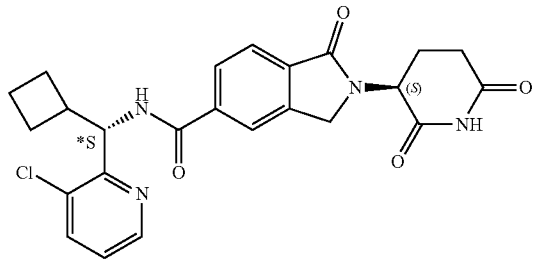
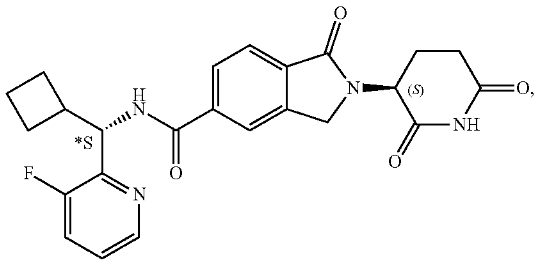
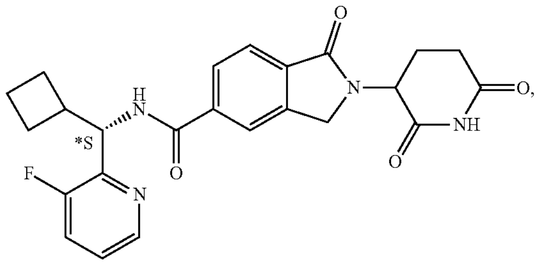
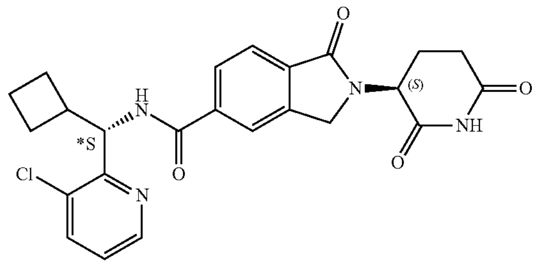
-continued
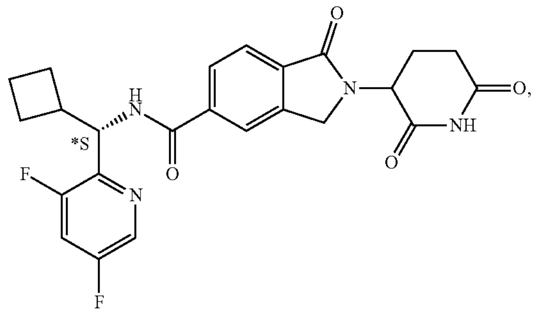
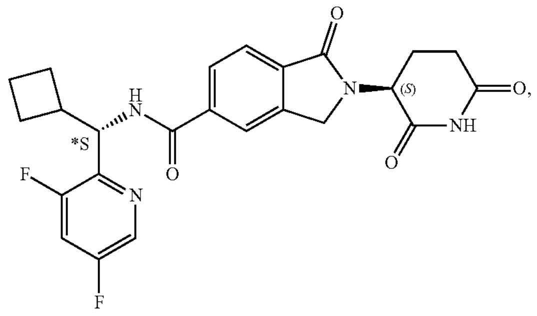
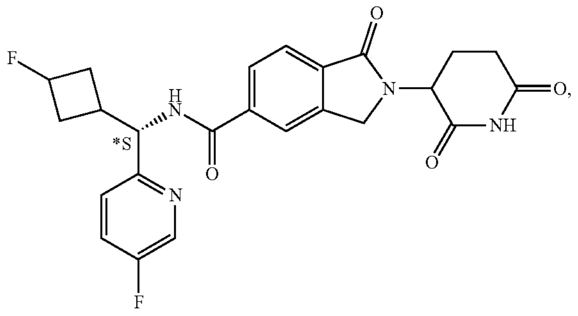
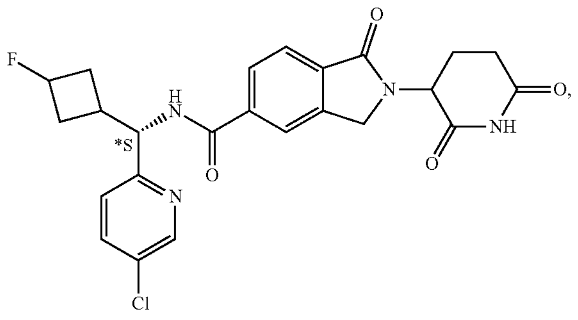
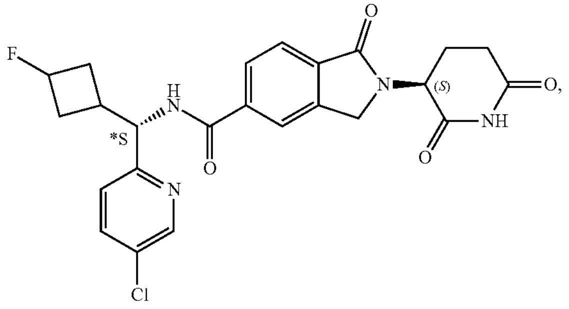

-continued

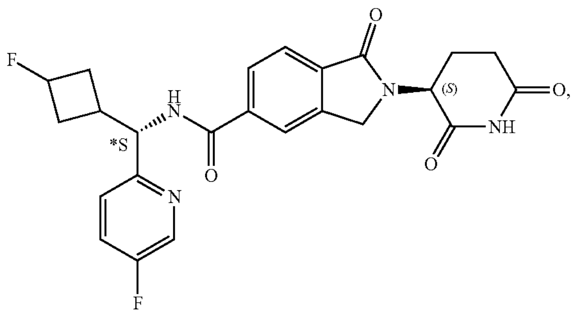

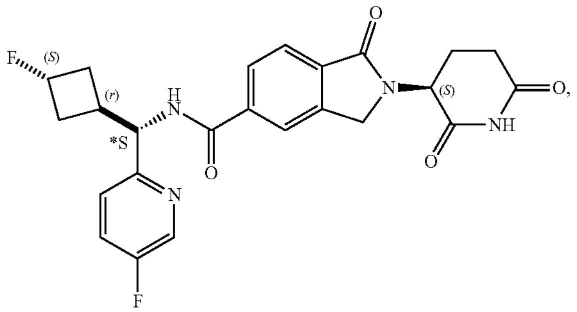

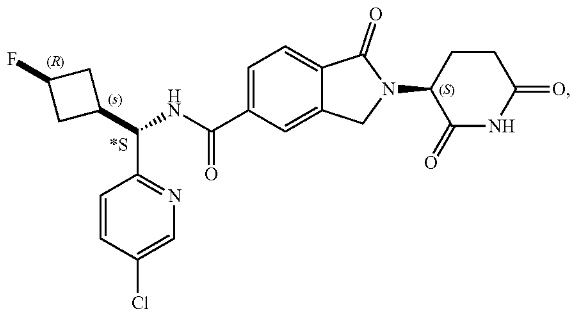

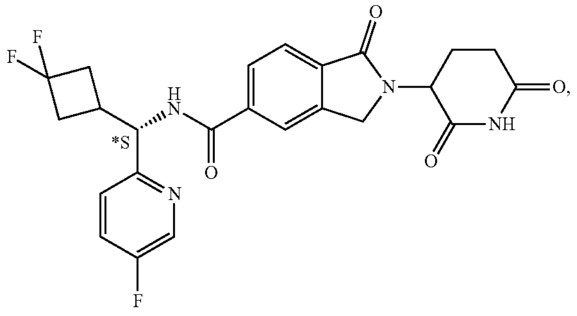

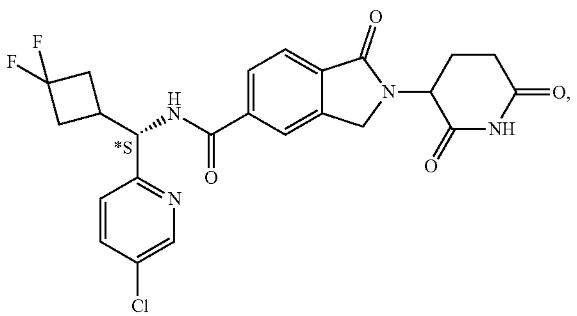

-continued

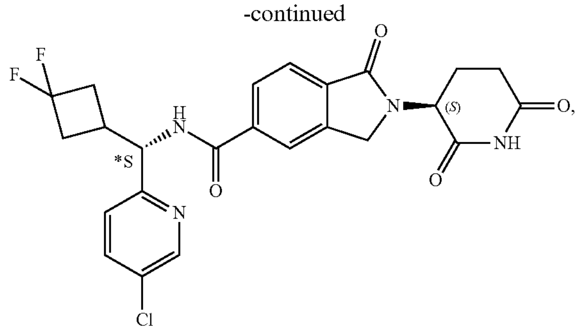

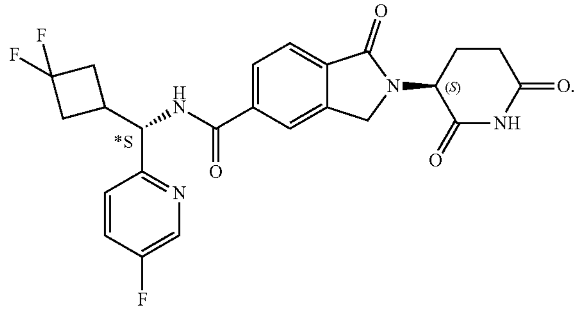

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

The invention also includes various isomers and mixtures thereof. Certain of the compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

The compounds of the invention may be prepared as individual isomers by either isomer specific synthesis or resolved from an isomeric mixture.

The disclosed compounds may possess one or more stereocenters, and each stereocenter may exist independently in either the R or S configuration. The stereochemical configuration may be assigned at indicated centers as (*) when the absolute stereochemistry is undetermined at the stereocenter although the compound itself has been isolated as a single stereoisomer and is enatiomerically/diastereomerically pure.

In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the disclosed compound described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography. When the absolute R or S stereochemistry of a compound cannot be determined, it can be identified by the retention time after chromatography under particular chromatographic conditions as determined by chromatography column, eluent, etc. In some embodiment, an asterisk (*) is used to indicate a chiral atom. In some embodiment, the asterisk "*" is used to indicate that a chiral atom is in a substantially single steric configuration while the absolute stereochemistry thereof is not determined (even if the bondis are drawn stereo specifically). The chiral atom can be a chiral carbon atom, a chiral nitogen atom or a chiaral phosphorus atom. The term "substantially" means variation in range of 5%, 2% or 1% or even 0.1% from the norm. The term "single steric configuration" can be single R configuration, or single S configuration.

Definitions

"Alkyl" is a branched or straight chain saturated aliphatic hydrocarbon group. In one embodiment, the alkyl contains from 1 to about 12 (1, 2, 3, 4, 5, 6, 7, 8, 9, 10, 11, 12) carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-$C_2$, $C_1$-$C_3$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$ cycloalkyl)$C_0$-$C_4$ alkyl, or —$C_0$-$C_4$alkyl($C_3$-$C_7$ cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl($C_3$-$C_7$ cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentyl, 3-methylpentyl, 2,2-dimethylbutyl and 2,3-dimethylbutyl. In one embodiment, the alkyl group is optionally substituted as described herein.

"Alkenyl" is a branched or straight chain aliphatic hydrocarbon group having one or more carbon-carbon double bonds that may occur at a stable point along the chain. Nonlimiting examples are $C_2$-$C_8$ alkenyl (such as $C_2$, $C_3$, $C_4$, $C_5$, $C_6$, $C_7$, $C_8$), $C_2$-$C_6$ alkenyl and $C_2$-$C_4$ alkenyl. The specified ranges as used herein indicate an alkenyl group having each member of the range described as an independent species, as described herein for the alkyl moiety. Examples of alkenyl include, but are not limited to, ethenyl, propenyl, butadienyl (including 1,2-butadienyl and 1,3-butadienyl). In one embodiment, the alkenyl group is optionally substituted as described herein.

"Alkynyl" is a branched or straight chain aliphatic hydrocarbon group having one or more carbon-carbon triple bonds that may occur at any stable point along the chain, for example, $C_2$-$C_8$alkynyl (such as $C_2$, $C_3$, $C_4$, $C_5$, $C_6$, $C_7$, $C_8$) or $C_2$-$C_6$alkynyl. The specified ranges as used herein indicate an alkynyl group having each member of the range described as an independent species, as described herein for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described herein.

"Alkoxy" is an alkyl group as defined above with the indicated number of carbon atoms covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described herein.

"Alkenyloxy" is an alkenyl group as defined above with the indicated number of carbon atoms covalently bound to the group it substitutes by an oxygen bridge (—O—).

"Alkynyloxy" is an alkynyl group as defined above with the indicated number of carbon atoms covalently bound to the group it substitutes by an oxygen bridge (—O—).

"Alkanoyl" is an alkyl group as defined above with the indicated number of carbon atoms covalently bound through a carbonyl (C═O) bridge. The carbonyl carbon is included in the number of carbons, that is $C_2$alkanoyl is a $CH_3(C{=}O)$— group. In one embodiment, the alkanoyl group is optionally substituted as described herein.

"Alkylester" is an alkyl group as defined with the indicated number of carbon atoms covalently bound through an ester linkage. The ester linkage may be in either orientation, e.g., a group of the formula-O(C═O)alkyl or a group of the formula —(C═O)Oalkyl.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, $C_{3-8}$ cycloalkyl has from 3 to 8 ring carbon atoms (such as, 3, 4, 5, 6, 7 or 8 ring carbon atoms). Examples of cycloalkyl groups include cyclopropyl, cyclobutyl, cyclopentyl, cyclohexyl, cycloheptyl, cyclooctyl, and partially unsaturated groups such as cyclopentenyl and cyclohexenyl.

"Amide" or "carboxamide" is —C(O)N$R^cR^d$ wherein $R^c$ and $R^d$ are each independently selected from hydrogen, alkyl, for example, $C_1$-$C_6$alkyl, alkenyl, for example, $C_2$-$C_6$ alkenyl, alkynyl, for example, $C_2$-$C_6$alkynyl, —$C_0$-$C_4$alkyl($C_3$-$C_7$ cycloalkyl), —$C_0$-$C_4$alkyl($C_3$-$C_7$heterocycloalkyl), —$C_0$-$C_4$alkyl(aryl), and —$C_0$-$C_4$alkyl(heteroaryl); or together with the nitrogen to which they are bonded, $R^c$ and $R^d$ can form a $C_3$-$C_7$heterocyclic ring. In one embodiment, the $R^c$ and $R^d$ groups are each independently optionally substituted as described herein.

"Carbocyclyl", "Carbocyclic group", "carbocyclic ring", or "cycloalkyl" is a saturated or partially unsaturated (i.e., not aromatic) group containing all carbon ring atoms. A carbocyclic group typically contains 1 ring of 3 to 7 carbon atoms or 2 fused rings each containing 3, 4, 5, 6 or 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described herein. In one embodiment, the cycloalkyl is a partially unsaturated (i.e., not aromatic) group containing all carbon ring atoms. In another embodiment, the cycloalkyl is a saturated group containing all carbon ring atoms.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Thioalkyl" indicates both branched and straight-chain alkyl groups substituted with 1 or more sulphur atoms, up to the maximum allowable number of halogen atoms.

"Halo" or "halogen" indicates independently any of fluoro, chloro, bromo, and iodo.

"Aryl" indicates aromatic groups containing only carbon in the aromatic ring or rings. In one embodiment, the aryl groups contain 1 to 3 separate or fused rings and is 6 to about 18 ring atoms (such as 6, 7, 8, 9, 10, 11, 12, 13, 14, 15, 16, 17, or 18 ring atoms), without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxyphenyl group. Aryl groups include, for example, phenyl, naphthyl, including 1-naphthyl and 2-naphthyl, fluorenyl, and anthryl. In one embodiment, aryl groups are pendant. An example of a pendant ring is a phenyl group substituted with a phenyl group. In one embodiment, the aryl group is optionally substituted as described herein.

The term "heterocyclyl", "heterocycle" or "heterocyclic ring" as used herein refers to a saturated or a partially unsaturated (i.e., having one or more double and/or triple bonds within the ring without aromaticity) monocyclic or bicyclic radical of 4, 5, 6, 7, 8, 9, or 10 ring atoms in which at least one ring atom is a heteroatom selected from nitrogen, oxygen, and sulfur, the remaining ring atoms being C, where one or more ring atoms is optionally substituted independently with one or more substituents described above. In one embodiment, the only heteroatom is oxygen. A heterocycle may be a monocycle having 4 to 7 ring members (2 to 6 carbon atoms and 1 to 4 heteroatoms selected from N, O, and S) or a bicycle having 6 to 10 ring members (4 to 9 carbon atoms and 1 to 6 heteroatoms selected from N, O, and S), for example: a bicyclo [4,5], [5,5], [5,6], or [6,6] system. In one embodiment, the only heteroatom is sulfur. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (═O) moieties are pyrimidinonyl and 1,1-dioxo-thiomorpholinyl. The heterocycle groups herein are optionally substituted independently with one or more substituents described herein.

"Heterocyclicoxy group" is a monocyclic heterocyclic ring or a bicyclic heterocyclic group as described previously linked to the group it substitutes via an oxygen, —O—, linker.

"Heteroaryl" can be a stable monocyclic aromatic ring which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. The 5 to 18 membered heteroaryl described herein may contain 5, 6, 7, 8, 9, 10, 11, 12, 13, 14, 15, 16, 17, or 18 ring atoms. In one embodiment, the only heteroatom is nitrogen. In one embodiment, the only heteroatom is oxygen. In one embodiment, the only heteroatom is sulfur. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-pyridinyl, 2-hydroxypyridinyl, 3-pyridinyl, 3-hydroxypyridinyl, 4-pyridinyl, 4-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein.

"Heteroaryloxy" is a heteroaryl group as described bound to the group it substituted via an oxygen, —O—, linker.

"Heterocycloalkyl" is a saturated ring group. It may have, for example, 1, 2, 3, or 4 heteroatoms independently chosen from N, S, and O, with remaining ring atoms being carbon. In a typical embodiment, nitrogen is the heteroatom. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "mono- and/or di-alkylamino" indicates secondary or tertiary alkylamino groups, wherein the alkyl groups are independently chosen alkyl groups, as defined herein. The point of attachment of the alkylamino group is on the nitrogen. Examples of mono- and di-alkylamino groups include ethylamino, dimethylamino, and methyl-propylamino.

The term "substituted", as used herein, means that any one or more hydrogens on the designated atom or group is replaced with a moiety selected from the indicated group, provided that the designated atom's normal valence is not exceeded.

When a stereocenter is designated as "*R" or "*S", it means that the absolute stereochemistry for such a stereocenter is undetermined (even if the bonds are drawn stereo specifically) although it is in a substantially single steric configuration. In other word, "*R" can be absolute R configuration, or absolute S configuration. Similarly, "*S" can be absolute R configuration, or absolute S configuration. "*R" or "*S" is assigned randomly for such molecules. A stereocenter designated as "*R" can be in a single steric configuration same as or different from that of another stereocenter designated as "*S". A stereocenter designated as "*R" can be in a single steric configuration same as or different from that of another stereocenter designated as "*R". A stereocenter designated as "*S" can be in a single steric configuration same as or different from that of another stereocenter designated as "*S". For example, it will be clear that the absolute stereochemistry of Compound 5

Compound 5

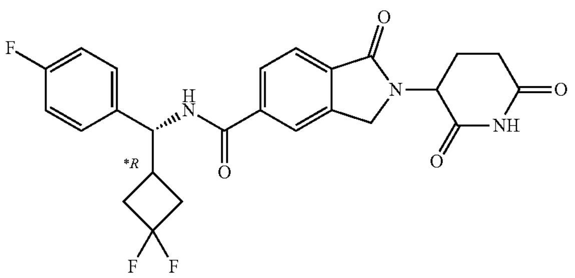

is one of the following structal formulae, while the absolute stereochemistry of Compound 6

Compound 6

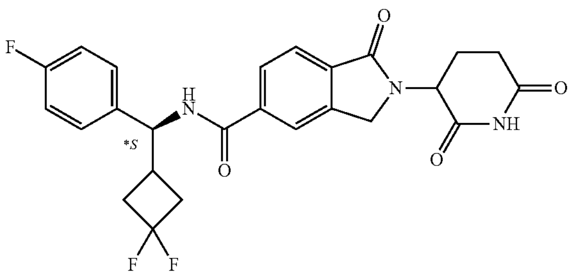

is the other of the following structal formulae:

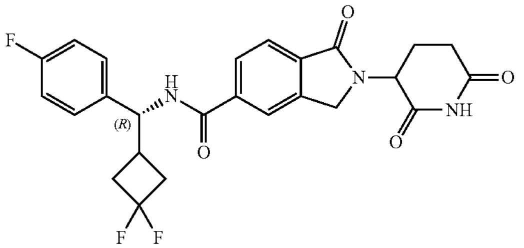

Or

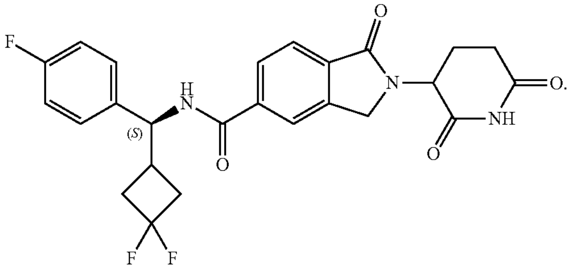

The stereocenter designated as "(R)" refers to absolute R configuration. The stereocenter designated "(S)" refers to absolute S configuration.

When "*R" or "*S" for a first stereocenter occurs together with a second stereocenter which is designated "(R)" or "(S)" (known absolute stereochemistry for the second stereocenter) in the same molecule, the absolute stereochemistry of the first stereocenter designated as "*R" or "*S" is undetermined (even if the bonds are drawn stereo specifically) although the first stereocenter is in a substantially single steric configuration. For example, it will be clear that Compound 82

Compound 82

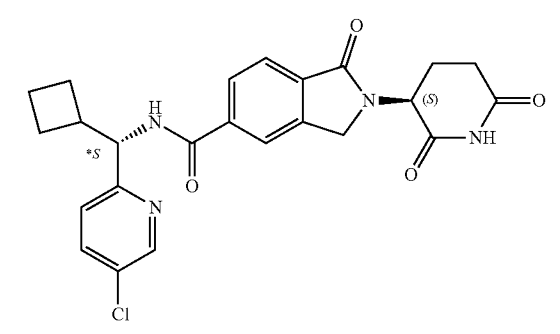

is

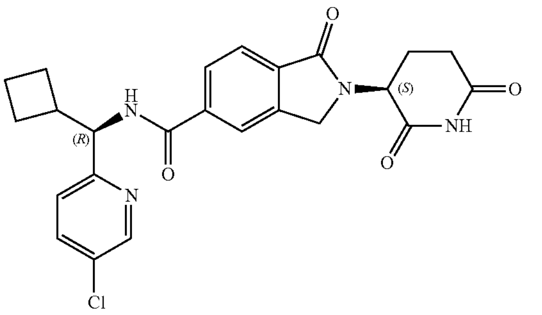

Or

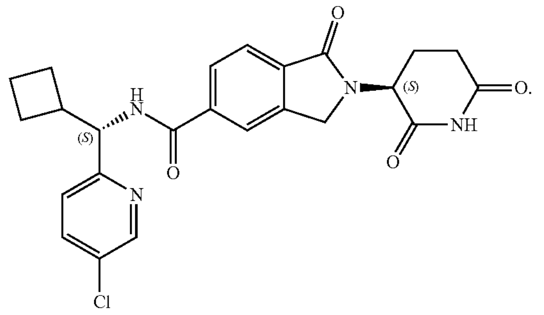

The compounds described herein or salts thereof are useful in the treatment of a proliferative disorder. The present invention provides the use of the compounds described herein or a pharmaceutically acceptable salt thereof in the manufacture of a medicament for the treatment of a proliferative disorder. The present invention further provides a compound described herein or a pharmaceutically acceptable salt thereof, for use in the treatment of a proliferative disorder. The present application further provides a method of treating a proliferative disorder, comprising administering to a subject in need thereof a therapeutically effective amount of the compounds described herein or a pharmaceutically acceptable salt thereof.

Applicant found that the compound described herein or a salt thereof can effectively degrade CK1α. Hence, the compound described herein or a salt thereof can be used to treat a proliferative disorder. Moreover, applicant also found the compound described herein or a salt thereof will not inhibit/degrade GSPT1 at the same time, when degrading CK1α. In other word, the compound described herein or a salt thereof can selectively degrade CK1α, having lowered or no impact on other protein/kinase, so as to exhibit lowered or no toxic side effects as compared with the previous CK1α degraders/inhibitors.

The term “proliferative disorder” or “cell proliferative disorder” refers to disorders that are associated with some degree of abnormal cell proliferation, whether malignant or benign. In some embodiments, the proliferative disorder is a cancer. In some aspects, the cancer is a solid tumor. In some aspects, the cancer is a hematologic malignancy. The terms “proliferative disorder”, “cell proliferative disorder”, “cancer,” “cancerous,” and “tumor” are not mutually exclusive as referred to herein.

A “cancer” comprises cancerous cells, and/or benign or pre-cancerous cells. Examples of cancer include, but are not limited to, breast cancer, colon cancer, brain cancer, prostate cancer, kidney cancer, pancreatic cancer, ovarian cancer, head and neck cancer, melanoma, colorectal cancer, gastric cancer, squamous cancer, small-cell lung cancer, non small-cell lung cancer, testicular cancer, Merkel cell carcinoma, glioblastoma, neuroblastoma, cancers of lymphatic organs and hematological malignancy including Leukemia (Acute lymphoblastic leukemia (ALL), Acute myelogenous leukemia (AML), Chronic lymphocytic leukemia (CLL), Chronic myelogenous leukemia (CML), Acute monocytic leukemia (AMOL), Hairy cell leukemia (HCL), T-cell prolymphocytic leukemia (T-PLL), Large granular lymphocytic leukemia, Adult T-cell leukemia), Lymphoma (small lymphocytic lymphoma (SLL), Hodgkin’s lymphomas (Nodular sclerosis, Mixed cellularity, Lymphocyte-rich, Lymphocyte depleted or not depleted, and Nodular lymphocyte-predominant Hodgkin lymphoma), Non-Hodgkin’s lymphomas (all subtypes), Chronic lymphocytic leukemia/Small lymphocytic lymphoma, B-cell prolymphocytic leukemia, Lymphoplasmacytic lymphoma (such as Waldenström macroglobulinemia), Splenic marginal zone lymphoma, Plasma cell neoplasms (Plasma cell myeloma, Plasmacytoma, Monoclonal immunoglobulin deposition diseases, Heavy chain diseases), Extranodal marginal zone B cell lymphoma (MALT lymphoma), Nodal marginal zone B cell lymphoma (NMZL), Follicular lymphoma, Mantle cell lymphoma, Diffuse large B cell lymphoma, Mediastinal (thymic) large B cell lymphoma, Intravascular large B cell lymphoma, Primary effusion lymphoma, Burkitt lymphoma/leukemia, T cell prolymphocytic leukemia, T cell large granular lymphocytic leukemia, Aggressive NK cell leukemia, Adult T cell leukemia/lymphoma, Extranodal NK/T cell lymphoma (nasal type), Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorders, Primary cutaneous anaplastic large cell lymphoma, Lymphomatoid papulosis, Angioimmunoblastic T cell lymphoma, Peripheral T cell lymphoma (unspecified), Anaplastic large cell lymphoma), multiple myeloma (plasma cell myeloma or Kahler’s disease).

The present invention further provides a pharmaceutical composition comprising the compound described herein or a pharmaceutically acceptable salt thereof, and optionally a pharmaceutically acceptable carrier. The pharmaceutical composition described herein may be a tablet, a capsule, a granule, a syrup, a suspension, a solution, a dispersion, a slow release preparation for oral or non-oral administration, an intravenous injection preparation, a subcutaneous injection preparation, an inhalation preparation, a transdermal preparation, a rectal or vaginal suppository.

The pharmaceutically acceptable carrier described herein refers to a pharmaceutically acceptable carrier well known to those skilled in the art, and the pharmaceutically acceptable carrier of the present invention includes, but is not limited to, a filler, a wetting agent, a binder, a disintegrating agent, a lubricant, a binder, a glidant, a flavoring agent, a surfactant, a preservative, and the like. Fillers include, but are not limited to, lactose, microcrystalline cellulose, starch, powdered sugar, dextrin, mannitol, calcium sulfate, and the like. Wetting agents and binders include, but are not limited to, sodium carboxymethylcellulose, hydroxypropylcellulose, hydroxypropyl methyl cellulose, gelatin, sucrose, polyvinylpyrrolidone, and the like. Disintegrating agents include, but are not limited to, sodium carboxymethyl starch, crosslinked polyvinylpyrrolidone, croscarmellose sodium, low substituted hydroxypropylcellulose, and the like. Lubricants include, but are not limited to, magnesium stearate, aerosil, talc, hydrogenated vegetable oil, polyethylene glycol, magnesium lauryl sulfate, and the like. Binders include, but are not limited to, gum arabic, alginic acid, calcium carboxymethylcellulose, sodium carboxymethylcellulose, glucose, dextrin, dextrose, ethylcellulose, gelatin, liquid glucose, guar gum, hydroxyethyl cellulose, hydroxypropyl cellulose, hydroxypropyl methyl cellulose, magnesium aluminum silicate, maltodextrin, methyl cellulose, polymethacrylate, polyvinylpyrrolidone, pregelatinized starch, sodium alginate, sorbitol, starch, syrup and tragacanth.

Glidants include, but are not limited to, colloidal silica, powdered cellulose, magnesium trisilicate, silica, and talc. Flavoring agents include, but are not limited to, aspartame, stevioside, fructose, glucose, syrup, honey, xylitol, mannitol, lactose, sorbitol, maltitol, glycyrrhizin. Surfactants include, but are not limited to, Tween-80, poloxamer. Preservatives include, but are not limited to, paraben, sodium benzoate, potassium sorbate, and the like.

Methods of preparing various pharmaceutical compositions containing various amounts of active ingredients are known, or will be apparent to those skilled in the art in light of this disclosure, as described in REMINGTON'S PHARMACEUTICAL SCIENCES, Martin, E. W., ed., Mack Publishing Company, 19th ed. (1995). Methods of preparing the pharmaceutical compositions include incorporation of suitable pharmaceutical excipients, carriers, diluents and the like. The pharmaceutical compositions described herein are made in a known manner, including conventional methods of mixing, dissolving or lyophilizing.

In the pharmaceutical compositions described herein, the amount of active ingredient may vary from about 0.01% to about 99% by weight of a given unit dosage form. In such therapeutically useful pharmaceutical composition formulations, the active ingredient is in an amount such that an effective dosage level can be obtained.

The tablet, capsule and the like described herein may comprise: a binder such as tragacanth, gum arabic, corn starch or gelatin; an excipient such as dicalcium phosphate; a disintegrating agent such as corn starch, potato starch, alginic acid, etc.; a lubricant such as magnesium stearate; and a sweetener such as sucrose, fructose, lactose or aspartame; or a flavoring agent such as mint, wintergreen or cherry flavor. When the unit dosage form is a capsule, it may contain, in addition to materials of the above types, a liquid carrier such as vegetable oil or polyethylene glycol. Various other materials may be present, as a coating, or otherwise alter the physical form of the solid unit dosage form. For example, tablets or capsules may be coated with gelatin, wax, shellac or sugar, etc. The syrup may contain an active ingredient, sucrose or fructose as a sweetener, methylparaben or propylparaben as a preservative, a dye and a flavoring agent such as cherry or orange flavor. Of course, any material used to prepare any unit dosage form should be pharmaceutically acceptable and non-toxic in the amounts employed. In addition, the active ingredient can be incorporated into a slow release formulations and a slow release device.

The active ingredient can also be administered intravenously or intraperitoneally by infusion or injection. An aqueous solution of the active ingredient or a salt thereof can be prepared, optionally with a non-toxic surfactant. Dispersions in glycerol, liquid polyethylene glycol, triacetin and mixtures thereof, and oils can also be prepared. Under ordinary conditions of storage and use, these formulations contain a preservative to prevent the growth of microorganisms.

Pharmaceutical composition dosage forms suitable for injection or infusion may comprise sterile aqueous solution or dispersion or sterile powder comprising an active ingredient suitable for the ready-to-use preparation of a sterile, injectable or infusible solution or dispersion (optionally encapsulated in a liposome). In all cases, the final dosage forms must be sterile, liquid, and stable under the conditions of manufacture and storage. The liquid carrier may be a solvent or liquid dispersion medium including, for example, water, ethanol, polyols (for example, glycerol, propylene glycol, liquid polyethylene glycol, and the like), vegetable oils, non-toxic glycerides, and suitable mixtures thereof. Proper fluidity can be maintained, for example, by liposome formation, by maintaining the desired particle size in the case of dispersion, or by the use of a surfactant. The prevention of microorganisms can be achieved by using various antibacterial and antifungal agents such as parabens, chlorobutanol, phenol, sorbic acid, thimerosal, and the like. In many cases, it will be preferred to include isotonic agents, such as sugars, buffers or sodium chloride. Prolonged absorption of the injectable composition can be brought about by the use of a composition that comprises an absorption delaying agent (for example, aluminum monostearate and gelatin).

Sterile injectable solutions are prepared by combining the active ingredient in a desired amount in a suitable solvent with the various other ingredients listed above, followed by filter sterilization. In the case of sterile powders for the preparation of sterile injectable solutions, the preferred preparation methods are vacuum drying and lyophilization techniques which result in powders of the active ingredient plus any additionally desired ingredients present in the sterile filtration solution.

Useful solid carriers include comminuted solids (e.g., talc, clay, microcrystalline cellulose, silica, alumina, etc.). Useful liquid carriers include water, ethanol or ethylene glycol or a water-ethanol/ethylene glycol mixture, and the pharmaceutical compositions of the present invention may be dissolved or dispersed in the liquid carriers in an effective amount, optionally with the aid of a non-toxic surfactant. Adjuvants (such as fragrances) and additional antimicrobial agents can be added to optimize the properties for a given use.

Thickeners (such as synthetic polymers, fatty acids, fatty acid salts and esters, fatty alcohols, modified celluloses or modified inorganic materials) can also be used with liquid carriers to form coatable pastes, gels, ointments, soaps, etc. that are used directly on the user's skin.

The therapeutically effective amount of the active ingredient will depend not only on the particular salt selected, but also on the administration route, the property of the disease to be treated, and the age and conditions of the patient, and will ultimately depend on the decision of the attending physician or clinician.

The above formulations may be presented in unit dosage form, which is a physically discrete unit containing a unit dose suitable for administration to humans and other mammalian bodies. The unit dosage form may be a capsule or a tablet. The amount of active ingredient in the unit dose may vary or be adjusted between about 0.01 to about 1000 mg or more, depending on the particular treatment involved.

The term "treated", "treating" or "treatment" as used herein generally refers to the acquisition of the desired pharmacological and/or physiological effect. The effect may be prophylactic according to the prevention of the disease or its symptoms in whole or in part; and/or may be therapeutic according to the partial or complete stabilization or cure of the disease and/or the side effect due to the disease. As used herein, "treated", "treating" or "treatment" encompasses any treatment for the disease of a patient, including: (a) prevention of the disease or condition in the patient that may be predisposed to the disease or condition but has not yet been diagnosed; (b) inhibition of the symptoms of the disease, i.e., preventing its development; or (c) remission of the symptoms of the disease, i.e., causing regression of the disease or symptoms in whole or in part.

The compound described herein, or a pharmaceutically acceptable salt thereof, may also be administered in combination with one or more additional therapeutic agents for the treatment of cancers. Such additional therapeutic agents include, but are not limited to, anthracyclines, cyclophosphamide, 5-fluorouracil, cisplatin, and the like.

Unless otherwise specified, the percentages, proportions, ratios or parts used in the present application are by weight or volume. The amount used in the present application is a weight or volume amount. It can be determined easily by those skilled in the art.

Hereinafter, the present application will demonstrate the beneficial effects of the present application by way of examples. Those skilled in the art will recognize that these examples are illustrative and not restrictive. These examples will do not limit the scope of the present application in any way. The experimental methods described in the following examples, unless otherwise specified, are conventional methods; the reagents and materials, unless otherwise specified, are commercially available.

Methods for Making Isoindolinone Carboxamide Compounds

General scheme 1:

Scheme 1

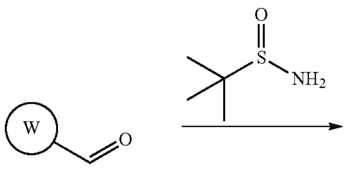

A

-continued

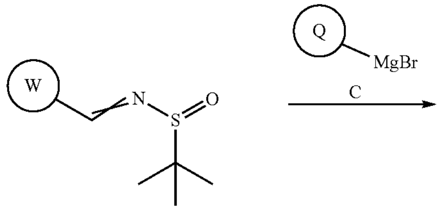

B

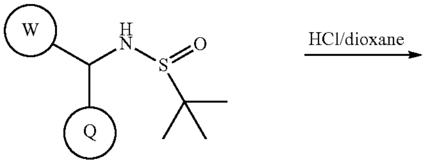

D

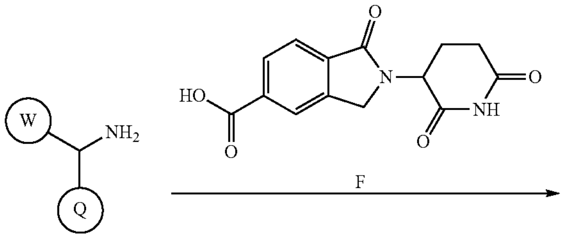

E

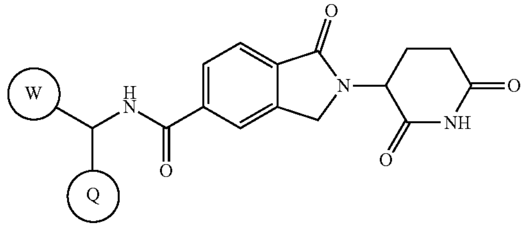

(I)

As shown in Scheme 1, the isoindolinone compounds of formula (I) can be made using conventional organic syntheses and commercially available starting materials. To a solution of compound A in an organic solvent (for example, THF, DCM), is added 2-methylpropane-2-sulfinamide in the presence of $CuSO_4$ or $Ti(OEt)_4$ to afford compound B. The imine intermediate in a solvent, such as THF, DCM, is subjected to a Grignard reagent C to form sulfinamide intermediate D. Deprotection of the sulfinamide is achieved by treatment with an acidic agent, for example, HCl in dioxane solution, to provide amine compound E. Coupling of the carboxylic acid F in a solvent, such as DMF, THF, and DCM in the presence of a coupling agent, such as $T_3P$, HATU, and EDCI and a base, such as DIEA and TEA, provides compounds of formula (I), wherein ring group W and ring group Q are as defined herein. The crude mixture is further purified by chiral HPLC or SFC to isolate optical isomers if needed.

General Scheme 2:

Scheme 2

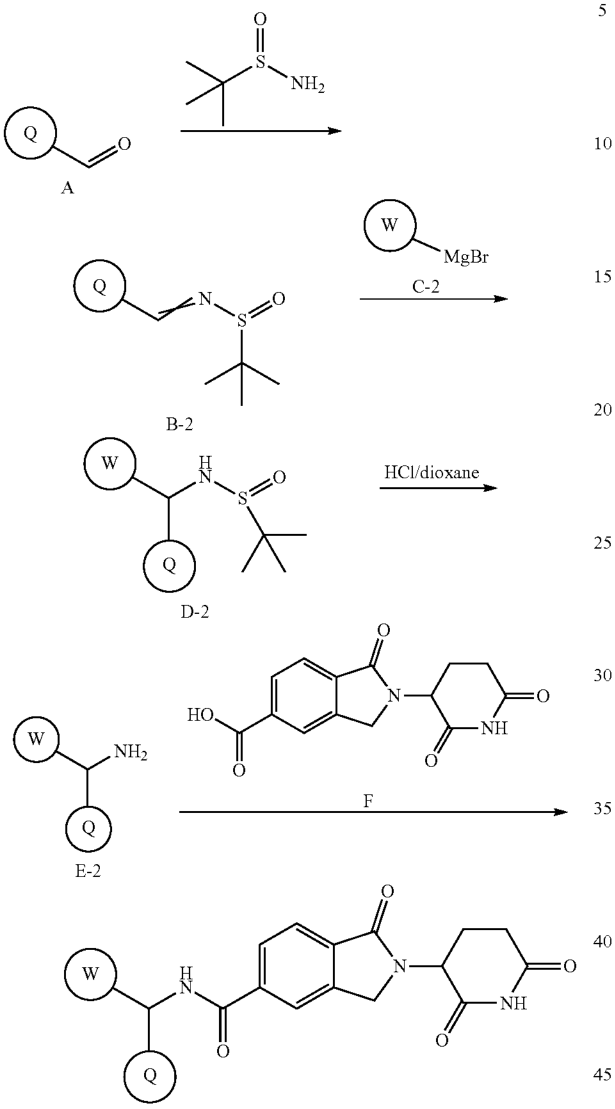

(I)

An alternative route to compounds of formula (I) is shown in Scheme 2. The isoindolinone compounds of formula (I) can be made using conventional organic syntheses and commercially available starting materials. To a solution of compound A-2 in an organic solvent (for example, THF, DCM), is added 2-methylpropane-2-sulfinamide in the presence of $CuSO_4$ or $Ti(OEt)_4$ to afford compound B-2. The imine intermediate in a solvent, such as THF, DCM, is subjected to a Grignard reagent C-2 to form sulfinamide intermediate D-2. Deprotection of the sulfinamide is achieved by treatment with an acidic agent, for example, HCl in dioxane solution, to provide amine compound E-2. Coupling of the carboxylic acid F in a solvent, such as DMF, THF, and DCM in the presence of a coupling agent, such as $T_3P$, HATU, and EDCI and a base, such as DIEA and TEA, provides compounds of formula (I), wherein ring group W and ring group Q are as defined herein. The crude mixture is further purified by chiral HPLC or SFC to isolate optical isomers if needed.

Chemistry

Several methods for preparing the compounds of this invention are illustrated hereinbelow. Unless otherwise noted, all starting materials were obtained from commercial suppliers and used without further purification.

Hereinafter, ACN means acetonitrile, AcOH means acetic acid, Boc means tert-butyloxycarbonyl, Bn means benzyl, calcd. means calculated, Cbz means benzyloxycarbonyl, col. means column, conc. means concentrated, DCM means dichloromethane, DEA means diethanolamine, DIPEA means N,N-diisopropylethyl amine, DMF means dimethylformamide, DMP means Dess-Martin periodinane, DMSO means dimethyl sulphoxide, DPPP means 1,3-bis(diphenylphosphine)propane, $Et_3N$ means triethylamine, EtOAc means ethyl acetate, ee means enantiomeric excess, ESI means electrospray ionization, HATU means 2-(7-azabenzotriazol-1-yl)-N,N,N',N'-tetramethyluronium hexafluorophosphate, Hex means hexane, HNMR means $^1H$ NMR, HPLC means high performance liquid chromatography, IPA means isopropyl alcohol, LC-MS or LCMS means liquid chromatography-mass spectrometry, LDA means lithium diisopropylamide, Ms means methanesulfonyl, PE means petroleum ether, PMB means 4-methoxybenzyl, PPTS means pyridinium p-toluenesulfonate, prep. means preparative, Prep-HPLC means preparative HPLC, $^tR$ or Rt mean retention time, (s) or (s) mean solid, sat. means saturated, SFC means supercritical fluid chromatography, TBAF means tetrabutylammonium fluoride, TBS means tert-butyldimethylsilyl, TEA means triethylamine, $T_3P$ means n-Propylphosphonic cyclic anhydride, THE means tetrahydrofuran, T or Temp mean temperature, TsCl means 4-toluenesulfonyl chloride, t-BuOK means potassium tert-butoxide, W means wavelength.

Example 1

Synthesis of Intermediate 1

Preparation of Intermediate 1: 2-(2,6-dioxopiperidin-3-yl)-1-oxoisoindoline-5-carboxylic acid Scheme 3

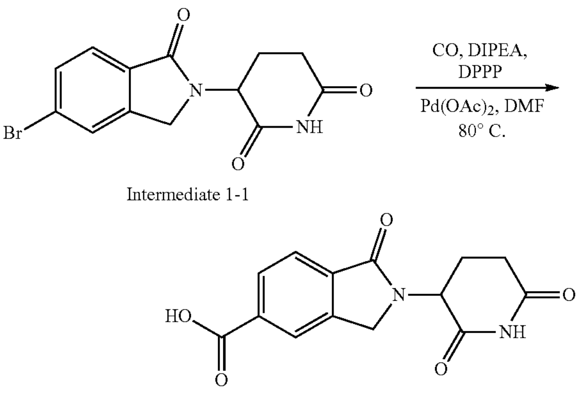

Intermediate 1

In a 2 L high-pressure reaction vessel was equipped with magnetic stirred bar, starting material of Intermediate 1-1 (100 g, 0.31 mmol), DIPEA (140 g, 1.08 mol), DPPP (76.7 g, 0.186 mmol), $Pd(OAc)_2$ (35.0 g, 0.155 mol), DMF (1200 mL) and water (50 mL). The mixture was heated to 80° C.

under CO atmosphere (80 MPa) overnight. The mixture was cooled to room temperature, and DMF was removed in vacuo. The residue was diluted with DCM (2.0 L) and slurried by stirring. The mixture was filtered and the filtrate was washed with solution of $NaHCO_3$, and the aqueous layer was acidified with conc.HCl to pH=1.0, the resulted solid was filtered, and collected. The crude of filter cake was dissolved with solution of $NaHCO_3$, the resulted solution was filtered and the filtrate was acidified with conc. HCl to pH:=1.0, the resulted solid was filtered and collected too. The collectors was combined and dried to give 2-(2,6-dioxopiperidin-3-yl)-1-oxoisoindoline-5-carboxylic acid (70.0 g, 78%) as a white solid $^1$H NMR (400 MHz, $CDCl_3$) δ 13.25 (brs, 1H), 11.02 (s, 1H), 8.18 (s, 1H), 8.07 (d, J=8.0 Hz, 1H), 7.83 (d, J=8.0 Hz, 1H), 5.17-5.13 (m, 1H), 4.48 (d, J=17.6 Hz, 1H), 4.42 (d, J=17.6 Hz, 1H), 2.92-2.89 (m, 1H), 2.63-2.50 (m, 1H), 2.43-2.40 (m, 1H), 2.05-2.03 (m 1H). LCMS (ESI$^+$): m/z: 287 [M−H]+

Synthesis of Intermediate 2

Scheme 3-1

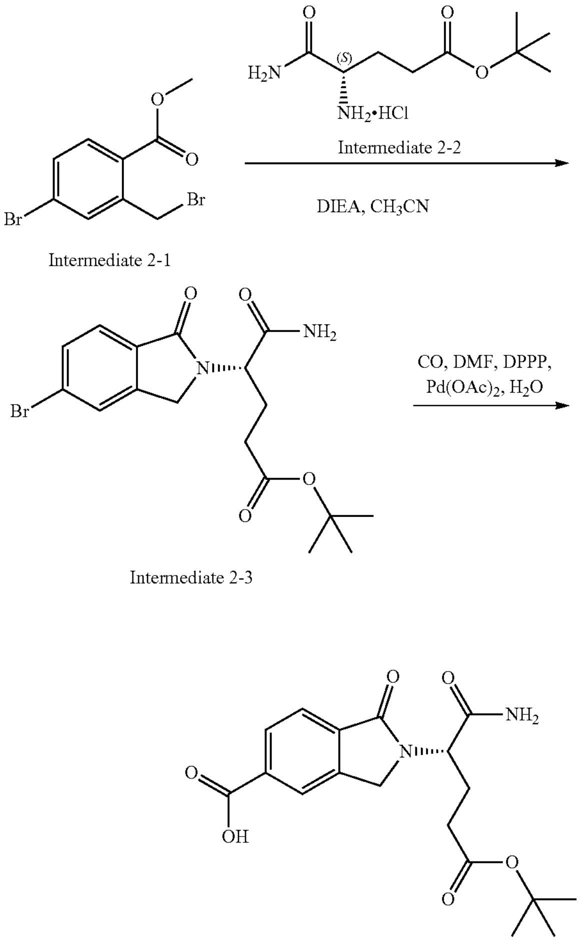

Intermediate 2-2
Intermediate 2-1
Intermediate 2-3
Intermediate 2

Step 1. Synthesis of tert-butyl (4S)-5-amino-4-(5-bromo-1-oxo-isoindolin-2-yl)-5-oxo-pentanoate (Intermediate 2-3)

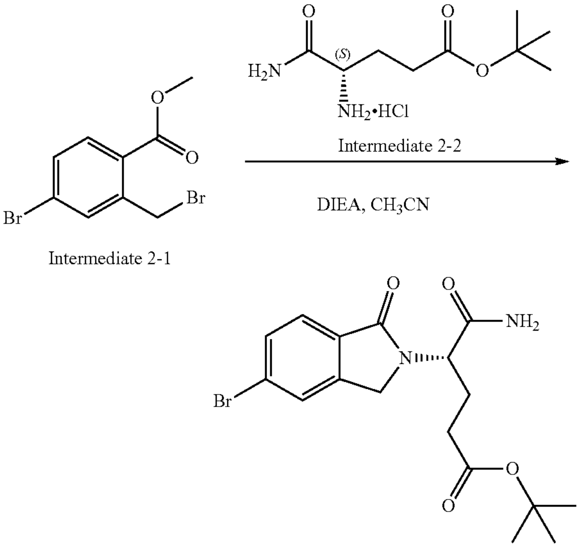

Intermediate 2-2
Intermediate 2-1
Intermediate 2-3

To a solution of (S)-tert-butyl 4, 5-diamino-5-oxopentanoate hydrochloride (139.68 g, 585.13 mmol, 1.06 eq) in $CH_3CN$ (900 mL) was stirred at 0° C. for 0.5 hr. Then DIEA (142.69 g, 1.10 mol, 192.30 mL, 2 eq) was dropwised added to the mixture. Then methyl 4-bromo-2-(bromomethyl) benzoate (170 g, 552.01 mmol, 1 eq) in $CH_3CN$ (800 mL) was added dropwise to the solution. The mixture was stirred at 60° C. for 12 hrs. LC-MS showed the desired compound was detected. The reaction mixture was concentrated under reduced pressure to remove solvent. The residue was added to $H_2O$ (2000 mL) under ultrasonic for 1 hr. Then the mixture was filtered. The filter cake was triturated with PE:EtOAc (5:1, 500 mL) under ultrasound for 1 hr. The mixture was filtered and the filter cake was collected. The crude product was used to the next step without further purification. Compound tert-butyl (4S)-5-amino-4-(5-bromo-1-oxo-isoindolin-2-yl)-5-oxo-pentanoate (220 g, 526.10 mmol, 95.3% yield, 95% purity) was obtained as a white solid.

LCMS (ESI) m/z 397.0 [M+H]

Step 2. Synthesis of 2-[(1S)-4-tert-butoxy-1-carbamoyl-4-oxo-butyl]-1-oxo-isoindoline-5-carboxylic acid (Intermediate 2)

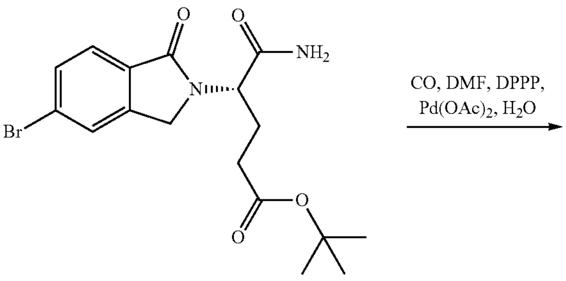

Intermediate 2-3

-continued

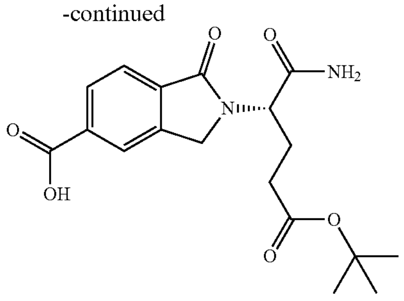

Intermediate 2

A mixture of tert-butyl (4S)-5-amino-4-(5-bromo-1-oxo-isoindolin-2-yl)-5-oxo-pentanoate (110 g, 276.89 mmol, 1 eq), TEA (224.15 g, 2.22 mol, 308.32 mL, 8 eq), DPPP (22.84 g, 55.38 mmol, 0.2 eq), and $Pd(OAc)_2$ (9.95 g, 44.30 mmol, 0.16 eq) in DMF (450 mL) and $H_2O$ (125 mL) was degassed and purged with $N_2$ for 3 times. And then the mixture was stirred at 80° C. for 12 hr under CO with 50 psi. LC-MS showed the desired compound was detected. The mixture was concentrated under reduced pressure to give a residue and poured into 2 M aq. $Na_2CO_3$ (dissolved with 6 L water), then the precipitate was formed. Filtered to remove solid to give a yellow solution. The filtrate was extracted with EtOAc (1 Lx3) and the organic layers were discarded and the aqueous solution was collected. The aqueous was neutralized with 6 N HCl to pH=4-5 and extracted with EtOAc (3 Lx2), combined the organic phases, dried over $Na_2SO_4$, filtered and concentrated under reduced pressure to give crude product. The crude was triturated with MTBE (500 mL) with stirring for 2 hrs. Filtered to afford target product. Compound 2-[(1S)-4-tert-butoxy-1-carbamoyl-4-oxo-butyl]-1-oxo-isoindoline-5-carboxylic acid (76.3 g, 205.74 mmol, 74.3% yield, 97.8% purity) was obtained as a white solid.

LCMS (ESI) m/z 363.4 [M+H]

$^1H$ NMR (400 MHz, DMSO-$d_6$) δ 13.29 (br s, 1H), 8.17 (s, 1H), 8.04 (d, J=8.8 Hz, 1H), 7.79 (d, J=7.9 Hz, 1H), 7.60 (br s, 1H), 7.22 (s, 1H), 4.75 (dd, J=4.2, 10.4 Hz, 1H), 4.69-4.50 (m, 2H), 2.26-2.09 (m, 3H), 2.06-1.92 (m, 1H), 1.32 (s, 9H)

Example 2

Preparation of compound 1: N-(-cyclopropyl(2,4-difluorophenyl)methyl)-2-(2,6-dioxopiperidin-3-yl)-1-oxoisoindoline-5-carboxamide Scheme 4

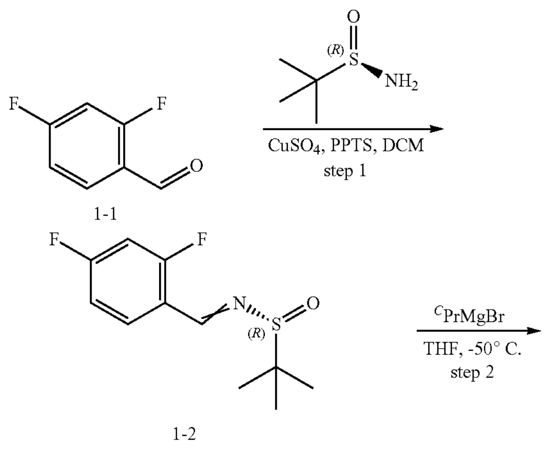

-continued

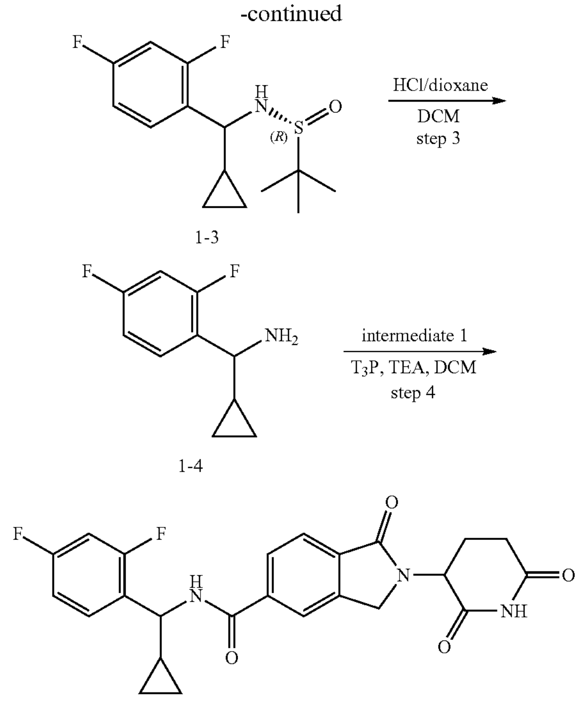

compound 1

Step 1: (R)—N-(2,4-difluorobenzylidene)-2-methyl-propane-2-sulfinamide 1-2

To a mixture of 2,4-difluorobenzaldehyde (1.00 g, 7.04 mmol), $CuSO_4$ (2.25 g, 14.1 mmol), PPTS (177 mg, 704 μmol) in DCM (10 mL) was added (R)-2-methylpropane-2-sulfinamide (768 mg, 6.34 mmol) at 25° C. The mixture was stirred at 25° C. for 20 hours. The reaction mixture was filtered and concentrated in vacuo to give a residue which was purified by chromatography on silica gel with petroleum ether and ethyl acetate as gradient eluent to obtained the titled product (1.59 g, 83% yield) as a colorless oil. $^1H$ NMR (400 MHz, $CDCl_3$) δ 8.84 (s, 1H), 8.11-7.97 (m, 1H), 7.05-6.87 (m, 2H), 1.27 (s, 9H). LCMS ($ESI^+$): m/z 246.01 $[M+H]^+$.

Step 2: (R)—N-(cyclopropyl(2,4-difluorophenyl) methyl)-2-methylpropane-2-sulfinamide 1-3

To a solution of (R)—N-(2,4-difluorobenzylidene)-2-methylpropane-2-sulfinamide (400 mg, 1.63 mmol) in THF (5 mL) was added dropwise cyclopropylmagnesium bromide (0.5 M, 6.52 mL) at −50° C. under $N_2$ atmosphere. After addition, the mixture was stirred at this temperature for 2 hours. The residue was poured into ice-sat. $NH_4Cl$ (10 mL) and stirred for 5 mins. The aqueous phase was extracted with ethyl acetate (10 mLx2). The combined organic phase was washed with brine (10 mL), dried with anhydrous $Na_2SO_4$, filtered and concentrated in vacuo to give the residue which was purified by chromatography on silica gel with petroleum ether and ethyl acetate as gradient eluent to obtained the titled product (165 mg, 28% yield) as colorless oil. $^1H$ NMR (400 MHz, $CDCl_3$) δ 7.42-7.32 (m, 1H), 6.91-6.77 (m, 2H), 3.90-3.83 (m, 1H), 3.59 (s, 1H), 1.45-1.38 (m, 1H), 1.22-1.17 (m, 9H), 0.77-0.64 (m, 1H), 0.59-0.36 (m, 3H). LCMS ($ESI^+$): m/z 288.04 $[M+H]^+$.

Step 3: cyclopropyl(2,4-difluorophenyl)methanamine 1-4

A mixture of (R)—N—((S)-cyclopropyl(2,4-difluorophenyl)methyl)-2-methylpropane-2-sulfinamide (160 mg, 557 μmol) in DCM (1 mL) and 4 N HCl/dioxane (1 mL) was degassed and purged with $N_2$ for 3 times. Then the mixture was stirred at 20° C. for 1 hour under $N_2$ atmosphere. The reaction mixture was concentrated under reduced pressure to give the title compound (180 mg, HCl salt, crude) as a yellow solid, which was used directly in the next step without further purification.

Step 4: N-(cyclopropyl(2,4-difluorophenyl)methyl)-2-(2,6-dioxopiperidin-3-yl)-1-oxoisoindoline-5-carboxamide compound 1

A mixture of cyclopropyl-(2,4-difluorophenyl)methanamine (50.0 mg, 228 μmol), 2-(2,6-dioxopiperidin-3-yl)-1-oxoisoindoline-5-carboxylic acid (54.6 mg, 190 μmol), $Et_3N$ (57.6 mg, 569 μmol), $T_3P$ (181 mg, 285 μmol) in DCM (2 mL) was degassed and purged with $N_2$ for 3 times, and then the mixture was stirred at 20° C. for 16 hours under $N_2$ atmosphere. The reaction mixture was concentrated under reduced pressure to remove solvent. The residue was purified by prep-HPLC to give the titled product (34.2 mg, 39.8% yield) as a white solid. $^1H$ NMR (400 MHz, DMSO-$d_6$) δ 11.01 (s, 1H), 9.33-9.14 (m, 1H), 8.08 (s, 1H), 8.03-7.95 (m, 1H), 7.85-7.79 (m, 1H), 7.72-7.63 (m, 1H), 7.24-7.15 (m, 1H), 7.14-7.05 (m, 1H), 5.24-5.04 (m, 1H), 4.70-4.62 (m, 1H), 4.56-4.48 (m, 1H), 4.44-4.35 (m, 1H), 2.99-2.85 (m, 1H), 2.63 (br s, 1H), 2.45-2.39 (m, 1H), 2.07-1.96 (m, 1H), 1.43-1.31 (m, 1H), 0.64-0.27 (m, 4H). LCMS ($ESI^+$): m/z 454.1 $[M+H]^+$.

Example 3

Compound 10 and 11 were prepared by condensation of similar procedure as described for compound 1, with commercially available chiral amine and intermediate 1.

TABLE 1

| No. | Structure | Compound name and characterization |
|---|---|---|
| 10 | 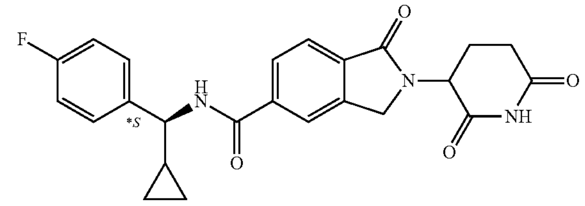 [SMILES: O=C1CCC(N2Cc3cc(C(=O)N[C@H](c4ccc(F)cc4)C4CC4)ccc3C2=O)C(=O)N1] | N-((*S)-cyclopropyl(4-fluorophenyl)methyl)-2-(2,6-dioxopiperidin-3-yl)-1-oxoisoindoline-5-carboxamide $^1H$ NMR (400 MHz, DMSO-$d_6$): δ 11.02 (bs., 1H), 9.30-9.17 (m, 1H), 8.09 (s, 1H), 8.02 (s, 1H), 7.85-7.80 (m, 1H), 7.55-7.46 (m, 2H), 7.21-7.12 (m, 2H), 5.15 (dd, J = 5.2, 13.2 Hz, 1H), 4.58-4.48 (m, 1H), 4.44-4.33 (m, 2H), 2.98-2.85 (m, 1H), 2.65-2.56 (m, 1H), 2.45-2.35 (m, 1H), 2.07-1.97 (m, 1H), 1.39-1.27 (m, 1H), 0.61-0.51 (m, 2H), 0.49-0.34 (m, 2H). LCMS ($ESI^+$): m/z 436.1 $[M + H]^+$. |
| 11 | 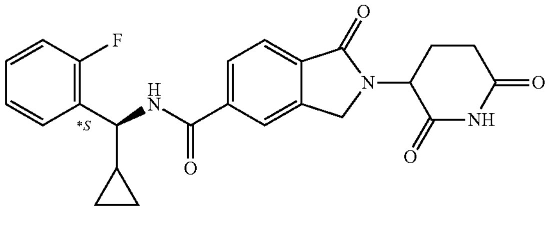 [SMILES: O=C1CCC(N2Cc3cc(C(=O)N[C@H](c4ccccc4F)C4CC4)ccc3C2=O)C(=O)N1] | N-((*S)-cyclopropyl(2-fluorophenyl)methyl)-2-(2,6-dioxopiperidin-3-yl)-1-oxoisoindoline-5-carboxamide $^1H$ NMR (400 MHz, DMSO-$d_6$) δ 11.04 (br. s., 1H), 9.28 (d, J = 7.6 Hz, 1H), 8.09 (s, 1H), 8.01 (d, J = 8.0 Hz, 1H), 7.83 (d, J = 8.0 Hz, 1H), 7.65 (t, J = 7.2 Hz, 1H), 7.36-7.11 (m, 3H), 5.15 (dd, J = 4.8, 13.2 Hz, 1H), 4.71 (t, J = 8.4 Hz, 1H), 4.58-4.34 (m, 2H), 2.99-2.85 (m, 1H), 2.67-2.57 (m, 1H), 2.47-2.35 (m, 1H), 2.10-1.98 (m, 1H), 1.43-1.32 (m, 1H), 0.65-0.30 (m, 4H); LCMS ($ESI^+$): m/z 436.1 $[M + H]^+$. |

Example 4

The following compounds were prepared according to similar procedure as described for compound 1 with corresponding starting materials of aldehydes and Grignard reagents. For compounds 12, 13, 17, 18, 21, 24, 64 and 71, the corresponding major diastereomer intermediate of step 2 was separated by prep-HPLC or SFC before the following step 3 and 4.

TABLE 2

| No. | Structure | Compound name and characterization |
|---|---|---|
| 12 | 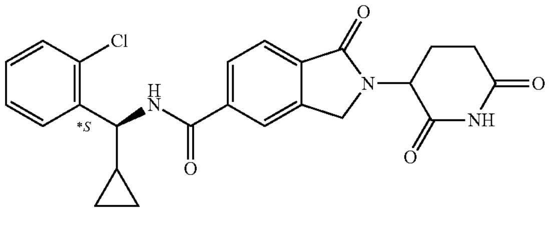 [SMILES: O=C1CCC(N2Cc3cc(C(=O)N[C@H](c4ccccc4Cl)C4CC4)ccc3C2=O)C(=O)N1] | N-((*S)-(2-chlorophenyl)(cyclopropyl)methyl)-2-(2,6-dioxopiperidin-3-yl)-1-oxoisoindoline-5-carboxamide $^1H$ NMR (400 MHz, DMSO-$d_6$) δ 11.03 (br. s., 1 H), 9.19 (d, J = 7.6 Hz, 1 H), 7.95-8.15 (m, 2 H), 7.72-7.87 (m, 2 H), 7.23-7.47 (m, 3 H), 5.15 (dd, J =13.2, 4.8 Hz, 1 H), 4.96 (t, J = 8.4 Hz, 1 H), 4.35-4.58 (m, 2 H), 2.87-2.99 (m, 1 H), 2.59-2.72 (m, 1 H), 2.32-2.45 (m, 1 H), 1.98-2.07 (m, 1 H), 1.31-1.43 (m, 1 H), 0.39-0.63 (m, 4 H); LCMS ($ESI^+$): m/z 452.0 $[M + H]^+$. |

TABLE 2-continued

| No. | Structure | Compound name and characterization |
|---|---|---|
| 13 | 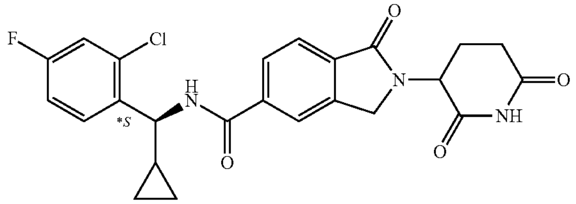 [SMILES: O=C1CCC(N2Cc3cc(C(=O)N[C@H](c4ccc(F)cc4Cl)C4CC4)ccc3C2=O)C(=O)N1] | N-((*S)-(2-chloro-4-fluorophenyl)(cyclopropyl)-yl)methyl)-2-(2,6-dioxopiperidin-3-yl)-1-oxoiso-indoline-5-carboxamide $^1$H NMR (400 MHz, DMSO-$d_6$) δ 11.01 (s, 1H), 9.33-9.14 (m, 1H), 8.08 (s, 1H), 8.03-7.95 (m, 1H), 7.85-7.79 (m, 1H), 7.72-7.63 (m, 1H), 7.24-7.15 (m, 1H), 7.14-7.05 (m, 1H), 5.24-5.04 (m, 1H), 4.70-4.62 (m, 1H), 4.56-4.48 (m, 1H), 4.44-4.35 (m, 1H), 2.99-2.85 (m, 1H), 2.63 (br s, 1H), 2.45-2.39 (m, 1H), 2.07-1.96 (m, 1H), 1.43-1.31 (m, 1H), 0.64-0.27 (m, 4H); LCMS (ESI$^+$): m/z 470.1 [M + H]$^+$. |
| 14 | 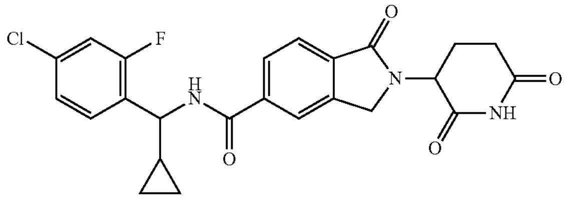 [SMILES: O=C1CCC(N2Cc3cc(C(=O)NC(c4ccc(Cl)cc4F)C4CC4)ccc3C2=O)C(=O)N1] | N-((4-chloro-2-fluorophenyl)(cyclopropyl)meth-yl)-2-(2,6-dioxopiperidin-3-yl)-1-xoisoindoline-5-carboxamide $^1$H NMR (400 MHz, DMSO-$d_6$) δ 11.02 (s, 1H), 9.28 (d, J = 7.6 Hz, 1H), 8.08 (s, 1H), 8.00 (d, J = 8.0 Hz, 1H), 7.82 (d, J = 8.0 Hz, 1H), 7.65 (t, J = 8.0 Hz, 1H), 7.40 (d, J = 10.4 Hz, 1H), 7.32 (d, J = 8.4 Hz, 1H), 5.21-5.08 (m, 1H), 4.64 (t, J = 8.4 Hz, 1H), 4.57-4.47 (m, 1H), 4.44-4.34 (m, 1H), 3.00-2.83 (m, 1H), 2.65-2.57 (m, 1H), 2.45-2.36 (m, 1H), 2.07-1.98 (m, 1H), 1.41-1.30 (m, 1H), 0.64-0.56 (m, 1H), 0.56-0.47 (m, 1H), 0.46-0.38 (m, 1H), 0.37-0.28 (m, 1H). LCMS (ESI+): m/z 470.0 [M + H]+. |
| 15 | 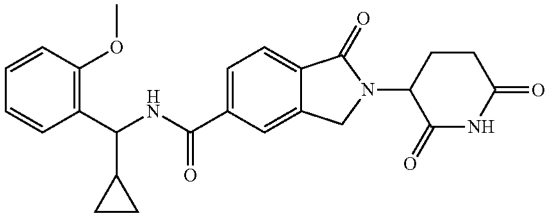 [SMILES: COc1ccccc1C(NC(=O)c1ccc2c(c1)CN(C1CCC(=O)NC1=O)C2=O)C1CC1] | N-(cyclopropyl(2-methoxyphenyl)methyl)-2-(2,6-dioxopiperidin-3-yl)-1-oxoisoindoline-5-carboxamide $^1$H NMR (400 MHz, DMSO-$d_6$) δ 11.03 (br. s, 1H), 8.98 (d, J = 8.4 Hz, 1H), 8.07 (s, 1H), 7.99 (d, J = 8.0 Hz, 1H), 7.82 (d, J = 8.0 Hz, 1H), 7.53 (d, J = 7.2 Hz, 1H), 7.30-7.19 (m, 1H), 7.04-6.88 (m, 2H), 5.15 (dd, J = 5.2, 13.2 Hz, 1H), 4.95 (t, J = 8.8 Hz, 1H), 4.58-4.34 (m, 2H), 3.81 (s, 3H), 3.00-2.86 (m, 1H), 2.63-2.59 (m, 1H), 2.46-2.35 (m, 1H), 2.09-1.96 (m, 1H), 1.37-1.20 (m, 1H), 0.54-0.26 (m, 4H); LCMS (ESI$^+$): m/z 448.1 [M + H]$^+$. |
| 16 | 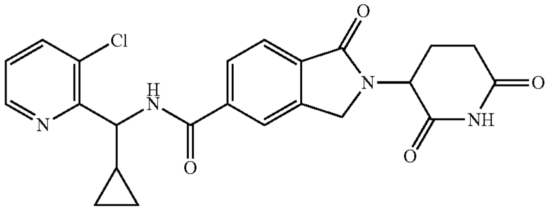 [SMILES: O=C1CCC(N2Cc3cc(C(=O)NC(c4ncccc4Cl)C4CC4)ccc3C2=O)C(=O)N1] | N-((3-chloropyridin-2-yl)(cyclopropyl)methyl)-2-(2,6-dioxopiperidin-3-yl)-1-oxoisoindoline-5-carboxamide $^1$H NMR (400 MHz, DMSO-$d_6$) δ 11.10-10.97 (m, 1H), 9.17 (d, J = 8.0 Hz, 1H), 8.57-8.52 (m, 1H), 8.10 (s, 1H), 8.03-7.97 (m, 1H), 7.94-7.90 (m, 1H), 7.79 (d, J = 8.0 Hz, 1H), 7.38-7.33 (m, 1H), 5.18-5.10 (m, 1H), 5.00 (t, J = 8.0 Hz, 1H), 4.55-4.47 (m, 1H), 4.43-4.34 (m, 1H), 2.96-2.87 (m, 1H), 2.65-2.56 (m, 1H), 2.46-2.39 (m, 1H), 2.07-1.97 (m, 1H), 1.59-1.36 (m, 1H), 0.60-0.54 (m, 1H), 0.51-0.43 (m, 3H); LCMS (ESI$^+$): m/z 453.1 [M + H]$^+$. |
| 17 | 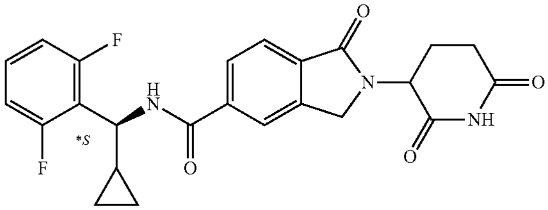 [SMILES: O=C1CCC(N2Cc3cc(C(=O)N[C@H](c4c(F)cccc4F)C4CC4)ccc3C2=O)C(=O)N1] | N-((*S)-cyclopropyl(2,6-difluorophenyl)meth-yl)-2-(2,6-dioxopiperidin-3-yl)-1-oxoisoindo-line-5-carboxamide $^1$H NMR (400 MHz, DMSO-$d_6$) δ 11.02 (s, 1H), 9.34 (d, J = 6.8 Hz, 1H), 8.07 (s, 1H), 7.99 (d, J = 8.0 Hz, 1H), 7.80 (d, J = 7.6 Hz, 1H), 7.39-7.28 (m, 1H), 7.13-7.01 (m, 2H), 5.18-5.10 (m, 1H), 4.55-4.46 (m, 2H), 4.42-4.34 (m, 1H), 2.98-2.86 (m, 1H), 2.68-2.58 (m, 1H), 2.45-2.32 (m, 1H), 2.06-1.97 (m, 1H), 1.65-1.54 (m, 1H), 0.69-0.61 (m, 1H), 0.57-0.49 (m, 1H), 0.49-0.41 (m, 1H), 0.29-0.21 (m, 1H); LCMS (ESI$^+$): m/z 454.1 [M + H]$^+$. |
| 18 | 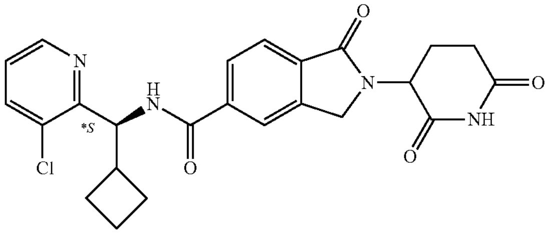 [SMILES: O=C1CCC(N2Cc3cc(C(=O)N[C@H](c4ncccc4Cl)C4CCC4)ccc3C2=O)C(=O)N1] | N-((*S)-(3-chloropyridin-2-yl)(cyclobutyl)-methyl)-2-(2,6-dioxopiperidin-3-yl)-1-oxoiso-indoline-5-carboxamide $^1$H NMR (400 MHz, DMSO-$d_6$) δ 11.01 (s, 1H), 8.90-8.81 (m, 1H), 8.56-8.47 (m, 1H), 8.11-8.03 (m, 1H), 8.01-7.94 (m, 1H), 7.93-7.88 (m, 1H), 7.81-7.75 (m, 1H), 7.42-7.25 (m, 1H), 5.68-5.57 (m, 1H), 5.20-5.08 (m, 1H), 4.57-4.44 (m, 1H), 4.43-4.31 (m, 1H), 3.06-2.83 (m, 2H), 2.65-2.56 (m, 1H),2.45-2.35 (m, 1H), 2.12-1.89 (m, 3H), 1.88-1.67 (m, 4H). LCMS (ESI$^+$): m/z 467.1 [M + H]$^+$ |

TABLE 2-continued

| No. | Structure | Compound name and characterization |
|---|---|---|
| 19 | 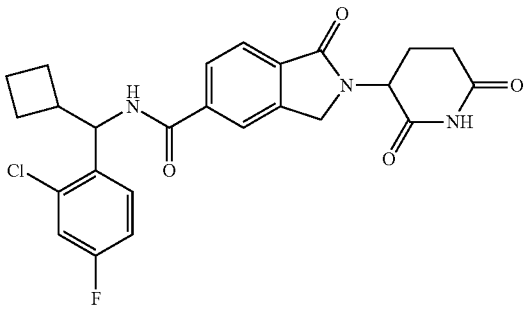 [SMILES: O=C1CCC(N2Cc3cc(C(=O)NC(c4ccc(F)cc4Cl)C4CCC4)ccc3C2=O)C(=O)N1] | N-((2-chloro-4-fluorophenyl)(cyclobutyl)-methyl)-2-(2,6-dioxopiperidin-3-yl)-1-oxoiso-indoline-5-carboxamide $^1$H NMR (400 MHz, DMSO-$d_6$) δ 11.01 (br s, 1 H) 8.90 (d, J = 8.00 Hz, 1 H) 8.03 (s, 1 H) 7.95 (d, J = 8.00 Hz, 1 H) 7.81 (d, J = 8.00 Hz, 1 H) 7.59-7.66 (m, 1 H) 7.35-7.43 (m, 1 H) 7.20-7.28 (m, 1 H) 5.40-5.57 (m, 1 H) 5.02-5.23 (m, 1 H) 4.28-4.61 (m, 2 H) 2.78-2.97 (m, 2 H) 2.56-2.65 (m, 1 H) 2.35-2.44 (m, 1 H) 1.97-2.14 (m, 2 H) 1.73-1.93 (m, 5 H). LCMS (ESI$^+$): m/z 484.1 [M + H]$^+$. |
| 50 | 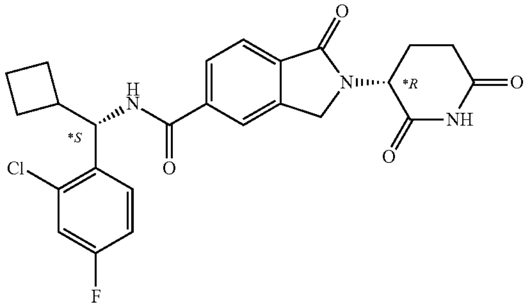 [SMILES: O=C1CC[C@@H](N2Cc3cc(C(=O)N[C@H](c4ccc(F)cc4Cl)C4CCC4)ccc3C2=O)C(=O)N1] | N-((*S)-(2-chloro-4-fluorophenyl)(cyclobutyl)-methyl)-2-((*R)-2,6-dioxopiperidin-3-yl)-1-oxoisoindoline-5-carboxamide $^1$H NMR (400 MHz, DMSO-$d_6$) δ 11.01 (br s, 1H), 8.89 (d, J = 8.0 Hz, 1H), 8.02 (s, 1H), 7.95 (d, J = 8.0 Hz, 1H), 7.81 (d, J = 8.0 Hz, 1H), 7.65-7.59 (m, 1H), 7.43-7.35 (m, 1H), 7.28-7.18 (m, 1H), 5.55-5.41 (m, 1H), 5.22-4.99 (m, 1H), 4.56-4.45 (m, 1H), 4.44-4.33 (m, 1H), 2.94-2.80 (m, 2H), 2.62 (s, 1H), 2.44-2.37 (m, 1H), 2.06-1.98 (m, 2H), 1.91-1.72 (m, 5H). LCMS (ESI$^+$): m/z 484.1 [M + H]$^+$. The compound was separated by SFC with the corresponding racemic mixture: chiral column: (S,S)Whelk-01, 100 * 4.6 mm I.D., 5 um, gradient mobile phase: $CO_2$: MeOH (0.05% DEA), tR: 2.571 min, chiral purity: 93% |
| 51 | 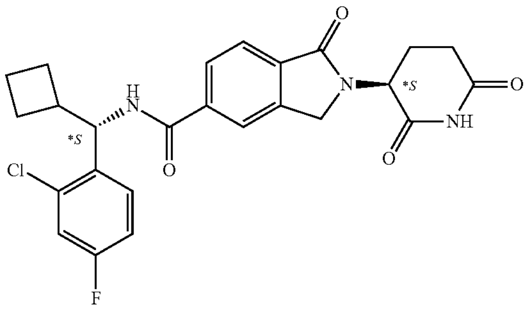 | N-((*S)-(2-chloro-4-fluorophenyl)(cyclobutyl)-methyl)-2-((*S)-2,6-dioxopiperidin-3-yl)-1-oxoisoindoline-5-carboxamide $^1$H NMR (400 MHz, DMSO-$d_6$) δ 11.01 (br s, 1H), 8.89 (d, J = 8.0 Hz, 1H), 8.03 (s, 1H), 7.95 (d, J = 8.0 Hz, 1H), 7.81 (d, J = 8.0 Hz, 1H), 7.66-7.59 (m, 1H), 7.42-7.36 (m, 1H), 7.28-7.19 (m, 1H), 5.54-5.41 (m, 1H), 5.21-5.04 (m, 1H), 4.57-4.46 (m, 1H), 4.44-4.33 (m, 1H), 2.93-2.77 (m, 2H), 2.64-2.57(m, 1H), 2.42-2.38 (m, 1H), 2.14-1.97 (m, 2H), 1.86-1.65 (m, 5H). LCMS (ESI$^+$): m/z 484.1 [M + H]$^+$. The compound was separated by SFC with the corresponding racemic mixture: chiral column: (S,S)Whelk-01, 100 * 4.6 mm I.D., 5 um, gradient mobile phase: $CO_2$: MeOH (0.05% DEA), tR: 2.571 min, chiral purity: 91% |
| 52 | 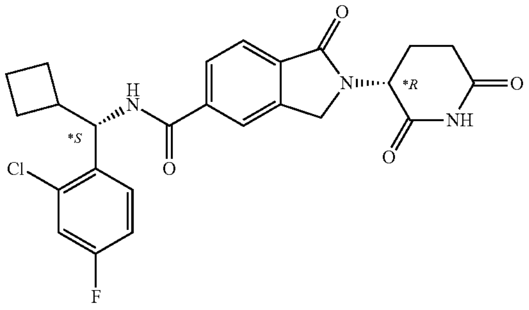 [SMILES: O=C1CC[C@@H](N2Cc3cc(C(=O)N[C@H](c4ccc(F)cc4Cl)C4CCC4)ccc3C2=O)C(=O)N1] | N-((*S)-(2-chloro-4-fluorophenyl)(cyclobutyl)-methyl)-2-((*R)-2,6-dioxopiperidin-3-yl)-1-oxoisoindoline-5-carboxamide $^1$H NMR (400 MHz, DMSO-$d_6$) δ 11.01 (br s, 1H), 8.89 (d, J = 8.0 Hz, 1H), 8.03 (s, 1H), 7.95 (d, J = 8.0 Hz, 1H), 7.81 (d, J = 8.0 Hz, 1H), 7.66-7.59 (m, 1H), 7.42-7.36 (m, 1H), 7.28-7.20 (m, 1H), 5.62-5.28 (m, 1H), 5.18-5.09 (m, 1H), 4.55-4.47 (m, 1H), 4.44-4.35 (m, 1H), 2.98-2.76 (m, 2H), 2.65-2.57(m, 1H), 2.45-2.37 (m, 1H), 2.12-1.97 (m, 2H), 1.93-1.71 (m, 5H). LCMS (ESI$^+$): m/z 484.1 [M + H]$^+$. The compound was separated by SFC with the corresponding racemic mixture: chiral column: (S,S)Whelk-01, 100 * 4.6 mm I.D., 5 um, gradient mobile phase: $CO_2$: MeOH (0.05% DEA), tR: 2.571 min, chiral purity: 94% |

TABLE 2-continued

| No. | Structure | Compound name and characterization |
|---|---|---|
| 53 | 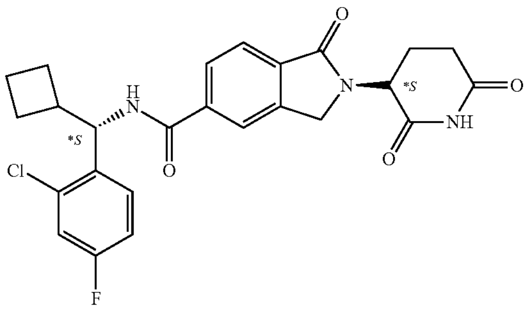 | N-((*S)-(2-chloro-4-fluorophenyl)(cyclobutyl)-methyl)-2-((*S)-2,6-dioxopiperidin-3-yl)-1-oxoisoindoline-5-carboxamide $^1$H NMR (400 MHz, DMSO-$d_6$) δ 11.00 (br s, 1H), 8.89 (d, J = 8.0 Hz, 1H), 8.02 (s, 1H), 7.95 (d, J = 8.0 Hz, 1H), 7.81 (d, J = 8.0 Hz, 1H), 7.67-7.58 (m, 1H), 7.42-7.36 (m, 1H), 7.28-7.19 (m, 1H), 5.53-5.41 (m, 1H), 5.19-5.07 (m, 1H), 4.56-4.46 (m, 1H), 4.43-4.33 (m, 1H), 2.93-2.77 (m, 2H), 2.64-2.58 (m, 1H), 2.45-2.37 (m, 1H), 2.13-1.98 (m, 2H), 1.97-1.68 (m, 5H). LCMS (ESI$^+$): m/z 484.1 [M + H]$^+$. The compound was separated by SFC with the corresponding racemic mixture: chiral column: (S,S)Whelk-01, 100 * 4.6 mm I.D., 5 um, gradient mobile phase: $CO_2$: MeOH (0.05% DEA), tR: 2.571 min, chiral purity: 88% |
| 20 | 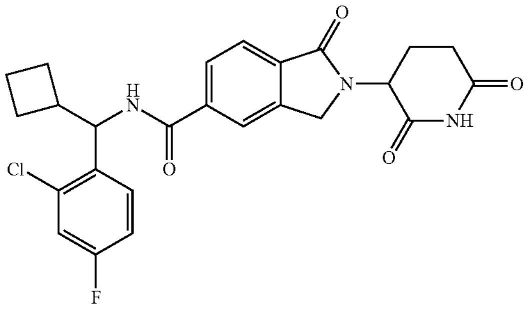 [SMILES: O=C1CCC(N2Cc3cc(C(=O)NC(c4ccc(F)cc4Cl)C4CCC4)ccc3C2=O)C(=O)N1] | N-((4-chloro-2-fluorophenyl)(cyclobutyl)methyl)-2-(2,6-dioxopiperidin-3-yl)-1-oxoisoindoline-5-carboxamide $^1$H NMR (400 MHz, DMSO-$d_6$) δ 11.02 (s, 1 H), 8.90-9.05 (m, 1 H), 8.02-8.08 (m, 1 H), 7.93-7.99 (m, 1 H), 7.80-7.86 (m, 1 H), 7.50-7.58 (m, 1 H), 7.36-7.44 (m, 1 H), 7.27-7.33 (m, 1 H), 5.23-5.35 (m, 1 H), 5.09-5.19 (m, 1 H), 4.35-4.55 (m, 2 H), 2.88-2.98 (m, 1 H), 2.77-2.86 (m, 1 H), 2.59-2.65 (m, 1 H), 2.34-2.45 (m, 1 H), 2.07-2.15 (m, 1 H), 1.97-2.06 (m, 1 H), 1.63-1.86 (m, 5 H). LCMS (ESI+): m/z 484.0 [M + 1]$^+$. |
| 54 | 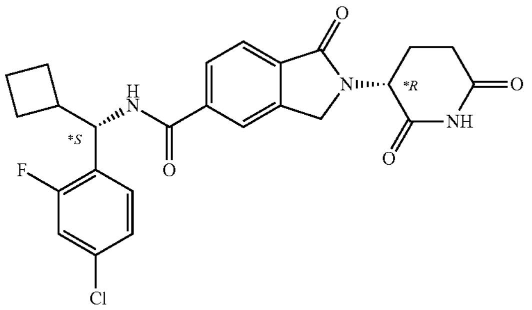 [SMILES: O=C1CC[C@@H](N2Cc3cc(C(=O)N[C@H](c4ccc(Cl)cc4F)C4CCC4)ccc3C2=O)C(=O)N1] | N-((*S)-(4-chloro-2-fluorophenyl)(cyclobutyl)-methyl)-2-((*R)-2,6-dioxopiperidin-3-yl)-1-oxo-isoindoline-5-carboxamide $^1$H NMR (400 MHz, DMSO-$d_6$) δ 11.01 (s, 1 H), 8.92-9.03 (m, 1 H), 8.04 (s, 1 H), 7.91-7.98 (m, 1 H), 7.82 (s, 1 H), 7.49-7.58 (m, 1 H), 7.34-7.43 (m, 1 H), 7.24-7.33 (m, 1 H), 5.22-5.32 (m, 1 H), 5.14-5.18 (m, 1 H), 4.35-4.56 (m, 2 H), 2.86-2.98 (m, 1 H), 2.75-2.85 (m, 1 H), 2.59-2.68 (m, 1 H), 2.35-2.46 (m, 1 H), 2.07-2.15 (m, 1 H), 1.98-2.06 (m, 1 H), 1.63-1.89 (m, 5 H); LCMS (ESI$^+$): m/z 484.1 [M + 1]$^+$. The compound was separated by SFC with the corresponding racemic mixture: chiral column: (S,S)Whelk-01, 100 * 4.6 mm I.D., 5 um, gradient mobile phase: $CO_2$: MeOH (0.05% DEA), tR: 2.571 min, chiral purity: 98% |
| 55 | 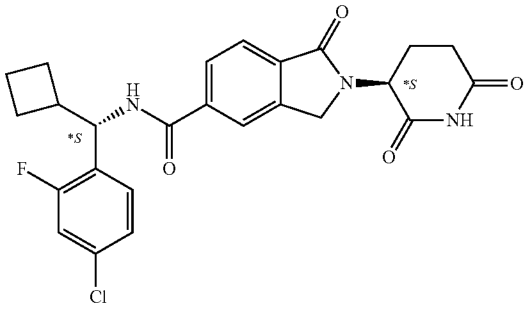 [SMILES: O=C1CC[C@H](N2Cc3cc(C(=O)N[C@H](c4ccc(Cl)cc4F)C4CCC4)ccc3C2=O)C(=O)N1] | N-((*S)-(4-chloro-2-fluorophenyl)(cyclobutyl)-methyl)-2-((*S)-2,6-dioxopiperidin-3-yl)-1-oxo-isoindoline-5-carboxamide $^1$H NMR (400 MHz, DMSO-$d_6$) δ 11.02 (s, 1 H), 8.90-9.09 (m, 1 H), 8.04 (s, 1 H), 7.93-8.00 (m, 1 H), 7.80-7.86 (m, 1 H), 7.51-7.58 (m, 1 H), 7.37-7.43 (m, 1 H), 7.27-7.32 (m, 1 H), 5.23-5.33 (m, 1 H), 5.08-5.19 (m, 1 H), 4.34-4.58 (m, 2 H), 2.86-2.99 (m, 1 H), 2.75-2.85 (m, 1 H), 2.58-2.68(m, 1 H), 2.31-2.45 (m, 1 H), 2.07-2.16 (m, 1 H), 1.96-2.07 (m, 1 H), 1.53-1.90 (m, 5 H); LCMS (ESI+): m/z 484.1 [M + 1]$^+$. The compound was separated by SFC with the corresponding racemic mixture: chiral column: (S,S)Whelk-01, 100 * 4.6 mm I.D., 5 um, gradient mobile phase: $CO_2$: MeOH (0.05% DEA), tR: 3.06 min, chiral purity: 96% |

TABLE 2-continued

| No. | Structure | Compound name and characterization |
|---|---|---|
| 56 | 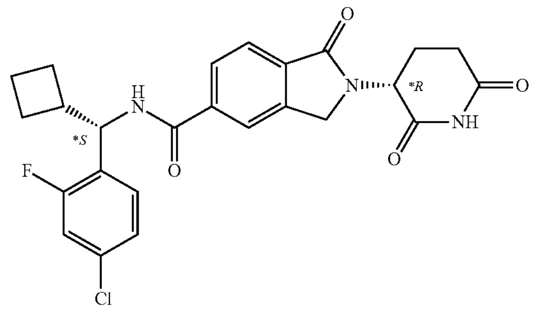 [SMILES: O=C1CC[C@@H](N2Cc3cc(C(=O)N[C@H](c4ccc(Cl)cc4F)C4CCC4)ccc3C2=O)C(=O)N1] | N-((*S)-(4-chloro-2-fluorophenyl)(cyclobutyl)-methyl)-2-((*R)-2,6-dioxopiperidin-3-yl)-1-oxoisoindoline-5-carboxamide $^1$H NMR (400 MHz, DMSO-$d_6$) δ 11.00 (s, 1 H), 8.87-9.07 (m, 1 H), 8.05 (s, 1 H), 7.96-8.01 (m, 1 H), 7.75-7.86 (m, 1 H), 7.51-7.61 (m, 1 H), 7.35-7.43 (m, 1 H), 7.26-7.32 (m, 1 H), 5.23-5.33 (m, 1 H), 5.10-5.18 (m, 1 H), 4.26-4.59 (m, 2 H), 2.87-3.03 (m, 1 H), 2.76-2.86 (m, 1 H), 2.56-2.69 (m, 1 H), 2.32-2.45 (m, 1 H), 2.07-2.17 (m, 1 H), 1.98-2.06 (m, 1 H), 1.61-1.88 (m, 5 H); LCMS (ESI+): m/z 484.1 $[M + 1]^+$. The compound was separated by SFC with the corresponding racemic mixture: chiral column: (S,S)Whelk-01, 100 * 4.6 mm I.D., 5 um, gradient mobile phase: $CO_2$: MeOH (0.05% DEA), tR: 4.34 min, chiral purity: 100% |
| 57 | 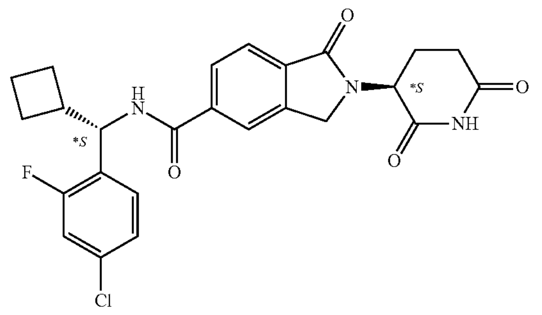 [SMILES: O=C1CC[C@H](N2Cc3cc(C(=O)N[C@H](c4ccc(Cl)cc4F)C4CCC4)ccc3C2=O)C(=O)N1] | N-((*S)-(4-chloro-2-fluorophenyl)(cyclobutyl)-methyl)-2-((*S)-2,6-dioxopiperidin-3-yl)-1-oxoisoindoline-5-carboxamide $^1$H NMR (400 MHz, DMSO-$d_6$) δ 11.01 (s, 1 H), 8.80-9.15 (m, 1 H), 8.05 (s, 1 H), 7.93-8.00 (m, 1 H), 7.78-7.85 (m, 1 H), 7.50-7.59 (m, 1 H), 7.36-7.43 (m, 1 H), 7.25-7.32 (m, 1 H), 5.23-5.36 (m, 1 H), 5.05-5.20 (m, 1 H), 4.47-4.58 (m, 2 H), 2.87-2.98 (m, 1 H), 2.78-2.85 (m, 1 H), 2.58-2.69 (m, 1 H), 2.32-2.45 (m, 1 H), 2.08-2.16 (m, 1 H), 1.97-2.07 (m, 1 H), 1.59-1.93 (m, 5 H); LCMS (ESI+): m/z 484.1 $[M + 1]^+$. The compound was separated by SFC with the corresponding racemic mixture: chiral column: (S,S)Whelk-01, 100 * 4.6 mm I.D., 5 um, gradient mobile phase: $CO_2$: MeOH (0.05% DEA), tR: 5.47 min, chiral purity: 100% |
| 21 | 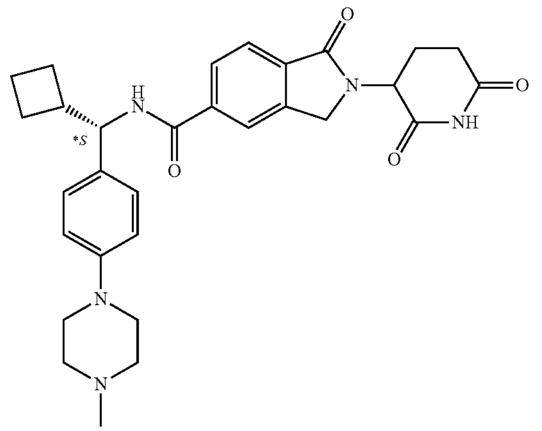 [SMILES: CN1CCN(c2ccc([C@@H](NC(=O)c3ccc4c(c3)CN(C3CCC(=O)NC3=O)C4=O)C3CCC3)cc2)CC1] | N-((*S)-cyclobutyl(4-(4-methylpiperazin-1-yl)-phenyl)methyl)-2-(2,6-dioxopiperidin-3-yl)-1-oxoisoindoline-5-carboxamide $^1$H NMR (400 MHz, DMSO-$d_6$) δ 11.01 (s, 1H), 8.76 (d, J = 8.4 Hz, 1H), 8.09-8.00 (m, 1H), 7.94 (d, J = 8.0 Hz, 1H), 7.80 (d, J = 8.0 Hz, 1H), 7.22 (d, J = 8.4 Hz, 2H), 6.86 (d, J = 8.8 Hz, 2H), 5.25-5.06 (m, 1H), 5.00-4.83 (m, 1H), 4.63-4.31 (m, 2H), 3.09-3.00 (m, 4H), 2.97-2.88 (m, 1H), 2.82-2.75 (m, 1H), 2.58 (br s, 1H), 2.46-2.43 (m, 4H), 2.41-2.38 (m, 1H), 2.21 (s, 3H), 2.12-1.95 (m, 2H), 1.81-1.67 (m, 4H), 1.54-1.37 (m, 1H). LCMS ($ESI^+$): m/z 530.2 $[M + H]^+$ |
| 22 | 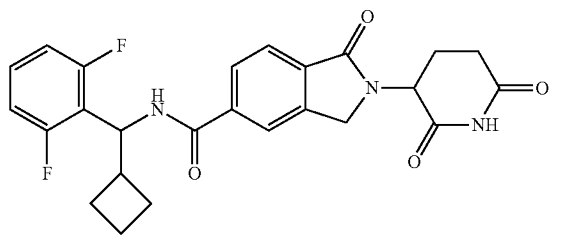 [SMILES: O=C1CCC(N2Cc3cc(C(=O)NC(c4c(F)cccc4F)C4CCC4)ccc3C2=O)C(=O)N1] | N-(cyclobutyl(2,6-difluorophenyl)methyl)-2-(2,6-dioxopiperidin-3-yl)-1-oxoisoindoline-5-carboxamide $^1$H NMR (400 MHz, DMSO-$d_6$) δ 11.02 (s, 1H), 8.92 (d, J = 6.8 Hz, 1H), 8.02 (d, J = 3.2 Hz, 1H), 7.97-7.92 (m, 1H), 7.80 (d, J = 8.0 Hz, 1H), 7.37-7.27 (m, 1H), 7.10-7.00 (m, 2H), 5.33-5.23 (m, 1H), 5.18-5.08 (m, 1H), 4.56-4.32 (m, 2H), 3.08-2.86 (m, 2H), 2.68-2.56 (m, 1H), 2.43-2.31 (m, 1H), 2.25-2.14 (m, 1H), 2.06-1.96 (m, 1H), 1.90-1.73 (m, 4H), 1.67-1.56 (m, 1H); LCMS ($ESI^+$): m/z 468.1 $[M + H]^+$. |

TABLE 2-continued

| No. | Structure | Compound name and characterization |
|---|---|---|
| 23 | 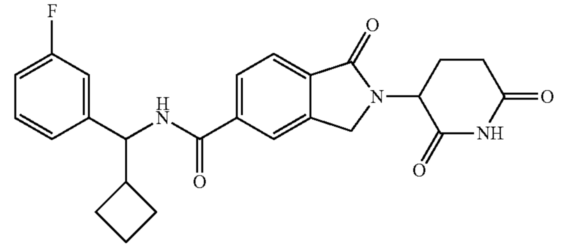 [SMILES: O=C1CCC(N2Cc3cc(C(=O)NC(c4cccc(F)c4)C4CCC4)ccc3C2=O)C(=O)N1] | N-(cyclobutyl(3-fluorophenyl)methyl)-2-(2,6-dioxopiperidin-3-yl)-1-oxoisoindoline-5-carboxamide $^{1}$H NMR (400 MHz, DMSO-$d_6$) δ 11.03 (s, 1H), 8.91 (d, J = 8.4 Hz, 1H), 8.06 (s, 1H), 7.98 (d, J = 7.6 Hz, 1H), 7.83 (d, J = 8.0 Hz, 1H), 7.42-7.33 (m, 1H), 7.25 (d, J = 7.6 Hz, 2H), 7.10-7.01 (m, 1H), 5.15 (dd, J = 4.8, 13.2 Hz, 1H), 5.07-4.93 (m, 1H), 4.58-4.46 (m, 1H), 4.45-4.33 (m, 1H), 3.01-2.87 (m, 1H), 2.83-2.74 (m, 1H), 2.66-2.56 (m, 1H), 2.45-2.36 (m, 1H), 2.12-1.99 (m, 2H), 1.86-1.71 (m, 5H); LCMS (ESI+): m/z 450.1 $[M + H]^+$ |
| 24 | 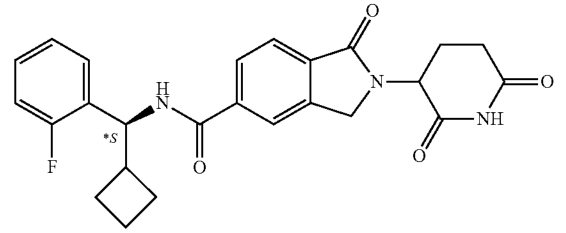 [SMILES: O=C1CCC(N2Cc3cc(C(=O)N[C@H](c4ccccc4F)C4CCC4)ccc3C2=O)C(=O)N1] | N-((*S)-cyclobutyl(3-fluoropyridin-2-yl)methyl)-2-(2,6-dioxopiperidin-3-yl)-1-oxoisoindoline-5-carboxamide $^{1}$H NMR (400 MHz, DMSO-$d_6$) δ 11.22 (s, 1 H), 8.85-9.02 (m, 1 H), 8.32-8.54 (m, 1 H), 8.07 (m, 1 H), 7.98 (m, 1 H), 7.81 (m, 1 H), 7.70 (m, 1 H), 7.27-7.44 (m, 1 H), 5.35-5.53 (m, 1 H), 5.09-5.25 (m, 1 H), 4.27-4.57 (m, 2 H), 2.85-2.99 (m, 2 H), 2.56-2.70 (m, 2 H), 2.32-2.44 (m, 1 H), 1.98-2.14 (m, 2 H), 1.68-1.86 (m, 4 H). LCMS (ESI+): m/z 451.1 $[M + 1]^+$. |
| 64 | 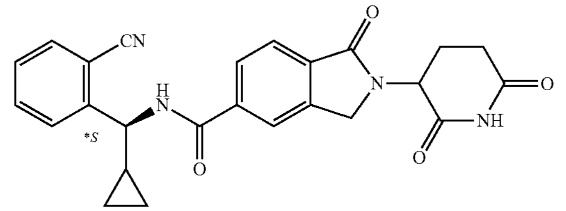 [SMILES: N#Cc1ccccc1[C@@H](NC(=O)c1ccc2c(c1)CN(C1CCC(=O)NC1=O)C2=O)C1CC1] | N-((*S)-(2-cyanophenyl)(cyclopropyl)methyl)-2-(2,6-dioxopiperidin-3-yl)-1-oxoisoindoline-5-carboxamide $^{1}$H NMR (400 MHz, DMSO-$d_6$) δ 11.03 (s, 1H), 9.46 (d, J = 8.0 Hz, 1H), 8.49 (s, 0.29H), 8.09 (s, 1H), 8.01 (d, J = 8.0 Hz, 1H), 7.87-7.77 (m, 3H), 7.76-7.69 (m, 1H), 7.46 (t, J = 8.0 Hz, 1H), 5.20-5.08 (m, 1H), 4.62 (t, J = 7.2 Hz, 1H), 4.56-4.48 (m, 1H), 4.44-4.35 (m, 1H), 2.97-2.87 (m, 1H), 2.65-2.56 (m, 1H), 2.44-2.36 (m, 1H), 2.07-1.97 (m, 1H), 1.43-1.32 (m, 1H), 0.72-0.39 (m, 4H). LCMS (ESI+): m/z 443.1 [M + H]+. |
| 71 | 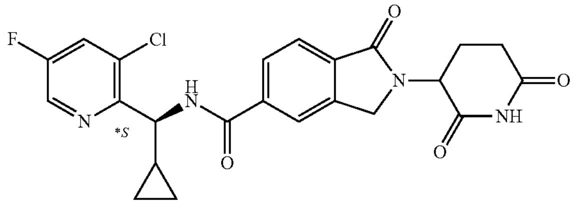 [SMILES: O=C1CCC(N2Cc3cc(C(=O)N[C@H](c4ncc(F)cc4Cl)C4CC4)ccc3C2=O)C(=O)N1] | N-((*S)-(3-chloro-5-fluoropyridin-2-yl)(cyclopropyl)methyl)-2-(2,6-dioxopiperidin-3-yl)-1-oxoisoindoline-5-carboxamide $^{1}$H NMR (400 MHz, DMSO-$d_6$) δ 11.02 (br s, 1H), 9.22 (d, J = 7.2 Hz, 1H), 8.61 (d, J = 2.4 Hz, 1H), 8.13-8.05 (m, 2H), 8.03-7.97 (m, 1H), 7.79 (d, J = 8.0 Hz, 1H), 5.18-5.10 (m, 1H), 4.98-4.90 (m, 1H), 4.55-4.46 (m, 1H), 4.42-4.33 (m, 1H), 2.99-2.85 (m, 1H), 2.60 (d, J = 15.6 Hz, 1H), 2.46-2.36 (m, 1H), 2.06-1.97 (m, 1H), 1.51-1.41 (m, 1H), 0.62-0.54 (m, 1H), 0.53-0.41 (m, 3H). LCMS ($ESI^+$): m/z 471.0 $[M + H]^+$. |
| 43 | 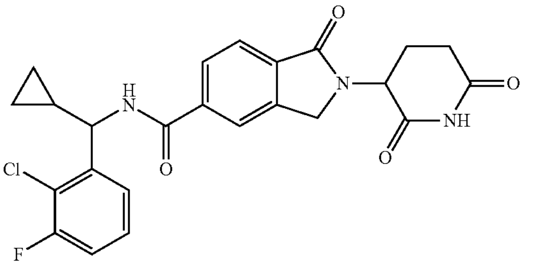 [SMILES: O=C1CCC(N2Cc3cc(C(=O)NC(c4cccc(F)c4Cl)C4CC4)ccc3C2=O)C(=O)N1] | N-((2-chloro-3-fluorophenyl)(cyclopropyl)methyl)-2-(2,6-dioxopiperidin-3-yl)-1-oxoisoindoline-5-carboxamide $^{1}$H NMR (400 MHz, DMSO-$d_6$) δ 11.02 (s, 1 H) 9.25 (d, J = 7.6 Hz, 1 H) 8.07 (s, 1 H) 7.99 (d, J = 8.0 Hz, 1 H) 7.82 (d, J = 8.0 Hz, 1 H) 7.58 (d, J = 7.7 Hz, 1 H) 7.41 (td, J = 8.0, 5.6 Hz, 1 H) 7.26-7.35 (m, 1 H) 5.14 (dd, J = 13.3, 5.0 Hz, 1 H) 4.90 (t, J = 8.3 Hz, 1 H) 4.28-4.59 (m, 2 H) 2.87-2.97 (m, 1 H) 2.61 (br d, J = 15.5 Hz, 1 H) 2.39-2.45 (m, 1 H) 1.96-2.09 (m, 1 H) 1. LCMS ($ESI^+$): m/z 470.1 $[M + H]^+$. |
| 44 | 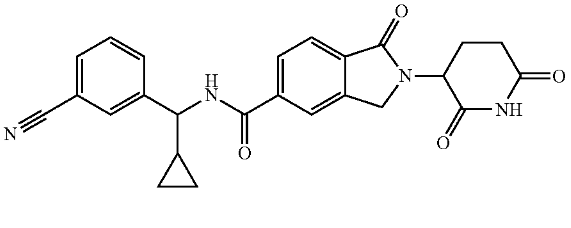 [SMILES: N#Cc1cccc(C(NC(=O)c2ccc3c(c2)CN(C2CCC(=O)NC2=O)C3=O)C2CC2)c1] | N-((3-cyanophenyl)(cyclopropyl)methyl)-2-(2,6-dioxopiperidin-3-yl)-1-oxoisoindoline-5-carboxamide $^{1}$H NMR (400 MHz, DMSO-$d_6$) δ 11.03 (br s, 1H), 9.30 (d, J = 8.0 Hz, 1H), 8.10 (s, 1H), 8.02 (d, J = 8.0 Hz, 1H), 7.94 (s, 1H), 7.88-7.79 (m, 2H), 7.74 (d, J = 7.2 Hz, 1H), 7.61-7.53 (m, 1H), 5.22-5.08 (m, 1H), 4.57-4.46 (m, 1H), 4.46-4.35 (m, 2H), 2.95-2.87 (m, 1H), 2.63 (br s, 1H), 2.45-2.39 (m, 1H), 2.08-1.95 (m, 1H), 1.34 (d, J = 4.4 Hz, 1H), 0.67-0.37 (m, 4H) LCMS ($ESI^+$): m/z 443.1 $[M + H]^+$. |

TABLE 2-continued

| No. | Structure | Compound name and characterization |
|---|---|---|
| 45 | 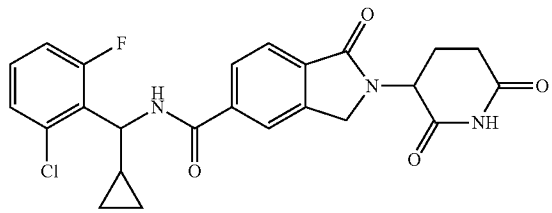 [SMILES: O=C1CCC(N2Cc3cc(C(=O)NC(c4c(F)cccc4Cl)C4CC4)ccc3C2=O)C(=O)N1] | N-((2-chloro-6-fluorophenyl)(cyclopropyl)methyl)-2-(2,6-dioxopiperidin-3-yl)-1-oxoisoindoline-5-carboxamide $^1H$ NMR (400 MHz, DMSO-$d_6$) δ 11.01 (br s, 1H), 9.33 (d, J = 6.0 Hz, 1H), 8.06 (s, 1H), 7.98 (br d, J = 8.0 Hz, 1H), 7.80 (d, J = 8.0 Hz, 1H), 7.37-7.25 (m, 2H), 7.24-7.15 (m, 1H), 5.21-5.07 (m, 1H), 4.74-4.60 (m, 1H), 4.57-4.47 (m, 1H), 4.45-4.32 (m, 1H), 2.91 (t, J = 12.8 Hz, 1H), 2.60 (d, J = 17.2 Hz, 1H), 2.44-2.36 (m, 1H), 2.08-1.92 (m, 1H), 1.63 (br s, 1H), 0.73-0.28 (m, 4H). LCMS (ESI$^+$): m/z 470.1 [M + H]$^+$. |
| 39 | 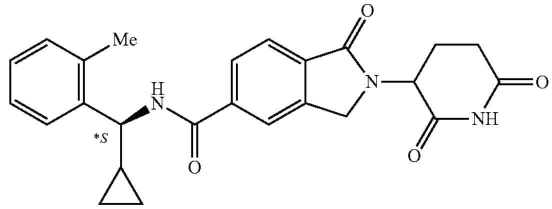 | N-((*S)-cyclopropyl(o-tolyl)methyl)-2-(2,6-dioxopiperidin-3-yl)-1-oxoisoindoline-5-carboxamide $^1H$ NMR (400 MHz, DMSO-$d_6$) δ 11.02 (s, 1H), 9.05 (d, J = 8.0 Hz, 1H), 8.06 (s, 1H), 7.98 (d, J = 8.0 Hz, 1H), 7.80 (d, J = 8.0 Hz, 1H), 7.63 (d, J = 7.6 Hz, 1H), 7.25-7.17 (m, 1H), 7.14 (d, J = 4.0 Hz, 2H), 5.18-5.08 (m, 1H), 4.75 (t, J = 8.0 Hz, 1H), 4.56-4.46 (m, 1H), 4.43-4.33 (m, 1H), 2.99-2.85 (m, 1H), 2.64-2.58 (m, 1H), 2.45-2.38 (m, 1H), 2.34 (s, 3H), 2.07-1.96 (m, 1H), 1.45-1.34 (m, 1H), 0.62-0.45 (m, 2H), 0.45-0.37 (m, 1H), 0.32-0.23 (m, 1H). LCMS (ESI$^+$): m/z 432.1 [M + H]$^+$. |

Example 5

Preparation of compound 2 and compound 3: N—((*R)-(4-chlorophenyl)(cyclopropyl)methyl)-2-(2,6-dioxopiperidin-3-yl)-1-oxoisoindoline-5-carboxamide and N—((*S)-(4-chlorophenyl)(cyclopropyl)methyl)-2-(2,6-dioxopiperidin-3-yl)-1-oxoisoindoline-5-carboxamide Scheme 5

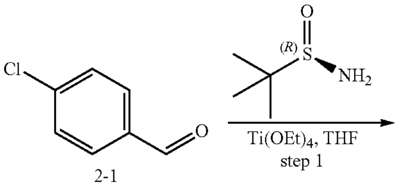

2-1

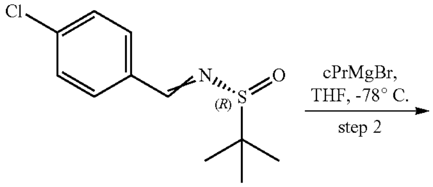

2-2

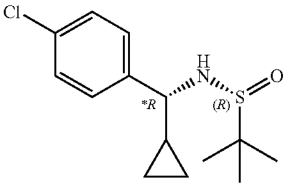

+

2-3-1

-continued

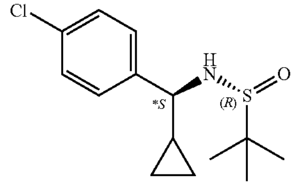

2-3-2

2-3-1 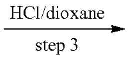

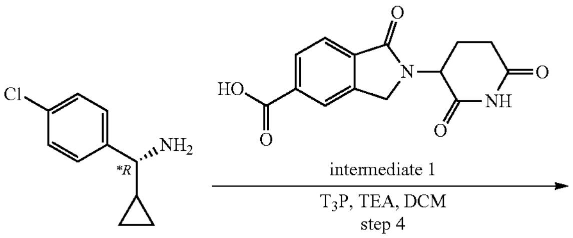

2-4-1

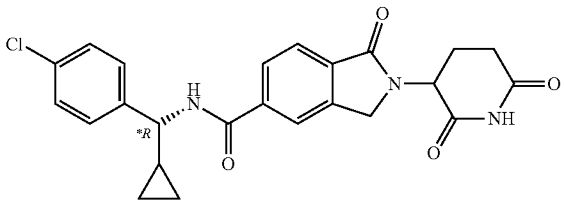

compound 2

2-3-2 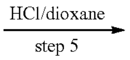

-continued

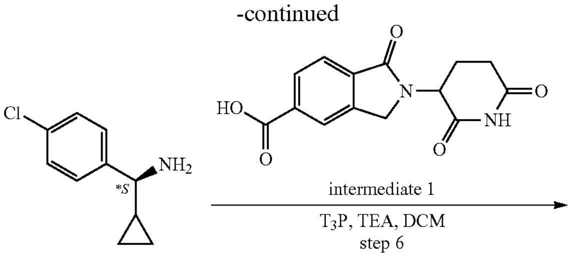

2-4-2

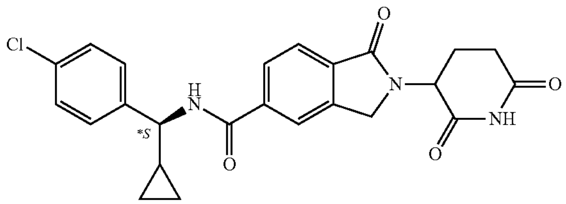

compound 3

Step 1: (R)—N-(4-chlorobenzylidene)-2-methylpropane-2-sulfinamide 2-2

2-2 was prepared according to the similar procedure of 1-2 as described for compound 1.

$^1$H NMR (400 MHz, $CDCl_3$) δ 8.48 (s, 1H), 7.72 (d, J=8.4 Hz, 2H), 7.38 (d, J=8.4 Hz, 2H), 1.19 (s, 9H); LCMS ($ESI^+$): m/z 244.1 $[M+H]^+$.

Step 2: (R)—N—((*R)-(4-chlorophenyl)(cyclopropyl)methyl)-2-methylpropane-2-sulfinamide (2-3-1) and (R)—N—((*S)-(4-chlorophenyl)(cyclopropyl) methyl)-2-methylpropane-2-sulfinamide (2-3-2)

To a solution of (R)—N-[(4-chlorophenyl)methylene]-2-methyl-propane-2-sulfinamide 2-2 (3 g, 12.3 mmol) in THE (15 mL) was added dropwise cyclopropylmagnesium bromide (1 M, 36.9 mL) at −78° C. After addition, the mixture was stirred at 25° C. for 2 hr. The reaction mixture was quenched with water (10 mL) and extracted with EA (20 mL×3). The combined organic phase was washed with water (5 mL), dried over anhydrous $Na_2SO_4$ and concentrated under reduced pressure. The residue was purified by flash silica gel chromatography ($SiO_2$, PE/EtOAc=1:0 to 3:1) and further purified by SFC (DAICEL CHIRALPAK AS (250 mm*30 mm, 10 um), 0.1% $NH_3 \cdot H_2O$ ETOH, B: 10%, Flowrate: 60 mL/min) to give the titled product 2-3-1 (500 mg, 13% yield) as a white solid and 2-3-2 (200 mg, 5% yield) as a colorless oil.

2-3-1: $^1$H NMR (400 MHz, DMSO-$d_6$) δ 7.29-7.07 (m, 4H), 5.52 (d, J=7.2 Hz, 1H), 3.35-3.23 (m, 1H), 0.87 (s, 10H), 0.40-0.28 (m, 1H), 0.25-0.14 (m, 2H), 0.10-0.01 (m, 1H); LCMS ($ESI^+$): m/z 286.01 $[M+H]^+$.

2-3-2: $^1$H NMR (400 MHz, DMSO-$d_6$) δ 7.20-7.09 (m, 4H), 5.13 (d, J=5.6 Hz, 1H), 3.28 (dd, J=5.6, 9.2 Hz, 1H), 0.97-0.82 (m, 10H), 0.37-0.31 (m, 1H), 0.25-0.09 (m, 3H); LCMS ($ESI^+$): m/z 286.2 $[M+H]^+$.

Step 3: (*R)-(4-chlorophenyl)(cyclopropyl)methanamine 2-4-1

HCl/dioxane (2 mL, 4M) was added to a mixture of N—[(*R)-(4-chlorophenyl)-cyclopropyl-methyl]-2-methyl-propane-2-sulfinamide (150 mg, 525 umol) and DCM (2 mL). The reaction mixture was stirred at 25° C. for 1 hr. The reaction mixture was concentrated under reduced pressure to give the crude product (150 mg, 69% yield, HCl) as a white solid. LCMS ($ESI^+$): m/z 164.93 $[M-NH_2]^+$.

(*S)-(4-chlorophenyl)(cyclopropyl)methanamine 2-4-2

Intermediate 2-4-2 was prepared according to the similar procedure of intermediate 2-4-1 with the respected starting material of intermediate 2-3-2.

Preparation of compound 2: N—((*R)-(4-chlorophenyl)(cyclopropyl)methyl)-2-(2,6-dioxopiperidin-3-yl)-1-oxoisoindoline-5-carboxamide Compound 2 was prepared according to the similar procedure of compound 1 with the respective starting material of intermediate 2-3-1. $^1$H NMR (400 MHz, DMSO-$d_6$) δ 11.03 (br. s., 1H), 9.26 (d, J=8.0 Hz, 1H), 8.10 (s, 1H), 8.05-7.99 (m, 1H), 7.86-7.80 (m, 1H), 7.53-7.46 (m, 2H), 7.44-7.36 (m, 2H), 5.23-5.09 (m, 1H), 4.60-4.48 (m, 1H), 4.47-4.30 (m, 2H), 3.00-2.84 (m, 1H), 2.74-2.58 (m, 1H), 2.46-2.29 (m, 1H), 2.11-1.96 (m, 1H), 1.42-1.25 (m, 1H), 0.65-0.51 (m, 2H), 0.49-0.33 (m, 2H). LCMS ($ESI^+$): m/z 452.0 $[M+H]^+$.

Preparation of compound 3: N—((*S)-(4-chlorophenyl)(cyclopropyl)methyl)-2-(2,6-dioxopiperidin-3-yl)-1-oxoisoindoline-5-carboxamide Compound 3 was prepared according to the similar procedure of compound 2 with the respective starting material of intermediate 2-3-1. $^1$H NMR (400 MHz, DMSO-$d_6$): 11.03 (br. s., 1H), 9.31 (d, J 8.0 Hz, 1H), 8.06 (s, 1H), 8.03-7.95 (m, 1H), 7.86-7.78 (m, 1H), 7.51-7.44 (m, 2H), 7.42-7.34 (i, 2H), 5.18-5.05 (i, 1H), 4.58-4.48 (m, 1H), 4.45-4.26 (m, 2H), 2.98-2.81 (m, 1H), 2.71-2.57 (m, 1H), 2.48-2.31 (m, 1H), 2.09-1.97 (mi, 1H), 1.40-1.24 (m, 1H), 0.63-0.49 (m, 2H), 0.47-0.31 (m, 2H). LCMS ($ESI^+$): m/z 452.0 $[M+H]^+$.

Example 6

The following compounds were prepared according to similar procedure as described for compound 2 with corresponding starting materials of aldehydes and Grignard reagents (Example 5).

TABLE 3

| No | Structure | Compound name and characterization |
| --- | --- | --- |
| 25 | 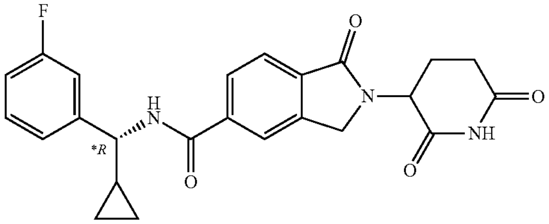 [SMILES: O=C1CCC(N2Cc3cc(C(=O)N[C@@H](c4cccc(F)c4)C4CC4)ccc3C2=O)C(=O)N1] | N-((*R)-cyclopropyl(3-fluorophenyl)methyl)-2-(2,6-dioxopiperidin-3-yl)-1-oxoisoindoline-5-carboxamide<br>$^1$H NMR (400 MHz, DMSO-$d_6$) δ 11.02 (br. s., 1 H), 9.19-9.34 (m, 1 H), 8.10 (s, 1 H), 7.98-8.05 (m, 1 H), 7.79-7.85 (m, 1 H), 7.35-7.42 (m, 1 H), 7.27-7.34 (m, 2 H), 7.04-7.11 (m, 1 H), 5.11-5.19 (m, 1 H), 4.35-4.58 (m, 3 H), 2.84-2.97 (m, 1 H), 2.52-2.68 (m, 2 H), 1.97-2.08 (m, 1 H), 1.27-1.38 (m, 1 H), 0.51-0.59 (m, 2 H), 0.36-0.50 (m, 2 H); LCMS (ESI$^+$): m/z 436.1.0 $[M + H]^+$. |
| 26 | 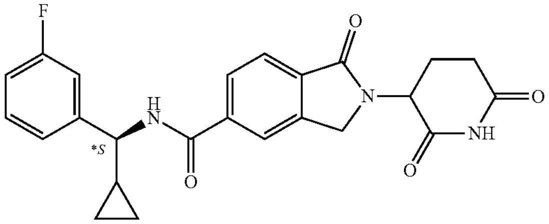 [SMILES: O=C1CCC(N2Cc3cc(C(=O)N[C@H](c4cccc(F)c4)C4CC4)ccc3C2=O)C(=O)N1] | N-((*S)-cyclopropyl(3-fluorophenyl)methyl)-2-(2,6-dioxopiperidin-3-yl)-1-oxoisoindoline-5-carboxamide<br>$^1$H NMR (400 MHz, DMSO-$d_6$) δ 11.03 (br. s. 1 H), 9.26 (s, 1 H), 8.11 (s, 1 H), 8.03 (d, J = 7.6 Hz, 1 H), 7.81-7.88 (m, 1 H), 7.38 (s, 1 H), 7.24-7.34 (m, 2H), 7.07-7.08 (m, 1 H), 5.10-5.23 (m, 1 H), 4.47-4.57 (m, 3 H), 2.86-3.02 (m, 1 H), 2.56-2.72 (m, 2 H), 1.98-2.09 (m, 1 H), 1.29-1.41 (m, 1 H), 0.54-0.65 (m, 2 H), 0.45-0.52 (m, 1 H), 0.36-0.45 (m, 1 H); LCMS (ESI$^+$): m/z 436.1 $[M + H]^+$. |
| 27 | 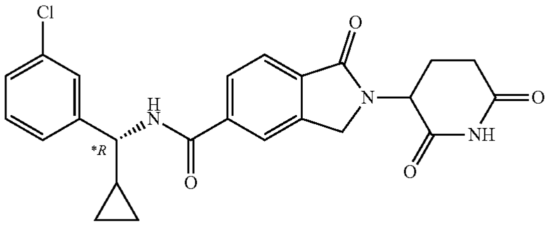 [SMILES: O=C1CCC(N2Cc3cc(C(=O)N[C@@H](c4cccc(Cl)c4)C4CC4)ccc3C2=O)C(=O)N1] | N-((*R)-(3-chlorophenyl)(cyclopropyl)methyl)-2-(2,6-dioxopiperidin-3-yl)-1-oxoisoindoline-5-carboxamide<br>$^1$H NMR (400 MHz, DMSO-$d_6$) δ 11.03 (s, 1H), 9.27 (d, J = 8.0 Hz, 1H), 8.11 (s, 1H), 8.03 (d, J = 8.0 Hz, 1H), 7.84 (d, J = 8.0 Hz, 1H), 7.55 (s, 1H), 7.46-7.29 (m, 3H), 5.15 (dd, J = 4.8, 13.2 Hz, 1H), 4.58-4.49 (m, 1H), 4.46-4.33 (m, 2H), 3.00-2.86 (m, 1H), 2.62 (d, J = 16.8 Hz, 1H), 2.46-2.35 (m, 1H), 2.09-1.97 (m, 1H), 1.41-1.29 (m, 1H), 0.63-0.53 (m, 2H), 0.51-0.37 (m, 2H); LCMS (ESI$^+$): m/z 454.1 $[M + H]^+$. |
| 28 | 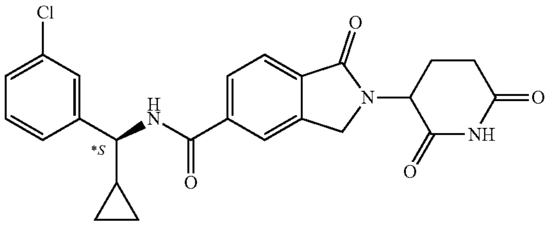 | N-((*S)-(3-chlorophenyl)(cyclopropyl)methyl)-2-(2,6-dioxopiperidin-3-yl)-1-oxoisoindoline-5-carboxamide<br>$^1$H NMR (400 MHz, DMSO-$d_6$) δ 11.02 (s, 1H), 9.26 (d, J = 8.0 Hz, 1H), 8.11 (s, 1H), 8.03 (d, J = 8.0 Hz, 1H), 7.84 (d, J = 8.0 Hz, 1H), 7.55 (s, 1H), 7.45-7.27 (m, 3H), 5.15 (dd, J = 5.2, 13.2 Hz, 1H), 4.59-4.50 (m, 1H), 4.41-4.35 (m, 1H), 3.00-2.85 (m, 1H), 2.60-2.59 (m, 1H), 2.45-2.43 (m, 1H), 2.13-1.92 (m, 1H), 1.39-1.36 (m, 1H), 0.60-0.55 (m, 2H), 0.50-0.39 (m, 2H); LCMS (ESI$^+$): m/z 454.0 $[M + H]^+$. |
| 29 | 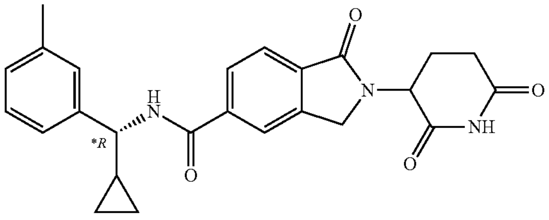 | N-((*R)-cyclopropyl(m-tolyl)methyl)-2-(2,6-dioxopiperidin-3-yl)-1-oxoisoindoline-5-carboxamide<br>$^1$H NMR (400 MHz, DMSO-$d_6$) δ 11.01 (br. s., 1H), 9.25-9.12 (m, 1H), 8.11 (s, 1H), 8.08-7.99 (m, 1H), 7.89-7.77 (m, 1H), 7.34-7.18 (m, 3H), 7.12-7.02 (m, 1H), 5.15 (dd, J = 4.8, 13.2 Hz, 1H), 4.58-4.32 (m, 3H), 3.00-2.86 (m, 1H), 2.66-2.57 (m, 1H), 2.46-2.37 (m, 1H), 2.31 (s, 3H), 2.10-1.96 (m, 1H), 1.40-1.28 (m, 1H), 0.62-0.50 (m, 2H), 0.47-0.34 (m, 2H); LCMS (ESI$^+$): m/z 4321 $[M + H]^+$. |
| 30 | 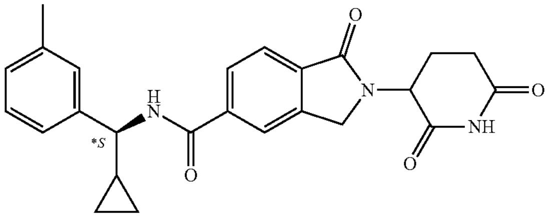 [SMILES: Cc1cccc([C@@H](NC(=O)c2ccc3c(c2)CN(C2CCC(=O)NC2=O)C3=O)C2CC2)c1] | N-((*S)-cyclopropyl(m-tolyl)methyl)-2-(2,6-dioxopiperidin-3-yl)-1-oxoisoindoline-5-carboxamide<br>$^1$H NMR (400 MHz, DMSO-$d_6$) δ 11.00 (br. s., 1H), 9.15-9.08 (m, 1H), 8.10 (s, 1H), 8.05-7.99 (m, 1H), 7.84-7.79 (m, 1H), 7.30-7.18 (m, 3H), 7.09-7.01 (m, 1H), 5.14 (dd, J = 5.2, 13.2 Hz, 1H), 4.57-4.31 (m, 3H), 2.99-2.83 (m, 1H), 2.67-2.57 (m, 1H), 2.48-2.36 (m, 1H), 2.30 (s, 3H), 2.10-1.97 (m, 1H), 1.42-1.28 (m, 1H), 0.62-0.47 (m, 2H), 0.45-0.32 (m, 2H); LCMS (ESI$^+$): m/z 432.1 $[M + H]^+$. |

TABLE 3-continued

| No | Structure | Compound name and characterization |
|---|---|---|
| 31 | 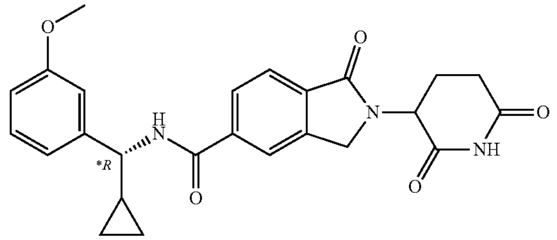 [SMILES: COc1cccc([C@H](NC(=O)c2ccc3c(c2)CN(C2CCC(=O)NC2=O)C3=O)C2CC2)c1] | N-((*R)-cyclopropyl(3-methoxyphenyl)methyl)-2-(2,6-dioxopiperidin-3-yl)-1-oxoisoindoline-5-carboxamide $^1$H NMR (400 MHz, DMSO-$d_6$) δ 11.02 (s, 1H), 9.18 (d, J = 8.4 Hz, 1H), 8.09 (s, 1H), 8.01 (d, J = 8.0 Hz, 1H), 7.82 (d, J = 8.0 Hz, 1H), 7.30-7.19 (m, 1H), 7.10-6.97 (m, 2H), 6.87-6.76 (m, 1H), 5.19-5.10 (m, 1H), 4.57-4.48 (m, 1H), 4.44-4.30 (m, 2H), 3.74 (s, 3H), 2.99-2.84 (m, 1H), 2.65-2.56 (m, 1H), 2.45-2.37 (m, 1H), 2.08-1.95 (m, 1H), 1.38-1.27 (m, 1H), 0.60-0.50 (m, 2H), 0.48-0.33 (m, 2H). LCMS (ESI+): m/z 448.1 $[M + H]^+$. |
| 32 | 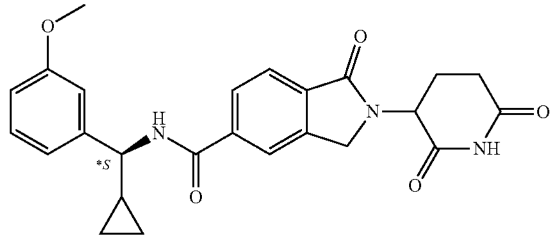 [SMILES: COc1cccc([C@@H](NC(=O)c2ccc3c(c2)CN(C2CCC(=O)NC2=O)C3=O)C2CC2)c1] | N-((*S)-cyclopropyl(3-methoxyphenyl)methyl)-2-(2,6-dioxopiperidin-3-yl)-1-oxoisoindoline-5-carboxamide $^1$H NMR (400 MHz, DMSO-$d_6$) δ 11.02 (br. s, 1H), 9.18 (d, J = 8.4 Hz, 1H), 8.09 (s, 1H), 8.01 (d, J = 8.0 Hz, 1H), 7.82 (d, J = 8.0 Hz, 1H), 7.29-7.20 (m, 1H), 7.09-6.99 (m, 2H), 6.86-6.78 (m, 1H), 5.22-5.08 (m, 1H), 4.57-4.48 (m, 1H), 4.45-4.31 (m, 2H), 3.74 (s, 3H), 2.99-2.84 (m, 1H), 2.68-2.58 (m, 1H), 2.44-2.32 (m, 1H), 2.08-1.98 (m, 1H), 1.38-1.26 (m, 1H), 0.58-0.49 (m, 2H), 0.47-0.33 (m, 2H). LCMS (ESI+): m/z 448.1 $[M + H]^+$. |
| 33 | 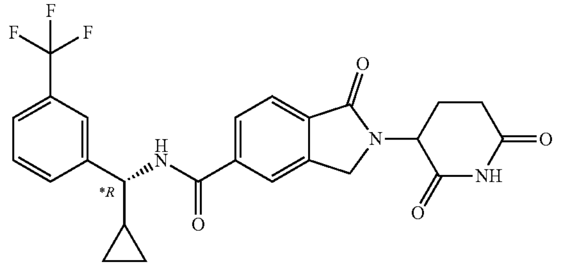 [SMILES: O=C1CCC(N2Cc3cc(C(=O)N[C@@H](c4cccc(C(F)(F)F)c4)C4CC4)ccc3C2=O)C(=O)N1] | N-((*R)-cyclopropyl(3-(trifluoromethyl)phenyl)methyl)-2-(2,6-dioxopiperidin-3-yl)-1-oxoisoindoline-5-carboxamide $^1$H NMR (400 MHz, DMSO-$d_6$) δ 11.03 (br. s., 1H), 9.36 (d, J = 7.6 Hz, 1H), 8.10 (s, 1H), 8.02 (d, J = 8.0 Hz, 1H), 7.89-7.81 (m, 2H), 7.78 (d, J = 6.8 Hz, 1H), 7.66-7.55 (m, 2H), 5.21-5.08 (m, 1H), 4.58-4.35 (m, 3H), 2.99-2.85 (m, 1H), 2.65-2.57 (m, 1H), 2.45-2.35 (m, 1H), 2.08-1.96 (m, 1H), 1.42-1.28 (m, 1H), 0.65-0.35 (m, 4H). LCMS (ESI+): m/z 486.1 $[M + H]^+$. |
| 34 | 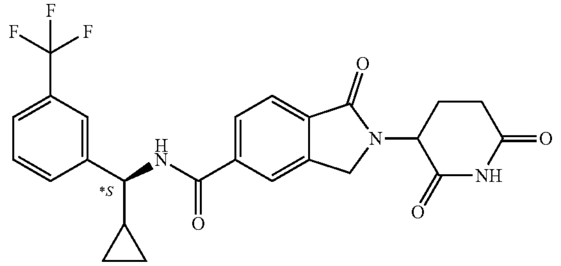 [SMILES: O=C1CCC(N2Cc3cc(C(=O)N[C@H](c4cccc(C(F)(F)F)c4)C4CC4)ccc3C2=O)C(=O)N1] | N-((*S)-cyclopropyl(3-(trifluoromethyl)phenyl)methyl)-2-(2,6-dioxopiperidin-3-yl)-1-oxoisoindoline-5-carboxamide $^1$H NMR (400 MHz, DMSO-$d_6$) δ 11.03 (br. s., 1H), 9.41-9.28 (m, 1H), 8.10 (s., 1H), 8.06-7.98 (m, 1H), 7.89-7.81 (m, 2H), 7.80-7.71 (m, 1H), 7.67-7.52 (m, 2H), 5.23-5.07 (m, 1H), 4.60-4.34 (m, 3H), 2.99-2.85 (m, 1H), 2.66-2.56 (m, 1H), 2.44-2.35 (m, 1H), 2.10-1.94 (m, 1H), 1.45-1.30 (m, 1H), 0.66-0.36 (m, 4H). LCMS (ESI+): m/z 486.1 $[M + H]^+$. |
| 72 | 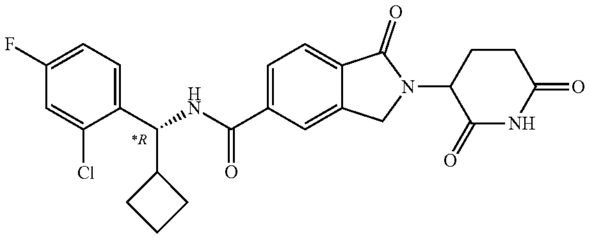 [SMILES: O=C1CCC(N2Cc3cc(C(=O)N[C@@H](c4ccc(F)cc4Cl)C4CCC4)ccc3C2=O)C(=O)N1] | N-((*R)-(2-chloro-4-fluorophenyl)(cyclobutyl)methyl)-2-(2,6-dioxopiperidin-3-yl)-1-oxoisoindoline-5-carboxamide $^1$H NMR (400 MHz, DMSO-$d_6$) δ 11.02 (s, 1H), 8.90 (d, J = 8.0 Hz, 1H), 8.03 (s, 1H), 7.95 (d, J = 7.6 Hz, 1H), 7.81 (d, J = 8.0 Hz, 1H), 7.67-7.56 (m, 1H), 7.47-7.31 (m, 1H), 7.28-7.20 (m, 1H), 5.53-5.43 (m, 1H), 5.18-5.10 (m, 1H), 4.55-4.35 (m, 2H), 2.98-2.77 (m, 2H), 2.65-2.58 (m, 1H), 2.43-2.35 (m, 1H), 2.13-1.98 (m, 2H), 1.93-1.70 (m, 5H). LCMS (ESI+): m/z 484.1 $[M + H]^+$. |
| 73 | 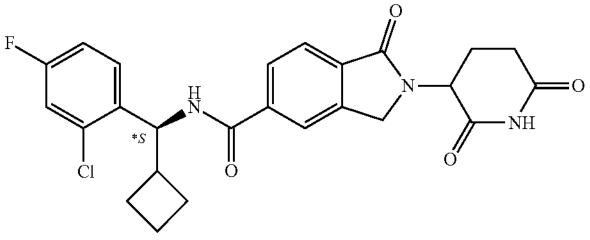 [SMILES: O=C1CCC(N2Cc3cc(C(=O)N[C@H](c4ccc(F)cc4Cl)C4CCC4)ccc3C2=O)C(=O)N1] | N-((*S)-(2-chloro-4-fluorophenyl)(cyclobutyl)methyl)-2-(2,6-dioxopiperidin-3-yl)-1-oxoisoindoline-5-carboxamide $^1$H NMR (400 MHz, DMSO-$d_6$) δ 11.02 (s, 1H), 8.90 (d, J = 8.0 Hz, 1H), 8.03 (s, 1H), 7.95 (d, J = 7.6 Hz, 1H), 7.81 (d, J = 8.0 Hz, 1H), 7.65-7.59 (m, 1H), 7.45-7.34 (m, 1H), 7.30-7.18 (m, 1H), 5.52-5.44 (m, 1H), 5.17-5.10 (m, 1H), 4.55-4.35 (m, 2H), 2.97-2.79 (m, 2H), 2.64-2.58 (m, 1H), 2.44-2.41 (m, 1H), 2.15-1.97 (m, 2H), 1.95-1.54 (m, 5H). LCMS (ESI+): m/z 484.1 $[M + H]^+$. |

TABLE 3-continued

| No | Structure | Compound name and characterization |
| --- | --- | --- |
| 74 | 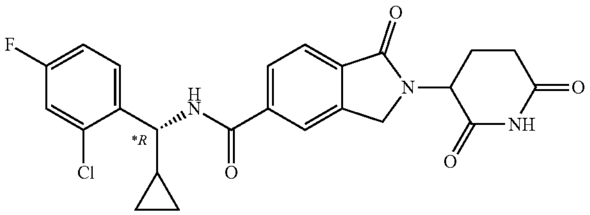 [SMILES: O=C1CCC(N2Cc3cc(C(=O)N[C@@H](c4ccc(F)cc4Cl)C4CC4)ccc3C2=O)C(=O)N1] | N-((*R)-(2-chloro-4-fluorophenyl)(cyclopropyl)methyl)-2-(2,6-dioxopiperidin-3-yl)-1-oxoisoindoline-5-carboxamide $^1$H NMR (400 MHz, DMSO-$d_6$) δ 11.02 (s, 1H), 9.17 (d, J = 7.6 Hz, 1H), 8.06 (s, 1H), 7.98 (d, J = 8.0 Hz, 1H), 7.86-7.75 (m, 2H), 7.40 (dd, J = 2.8, 8.8 Hz, 1H), 7.32-7.22 (m, 1H), 5.18-5.09 (m, 1H), 4.95-4.86 (m, 1H), 4.57-4.46 (m, 1H), 4.44-4.33 (m, 1H), 2.98-2.85 (m, 1H), 2.65-2.56 (m, 1H), 2.45-2.36 (m, 1H), 2.08-1.97 (m, 1H), 1.41-1.28 (m, 1H), 0.63-0.55 (m, 1H), 0.54-0.47 (m, 1H), 0.46-0.36 (m, 2H). LCMS (ESI+): m/z 470.1 $[M + H]^+$. |
| 75 | 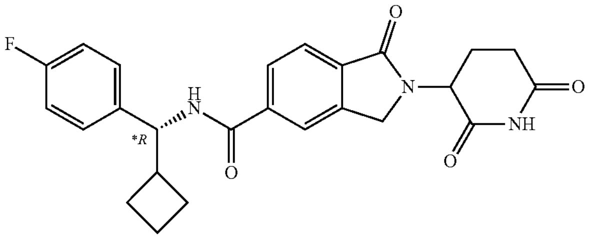 [SMILES: O=C1CCC(N2Cc3cc(C(=O)N[C@@H](c4ccc(F)cc4)C4CCC4)ccc3C2=O)C(=O)N1] | N-((*R)-cyclobutyl(4-fluorophenyl)methyl)-2-(2,6-dioxopiperidin-3-yl)-1-oxoisoindoline-5-carboxamide $^1$H NMR (400 MHz, DMSO-$d_6$) δ 11.03 (s, 1H), 8.90 (d, J = 8.4 Hz, 1H), 8.05 (s, 1H), 7.97 (d, J = 8.0 Hz, 1H), 7.82 (d, J = 8.0 Hz, 1H), 7.44 (dd, J = 5.6, 8.4 Hz, 2H), 7.14 (t, J = 8.8 Hz, 2H), 5.15 (dd, J = 5.2, 13.2 Hz, 1H), 5.05-4.95 (m, 1H), 4.60-4.34 (m, 2H), 2.98-2.87 (m, 1H), 2.84-2.72 (m, 1H), 2.62-2.59 (m, 1H), 2.46-2.36 (m, 1H), 2.15-1.97 (m, 2H), 1.86-1.71 (m, 5H); LCMS ($ESI^+$): m/z 450.1 $[M + H]^+$. |
| 66 | 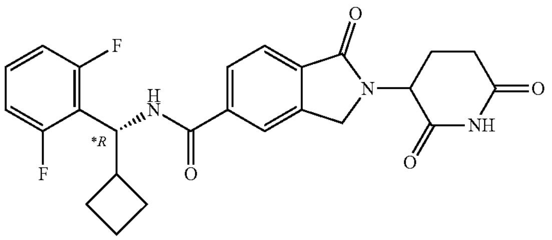 [SMILES: O=C1CCC(N2Cc3cc(C(=O)N[C@@H](c4c(F)cccc4F)C4CCC4)ccc3C2=O)C(=O)N1] | N-((*R)-cyclobutyl(2,6-difluorophenyl)methyl)-2-(2,6-dioxopiperidin-3-yl)-1-oxoisoindoline-5-carboxamide $^1$H NMR (400 MHz, DMSO-d6) δ 11.02 (s, 1H), 8.92 (d, J = 7.2 Hz, 1H), 8.03-7.99 (m, 1H), 7.97-7.91 (m, 1H), 7.79 (d, J = 8.0 Hz, 1H), 7.37-7.28 (m, 1H), 7.09-6.99 (m, 2H), 5.34-5.21 (m, 1H), 5.17-5.10 (m, 1H), 4.55-4.33 (m, 2H), 3.10-2.84 (m, 2H), 2.64-2.57 (m, 1H), 2.43-2.35 (m, 1H), 2.25-2.12 (m, 1H), 2.06-1.96 (m, 1H), 1.91-1.71 (m, 4H), 1.68-1.53 (m, 1H); LCMS ($ESI^+$): m/z 468.1 $[M + H]^+$. |
| 67 | 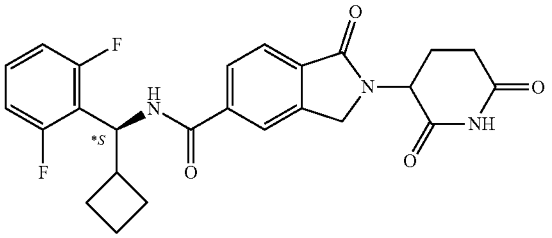 [SMILES: O=C1CCC(N2Cc3cc(C(=O)N[C@H](c4c(F)cccc4F)C4CCC4)ccc3C2=O)C(=O)N1] | N-((*S)-cyclobutyl(2,6-difluorophenyl)methyl)-2-(2,6-dioxopiperidin-3-yl)-1-oxoisoindoline-5-carboxamide $^1$H NMR (400 MHz, DMSO-$d_6$) δ 11.02 (s, 1H), 8.92 (d, J = 6.8 Hz, 1H), 8.02 (d, J = 3.2 Hz, 1H), 7.97-7.91 (m, 1H), 7.79 (d, J = 8.0 Hz, 1H), 7.37-7.26 (m, 1H), 7.09-6.99 (m, 2H), 5.33-5.22 (m, 1H), 5.17-5.09 (m, 1H), 4.55-4.31 (m, 2H), 3.06-2.86 (m, 2H), 2.63-2.56 (m, 1H), 2.44-2.39 (m, 1H), 2.25-2.14 (m, 1H), 2.07-1.96 (m, 1H), 1.89-1.74 (m, 4H), 1.66-1.57 (m, 1H); LCMS ($ESI^+$): m/z 468.1 $[M + H]^+$. |
| 41 | 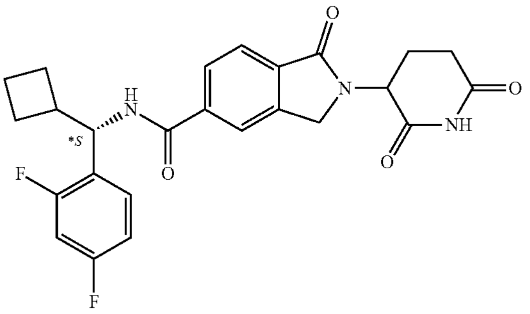 [SMILES: O=C1CCC(N2Cc3cc(C(=O)N[C@H](c4ccc(F)cc4F)C4CCC4)ccc3C2=O)C(=O)N1] | N-((*S)-cyclobutyl(2,4-difluorophenyl)methyl)-2-(2,6-dioxopiperidin-3-yl)-1-oxoisoindoline-5-carboxamide $^1$H NMR (400 MHz, DMSO-$d_6$) δ 11.02 (br s, 1H), 8.93 (d, J = 8.0 Hz, 1H), 8.04 (s, 1H), 7.96 (d, J = 8.0 Hz, 1H), 7.82 (d, J = 8.0 Hz, 1H), 7.61-7.52 (m, 1H), 7.24-7.15 (m, 1H), 7.13-7.04 (m, 1H), 5.33-5.23 (m, 1H), 5.18-5.11 (m, 1H), 4.56-4.48 (m, 1H), 4.44-4.34 (m, 1H), 3.00-2.86 (m, 1H), 2.86-2.76 (m, 1H), 2.66-2.56 (m, 1H), 2.45-2.36 (m, 1H), 2.17-1.98 (m, 2H), 1.91-1.63 (m, 5H) LCMS ($ESI^+$): m/z 468.1 $[M + H]^+$. |
| 42 | 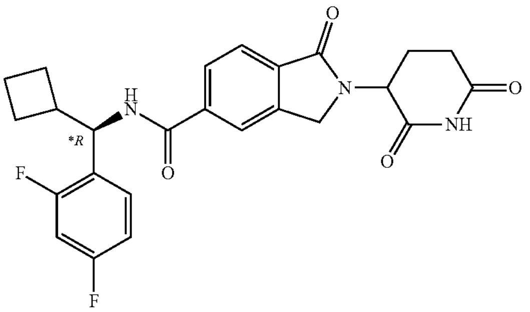 [SMILES: O=C1CCC(N2Cc3cc(C(=O)N[C@@H](c4ccc(F)cc4F)C4CCC4)ccc3C2=O)C(=O)N1] | N-((*R)-cyclobutyl(2,4-difluorophenyl)methyl)-2-(2,6-dioxopiperidin-3-yl)-1-oxoisoindoline-5-carboxamide $^1$H NMR (400 MHz, DMSO-$d_6$) δ 11.02 (s, 1H), 8.92 (d, J = 8.0 Hz, 1H), 8.03 (s, 1H), 7.95 (d, J = 8.0 Hz, 1H), 7.81 (d, J = 8.0 Hz, 1H), 7.63-7.50 (m, 1H), 7.23-7.14 (m, 1H), 7.12-7.04 (m, 1H), 5.34-5.23 (m, 1H), 5.20-5.10 (m, 1H), 4.56-4.47 (m, 1H), 4.44-4.33 (m, 1H), 2.97-2.86 (m, 1H), 2.85-2.75 (m, 1H), 2.65-2.56 (m, 1H), 2.44-2.35 (m, 1H), 2.15-1.96 (m, 2H), 1.88-1.62 (m, 5H) LCMS ($ESI^+$): m/z 468.1 $[M + H]^+$. |

TABLE 3-continued

| No | Structure | Compound name and characterization |
|---|---|---|
| 40 | 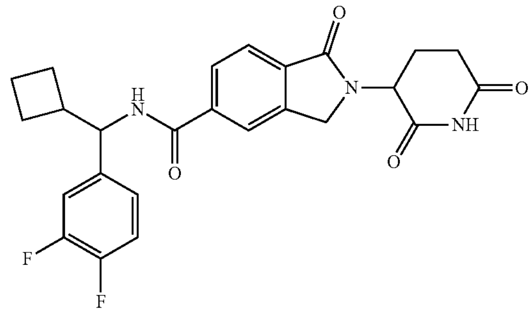 [SMILES: O=C1CCC(N2Cc3cc(C(=O)NC(c4ccc(F)c(F)c4)C4CCC4)ccc3C2=O)C(=O)N1] | N-(cyclobutyl(3,4-difluorophenyl)methyl)-2-(2,6-dioxopiperidin-3-yl)-1-oxoisoindoline-5-carboxamide $^1$H NMR (400 MHz, DMSO-$d_6$) δ 11.02 (s, 1H), 8.89 (d, J = 8.4 Hz, 1H), 8.04 (s, 1H), 7.96 (d, J = 8.0 Hz, 1H), 7.82 (d, J = 8.0 Hz, 1H), 7.54-7.44 (m, 1H), 7.42-7.33 (m, 1H), 7.32-7.21 (m, 1H), 5.21-5.09 (m, 1H), 5.03-4.94 (m, 1H), 4.56-4.48 (m, 1H), 4.44-4.35 (m, 1H), 2.95-2.86 (m, 1H), 2.75 (br d, J = 10.5 Hz, 1H), 2.61 (br d, J = 14.9 Hz, 1H), 2.44-2.35 (m, 1H), 2.11-1.96 (m, 2H), 1.87-1.67 (m, 6H). LCMS (ESI$^+$): m/z 468.1 [M + H]$^+$. |

Example 7

Preparation of Compound 4: N-((3,3-difluorocyclobutyl)(4-fluorophenyl)methyl)-2-(2,6-dioxopiperidin-3-yl)-1-oxoisoindoline-5-carboxamide Scheme 6

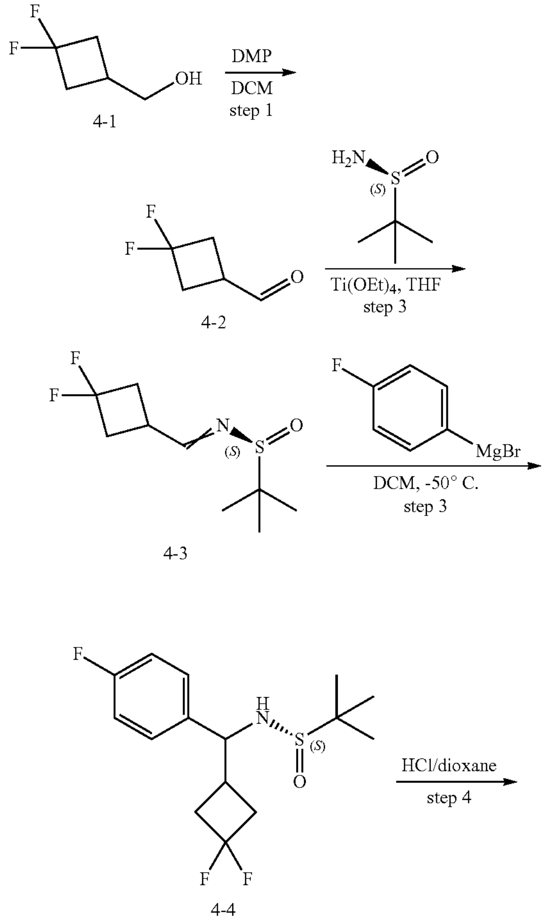

-continued

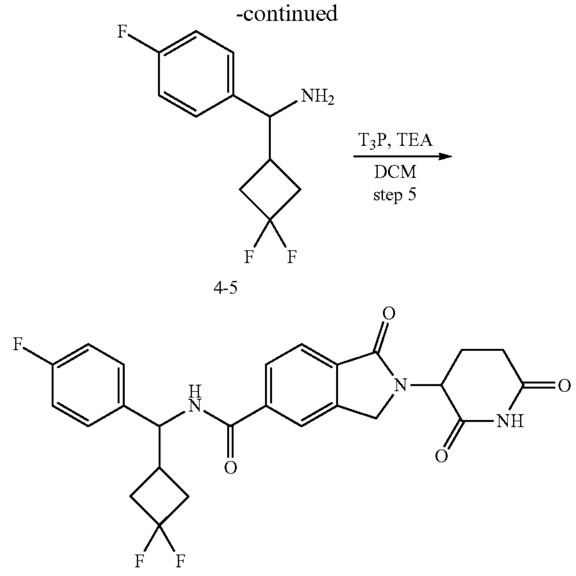

Compound 4

Step 1: 3,3-difluorocyclobutanecarbaldehyde 4-2

To a solution of (3,3-difluorocyclobutyl)methanol (2.00 g, 16.4 mmol) in DCM (30 mL) was added DMP (9.00 g, 21.2 mmol). The mixture was stirred at 25° C. for 16 hours. The reaction mixture was diluted with DCM and quenched by aq. $Na_2S_2O_3$ (100 mL) and sat. $NaHCO_3$ (100 mL). Then the mixture was extracted with DCM (150 mL×2). The combined organic layers were washed with brine (20 mL×2), dried over $Na_2SO_4$, filtered to give the filtrate and concentrated under 15° C. to give a solution of intermediate 4-2 in DCM (21 g in DCM, 14.4 mmol of intermediate 4-2, 88% yield), which was used directly in the next step without further purification.

Step 2: (S)—N-((3,3-difluorocyclobutyl)methylene)-2-methylpropane-2-sulfinamide 4-3

To a solution of 3,3-difluorocyclobutanecarbaldehyde (21 g in DCM, 14.4 mmol of intermediate 4-2) in DCM (20 mL) was added (S)-2-methylpropane-2-sulfinamide (1.74 g, 14.4 mmol) and $Ti(OEt)_4$ (7.22 g, 31.7 mmol). The mixture was stirred at 45° C. for 16 hours. The reaction mixture was cooled to 0° C., $H_2O$ (16 mL) was added to quench the reaction, and the solution was filtered through celite. The phases were separated, and the organic phase were washed with brine (20 mL), dried over $Na_2SO_4$ and concentrated to give a residue which was purified by column chromatography ($SiO_2$, Petroleum ether: Ethyl acetate=5:1 to 3:1) to give the titled product (912 mg, 28% yield) as a yellow oil.

$^1H$ NMR (400 MHz, $CDCl_3$) δ 8.21-8.09 (m, 1H), 3.29-3.13 (m, 1H), 2.96-2.62 (m, 4H), 1.21 (s, 9H). LCMS ($ESI^+$): m/z 224.01 $[M+H]^+$.

Step 3: (S)—N-((3,3-difluorocyclobutyl)(4-fluorophenyl)methyl)-2-methylpropane-2-sulfinamide 4-4

To a solution of (S)—N-[(3,3-difluorocyclobutyl)methylene]-2-methyl-propane-2-sulfinamide intermediate 4-3 (316 mg, 1.42 mmol) in DCM (2.4 mL) was added dropwise 4-fluorophenylmagnesium bromide (1 M, 3.54 mL) at −48° C. After addition, the mixture was stirred at this temperature for 5 hours. The resulting mixture was stirred at 25° C. for 16 hours. The reaction mixture was quenched by addition of sat. $NH_4Cl$ at 25° C., and then diluted with DCM (10 mL) and extracted with DCM (10 mL×2). The combined organic layers were washed with brine (15 mL×2), dried over $Na_2SO_4$, filtered and concentrated under reduced pressure to give a residue which was purified by column chromatography ($SiO_2$, PE/EtOAc=5/1 to 0/1) and further purified by prep-HPLC to give the titled product (340 mg, 75% yield) as a white solid. $^1H$ NMR (400 MHz, DMSO-$d_6$) δ 7.49-7.42 (m, 1H), 7.42-7.35 (m, 1H), 7.15 (t, J=8.8 Hz, 2H), 5.82-5.56 (m, 1H), 4.31-4.09 (m, 1H), 2.74-2.51 (m, 3H), 2.39-2.20 (m, 2H), 1.17-1.06 (m, 6H), 1.04 (s, 3H). LCMS ($ESI^+$): m/z 319.98 $[M+H]^+$.

Step 4: (3,3-difluorocyclobutyl)(4-fluorophenyl)methanamine 4-5

To a solution of (S)—N-((3,3-difluorocyclobutyl)(4-fluorophenyl)methyl)-2-methylpropane-2-sulfinamide intermediate 4-4 (100 mg, 313 μmol) in DCM (2 mL) was added HCl/dioxane (4 M, 2.00 mL). The mixture was stirred at 25° C. for 4 hours. Then the mixture was concentrated under reduced pressure to give the titled product as a white solid (90.0 mg, HCl salt, crude), which was used directly in the next step without further purification.

$^1H$ NMR (400 MHz, DMSO-$d_6$) δ 8.60 (s, 2H), 7.72-7.50 (m, 2H), 7.29 (t, J=8.8 Hz, 2H), 4.36 (s, 1H), 3.57 (s, 1H), 2.78-2.68 (m, 2H), 2.42-2.22 (m, 2H). LCMS ($ESI^+$): m/z 215.99 $[M+H]^+$.

Step 5: N-((3,3-difluorocyclobutyl)(4-fluorophenyl)methyl)-2-(2,6-dioxopiperidin-3-yl)-1-oxoisoindoline-5-carboxamide compound 4

To a solution of (3,3-difluorocyclobutyl)(4-fluorophenyl)methanamine intermediate 4-5 (40.0 mg, 159 μmol) and 2-(2,6-dioxopiperidin-3-yl)-1-oxo-isoindoline-5-carboxylic acid intermediate 1 (40.0 mg, 139 μmol) in DCM (2 mL) was added TEA (42.0 mg, 416 μmol) and $T_3P$ (177 mg, 278 μmol). The mixture was stirred at 25° C. for 16 hours. The reaction mixture was concentrated under reduced pressure to afford a residue which was purified by preparative HPLC to give the titled product compound 4 (50.0 mg, 74% yield) as a white solid. $^1H$ NMR (400 MHz, DMSO-$d_6$) δ 11.01 (s, 1H), 9.07 (d, J=8.4 Hz, 1H), 8.06 (s, 1H), 7.98 (d, J=8.0 Hz, 1H), 7.83 (d, J=7.6 Hz, 1H), 7.55-7.45 (m, 2H), 7.18 (t, J=8.4 Hz, 2H), 5.22-5.03 (m, 2H), 4.56-4.48 (m, 1H), 4.44-4.36 (m, 1H), 3.02-2.84 (m, 1H), 2.71 (s, 2H), 2.61 (d, J=16.8 Hz, 1H), 2.47-2.30 (m, 4H), 2.11-1.96 (m, 1H); LCMS ($ESI^+$): m/z 486.1 $[M+H]^+$.

Example 8

Preparation of Compound 5 and Compound 6: N—((*R)-(3,3-difluorocyclobutyl)(4-fluorophenyl)methyl)-2-(2,6-dioxopiperidin-3-yl)-1-oxoisoindoline-5-carboxamide and N—((*S)-(3,3-difluorocyclobutyl)(4-fluorophenyl)methyl)-2-(2,6-dioxopiperidin-3-yl)-1-oxoisoindoline-5-carboxamide Scheme 7

Compound 5

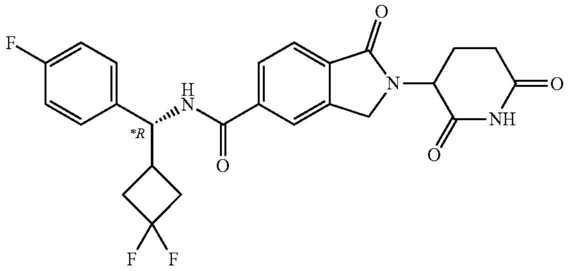

Compound 6

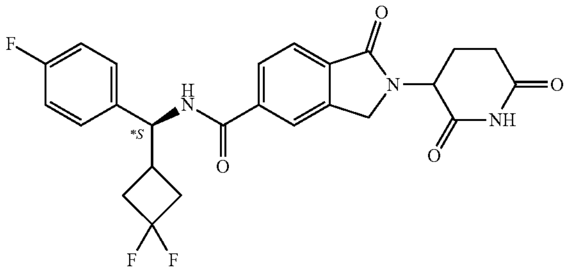

N-[(3,3-difluorocyclobutyl)-(4-fluorophenyl)methyl]-2-(2,6-dioxo-3-piperidyl)-1-oxo-isoindoline-5-carboxamide compound 4 (40.0 mg, 82.4 μmol) was purified by SFC (separation condition: DAICEL CHIRALPAK AD (250 mm×30 mm, 10 um); Mobile phase: A: Supercritical $CO_2$, B: EtOH, 40% B at 80 mL/min) to give compound 5 ($^tR$=0.686 min, 13 mg) and compound 6 ($^tR$=0.894 min, 25 mg) as white solids.

Compound 5: $^1$HNMR (400 MHz, DMSO-$d_6$) δ 11.03 (s, 1H), 9.07 (d, J=8.4 Hz, 1H), 8.04 (s, 1H), 7.97 (d, J=8.0 Hz, 1H), 7.83 (d, J=7.6 Hz, 1H), 7.54-7.45 (m, 2H), 7.17 (t, J=8.8 Hz, 2H), 5.19-5.04 (m, 2H), 4.56-4.46 (m, 1H), 4.43-4.33 (m, 1H), 2.98-2.85 (m, 1H), 2.69 (s, 2H), 2.60 (d, J=17.6 Hz, 1H), 2.47-2.35 (m, 4H), 2.07-1.95 (m, 1H). LCMS ($ESI^+$): m/z 486.1 [M+H]+.

Compound 6: H NMR (400 MHz, DMSO-$d_6$) δ 11.03 (s, 1H), 9.06 (d, J=8.8 Hz, 1H), 8.05 (s, 1H), 7.97 (d, J=7.6 Hz, 1H), 7.83 (d, J=8.0 Hz, 1H), 7.57-7.41 (m, 2H), 7.17 (t, J=8.8 Hz, 2H), 5.22-4.99 (m, 2H), 4.61-4.30 (m, 2H), 3.00-2.83 (m, 1H), 2.79-2.68 (m, 2H), 2.60 (d, J=18.8 Hz, 1H), 2.33 (s, 4H), 2.12-1.91 (m, 1H). LCMS ($ESI^+$): m/z 486.1 [M+H]+.

Example 9

Preparation of compound 7: N—((*S)-cyclobutyl(4-fluorophenyl)methyl)-2-(2,6-dioxopiperidin-3-yl)-1-oxoisoindoline-5-carboxamide Scheme 8

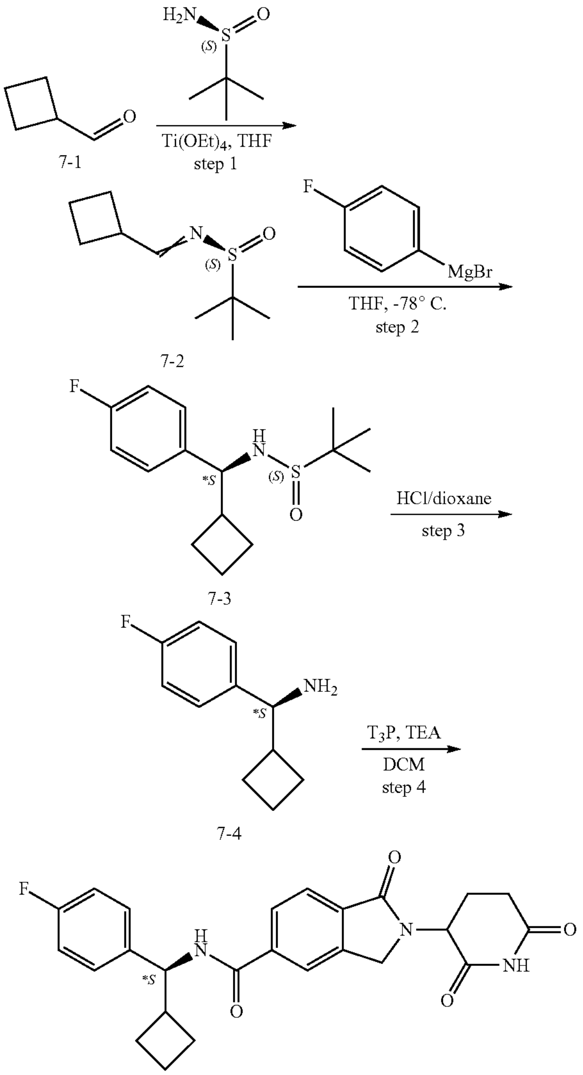

Compound 7

Step 1: Synthesis of (S)—N-(cyclobutylmethylene)-2-methylpropane-2-sulfinamide 7-2

To a mixture of cyclobutanecarbaldehyde (500 mg, 5.94 mmol) and (S)-2-methylpropane-2-sulfinamide (720 mg, 5.94 mmol) in THF (10 mL) was added $Ti(OEt)_4$ (1.36 g, 5.94 mmol) in one portion at 25° C. under $N_2$. The mixture was stirred at 25° C. for 12 hours. The reaction mixture was concentrated under reduced pressure. The residue was diluted with water (10 mL) and extracted with EtOAc (20 mL×3). The combined organic layers were washed with brine, dried over $Na_2SO_4$, filtered and concentrated under reduced pressure. The residue was purified by flash silica gel chromatography (ISCO®; 4 g SepaFlash® Silica Flash Column, Eluent of 0~50% Ethyl acetate/Petroleum ether gradient @ 30 mL/min). Compound (S)—N-(cyclobutylmethylene)-2-methyl-propane-2-sulfinamide intermediate 7-2 (600 mg, 3.20 mmol) was obtained as a colorless oil. $^1H$ NMR (400 MHz, $CDCl_3$) 8.04 (d, J=4.8 Hz, 1H), 3.37-3.25 (m, 1H), 2.23-1.82 (m, 6H), 1.13 (s, 9H).

Step 2: Synthesis of (S)—N—((*S)-cyclobutyl(4-fluorophenyl)methyl)-2-methylpropane-2-sulfinamide 7-3

To a mixture of (S)—N-(cyclobutylmethylene)-2-methyl-propane-2-sulfinamide intermediate 7-2 (600 mg, 3.20 mmol) in THE (10 mL) was added 1M bromo-(4-fluoro-phenyl)magnesium in THE (9.61 mL, 9.61 mmol) at −78° C. under $N_2$ atmosphere, and then the mixture was stirred at 25° C. for 12 h under $N_2$ atmosphere. The reaction was quenched with water (10 mL) and extracted with EtOAc (10 mL×2). The combined organic phase was washed with water (5 mL), dried over anhydrous $Na_2SO_4$ and concentrated under reduced pressure. The residue was purified by flash silica gel chromatography (ISCO®; 4 g SepaFlash® Silica Flash Column, Eluent of 0~100% Ethyl acetate/Petroleum ether gradient @ 30 mL/min). Compound (S)—N—[(S)-cyclobutyl-(4-fluorophenyl)methyl]-2-methyl-propane-2-sulfinamide intermediate 7-3 (90 mg, 9% yield) was obtained as a white oil. LCMS ($ESI^+$): m/z 284.3 $[M+H]^+$.

Step 3: Synthesis of (*S)-cyclobutyl(4-fluorophenyl)methanamine 7-4

To a solution of (S)—N—[(S)-cyclobutyl-(4-fluorophenyl)methyl]-2-methyl-propane-2-sulfinamide intermediate 7-3 (90.0 mg, 318 μmol) in DCM (20 mL) was added HCl/dioxane (4 M, 1.59 mL). The mixture was stirred at 25° C. for 0.5 h. The mixture was concentrated under reduced pressure. Compound (S)-cyclobutyl-(4-fluorophenyl)methanamine intermediate 7-4 (65 mg, crude, HCl salt) was obtained as a white solid. LCMS ($ESI^+$): m/z 180.2 $[M+H]^+$.

Step 4: N—((*S)-cyclobutyl(4-fluorophenyl)methyl)-2-(2,6-dioxopiperidin-3-yl)-1-oxoisoindoline-5-carboxamide compound 7

To a solution of (S)-cyclobutyl-(4-fluorophenyl)methanamine intermediate 7-4 (65.0 mg, 301 μmol) and 2-(2,6-dioxo-3-piperidyl)-1-oxo-isoindoline-5-carboxylic acid intermediate 1 (95.6 mg, 331 μmol) in DCM (5 mL) was added $T_3P$ (192 mg, 301 μmol) and TEA (30.5 mg, 301 μmol). The mixture was stirred at 25° C. for 12 h. The reaction mixture was concentrated under reduced pressure to afford a residue which was purified by preparative HPLC to give compound N—((S)-cyclobutyl(4-fluorophenyl)methyl)-2-(2,6-dioxopiperidin-3-yl)-1-oxoisoindoline-5-carboxamide compound 7 (80.9 mg, 60% yield) as a white solid. $^1H$ NMR (400 MHz, DMSO-$d_6$) δ 11.04 (s, 1H), 8.90 (d, J=8.4 Hz, 1H), 8.05 (s, 1H), 7.97 (d, J=8.0 Hz, 1H), 7.82 (d, J=7.0 Hz, 1H), 7.44 (dd, J=5.6, 8.4 Hz, 2H), 7.19-7.11 (m, 2H), 5.14 (dd, J=5.2, 13.2 Hz, 1H), 5.05-4.95 (m, 1H), 4.58-4.34 (m, 2H), 2.98-2.87 (m, 1H), 2.84-2.72 (m, 1H), 2.68-2.59 (m, 1H), 2.47-2.33 (m, 1H), 2.13-1.98 (m, 2H), 1.86-1.69 (m, 5H); LCMS ($ESI^+$): m/z 450.1 $[M+H]^+$.

Example 10

Preparation of Compound 8 and Compound 9: N—((*S)-cyclobutyl(4-fluorophenyl)methyl)-2-((R)-2,6-dioxopiperidin-3-yl)-1-oxoisoindoline-5-carboxamide and N—((*S)-cyclobutyl(4-fluorophenyl)methyl)-2-((S)-2,6-dioxopiperidin-3-yl)-1-oxoisoindoline-5-carboxamide Scheme 9

Compound 8

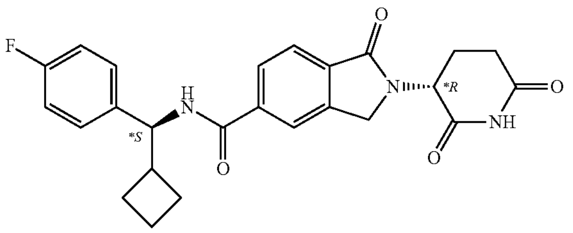

Compound 9

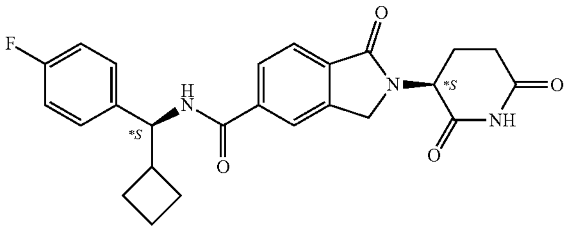

N—((*S)-cyclobutyl(4-fluorophenyl)methyl)-2-(2,6-dioxopiperidin-3-yl)-1-oxoisoindoline-5-carboxamide compound 7 (60.0 mg, 133 μmol) was purified by prep-SFC (Column: DAICEL CHIRALCEL OD (250 mm×30 mm, 10 um), Condition: 0.1% $NH_3H_2O$, EtOH, Begin B: 45%, Flow Rate: 80 ml/min) to afford compound 8 (14.8 mg, 100% purity) as a white solid and compound 9 (14.2 mg, 100% purity) as a white solid.

Compound 8: $^1H$ NMR (400 MHz, DMSO-$d_6$) δ 11.04 (br. s., 1H), 8.92 (d, J=8.4 Hz, 1H), 8.05 (s, 1H), 7.97 (d, J=7.6 Hz, 1H), 7.82 (d, J=8.0 Hz, 1H), 7.44 (dd, J=5.6, 8.4 Hz, 2H), 7.14 (t, J=8.8 Hz, 2H), 5.14 (dd, J=5.2, 13.2 Hz, 1H), 5.03-4.96 (m, 1H), 4.56-4.35 (m, 2H), 2.98-2.86 (m, 1H), 2.85-2.73 (m, 1H), 2.66-2.57 (m, 1H), 2.45-2.36 (m, 1H), 2.13-1.98 (m, 2H), 1.86-1.68 (m, 5H); LCMS ($ESI^+$): m/z 450.1 $[M+H]^+$;

Compound 9: $^1H$ NMR (400 MHz, DMSO-$d_6$) δ 11.03 (s, 1H), 8.91 (d, J=8.4 Hz, 1H), 8.05 (s, 1H), 7.97 (d, J=7.6 Hz, 1H), 7.82 (d, J=8.0 Hz, 1H), 7.50-7.37 (m, 2H), 7.14 (t, J=8.8 Hz, 2H), 5.15 (dd, J=4.8, 13.2 Hz, 1H), 4.99 (t, J=9.2 Hz, 1H), 4.58-4.36 (m, 2H), 2.98-2.86 (m, 1H), 2.84-2.73 (m, 1H), 2.68-2.58 (m, 1H), 2.45-2.35 (m, 1H), 2.14-1.98 (m, 2H), 1.86-1.70 (m, 5H); LCMS ($ESI^+$): m/z 450.1 $[M+H]^+$;

Example 11

The following compounds were prepared according to similar procedure as described for compound 4 with corresponding starting materials of aldehydes and Grignard reagents (Example 7). For compounds 35, 36, 38, 58, 59, 66, 67, 69, and 70, the corresponding major diastereomer intermediate of step 2 was separated by prep-HPLC or SFC before the following step 3 and 4.

TABLE 4

| No | Structure | Compound name and characterization |
|---|---|---|
| 35 | 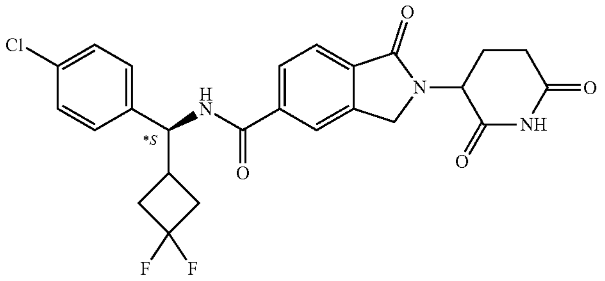 [SMILES: O=C1CCC(N2Cc3cc(C(=O)N[C@H](c4ccc(Cl)cc4)C4CC(F)(F)C4)ccc3C2=O)C(=O)N1] | N-((*S)-(4-chlorophenyl)(3,3-difluorocyclobutyl)methyl)-2-(2,6-dioxopiperidin-3-yl)-1-oxoisoindoline-5-carboxamide $^1H$ NMR (400 MHz, DMSO-$d_6$) δ 10.99 (s, 1H), 9.08 (d, J = 8.4 Hz, 1H), 8.05 (s, 1H), 7.97 (d, J = 8.0 Hz, 1H), 7.83 (d, J = 8.0 Hz, 1H), 7.53-7.44 (m, 2H), 7.44-7.38 (m, 2H), 5.19-5.03 (m, 2H), 4.57-4.47 (m, 1H), 4.44-4.34 (m, 1H), 2.98-2.85 (m, 1H), 2.78-2.56 (m, 3H), 2.48-2.34 (m, 4H), 2.08-1.96 (m, 1H). LCMS (ESI+): m/z 502.2 [M + H]+. |
| 36 | 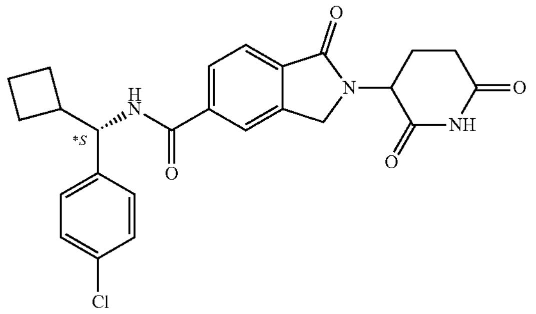 [SMILES: O=C1CCC(N2Cc3cc(C(=O)N[C@H](c4ccc(Cl)cc4)C4CCC4)ccc3C2=O)C(=O)N1] | N-((*S)-(4-chlorophenyl)(cyclobutyl)methyl)-2-(2,6-dioxopiperidin-3-yl)-1-oxoisoindoline-5-carboxamide $^1H$ NMR (400 MHz, DMSO-$d_6$) δ 11.02 (br. s, 1H), 8.92 (d, J = 8.0 Hz, 1H), 8.04 (s, 1H), 7.97 (d, J = 8.0 Hz, 1H), 7.82 (d, J = 8.0 Hz, 1H), 7.45-7.36 (m, 4H), 5.14 (dd, J = 5.2, 13.2 Hz, 1H), 5.03-4.93 (m, 1H), 4.56-4.36 (m, 2H), 2.98-2.85 (m, 1H), 2.80-2.76 (m, 1H), 2.63-2.59 (m, 1H), 2.44-2.40 (m, 1H), 2.13-1.99 (m, 2H), 1.83-1.71 (m, 5H); LCMS ($ESI^+$): m/z 466.1 $[M + H]^+$. |

TABLE 4-continued

| No | Structure | Compound name and characterization |
|---|---|---|
| 37 | 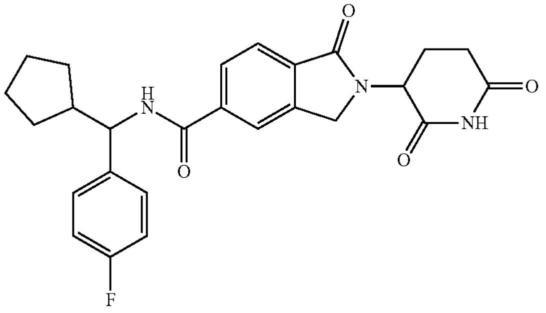 [SMILES: O=C1CCC(N2Cc3cc(C(=O)NC(c4ccc(F)cc4)C4CCCC4)ccc3C2=O)C(=O)N1] | N-(cyclopentyl(4-fluorophenyl)methyl)-2-(2,6-dioxopiperidin-3-yl)-1-oxoisoindoline-5-carboxamide $^{1}$H NMR (400 MHz, DMSO-d6) δ 11.01 (br s, 1H), 9.20-8.90 (m, 1H), 8.03 (s, 1H), 7.99-7.91 (m, 1H), 7.85-7.77 (m, 1H), 7.51-7.42 (m, 2H), 7.19-7.09 (m, 2H), 5.20-5.08 (m, 1H), 4.84-4.70 (m, 1H), 4.59-4.44 (m, 1H), 4.42-4.27 (m, 1H), 3.05-2.84 (m, 1H), 2.65-2.56 (m, 1H), 2.45-2.34 (m, 2H), 2.07-1.95 (m, 1H), 1.93-1.81 (m, 1H), 1.69-1.41 (m, 4H), 1.40-1.21 (m, 2H), 1.18-1.05 (m, 1H). LCMS (ESI+): m/z 464.1 [M + H]+ |
| 38 | 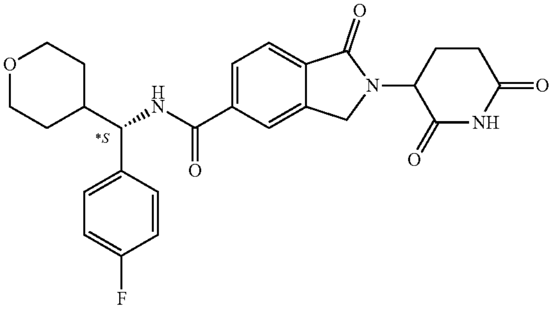 [SMILES: O=C1CCC(N2Cc3cc(C(=O)N[C@H](c4ccc(F)cc4)C4CCOCC4)ccc3C2=O)C(=O)N1] | 2-(2,6-dioxopiperidin-3-yl)-N-((*S)-(4-fluorophenyl)(tetrahydro-2H-pyran-4-yl)methyl)-1-oxoisoindoline-5-carboxamide $^{1}$H NMR (400 MHz, DMSO-$d_6$) δ 11.03 (br. s, 1H), 9.08-8.94 (m, 1H), 8.09-7.78 (m, 3H), 7.53-7.39 (m, 2H), 7.22-7.11 (m, 2H), 5.21-5.08 (m, 1H), 4.86-4.69 (m, 1H), 4.58-4.32 (m, 2H), 3.90-3.78 (m, 2H), 3.25-3.16 (m, 2H), 3.00-2.83 (m, 1H), 2.64-2.59 (m, 1H), 2.43-2.40 (m, 1H), 2.04-2.00 (m, 1H), 1.90-1.76 (m, 1H), 1.36-1.12 (m, 3H), 1.06-0.98 (m, 1H). LCMS (ESI+): m/z 480.1 $[M + H]^+$. |
| 46 | 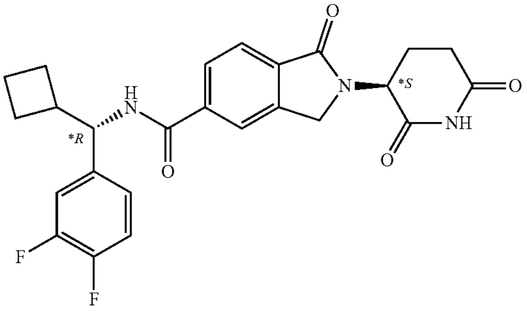 [SMILES: O=C1CC[C@H](N2Cc3cc(C(=O)N[C@H](c4ccc(F)c(F)c4)C4CCC4)ccc3C2=O)C(=O)N1] | N-((*R)-cyclobutyl(3,4-difluorophenyl)methyl)-2-((*S)-2,6-dioxopiperidin-3-yl)-1-oxoisoindoline-5-carboxamide $^{1}$H NMR (400 MHz, DMSO-$d_6$) 11.01 (br s, 1H), 8.88 (d, J = 8.4 Hz, 1H), 8.04 (s, 1H), 7.96 (d, J = 8.0 Hz, 1H), 7.82 (d, J = 8.0 Hz, 1H), 7.53-7.43 (m, 1H), 7.43-7.30 (m, 1H), 7.29-7.17 (m, 1H), 5.21-5.08 (m, 1H), 5.06-4.91 (m, 1H), 4.59-4.45 (m, 1H), 4.45-4.30 (m, 1H), 3.02-2.83 (m, 1H), 2.82-2.69 (m, 1H), 2.64-2.57 (m, 1H), 2.41-2.38 (m, 1H), 2.15-1.95 (m, 2H), 1.92-1.61 (m, 6H). LCMS (ESI+): m/z 468.1 [M + H]+. The compound was separated by SFC with the corresponding racemic mixture: chiral column: (S,S)Whelk-01, 100*4.6 mm I.D., 5 um, gradient mobile phase: $CO_2$: MeOH (0.05% DEA), $^{t}$R: 1.80 min, chiral purity: 95% |
| 47 | 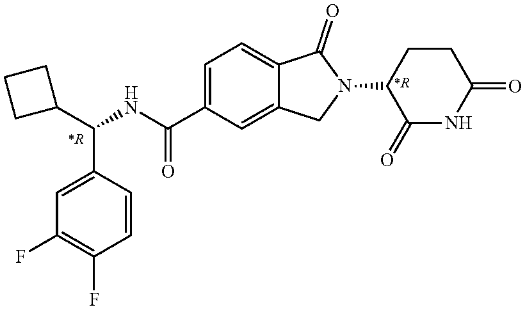 | N-((*R)-cyclobutyl(3,4-difluorophenyl)methyl)-2-((*R)-2,6-dioxopiperidin-3-yl)-1-oxoisoindoline-5-carboxamide $^{1}$H NMR (400 MHz, DMSO-$d_6$) δ 11.01 (br s, 1H), 8.87 (d, J = 8.4 Hz, 1H), 8.04 (s, 1H), 7.96 (d, J = 8.0 Hz, 1H), 7.82 (d, J = 8.0 Hz, 1H), 7.54-7.43 (m, 1H), 7.42-7.31 (m, 1H), 7.29-7.19 (m, 1H), 5.23-5.07 (m, 1H), 5.06-4.92 (m, 1H), 4.59-4.46 (m, 1H), 4.44-4.29 (m, 1H), 3.01-2.84 (m, 1H), 2.81-2.70 (m, 1H), 2.61-2.57 (m, 1H), 2.45-2.38 (m, 1H), 2.10-2.01 (m, 2H), 1.89-1.67 (m, 6H). LCMS (ESI+): m/z 468.1 [M + H]+. The compound was separated by SFC with the corresponding racemic mixture: chiral column: (S,S)Whelk-01, 100*4.6 mm I.D., 5 um, gradient mobile phase: $CO_2$: MeOH (0.05% DEA), $^{t}$R: 2.13 min, chiral purity: 66% |
| 48 | 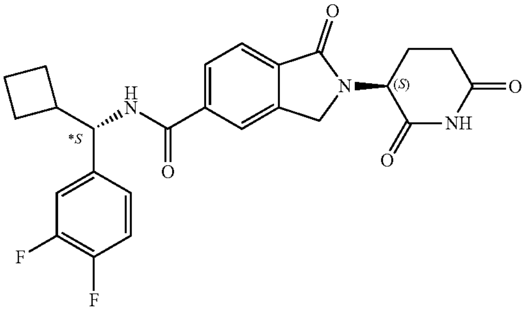 | N-((*S)-cyclobutyl(3,4-difluorophenyl)methyl)-2-((S)-2,6-dioxopiperidin-3-yl)-1-oxoisoindoline-5-carboxamide $^{1}$H NMR (400 MHz, DMSO-$d_6$) δ 11.01 (br s, 1H), 8.88 (d, J = 8.4 Hz, 1H), 8.05 (s, 1H), 7.96 (d, J = 8.0 Hz, 1H), 7.82 (d, J = 8.0 Hz, 1H), 7.53-7.43 (m, 1H), 7.42-7.32 (m, 1H), 7.29-7.20 (m, 1H), 5.21-5.09 (m, 1H), 5.06-4.92 (m, 1H), 4.58-4.47 (m, 1H), 4.44-4.34 (m, 1H), 2.98-2.85 (m, 1H), 2.82-2.69 (m, 1H), 2.65-2.57 (m, 1H), 2.44-2.38 (m, 1H), 2.14-1.95 (m, 2H), 1.90-1.64 (m, 6H). LCMS (ESI+): m/z 468.1 [M + H]+. The compound was separated by SFC with the corresponding racemic mixture: chiral column: (S,S)Whelk-01, 100*4.6 mm I.D., 5 um, gradient mobile phase: $CO_2$: MeOH (0.05% DEA), $^{t}$R: 3.82 min, chiral purity: 100% |

TABLE 4-continued

| No | Structure | Compound name and characterization |
| --- | --- | --- |
| 49 | 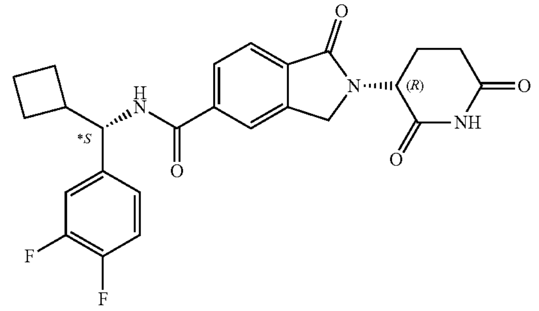 | N-((*S)-cyclobutyl(3,4-difluorophenyl)methyl)-2-((R)-2,6-dioxopiperidin-3-yl)-1-oxoisoindoline-5-carboxamide<br>$^{1}$H NMR (400 MHz, DMSO-$d_6$) 11.01 (br s, 1H), 8.88 (d, J = 8.4 Hz, 1H), 8.04 (s, 1H), 7.96 (d, J = 8.0 Hz, 1H), 7.82 (d, J = 8.0 Hz, 1H), 7.54-7.43 (m, 1H), 7.42-7.32 (m, 1H), 7.29-7.20 (m, 1H), 5.20-5.09 (m, 1H), 5.06-4.93 (m, 1H), 4.59-4.46 (m, 1H), 4.44-4.32 (m, 1H), 3.00-2.83 (m, 1H), 2.81-2.70 (m, 1H), 2.64-2.58 (m, 1H), 2.45-2.35 (m, 1H), 2.14-1.96 (m, 2H), 1.87-1.67 (m, 6H). LCMS (ESI+): m/z 468.1 [M + H]+. The compound was separated by SFC with the corresponding racemic mixture: chiral column: (S,S)Whelk-01, 100*4.6 mm I.D., 5 um, gradient mobile phase: CO2: MeOH (0.05% DEA), $^{t}$R: 4.89 min, chiral purity: 98% |
| 58 | 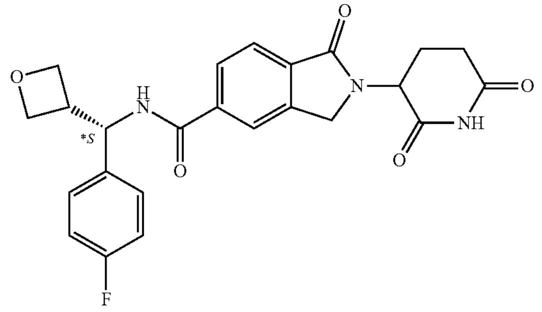 [SMILES: O=C1CCC(N2Cc3cc(C(=O)N[C@H](c4ccc(F)cc4)C4COC4)ccc3C2=O)C(=O)N1] | 2-(2,6-dioxo-3-piperidyl)-N-[(*S)-(4-fluorophenyl)-(oxetan-3-yl)methyl]-1-oxo-isoindoline-5-carboxamide<br>$^{1}$H NMR (400 MHz, DMSO-$d_6$) δ 11.02 (s, 1H), 9.03 (d, J = 8.4 Hz, 1H), 8.44 (br s, 0.28H), 8.04 (s, 1H), 7.96 (d, J = 8.4 Hz, 1H), 7.82 (d, J = 7.6 Hz, 1H), 7.49-7.40 (m, 2H), 7.21-7.12 (m, 2H), 5.51-5.36 (m, 1H), 5.20-5.07 (m, 1H), 4.72-4.66 (m, 1H), 4.55-4.46 (m, 2H), 4.45-4.35 (m, 2H), 4.30 (t, J = 6.4 Hz, 1H), 2.98-2.85 (m, 2H), 2.60 (d, J = 16.8 Hz, 1H), 2.46-2.37 (m, 1H), 2.07-1.91 (m, 1H); LCMS ($ESI^+$): m/z 452.1 $[M + H]^+$. |
| 59 | 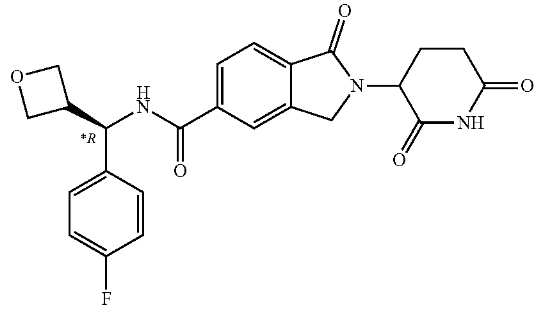 [SMILES: O=C1CCC(N2Cc3cc(C(=O)N[C@@H](c4ccc(F)cc4)C4COC4)ccc3C2=O)C(=O)N1] | 2-(2,6-dioxopiperidin-3-yl)-N-((*R)-(4-fluorophenyl)(oxetan-3-yl)methyl)-1-oxoisoindoline-5-carboxamide<br>$^{1}$H NMR (400 MHz, DMSO-$d_6$) δ 11.01 (br s, 1H), 9.02 (d, J = 8.0 Hz, 1H), 8.46 (s, 0.19H), 8.04 (s, 1H), 7.96 (d, J = 8.4 Hz, 1H), 7.82 (d, J = 8.0 Hz, 1H), 7.52-7.39 (m, 2H), 7.17 (t, J = 8.8 Hz, 2H), 5.51-5.40 (m, 1H), 5.21-5.07 (m, 1H), 4.69 (t, J = 7.6 Hz, 1H), 4.55-4.46 (m, 2H), 4.45-4.35 (m, 2H), 4.30 (t, J = 6.4 Hz, 1H), 3.59-3.45 (m, 1H), 2.97-2.85 (m, 1H), 2.61 (d, J = 16.8 Hz, 1H), 2.40 (d, J = 4.0 Hz, 1H), 2.06-1.97 (m, 1H); LCMS ($ESI^+$): m/z 452.1 $[M + H]^+$. |
| 60 | 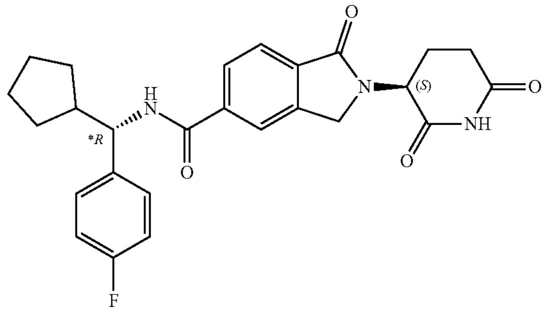 | N-((*R)-cyclopentyl(4-fluorophenyl)methyl)-2-((S)-2,6-dioxopiperidin-3-yl)-1-oxoisoindoline-5-carboxamide<br>$^{1}$H NMR (400 MHz, DMSO-$d_6$) δ 11.01 (br s, 1H), 9.06-8.92 (m, 1H), 8.03 (s, 1H), 7.97-7.92 (m, 1H), 7.84-7.78 (m, 1H), 7.49-7.42 (m, 2H), 7.17-7.09 (m, 2H), 5.19-5.04 (m, 1H), 4.81-4.69 (m, 1H), 4.57-4.45 (m, 1H), 4.43-4.32 (m, 1H), 2.93-2.90 (m, 1H), 2.64-2.61 (m, 1H), 2.47-2.35 (m, 2H), 2.07-1.96 (m, 1H), 1.93-1.82 (m, 1H), 1.67-1.42 (m, 4H), 1.30-1.21 (m, 2H), 1.17-1.09 (m, 1H). LCMS (ESI+): m/z 464.1 [M + H]+.<br>The compound was separated by SFC with the corresponding racemic mixture: chiral column: (S,S)Whelk-01, 100*4.6 mm I.D., 5 um, gradient mobile phase: $CO_2$: MeOH (0.05% DEA), $^{t}$R: 2.04 min, chiral purity: 58% |
| 61 | 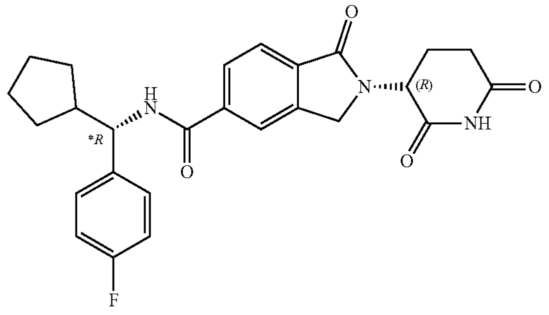 | N-((*S)-cyclopentyl(4-fluorophenyl)methyl)-2-((R)-2,6-dioxopiperidin-3-yl)-1-oxoisoindoline-5-carboxamide<br>$^{1}$H NMR (400 MHz, DMSO-$d_6$) δ 11.01 (br s, 1H), 9.06-8.92 (m, 1H), 8.03 (s, 1H), 7.97-7.92 (m, 1H), 7.84-7.78 (m, 1H), 7.49-7.42 (m, 2H), 7.17-7.09 (m, 2H), 5.19-5.04 (m, 1H), 4.81-4.69 (m, 1H), 4.57-4.45 (m, 1H), 4.43-4.32 (m, 1H), 2.93-2.90 (m, 1H), 2.64-2.61 (m, 1H), 2.47-2.35 (m, 2H), 2.07-1.96 (m, 1H), 1.93-1.82 (m, 1H), 1.65-1.49 (m, 4H), 1.30-1.21 (m, 2H), 1.17-1.11 (m, 1H). LCMS (ESI+): m/z 464.1 [M + H]+.<br>The compound was separated by SFC with the corresponding racemic mixture: chiral column: (S,S)Whelk-01, 100*4.6 mm I.D., 5 um, gradient mobile phase: $CO_2$: MeOH (0.05% DEA), $^{t}$R: 2.42 min, chiral purity: 76% |

TABLE 4-continued

| No | Structure | Compound name and characterization |
| --- | --- | --- |
| 62 | 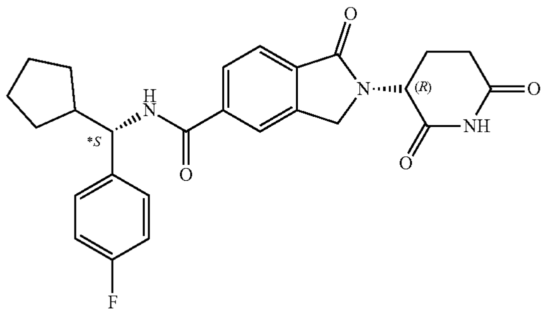 | N-((*S)-cyclopentyl(4-fluorophenyl)methyl)-2-((R)-2,6-dioxopiperidin-3-yl)-1-oxoisoindoline-5-carboamide<br>$^{1}$H NMR (400 MHz, DMSO-$d_6$) δ 11.01 (br s, 1H), 9.08-8.90 (m, 1H), 8.03 (s, 1H), 7.97-7.92 (m, 1H), 7.83-7.78 (m, 1H), 7.51-7.41 (m, 2H), 7.19-7.01 (m, 2H), 5.18-5.09 (m, 1H), 4.81-4.72 (m, 1H), 4.55-4.46 (m, 1H), 4.43-4.33 (m, 1H), 2.99-2.82 (m, 1H), 2.65-2.57 (m, 1H), 2.45-2.38 (m, 2H), 2.10-1.96 (m, 1H), 1.93-1.82 (m, 1H), 1.64-1.42 (m, 4H), 1.36-1.23 (m, 2H), 1.18-1.08 (m, 1H). LCMS (ESI+): m/z 464.1 [M + H]+.<br>The compound was separated by SFC with the corresponding racemic mixture: chiral column: (S,S)Whelk-01, 100*4.6 mm I.D., 5 um, gradient mobile phase: $CO_2$: MeOH (0.05% DEA), $^{t}$R: 5.30 min, chiral purity: 91% |
| 63 | 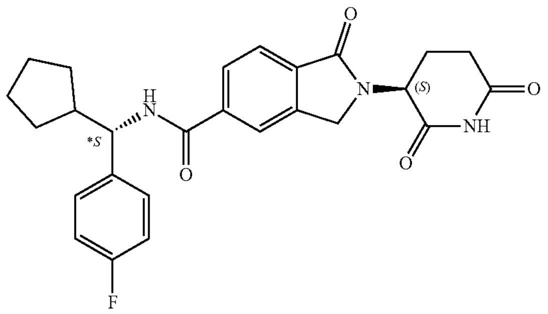 | N-((*S)-cyclopentyl(4-fluorophenyl)methyl)-2-((S)-2,6-dioxopiperidin-3-yl)-1-oxoisoindoline-5-carboxamide<br>$^{1}$H NMR (400 MHz, DMSO-$d_6$) δ 11.01 (br s, 1H), 9.05-8.95 (m, 1H), 8.02 (s, 1H), 7.98-7.91 (m, 1H), 7.84-7.77 (m, 1H), 7.53-7.42 (m, 2H), 7.19-7.09 (m, 2H), 5.19-5.07 (m, 1H), 4.81-4.71 (m, 1H), 4.57-4.47 (m, 1H), 4.44-4.33 (m, 1H), 2.96-2.86 (m, 1H), 2.65-2.53 (m, 1H), 2.45-2.39 (m, 2H), 2.06-1.96 (m, 1H), 1.94-1.81 (m, 1H), 1.66-1.46 (m, 4H), 1.38-1.23 (m, 2H), 1.15-1.08 (m, 1H). LCMS (ESI+): m/z 464.1 [M + H]+.<br>The compound was separated by SFC with the corresponding racemic mixture: chiral column: (S,S)Whelk-01, 100*4.6 mm I.D., 5 um, gradient mobile phase: $CO_2$: MeOH (0.05% DEA), $^{t}$R: 5.22 min, chiral purity: 97% |
| 68 | 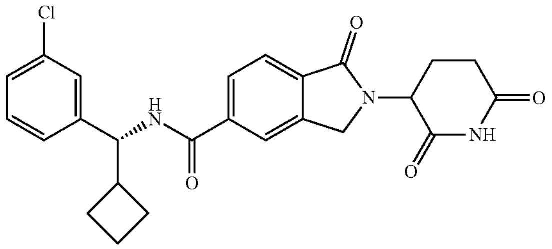 [SMILES: O=C1CCC(N2Cc3cc(C(=O)N[C@@H](c4cccc(Cl)c4)C4CCC4)ccc3C2=O)C(=O)N1] | N-((3-chlorophenyl)(cyclobutyl)methyl)-2-(2,6-dioxopiperidin-3-yl)-1-oxoisoindoline-5-carboxamide<br>$^{1}$H NMR (400 MHz, DMSO-d6) δ 11.02 (br s, 1H), 8.92 (d, J = 8.0 Hz, 1H), 8.05 (s, 1H), 7.97 (d, J = 8.0 Hz, 1H), 7.82 (d, J = 8.0 Hz, 1H), 7.47 (s, 1H), 7.37-7.32 (m, 1H), 7.37-7.32 (m, 1H), 7.31-7.27 (m, 1H), 5.18-5.11 (m, 1H), 5.02-4.95 (m, 1H), 4.57-4.47 (m, 1H), 4.43-4.35 (m, 1H), 2.97 2.87 (m, 1H), 2.82-2.72 (m, 1H), 2.65-2.55 (m, 1H), 2.44-2.36 (m, 1H), 2.13-1.96 (m, 2H), 1.84-1.70 (m, 5H). LCMS ($ESI^+$): m/z 466.1 $[M + H]^+$. |
| 69 | 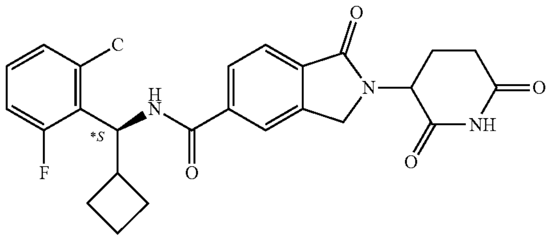 | N-((*S)-(2-chloro-6-fluorophenyl)(cyclobutyl)methyl)-2-(2,6-dioxopiperidin-3-yl)-1-oxoisoindoline-5-carboxamide<br>$^{1}$H NMR (400 MHz, DMSO-$d_6$) δ 11.01 (br s, 1H), 8.90 (d, J = 6.8 Hz, 1H), 8.02 (d, J = 3.2 Hz, 1H), 7.97-7.91 (m, 1H), 7.80 (d, J = 8.0 Hz, 1H), 7.35-7.25 (m, 2H), 7.22-7.12 (m, 1H), 5.55-5.44 (m, 1H), 5.22-5.07 (m, 1H), 4.56-4.45 (m, 1H), 4.43-4.30 (m, 1H), 3.16-3.03 (m, 1H), 2.99-2.84 (m, 1H), 2.60 (d, J = 15.6 Hz, 1H), 2.46-2.35 (m, 1H), 2.29-2.15 (m, 1H), 2.07-1.96 (m, 1H), 1.91-1.63 (m, 5H). LCMS ($ESI^+$): m/z 484.1 $[M + H]^+$. |
| 70 | 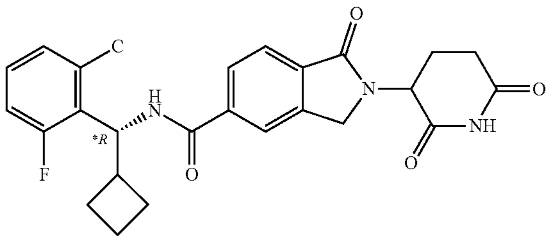 | N-((*R)-(2-chloro-6-fluorophenyl)(cyclobutyl)methyl)-2-(2,6-dioxopiperidin-3-yl)-1-oxoisoindoline-5-carboxamide<br>$^{1}$H NMR (400 MHz, DMSO-$d_6$) δ 11.03 (br s, 1H), 8.90 (d, J = 6.8 Hz, 1H), 8.02 (d, J = 2.8 Hz, 1H), 7.95 (d, J = 5.6 Hz, 1H), 7.80 (d, J = 8.0 Hz, 1H), 7.35-7.25 (m, 2H), 7.22-7.11 (m, 1H), 5.53-5.44 (m, 1H), 5.18-5.09 (m, 1H), 4.57-4.46 (m, 1H), 4.43-4.32 (m, 1H), 3.09 (d, J = 9.2 Hz, 1H), 2.98-2.85 (m, 1H), 2.60 (d, J = 17.2 Hz, 1H), 2.45-2.37 (m, 1H), 2.23 (br s, 1H), 2.08-1.96 (m, 1H), 1.92-1.64 (m, 5H). LCMS ($ESI^+$): m/z 484.1 $[M + H]^+$. |

Example 12

Preparation of Compound 65: 2-(2,6-dioxopiperidin-3-yl)-N—((R)-(4-fluorophenyl)(1-hydroxycyclopropyl)methyl)-1-oxoisoindoline-5-carboxamide Scheme 10

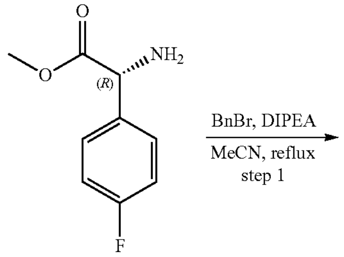

65-1

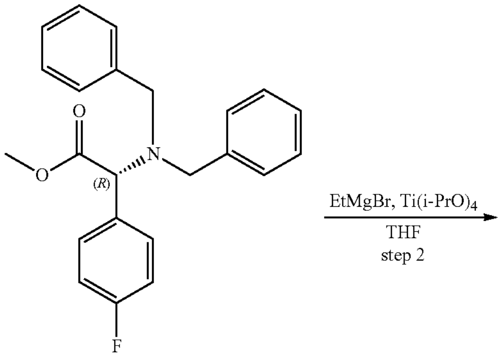

65-2

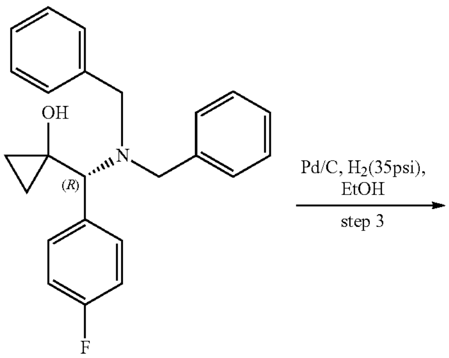

65-3

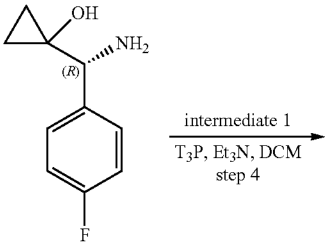

65-4

-continued

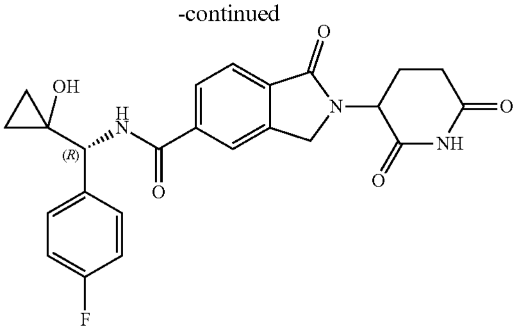

compound 65

Step 1: Synthesis of (R)-methyl 2-(dibenzylamino)-2-(4-fluorophenyl)acetate 65-2

To a solution of methyl (2R)-2-amino-2-(4-fluorophenyl) acetate (1.50 g, 8.19 mmol) in MeCN (15 mL) was added DIPEA (4.23 g, 32.8 mmol) and bromomethylbenzene (5.60 g, 32.8 mmol). The mixture was stirred at 90° C. for 21 hr. The reaction was concentrated under vacuum to give residue. The residue was purified by column chromatography ($SiO_2$, Petroleum ether: Ethyl acetate=1:0 to 10:1). Compound methyl (2R)-2-(dibenzylamino)-2-(4-fluorophenyl) acetate (1.73 g, 58% yield) was obtained as a yellow oil. $^1$H NMR (400 MHz, $CDCl_3$): δ 7.36-7.29 (m, 10H), 7.27 (s, 2H), 7.15-6.93 (m, 2H), 4.60 (s, 1H), 3.80 (s, 3H), 3.77-3.70 (m, 4H). LCMS ($ESI^+$): m/z 364.01 $[M+H]^+$.

Step 2: (R)-1-((dibenzylamino)(4-fluorophenyl)methyl)cyclopropanol 65-3

To a solution of methyl (2R)-2-(dibenzylamino)-2-(4-fluorophenyl)acetate (500 mg, 1.38 mmol) in THE (5 mL) was added $Ti(i\text{-}PrO)_4$ (193 mg, 678 umol) at 20° C. Then EtMgBr (3 M, 1.67 mL) was added to the reaction over 1.5 hours. After addition was complete, the reaction mixture was quenched with a saturated solution of $NH_4Cl$. After stirring at room temperature for an additional 30 minutes, the mixture was filtered through a pad of Celite, transferred to a separatory funnel, and diluted with ethyl acetate (250 mL). The layers were separated and the aqueous was extracted with ethyl acetate (50 mL×3). The combined organic extracts were dried over magnesium sulfate, filtered, concentrated under reduced pressure to give a residue. The residue was purified by prep-HPLC (TFA condition). Compound 1-[(R)-(dibenzylamino)-(4-fluorophenyl)methyl]cyclopropanol (269 mg, 32% yield) was obtained as a colorless oil. LCMS ($ESI^+$): m/z 362.10 $[M+H]^+$.

Step 3: (R)-1-(amino(4-fluorophenyl)methyl)cyclopropanol 65-4

To a solution of 1-[(R)-(dibenzylamino)-(4-fluorophenyl) methyl]cyclopropanol (80 mg, 221 umol) in EtOH (3 mL) was added Pd/C (10%, 50 mg) under $N_2$ atmosphere. The suspension was degassed and purged with $H_2$ for 3 times. The mixture was stirred under $H_2$ (35 Psi) at 25° C. for 20 hr. After 20 hours, Celite was added and the slurry was filtered. The filter cake was washed with ethanol (25 mL×5), the combined filtrate was added 4.0 M HCl/dioxane (0.12 mL) and concentrated, the residue was triturated with EtOAc (1 mL). Compound 1-[(R)-amino-(4-fluorophenyl)methyl]cyclopropanol (22 mg, crude, HCl) was obtained as a white solid. LCMS ($ESI^+$): m/z 182.1 $[M+H]^+$.

Step 4: 2-(2,6-dioxopiperidin-3-yl)-N—((R)-(4-fluorophenyl)(1-hydroxycyclopropyl)methyl)-1-oxoisoindoline-5-carboxamide compound 65

The compounds were prepared according to similar procedure as described for compound 1.

Compound 65:

$^1H$ NMR (400 MHz, DMSO-$d_6$) δ 11.02 (br s, 1H), 8.86 (d, J=8.0 Hz, 1H), 8.11 (s, 1H), 8.03 (d, J=8.0 Hz, 1H), 7.84 (d, J=8.0 Hz, 1H), 7.55-7.47 (m, 2H), 7.15 (t, J=8.8 Hz, 2H), 5.55 (s, 1H), 5.18-5.10 (m, 1H), 4.85 (d, J=8.8 Hz, 1H), 4.60-4.48 (m, 1H), 4.45-4.36 (m, 1H), 2.98-2.85 (m, 1H), 2.61 (d, J=17.2 Hz, 1H), 2.41 (d, J=4.4 Hz, 1H), 2.08-1.97 (m, 1H), 0.86-0.75 (m, 1H), 0.72-0.60 (m, 3H)). LCMS ($ESI^+$): m/z 452.1 $[M+H]^+$.

Example 13

Preparation of Compound 76 and Compound 77: N—((*S)-(5-chloropyridin-2-yl)(cyclobutyl)methyl)-2-(2,6-dioxopiperidin-3-yl)-1-oxoisoindoline-5-carboxamide and N—((*R)-(5-chloropyridin-2-yl)(cyclobutyl)methyl)-2-(2,6-dioxopiperidin-3-yl)-1-oxoisoindoline-5-carboxamide Scheme 11

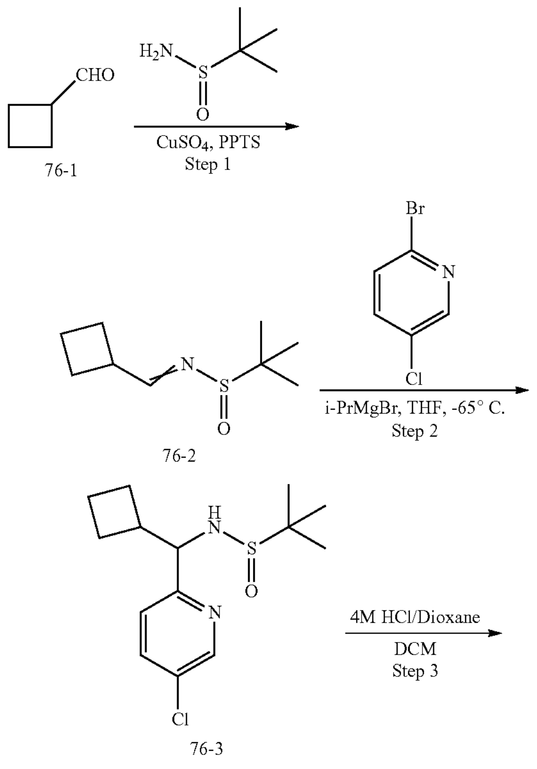

-continued

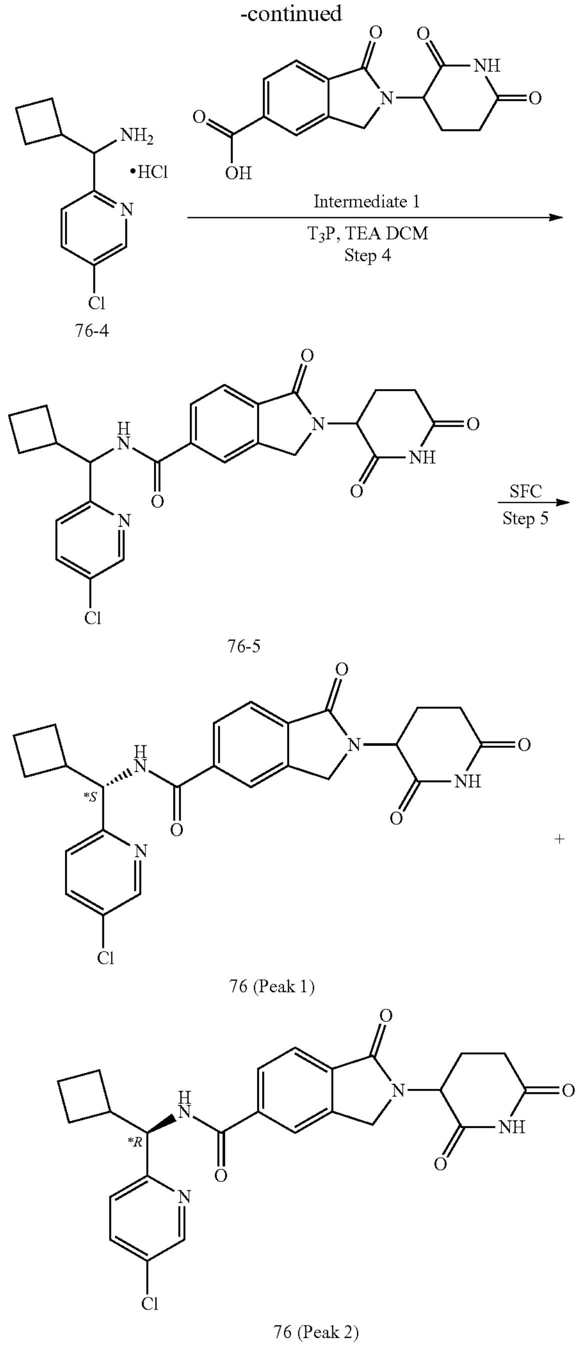

Step 1: Synthesis of N-(cyclobutylmethylene)-2-methylpropane-2-sulfinamide 76-2

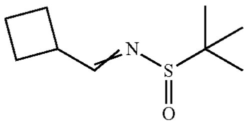

A mixture of cyclobutanecarbaldehyde (4.00 g, 47.6 mmol), 2-methylpropane-2-sulfinamide (5.19 g, 42.8 mmol), $CuSO_4$ (15.2 g, 95.1 mmol) and PPTS (1.20 g, 4.76 mmol) in DCM (10 mL) was degassed and purged with $N_2$ for 3 times. The mixture was stirred at 20° C. for 3 h under $N_2$ atmosphere. The mixture was filtered and the filtrate was concentrated under reduced pressure to remove DCM. The residue was purified by flash silica gel chromatography (ISCO®; 80 g SepaFlash® Silica Flash Column, Eluent of 0~10% Ethyl acetate/Petroleum ether gradient @ 40 mL/min). Compound N-(cyclobutylmethylene)-2-methyl-propane-2-sulfinamide (8.00 g, 89.8% yield) was obtained as a colorless oil.

$^1$HNMR (400 MHz, DMSO-$d_6$) δ 7.99 (d, J=4.4 Hz, 1H), 3.43-3.35 (m, 1H), 2.26-2.02 (m, 5H), 1.90-1.79 (m, 1H), 1.11 (s, 9H).

Step 2: Synthesis of N-((5-chloropyridin-2-yl)(cyclobutyl)methyl)-2-methylpropane-2-sulfinamide 76-3

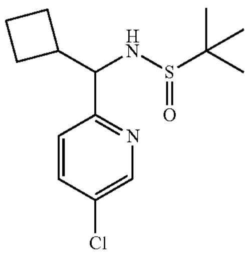

To a solution of 2-bromo-5-chloro-pyridine (9.25 g, 48.1 mmol) in THE (15 mL) was added bromo(isopropyl)magnesium (2.8 M, 17.2 mL) at −65° C. under $N_2$ atmosphere. The mixture was stirred at 20° C. for 2 h. The crude (5-chloropyridin-2-yl)magnesium bromide solution was added dropwise to the mixture of N-(cyclobutylmethylene)-2-methylpropane-2-sulfinamide (2.00 g, 10.7 mmol) in THE (20 mL) at −78° C. under $N_2$ atmosphere. The mixture was stirred at 20° C. for 2 h. The reaction mixture was quenched with saturated $NH_4Cl$ (15 mL) at 0° C. and extracted with EA (25 mL×3). The combined organic layers were washed with brine (30 mL×2), dried over anhydrous $Na_2SO_4$, filtered and concentrated under reduced pressure to give a residue. The residue purified by flash silica gel chromatography (ISCO®; 20 g SepaFlash® Silica Flash Column, Eluent of 0~40% Ethyl acetate/Petroleum ether gradient @ 15 mL/min). Compound N-((5-chloropyridin-2-yl)(cyclobutyl)methyl)-2-methylpropane-2-sulfinamide (600 mg, 18.7% yield) was obtained as a colorless oil. LCMS ($ESI^+$): m/z 301.3 $[M+H]^+$.

Step 3: Synthesis (5-chloropyridin-2-yl)(cyclobutyl)methanamine 76-4

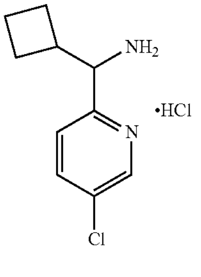

To a solution of N-((5-chloropyridin-2-yl)(cyclobutyl)methyl)-2-methylpropane-2-sulfinamide (150 mg, 499 umol) in DCM (3 mL) was added HCl/dioxane (4 M, 5.00 mL). The mixture was stirred at 20° C. for 1 h. The mixture was concentrated under reduce pressure. Compound (5-chloropyridin-2-yl)(cyclobutyl)methanamine (78 mg, crude, HCl salt) was obtained as a white solid, which was directly used for the next step without further purification. LCMS ($ESI^+$): m/z 197.2 $[M+H]^+$.

Step 4: Synthesis of N-((5-chloropyridin-2-yl)(cyclobutyl)methyl)-2-(2,6-dioxopiperidin-3-yl)-1-oxoisoindoline-5-carboxamide 76-5

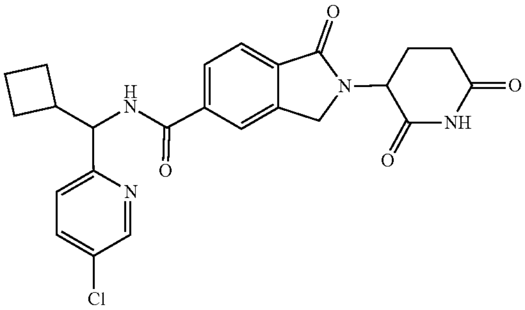

A mixture of (5-chloropyridin-2-yl)(cyclobutyl)methanamine (78 mg, 334 umol, HCl salt), 2-(2,6-dioxopiperidin-3-yl)-1-oxoisoindoline-5-carboxylic acid (106 mg, 368 umol), $T_3P$ (212 mg, 334 umol) in DCM (5 mL) was added TEA (67.3 mg, 669 umol). The mixture was stirred at 20° C. for 12 h under $N_2$ atmosphere. The mixture was concentrated under reduced pressure to remove DCM. Then the crude product was purified by prep-HPLC (FA condition). Compound N-((5-chloropyridin-2-yl)(cyclobutyl)methyl)-2-(2,6-dioxopiperidin-3-yl)-1-oxoisoindoline-5-carboxamide (60 mg, 26.0% yield) was obtained as a white solid. LCMS ($ESI^+$): m/z 467.13 $[M+H]^+$.

Step 5: Synthesis of N—((*S)-(5-chloropyridin-2-yl)(cyclobutyl)methyl)-2-(2,6-dioxopiperidin-3-yl)-1-oxoisoindoline-5-carboxamide (Compound 76, peak 1) & N—((*R)-(5-chloropyridin-2-yl)(cyclobutyl)methyl)-2-(2,6-dioxopiperidin-3-yl)-1-oxoisoindoline-5-carboxamide (Compound 77, peak 2)

76

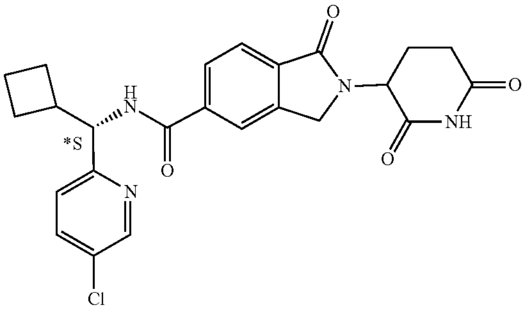

(Peak 1)

-continued

77

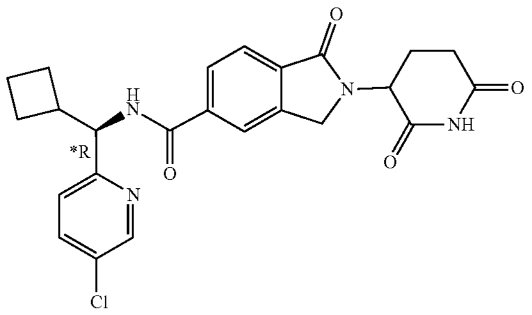

(Peak 2)

N-((5-chloropyridin-2-yl)(cyclobutyl)methyl)-2-(2,6-dioxopiperidin-3-yl)-1-oxoisoindoline-5-carboxamide (60 mg, 129 umol) was purified by SFC (Column: (s,s) WHELK-O1 (250 mm×30 mm, 5 um); Mobile phase: Neu-ETOH; B %: 50%, Flow Rate 80 mL/min). The first eluted peak during SFC separation was assigned as Compound 76 and second eluted peak was assigned as Compound 77. Compound N-((5-chloropyridin-2-yl)(cyclobutyl)methyl)-2-(2,6-dioxopiperidin-3-yl)-1-oxoisoindoline-5-carboxamide (Compound 76, peak 1) (15.62 mg, 26.0% yield) was obtained as a white solid. ($R_t$=3.577 min and 4.993 min; de %: 100.00%); $^1$HNMR (400 MHz, DMSO-$d_6$) 11.03 (br. s., 1H), 9.04-8.79 (m, 1H), 8.56 (d, J=2.4 Hz, 1H), 8.08 (s, 1H), 8.03-7.97 (m, 1H), 7.90 (dd, J=2.4, 8.4 Hz, 1H), 7.82 (d, J=7.6 Hz, 1H), 7.50 (d, J=8.4 Hz, 1H), 5.19-5.07 (m, 2H), 4.61-4.24 (m, 2H), 3.00-2.80 (m, 2H), 2.64-2.58 (m, 1H), 2.47-2.37 (m, 1H), 2.14-1.97 (m, 2H), 1.95-1.71 (m, 5H); LCMS (ESI$^+$): m/z 467.3 [M+H]$^+$.

Compound N-((5-chloropyridin-2-yl)(cyclobutyl)methyl)-2-(2,6-dioxopiperidin-3-yl)-1-oxoisoindoline-5-carboxamide (Compound 77, peak 2) (12.14 mg, 20.23% yield) was obtained as a white solid. ($R_t$=2.184 min and 2.833 min; de %: 100%); $^1$HNMR (400 MHz, DMSO-$d_6$) 11.03 (br. s., 1H), 8.98-8.86 (m, 1H), 8.61-8.49 (m, 1H), 8.08 (s, 1H), 8.02-7.97 (m, 1H), 7.93-7.87 (m, 1H), 7.84-7.79 (m, 1H), 7.53-7.48 (m, 1H), 5.20-5.05 (m, 2H), 4.57-4.34 (m, 2H), 2.97-2.81 (m, 2H), 2.65-2.58 (m, 1H), 2.45-2.37 (m, 1H), 2.11-1.99 (m, 2H), 1.92-1.72 (m, 5H); LCMS (ESI$^+$): m/z 467.2 [M+H]$^+$.

(Note: Compound 76 can be further separated by optimized SFC conditions to obtain two stereoisomers. So, Compound 76 was a mixture of two isomers with unknown stereochemistry.)

Example 14

The following compounds were prepared according to similar procedure as described for compound 76 and 77 with corresponding starting materials of aldehydes, Grignard reagents and the following coupling steps (Example 13).

For compounds 77, 78, 79, 80, and 81, the corresponding diastereomer intermediate was separated by prep-HPLC or SFC before the following step.

TABLE 5

| | | |
|---|---|---|
| 78 | 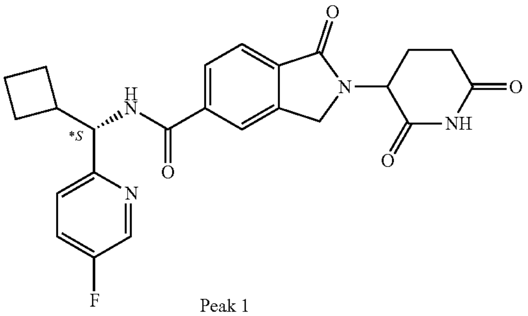 [SMILES: O=C1CCC(N2Cc3cc(C(=O)N[C@H](c4ccc(F)cn4)C4CCC4)ccc3C2=O)C(=O)N1] Peak 1 | N-((*S)-cyclobutyl(5-fluoropyridin-2-yl)methyl)-2-(2,6-dioxopiperidin-3-yl)-1-oxoisoindoline-5-carboxamide $^1$H NMR (400 MHz, DMSO-$d_6$) δ 11.01 (s, 1H), 8.89 (d, J = 8.0 Hz, 1H), 8.49 (d, J = 8.0 Hz, 1H), 8.06 (s, 1H), 7.98 (d, J = 8.4 Hz, 1H), 7.81 (d, J = 8.0 Hz, 1H), 7.72-7.65 (m, 1H), 7.55-7.49 (m, 1H), 5.17-5.08 (m, 2H), 4.55-4.48 (m, 1H), 4.43-4.34 (m, 1H), 2.98-2.92 (m, 1H), 2.57 (d, J = 6.4 Hz, 2H), 2.47-2.45 (m, 1H), 2.13-1.96 (m, 2H), 1.90-1.71 (m, 5H). LCMS (ESI+): m/z 451.3 [M + H]$^+$. Retention time: 2.706 min; SFC: Retention time: 2.888 min, 3.661 min. |
| 79 | 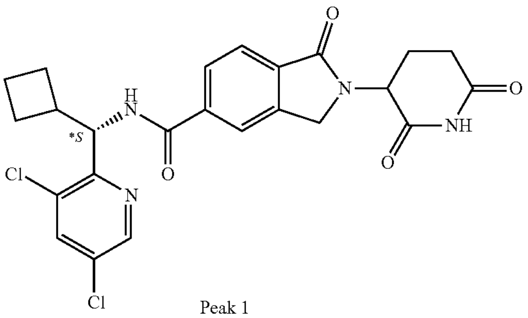 [SMILES: O=C1CCC(N2Cc3cc(C(=O)N[C@H](c4ncc(Cl)cc4Cl)C4CCC4)ccc3C2=O)C(=O)N1] Peak 1 | N-((*S)-cyclobutyl(3,5-dichloropyridin-2-yl)methyl)-2-(2,6-dioxopiperidin-3-yl)-1-oxoisoindoline-5-carboxamide $^1$H NMR (400 MHz, DMSO-$d_6$) δ 11.01 (s, 1H), 8.90 (d, J = 7.6 Hz, 1H), 8.60 (d, J = 2.0 Hz, 1H), 8.21 (d, J = 2.0 Hz, 1H), 8.05 (s, 1H), 7.97 (d, J = 3.6, 7.9 Hz, 1H), 7.79 (d, J = 8.0 Hz, 1H), 5.55 (d, J = 7.6, 9.6 Hz, 1H), 5.13 (d, J = 5.2, 13.2 Hz, 1H), 4.48 (s, 1H), 4.44-4.33 (m, 1H), 3.06-2.85 (m, 2H), 2.44-2.42 (m, 2H), 2.15-1.93 (m, 3H), 1.86-1.76 (m, 4H). LCMS (ESI+): m/z 451.3 [M + H]$^+$. Retention time: 1.711 min; SFC: Retention time: 1.413 min, 1.702 min. |

TABLE 5-continued

| | | |
|---|---|---|
| 80 | 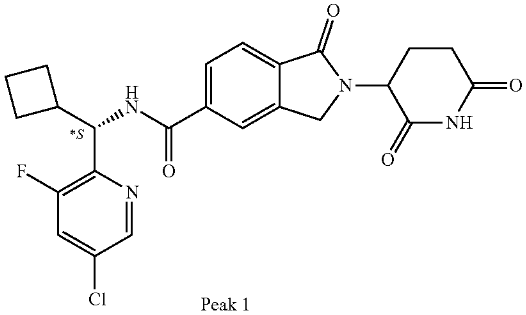 [SMILES: O=C1CCC(N2Cc3cc(C(=O)N[C@H](c4ncc(Cl)cc4F)C4CCC4)ccc3C2=O)C(=O)N1] Peak 1 | N-((*S)-(5-chloro-3-fluoropyridin-2-yl)(cyclobutyl)methyl)-2-(2,6-dioxopiperidin-3-yl)-1-oxoisoindoline-5-carboxamide $^1$HNMR (400 MHz, DMSO-$d_6$) 11.03 (br. s., 1H), 9.02-8.92 (m, 1H), 8.51-8.48 (m, 1H), 8.11-8.04 (m, 2H), 8.00-7.95 (m, 1H), 7.82-7.77 (m, 1H), 5.39-5.31 (m, 1H), 5.18-5.11 (m, 1H), 4.54-4.35 (m, 2H), 3.02-2.87 (m, 2H), 2.64-2.57 (m, 1H), 2.46-2.36 (m, 1H), 2.20-2.09 (m, 1H), 2.07-1.98 (m, 1H), 1.95-1.66 (m, 5H); LCMS (ESI$^+$): m/z 485.2 [M + H]$^+$, Retention time: 1.910 min; SFC Retention time: 1.251 min and 1.500 min. |
| 81 | 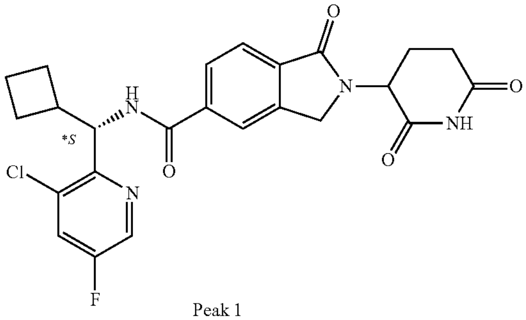 [SMILES: O=C1CCC(N2Cc3cc(C(=O)N[C@H](c4ncc(F)cc4Cl)C4CCC4)ccc3C2=O)C(=O)N1] Peak 1 | N-((*S)-(3-chloro-5-fluoropyridin-2-yl)(cyclobutyl)methyl)-2-(2,6-dioxopiperidin-3-yl)-1-oxoisoindoline-5-carboxamide $^1$HNMR (400 MHz, DMSO-$d_6$) 11.01 (br. s., 1H), 8.87 (d, J = 7.6 Hz, 1H), 8.59 (d, J = 2.4 Hz, 1H), 8.10-8.04 (m, 2H), 8.00-7.93 (m, 1H), 7.79 (d, J = 7.6 Hz, 1H), 5.64-5.52 (m, 1H), 5.22-5.06 (m, 1H), 4.58-4.30 (m, 2H), 3.02-2.87 (m, 2H), 2.64-2.60 (m, 1H), 2.45-2.40 (m, 1H), 2.11-1.94 (m, 3H), 1.86-1.75 (m, 4H); LCMS (ESI$^+$): m/z 485.3 [M + H]$^+$, Retention time: 3.298 min; SFC Retention time: 3.341 min and 4.428 min. |

Example 15

Preparation of Compound 82: N—((*S)-(5-chloropyridin-2-yl)(cyclobutyl)methyl)-2-((S)-2,6-dioxopiperidin-3-yl)-1-oxoisoindoline-5-carboxamide Scheme 12

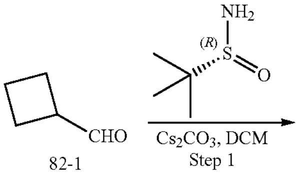

82-1

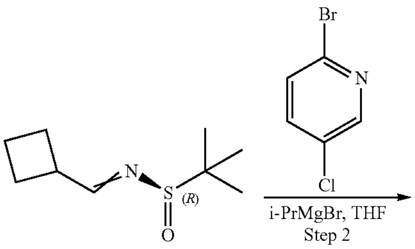

82-2

-continued

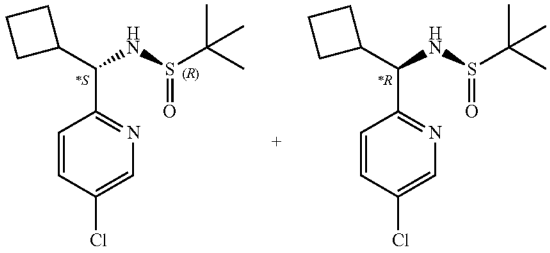

82-3
Major product

Minor product 82-3

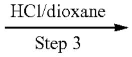

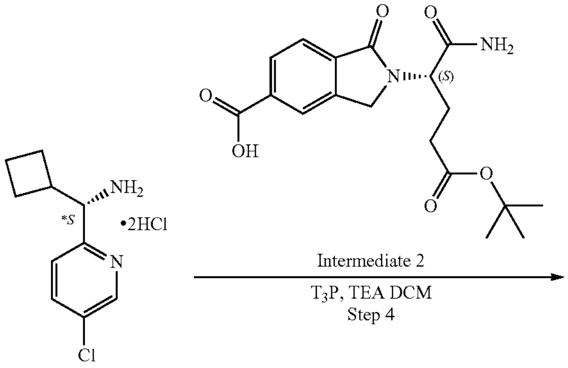

82-4

-continued

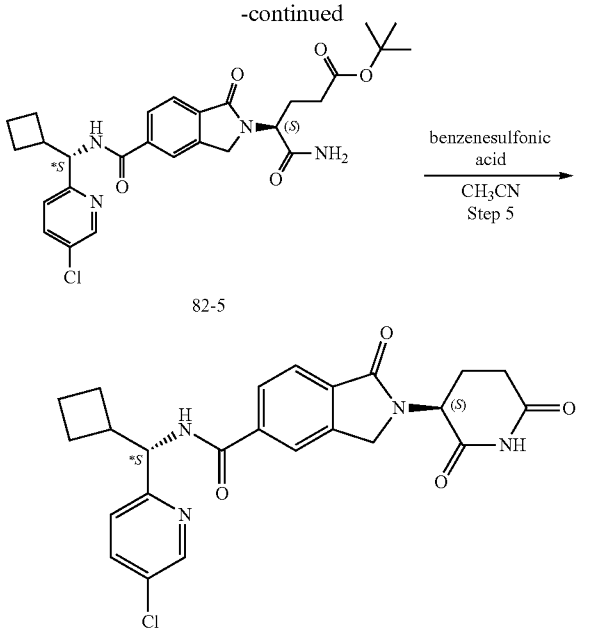

82-5

Compound 82

Step 1: Synthesis of (R)—N-(cyclobutylmethylene)-2-methylpropane-2-sulfinamide 82-2

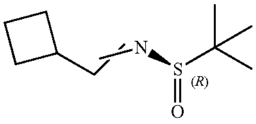

To a mixture of cyclobutanecarbaldehyde (10 g, 0.119 mol), (R)-2-methylpropane-2-sulfinamide (14.4 g, 0.119 mol) in DCM (100 mL) was added cesium carbonate (44.5 g, 0.137 mol). The mixture was stirred at 20° C. for 12 h under $N_2$ atmosphere. The mixture was filtered and the filtrate was concentrated under reduced pressure to remove DCM. The residue was purified by chromatography on a silica gel eluted with petroleum ether: ethyl acetate (from 0 to 10%) to give (R)—N-(cyclobutylmethylene)-2-methylpropane-2-sulfinamide (19 g, 85.0% yield) as a colorless oil.

$^1$H NMR (400 MHz, DMSO-$d_6$) δ 8.15-7.82 (m, 1H), 3.44-3.36 (m, 1H), 2.53-2.45 (m, 1H), 2.24-1.94 (m, 5H), 1.11 (s, 9H)

Step 2: Synthesis of (R)—N—((*S)-(5-chloropyridin-2-yl)(cyclobutyl)methyl)-2-methylpropane-2-sulfinamide 82-3

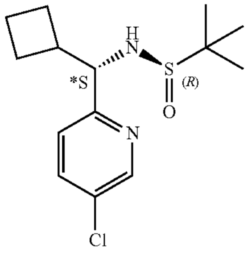

To a solution of 2-bromo-5-chloro-pyridine (28.9 g, 0.150 mol) in THE (100 mL) was added bromo(isopropyl)magnesium (3 M, 50 mL) at −65° C. under $N_2$ atmosphere. The mixture was stirred at 20° C. for 2 h. (R)—N-(cyclobutylmethylene)-2-methyl-propane-2-sulfinamide (10 g, 53.4 mmol) in THE (100 mL) was added to the mixture above at −65° under $N_2$ atmosphere. The mixture was stirred at 20° C. for 30 min. The reaction mixture was quenched with saturated $NH_4Cl$ (150 mL) at 0° C. and extracted with EA (100 mL×2). The combined organic layers were washed with brine (50 mL), dried over anhydrous $Na_2SO_4$, filtered and concentrated under reduced pressure to give a residue. The residue was purified by chromatography on a silica gel eluted with petroleum ether: ethyl acetate (from 50% to 100%). The crude product was purified by re-crystallization from PE (20 mL) at 0° C., the minor byproduct was removed in the process of re-crystallization which was confirmed by chiral analysis (CHIRALPAK IC-3 AS (150 mm×4.6 mm, 3 um), A: $CO_2$, B: Isopropanol (0.05% DEA), Flowrate: 2.5 mL/min), the compound of 82-3 de value was exceed to 98%. Compound (R)—N—((*S)-(5-chloropyridin-2-yl)(cyclobutyl)methyl)-2-methylpropane-2-sulfinamide (12.1 g, 31% yield) was obtained as a white solid.

$^1$H NMR (400 MHz, DMSO-$d_6$) δ 8.51 (d, J=2.4 Hz, 1H), 7.91 (dd, J=2.4, 8.4 Hz, 1H), 7.46 (d, J=8.4 Hz, 1H), 5.38 (d, J=6.8 Hz, 1H), 4.24 (dd, J=6.8, 9.6 Hz, 1H), 2.80-2.65 (m, 1H), 2.12-2.00 (m, 1H), 1.95-1.83 (m, 1H), 1.79-1.61 (m, 4H), 1.04 (s, 9H).

Step 3: Synthesis of (*S)-(5-chloropyridin-2-yl)(cyclobutyl)methanamine 82-4

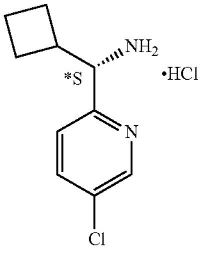

To a solution of (R)—N—((*S)-(5-chloropyridin-2-yl)(cyclobutyl)methyl)-2-methylpropane-2-sulfinamide (11 g, 36.6 mmol) in DCM (20 mL) was added HCl/dioxane (4 M, 30 mL). The mixture was stirred at 20° C. for 4 h. The mixture was concentrated under reduce pressure. The crude product was purified by re-crystallization from DCM (60 mL) at 20° C. Compound (*S)-(5-chloro-2-pyridyl)-cyclobutyl-methanamine (9 g, crude, HCl) was obtained as a white solid.

LCMS (ESI$^+$): m/z 197.1[M+H]$^+$.

Step 4: Synthesis of tert-butyl (S)-5-amino-4-(5-(((*S)-(5-chloropyridin-2-yl)(cyclobutyl)methyl)carbamoyl)-1-oxoisoindolin-2-yl)-5-oxopentanoate A mixture of (*S)-(5-chloro-2-pyridyl)-cyclobutyl-methanamine (3.25 g, 12.3 mmol, HCl salt), (S)-2-(1-amino-5-(tert-butoxy)-1,5-dioxopentan-2-yl)-1-oxoisoindoline-5-carboxylic acid (4.67 g, 12.9 mmol) and NMM (6.2 g, 61.3 mmol) in DMAC (50 mL) was added HATU (5.6 g, 14.7 mmol). The mixture was degassed and purged with $N_2$ for 3 times. The mixture was stirred at 25° C. for 12 h under $N_2$ atmosphere. The mixture was poured into saturated NaCl (100 mL), then filtered and washed with water (100 mL). Then the filter cake was dissolved in DCM (200 mL) and washed with saturated $NaHCO_3$ (100 mL), dried over anhydrous $Na_2SO_4$, filtered and concentrated under reduced pressure. Compound tert-butyl (S)-5-amino-4-(5-(((*S)-(5-chloropyridin-2-yl)(cyclobutyl)methyl)carbamoyl)-1-oxoisoindolin-2-yl)-5-oxopentanoate (6.5 g, 95.0% yield) was obtained as a white solid.

$^1$H NMR (400 MHz, DMSO-$d_6$) δ 8.96 (d, J=8.0 Hz, 1H), 8.61 (d, J=2.4 Hz, 1H), 8.12 (s, 1H), 8.03 (d, J=7.6 Hz, 1H), 7.96 (dd, J=2.4, 8.4 Hz, 1H), 7.84 (d, J=7.6 Hz, 1H), 7.67 (s, 1H), 7.56 (d, J=8.4 Hz, 1H), 7.29 (s, 1H), 5.30-5.11 (m, 1H), 4.81 (m, 1H), 4.75-4.52 (m, 2H), 2.98-2.86 (m, 1H), 2.27-2.12 (m, 4H), 1.98-1.78 (m, 6H), 1.39 (s, 9H); LCMS (ESI$^+$): m/z 541.4 [M+H]$^+$.

Step 5: Synthesis of Compound 82: N—((*S)-(5-chloropyridin-2-yl)(cyclobutyl)methyl)-2-((S)-2,6-dioxopiperidin-3-yl)-1-oxoisoindoline-5-carboxamide Compound 82

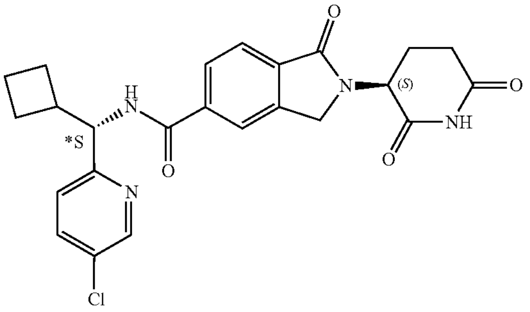

To a solution of tert-butyl (S)-5-amino-4-(5-(((*S)-(5-chloropyridin-2-yl)(cyclobutyl)methyl)carbamoyl)-1-oxoisoindolin-2-yl)-5-oxopentanoate (1.3 g, 2.4 mmol) in $CH_3CN$ (13 mL) was added benzenesulfonic acid (1.1 g, 7.21 mmol). The mixture was stirred at 70° C. for 14 h under $N_2$ atmosphere. The mixture was diluted with DCM (60 mL) and washed three times with saturated $NaHCO_3$ (30 mL×2), then washed with $H_2O$ (30 mL*2), dried over anhydrous $Na_2SO_4$, filtered and concentrated under reduced pressure to afford the crude product. Then the crude product was triturated with EA (5 mL) and then MTBE (5 mL) at 25° C. for 0.5 h. Compound N—((*S)-(5-chloropyridin-2-yl)(cyclobutyl)methyl)-2-((S)-2,6-dioxopiperidin-3-yl)-1-oxoisoindoline-5-carboxamide (0.79 g, 87% yield, 99% purity) was obtained as a white solid. $^1$H NMR (400 MHz, DMSO-$d_6$) δ 11.01 (s, 1H), 8.91 (d, J=8.0 Hz, 1H), 8.57-8.52 (m, 1H), 8.06 (s, 1H), 8.02-7.95 (m, 1H), 7.91-7.87 (m, 1H), 7.81 (d, J=8.0 Hz, 1H), 7.49 (d, J=8.4 Hz, 1H), 5.19-5.05 (m, 2H), 4.57-4.34 (m, 2H), 2.97-2.81 (m, 2H), 2.65-2.56 (m, 1H), 2.45-2.35 (m, 1H), 2.12-1.97 (m, 2H), 1.91-1.71 (m, 5H); LCMS (ESI$^+$): m/z 467.2 [M+H]$^+$, Retention time: 4.028 min; SFC Retention time: 4.593 min.

Example 16

Preparation of Compound 83: N—((*S)-cyclobutyl(3-(4-fluorophenyl)pyridin-2-yl)methyl)-2-(2,6-dioxopiperidin-3-yl)-1-oxoisoindoline-5-carboxamide Scheme 13

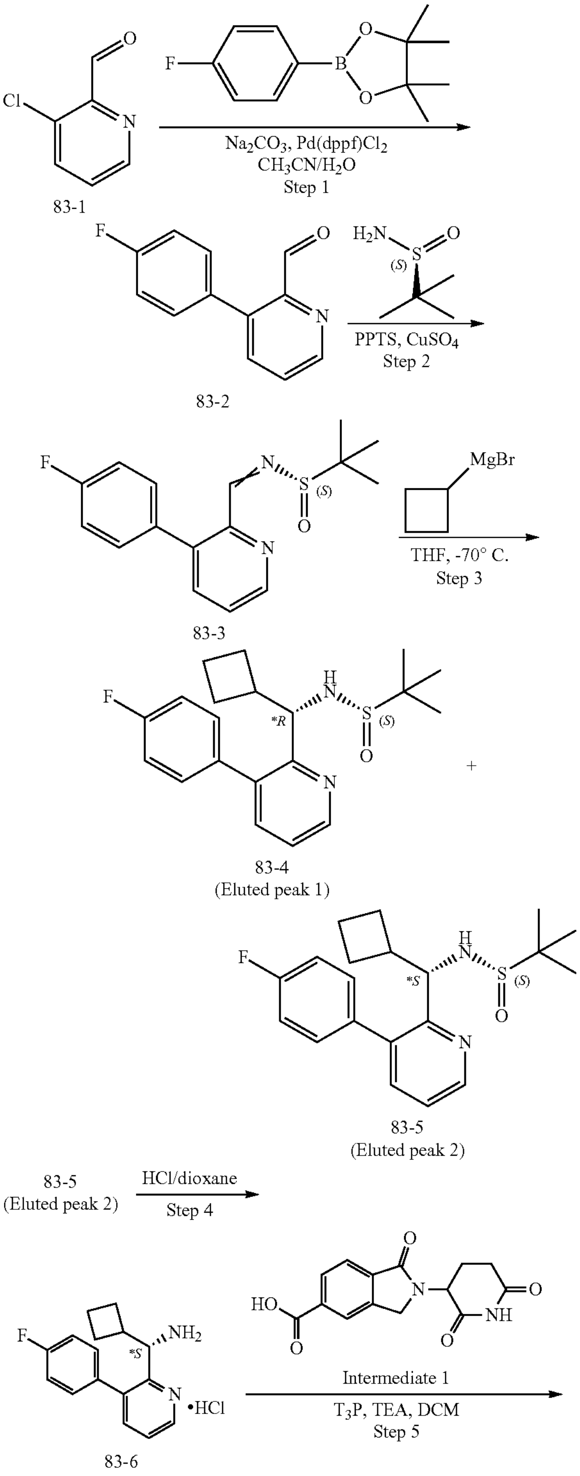

-continued

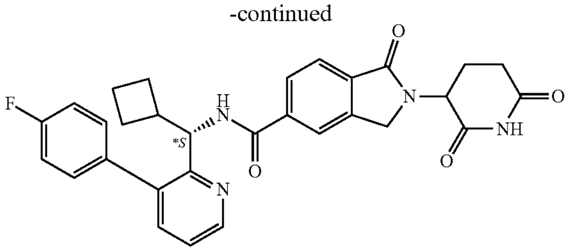

Compound 83

Step 1: Synthesis of 3-(4-fluorophenyl)picolinaldehyde 83-2

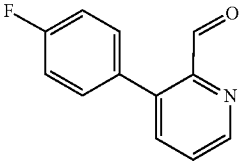

A mixture of 3-chloropicolinaldehyde (3.00 g, 21.2 mmol), 2-(4-fluorophenyl)-4,4,5,5-tetramethyl-1,3,2-dioxaborolane (5.65 g, 25.4 mmol), $Na_2CO_3$ (6.74 g, 63.6 mmol) and Pd(dppf)$Cl_2$ (1.55 g, 2.12 mmol) in $H_2O$ (6 mL) and $CH_3CN$ (30 mL) was degassed and purged with $N_2$ for 3 times, and then the mixture was stirred at 100° C. for 12 h under $N_2$ atmosphere. The reaction mixture was poured into water (10 mL) at 20° C. and extracted with EA (25 mL*3). The combined organic layers were washed with brine (30 mL×2), dried over anhydrous $Na_2SO_4$, filtered and concentrated under reduced pressure to give a residue. The residue was purified by flash silica gel chromatography (ISCO®; 40 g SepaFlash® Silica Flash Column, Eluent of 0~100% Ethyl acetate/Petroleum ether gradient @ 40 mL/min). Compound 3-(4-fluorophenyl) pyridine-2-carbaldehyde (4.20 g, 98.5% yield) was obtained as a colorless oil. $^1$HNMR (400 MHz, DMSO-$d_6$) δ 10.06-9.93 (m, 1H), 8.83 (dd, J=1.6, 4.4 Hz, 1H), 7.92 (dd, J=1.2, 7.6 Hz, 1H), 7.73 (dd, J=4.4, 7.6 Hz, 1H), 7.57-7.46 (m, 2H), 7.36-7.28 (m, 2H).

Step 2: Synthesis of (S)—N-((3-(4-fluorophenyl) pyridin-2-yl)methylene)-2-methylpropane-2-sulfinamide 83-3

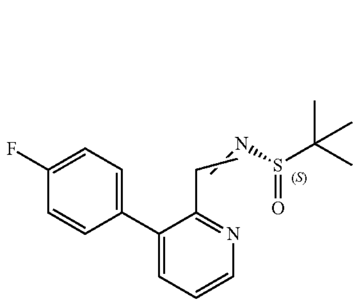

A mixture of 3-(4-fluorophenyl)picolinaldehyde (4.20 g, 21.0 mmol), (S)-2-methylpropane-2-sulfinamide (2.29 g, 18.9 mmol), PPTS (527 mg, 2.10 mmol), $CuSO_4$ (6.70 g, 41.9 mmol) in DCM (40 mL) was degassed and purged with $N_2$ for 3 times, and then the mixture was stirred at 20° C. for 12 h under $N_2$ atmosphere. The mixture was filtered and the filtrate was concentrated under reduced pressure to remove DCM. The residue was purified by flash silica gel chromatography (ISCO®; 40 g SepaFlash® Silica Flash Column, Eluent of 0~50% Ethyl acetate/Petroleum ether gradient @ 20 mL/min). Compound (S)—N-((3-(4-fluorophenyl)pyridin-2-yl)methylene)-2-methylpropane-2-sulfinamide (1.20 g, 18.8% yield) was obtained as a colorless oil. $^1$HNMR (400 MHz, DMSO-$d_6$) δ 8.80 (dd, J=1.6, 4.4 Hz, 1H), 8.53-8.37 (m, 1H), 7.89 (dd, J=1.6, 7.6 Hz, 1H), 7.65 (dd, J=4.4, 7.6 Hz, 1H), 7.51-7.41 (m, 2H), 7.37-7.25 (m, 2H), 1.06 (s, 9H).

Step 3: Synthesis of (*S)—N-(cyclobutyl(3-(4-fluorophenyl)pyridin-2-yl)methyl)-2-methylpropane-2-sulfinamide 83-4

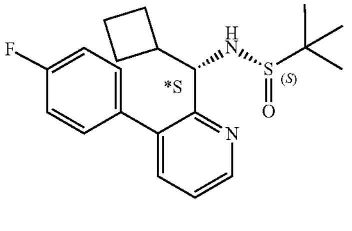

Eluated peak 2

To a solution of (S)—N-((3-(4-fluorophenyl)pyridin-2-yl) methylene)-2-methylpropane-2-sulfinamide (1.17 g, 3.84 mmol) in THF (10 mL) was added bromo(cyclobutyl)magnesium (0.5 M, 15.4 mL). The mixture was stirred at −70° C. for 3 h under $N_2$ atmosphere. The reaction mixture was quenched with saturated $NH_4Cl$ (20 mL) at 0° C. and extracted with ethyl acetate (25 mL×3). The combined organic layers were washed with brine (30 mL×2), dried over anhydrous $Na_2SO_4$, filtered and concentrated under reduced pressure to give a residue. The residue was purified by flash silica gel chromatography (ISCO®; 20 g SepaFlash® Silica Flash Column, Eluent of 0~50% Ethyl acetate/Petroleum ether gradient @ 40 mL/min) to give the desired the eluated peak 2, which was considered as compound 83-4 and the isomer was detected by chiral HPLC to make sure the retention time. Compound (*S)—N-(cyclobutyl(3-(4-fluorophenyl)pyridin-2-yl)methyl)-2-methylpropane-2-sulfinamide (45 mg, 3.25% yield) was obtained as a white solid. LCMS (ESI$^+$). m/z 363.3 [M+H]$^+$.

83-6

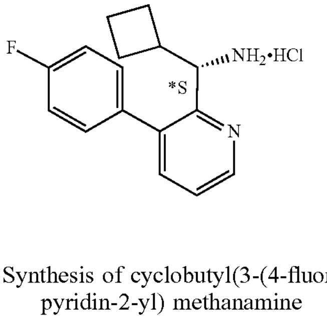

Step 4: Synthesis of cyclobutyl(3-(4-fluorophenyl) pyridin-2-yl) methanamine

To a solution of (*S)—N-(cyclobutyl(3-(4-fluorophenyl) pyridin-2-yl)methyl)-2-methylpropane-2-sulfinamide (40 mg, 111 umol) in DCM (10 mL) was added HCl/dioxane (4 M, 665 uL). The mixture was stirred at 20° C. for 1 h. The reaction mixture was concentrated under reduced pressure. Compound (*S)-cyclobutyl(3-(4-fluorophenyl) pyridin-2-yl) methanamine (32 mg, HCl salt, crude) was obtained as a white solid, which was used directly in the next step without further purification.

Step 5: Synthesis of N—((*S)-cyclobutyl(3-(4-fluorophenyl)pyridin-2-yl)methyl)-2-(2,6-dioxopiperidin-3-yl)-1-oxoisoindoline-5-carboxamide (compound 83)

Compound 83

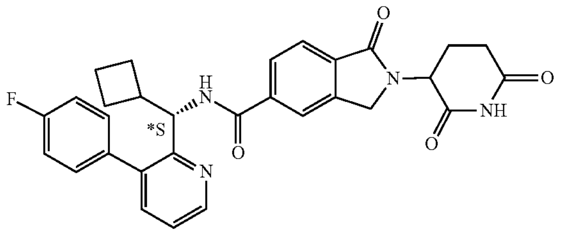

A mixture of cyclobutyl(3-(4-fluorophenyl) pyridin-2-yl) methanamine (32.0 mg, 109 umol, HCl), 2-(2,6-dioxopiperidin-3-yl)-1-oxoisoindoline-5-carboxylic acid (34.7 mg, 120 umol), $T_3P$ (69.6 mg, 109 umol) in DCM (5 mL) was added TEA (22.1 mg, 219 umol). The mixture was stirred at 20° C. for 12 h. The mixture was concentrated under reduced pressure to remove DCM. The residue was purified by prep-HPLC (FA condition). Compound N—((*S)-cyclobutyl(3-(4-fluorophenyl)pyridin-2-yl)methyl)-2-(2,6-dioxopiperidin-3-yl)-1-oxoisoindoline-5-carboxamide (9.66 mg, 16.8% yield) was obtained as a white solid.

$^1$HNMR (400 MHz, DMSO-$d_6$) 11.03 (br. s., 1H), 8.81 (d, J=7.6 Hz, 1H), 8.58 (d, J=4.2 Hz, 1H), 8.08 (s, 1H), 8.00 (d, J=7.2 Hz, 1H), 7.80 (d, J=7.6 Hz, 1H), 7.72 (dd, J=5.6, 8.4 Hz, 2H), 7.61 (dd, J=1.6, 7.6 Hz, 1H), 7.42-7.31 (m, 3H), 5.40-5.29 (m, 1H), 5.15 (dd, J=5.2, 13.2 Hz, 1H), 4.57-4.31 (m, 2H), 2.98-2.88 (m, 1H), 2.82-2.74 (m, 1H), 2.66 (d, J=17.2 Hz, 1H), 2.43-2.37 (m, 1H), 2.07-1.93 (m, 2H), 1.70-1.48 (m, 4H), 1.27-1.21 (m, 1H); LCMS (ESI$^+$): m/z 527.3 $[M+H]^+$.

Example 17

Preparation of Compound 84: N—((*S)-cyclobutyl (3-(1-methyl-1H-pyrazol-4-yl)pyridin-2-yl)methyl)-2-((S)-2,6-dioxopiperidin-3-yl)-1-oxoisoindoline-5-carboxamide Scheme 14

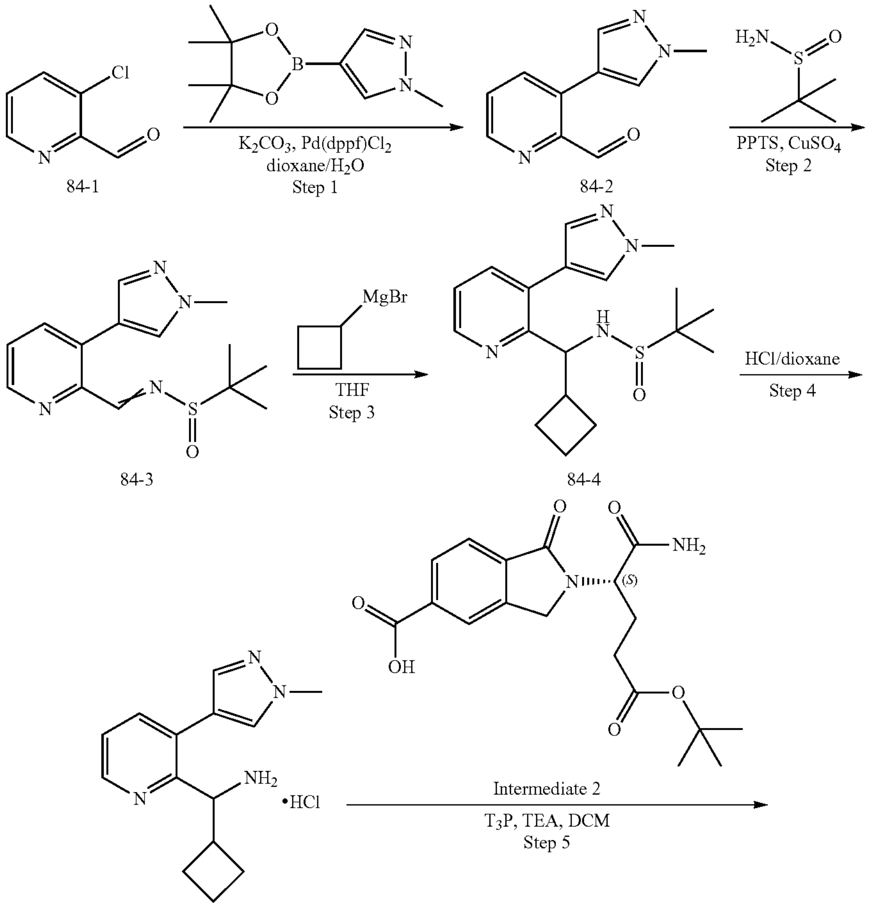

84-5

-continued

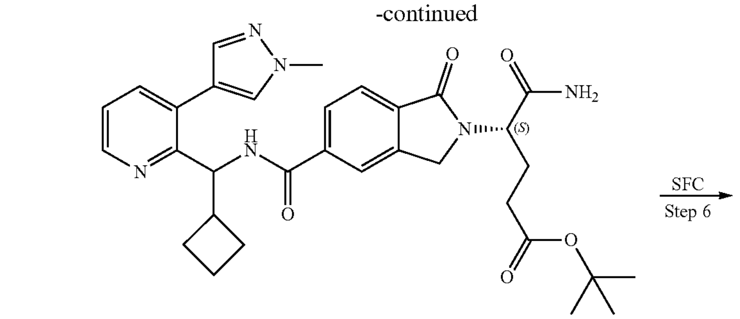

84-6

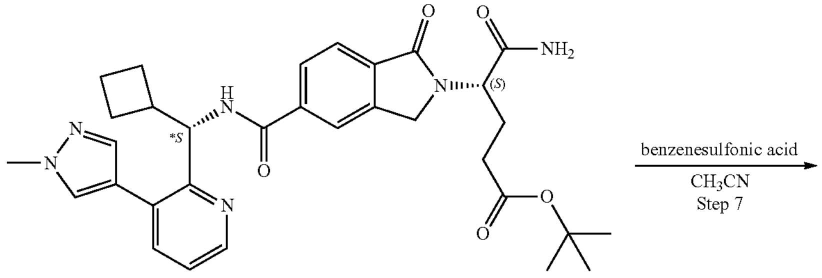

84-7
Peak 2

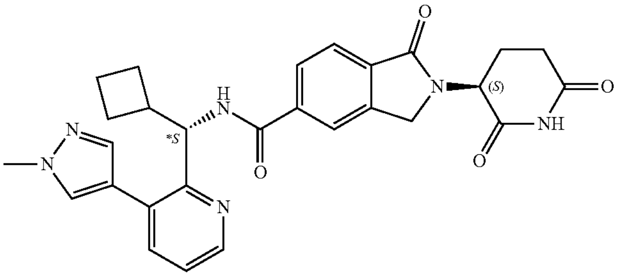

Compound 84

Step 1: Synthesis of 3-(1-methyl-1H-pyrazol-4-yl)picolinaldehyde 84-2

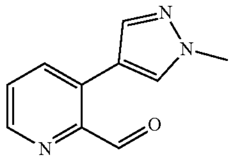

To a mixture of 3-chloropyridine-2-carbaldehyde (2.00 g, 14.1 mmol), 1-methyl-4-(4,4,5,5-tetramethyl-1,3,2-dioxaborolan-2-yl) pyrazole (3.53 g, 17.0 mmol), $K_2CO_3$ (3.91 g, 28.3 mmol) in dioxane (35 mL) and water (7 mL) was added Pd(dppf)$Cl_2$ (517 mg, 706 umol) at 25° C. under $N_2$ atmosphere. The mixture was stirred at 80° C. for 6 h under $N_2$ atmosphere. The reaction mixture was poured into water (20 mL) and extracted with EA (40 mL×2). The combined organic layers were dried over anhydrous $Na_2SO_4$, filtered and concentrated under reduced pressure. The residue was purified by flash silica gel chromatography (ISCO®; 40 g SepaFlash® Silica Flash Column, Eluent of 0~100% Ethyl acetate/Petroleum ether gradient @ 40 mL/min). Compound 3-(1-methylpyrazol-4-yl) pyridine-2-carbaldehyde (1.7 g, 64.28% yield) was obtained as a brown solid. $^1$H NMR (400 MHz, DMSO-$d_6$) δ 10.18-10.05 (m, 1H), 8.69 (dd, J=1.6, 4.4 Hz, 1H), 8.12 (s, 1H), 8.00 (dd, J=1.2, 7.6 Hz, 1H), 7.78 (s, 1H), 7.66 (m, 1H), 3.91 (m, 3H).

Step 2: Synthesis of 2-methyl-N-((3-(1-methyl-1H-pyrazol-4-yl) pyridin-2-yl)methylene)propane-2-sulfinamide 84-3

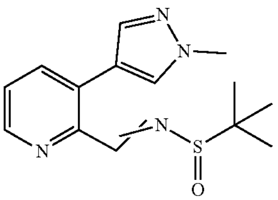

To a mixture of 3-(1-methylpyrazol-4-yl) pyridine-2-carbaldehyde (1.60 g, 8.55 mmol), $CuSO_4$ (2.73 g, 17.1 mmol), PPTS (215 mg, 855 umol) in DCM (10 mL) was added 2-methylpropane-2-sulfinamide (1.55 g, 12.8 mmol). The mixture was stirred at 25° C. for 12 h. The reaction mixture was filtered and concentrated under reduced pressure. The residue was purified by flash silica gel chromatography (ISCO®; 40 g SepaFlash® Silica Flash Column, Eluent of 0~20% Ethyl acetate/Petroleum ether gradient @ 20 mL/min). Compound 2-methyl-N-((3-(1-methyl-1H-pyrazol-4-yl)pyridin-2-yl)methylene)propane-2-sulfinamide (1.70 g, 94.44% yield) was obtained as a yellow oil.

$^1$HNMR (400 MHz, DMSO-$d_6$) δ 8.73-8.61 (m, 1H), 8.73-8.61 (m, 1H), 8.01 (s, 1H), 7.93 (dd, J=1.6, 8.0 Hz, 1H), 7.66-7.47 (m, 2H), 3.91 (s, 3H), 1.17 (s, 9H).

Step 3: Synthesis of N-(cyclobutyl(3-(1-methyl-1H-pyrazol-4-yl) pyridin-2-yl)methyl)-2-methylpropane-2-sulfinamide 84-4

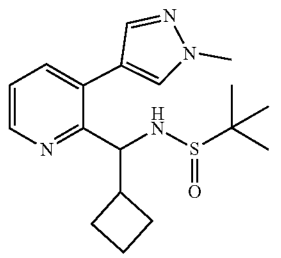

To a solution of 2-methyl-N-((3-(1-methyl-1H-pyrazol-4-yl)pyridin-2-yl)methylene)propane-2-sulfinamide (1.26 g, 3.04 mmol) in THE (10 mL) was added bromo(cyclobutyl) magnesium (0.5 M, 9.12 mL) at −70° C. under $N_2$ atmosphere. The mixture was stirred at 20° C. for 2 h. The reaction mixture was quenched with water (10 mL) at 0° C. and extracted with EA (25 mL×3). The combined organic layers were washed with brine (30 mL×2), dried over anhydrous $Na_2SO_4$, filtered and concentrated under reduced pressure to give a residue. The residue was purified by flash silica gel chromatography (ISCO®; 20 g SepaFlash® Silica Flash Column, Eluent of 0~30% Ethyl acetate/Petroleum ether gradient @ 20 mL/min to give N-(cyclobutyl(3-(1-methyl-1H-pyrazol-4-yl)pyridin-2-yl)methyl)-2-methylpropane-2-sulfinamide (150 mg, 14.2% yield) as a colorless oil.

$^1$H NMR (400 MHz, $CDCl_3$) δ 8.76 (d, J=5.6 Hz, 1H), 7.91 (d, J=7.6 Hz, 1H), 7.71 (s, 1H), 7.62 (s, 1H), 7.52 (dd, J=5.6, 7.6 Hz, 1H), 5.79 (d, J=8.4 Hz, 1H), 4.79-4.51 (m, 1H), 4.00 (s, 3H), 2.88-2.69 (m, 1H), 2.12-2.02 (m, 1H), 1.84-1.72 (m, 2H), 1.70-1.45 (m, 3H), 1.19 (s, 9H).

Step 4: Synthesis of cyclobutyl(3-(1-methyl-1H-pyrazol-4-yl) pyridin-2-yl) methanamine 84-5

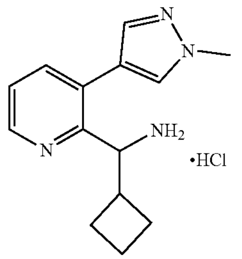

To a solution of N-(cyclobutyl(3-(1-methyl-1H-pyrazol-4-yl)pyridin-2-yl)methyl)-2-methylpropane-2-sulfinamide (100 mg, 288 umol) in DCM (3 mL) was added HCl/dioxane (4 M, 1.08 mL). The mixture was stirred at 20° C. for 1 h. The mixture was concentrated under reduce pressure. Compound cyclobutyl(3-(1-methyl-1H-pyrazol-4-yl)pyridin-2-yl)methanamine (150 mg, crude, HCl) was obtained as a white solid, which was used directly for next step without further purification. LCMS ($ESI^+$): m/z 242.9 $[M+H]^+$.

Step 5: Synthesis of tert-butyl (4S)-5-amino-4-(5-((cyclobutyl(3-(1-methyl-1H-pyrazol-4-yl) pyridin-2-yl) methyl) carbamoyl)-1-oxoisoindolin-2-yl)-5-oxopentanoate 84-6

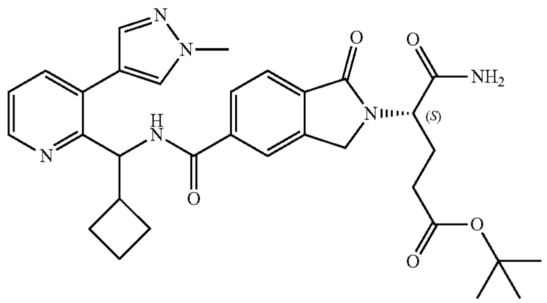

To a solution of cyclobutyl(3-(1-methyl-1H-pyrazol-4-yl) pyridin-2-yl)methanamine (150 mg, 538 umol, HCl salt) and (S)-2-(1-amino-5-(tert-butoxy)-1,5-dioxopentan-2-yl)-1-oxoisoindoline-5-carboxylic acid (214 mg, 592 umol) in DCM (10 mL) was added TEA (109 mg, 1.08 mmol) and $T_3P$ (342 mg, 538 umol). The mixture was stirred at 20° C. for 1 h. The mixture was concentrated under reduce pressure to give a residue. The mixture was concentrated under reduce pressure to give a residue. The residue was purified by flash silica gel chromatography (ISCO®; 20 g SepaFlash® Silica Flash Column, Eluent of 0~100% Ethyl acetate/Petroleum ether gradient @ 15 mL/min). Compound tert-butyl (4S)-5-amino-4-(5-((cyclobutyl(3-(1-methyl-1H-pyrazol-4-yl) pyridin-2-yl) methyl) carbamoyl)-1-oxoisoindolin-2-yl)-5-oxopentanoate (120 mg, 38.01% yield) was obtained as a white solid. LCMS ($ESI^+$): m/z 586.9 $[M+H]^+$.

Step 6: Synthesis of tert-butyl (S)-5-amino-4-(5-(((*S)-cyclobutyl(3-(1-methyl-1H-pyrazol-4-yl)pyridin-2-yl)methyl)carbamoyl)-1-oxoisoindolin-2-yl)-5-oxopentanoate 84-7

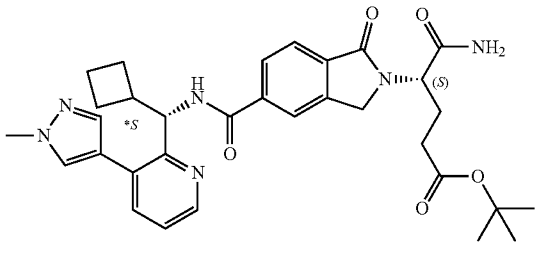

Peak 2

Tert-butyl (4S)-5-amino-4-(5-((cyclobutyl(3-(1-methyl-1H-pyrazol-4-yl) pyridin-2-yl) methyl) carbamoyl)-1-oxoisoindolin-2-yl)-5-oxopentanoate (120 mg, 256 umol) was purified by prep-SFC (Column: Phenomenex-Cellulose-2 (250 mm×30 mm, 10 um), Condition: 0.1% $NH_3H_2O$ MeOH, Begin B: 50%, Flow Rate: 80 ml/min). Compound tert-butyl (S)-5-amino-4-(5-((*R)-(cyclobutyl(3-(1-methyl-1H-pyrazol-4-yl)pyridin-2-yl)methyl)carbamoyl)-1-oxoisoindolin-2-yl)-5-oxopentanoate (75 mg, 50% yield) was obtained as with a white solid, considered as peak 1. ($R_t$=2.295 min; de %: 100%); Compound tert-butyl (S)-5-amino-4-(5-(((*S)-cyclobutyl(3-(1-methyl-1H-pyrazol-4-yl)pyridin-2-yl)methyl)carbamoyl)-1-oxoisoindolin-2-yl)-5-oxopentanoate (70 mg, 46.67% yield) was obtained as a white solid, considered as peak 2. ($R_t$=3.495 min; de %: 99.4%)

Step 7: Synthesis of N—((*S)-cyclobutyl(3-(1-methyl-1H-pyrazol-4-yl)pyridin-2-yl)methyl)-2-((S)-2,6-dioxopiperidin-3-yl)-1-oxoisoindoline-5-carboxamide (Compound 84)

Compound 84

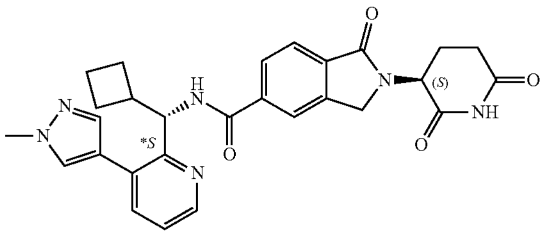

A mixture of tert-butyl (S)-5-amino-4-(5-(((*S)-cyclobutyl(3-(1-methyl-1H-pyrazol-4-yl)pyridin-2-yl)methyl) carbamoyl)-1-oxoisoindolin-2-yl)-5-oxopentanoate (70 mg, 119 umol) and benzenesulfonic acid (56.6 mg, 358 umol) in $CH_3CN$ (10 mL) was degassed and purged with $N_2$ for 3 times. The mixture was stirred at 90° C. for 3 h under $N_2$ atmosphere. The mixture was concentrated under reduce pressure. The crude product was purified by reversed-phase HPLC (FA condition). Compound N—((*S)-cyclobutyl(3-(1-methyl-1H-pyrazol-4-yl)pyridin-2-yl)methyl)-2-((S)-2,6-dioxopiperidin-3-yl)-1-oxoisoindoline-5-carboxamide (18.09 mg, 29.6% yield, 100% purity) was obtained as a white solid.

$^1H$ NMR (400 MHz, DMSO-$d_6$) δ 11.01 (br. s., 1H), 8.78 (d, J=8.4 Hz, 1H), 8.49 (d, J=3.6 Hz, 1H), 8.15 (s, 1H), 8.09 (s, 1H), 8.03-7.99 (m, 1H), 7.88 (s, 1H), 7.80 (d, J=7.6 Hz, 1H), 7.69-7.62 (m, 1H), 7.33-7.24 (m, 1H), 5.70-5.60 (m, 1H), 5.18-5.08 (m, 1H), 4.57-4.34 (m, 2H), 3.95 (s, 3H), 2.99-2.80 (m, 2H), 2.68-2.56 (m, 1H), 2.47-2.36 (m, 1H), 2.08-1.92 (m, 2H), 1.86-1.75 (m, 1H), 1.74-1.55 (m, 3H), 1.47-1.35 (m, 1H); LCMS ($ESI^+$): m/z 513.4 $[M+H]^+$, Retention time: 2.221 min; SFC Retention time: 3.581 min.

Example 18

Preparation of compound 85: N—((*R)-(3-chloro-5-fluoropyridin-2-yl)(1-fluorocyclobutyl)methyl)-2-(2,6-dioxopiperidin-3-yl)-1-oxoisoindoline-5-carboxamide Scheme 15

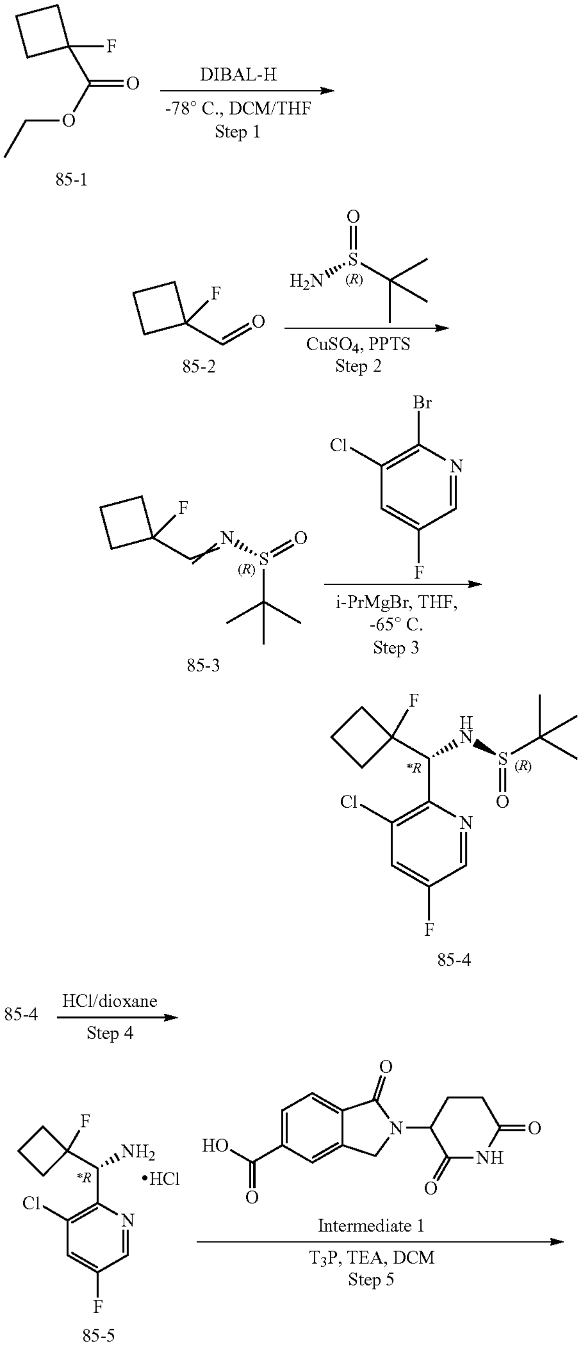

-continued

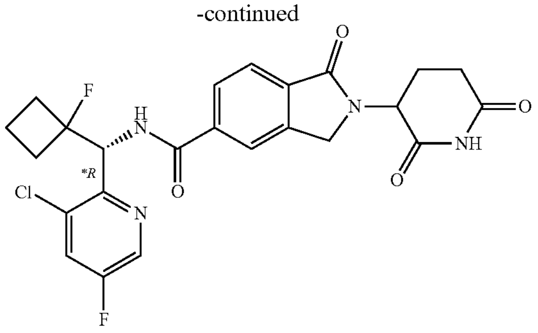

Compound 85

Step 1: Synthesis of 1-fluorocyclobutane-1-carbaldehyde 85-2

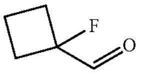

To a mixture of ethyl 1-fluorocyclobutanecarboxylate (4.00 g, 27.4 mmol) in DCM (40 mL) and THF (40 mL) was added DIBAL-H (1 M, 49.3 mL) dropwise at −78° C. under $N_2$ atmosphere. The mixture was stirred at −78° C. for 10 min under $N_2$ atmosphere. The mixture was quenched with water (2 mL), 15% NaOH (2 mL) and water (5 mL). Then it was stirred at 0° C. for 0.5 h and dried over anhydrous $Na_2SO_4$, filtered to give a crude residue. Compound 1-fluorocyclobutanecarbaldehyde (4 g, crude) was obtained as a yellow liquid, which was used into the next step without further purification.

Step 2: Synthesis of (R)—N-((1-fluorocyclobutyl)methylene)-2-methylpropane-2-sulfinamide 85-3

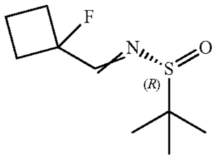

To a solution of 1-fluorocyclobutanecarbaldehyde (400 mg, 3.92 mmol, crude) and (R)-2-methylpropane-2-sulfinamide (950 mg, 7.83 mmol) in DCM (10 mL) was added PPTS (98.5 mg, 39.0 umol) and $CuSO_4$ (1.25 g, 7.83 mmol). The mixture was stirred at 20° C. for 12 h. The mixture was filtered and the filtrate was concentrated under reduce pressure. The residue was purified by flash silica gel chromatography (ISCO®; 20 g SepaFlash® Silica Flash Column, Eluent of 0~100% Ethyl acetate/Petroleum ether gradient @ 20 mL/min). Compound (R)—N-((1-fluorocyclobutyl)methylene)-2-methylpropane-2-sulfinamide (600 mg, 74.6% yield) was obtained as a colorless oil. LCMS ($ESI^+$) m/z 206.9 $[M+H]^+$.

Step 3: Synthesis of (R)—N—((*R)-(3-chloro-5-fluoropyridin-2-yl)(1-fluorocyclobutyl)methyl)-2-methylpropane-2-sulfinamide 85-4

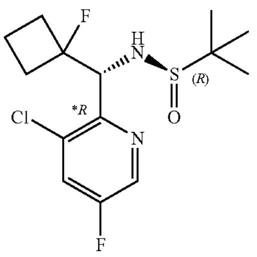

To a solution of 2-bromo-3-chloro-5-fluoro-pyridine (404 mg, 1.92 mmol) in THE (5 mL) was added bromo(isopropyl) magnesium (2.8 M, 686 uL) at −78° C. under $N_2$ atmosphere. The mixture was stirred at 20° C. for 2 h. The crude product was added to the mixture of (R)—N-((1-fluorocyclobutyl)methylene)-2-methylpropane-2-sulfinamide (90.0 mg, 438 umol) in THE (5 mL) at −65° C. under $N_2$ atmosphere. The mixture was stirred at 20° C. for 2 h. The reaction mixture was quenched with water (15 mL) at 0° C. and extracted with EA (25 mL×3). The combined organic layers were washed with brine (30 mL×2), dried over anhydrous $Na_2SO_4$, filtered and concentrated under reduced pressure. The residue was purified by flash silica gel chromatography (ISCO®; 20 g SepaFlash® Silica Flash Column, Eluent of 0~50% Ethyl acetate/Petroleum ether gradient @ 20 mL/min), and SFC was used to make sure the retention time to get the desired compound 85-4, only one compound was obtained. Compound (R)—N-((3-chloro-5-fluoropyridin-2-yl)(1-fluorocyclobutyl)methyl)-2-methylpropane-2-sulfinamide (60 mg, 42.93% yield) was obtained as a colorless oil.

$^1$HNMR (400 MHz, DMSO-$d_6$) δ 8.65 (d, J=2.4 Hz, 1H), 8.13 (dd, J=2.4, 8.8 Hz, 1H), 5.85 (d, J=10.4 Hz, 1H), 5.10-4.88 (m, 1H), 2.63-2.55 (m, 2H), 2.30-2.11 (m, 3H), 1.84-1.77 (m, 1H), 1.04 (s, 9H).

Step 4: Synthesis of (*R)-(3-chloro-5-fluoropyridin-2-yl)(1-fluorocyclobutyl)methanamine 85-5

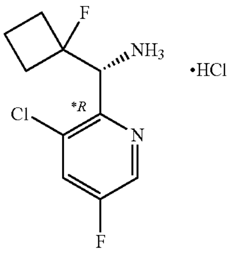

To a solution of (R)—N—((*R)-(3-chloro-5-fluoropyridin-2-yl)(1-fluorocyclobutyl)methyl)-2-methylpropane-2-sulfinamide (60.0 mg, 178 umol) in DCM (3 mL) was added HCl/dioxane (4 M, 5 mL). The mixture was stirred at 20° C. for 2 h. The mixture was concentrated under reduce pressure. Compound (*R)-(3-chloro-5-fluoro-2-pyridyl)-(1- fluorocyclobutyl)methanamine (45 mg, crude, HCl) was obtained as a white solid. LCMS (ESI$^+$) m/z 235 $[M+H]^+$.

Step 5: Synthesis of N—((*R)-(3-chloro-5-fluoro-pyridin-2-yl)(1-fluorocyclobutyl)methyl)-2-(2,6-dioxopiperidin-3-yl)-1-oxoisoindoline-5-carboxamide (compound 85)

Compound 85

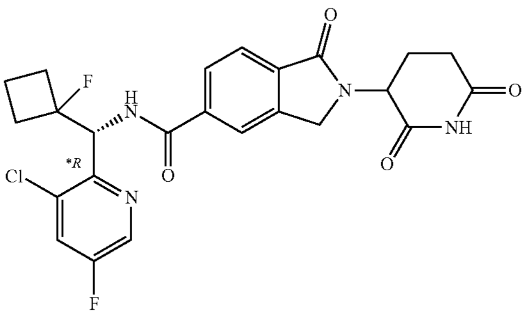

A mixture of (*R)-(3-chloro-5-fluoro-2-pyridyl)-(1-fluorocyclobutyl)methanamine (45.0 mg, 167 umol), 2-(2,6-dioxopiperidin-3-yl)-1-oxoisoindoline-5-carboxylic acid (53.0 mg, 184 umol), TEA (33.9 mg, 334 umol) in DCM (5 mL) was added $T_3P$ (106 mg, 167 umol) and then the mixture was stirred at 20° C. for 12 h. The mixture was concentrated under reduced pressure to remove DCM. The crude product was purified by reversed-phase HPLC (FA condition). Compound N—((*R)-(3-chloro-5-fluoropyridin-2-yl)(1-fluorocyclobutyl)methyl)-2-(2,6-dioxopiperidin-3-yl)-1-oxoisoindoline-5-carboxamide (39.29 mg, 46.72% yield) was obtained as a white solid.

$^1$HNMR (400 MHz, DMSO-$d_6$) δ 11.03 (s, 1H), 9.00 (d, J=8.4 Hz, 1H), 8.65 (s, 1H), 8.19-8.13 (m, 1H), 8.10 (s, 1H), 8.04-7.94 (m, 1H), 7.80 (d, J=7.6 Hz, 1H), 6.03 (dd, J=8.4, 17.6 Hz, H), 5.15 (dd, J=5.2, 13.2 Hz, 1H), 4.57-4.33 (mi, 2H), 2.98-2.86 (m, 1H), 2.67-2.59 (m, 2H), 2.47-2.37 (in, 2H), 2.33-2.19 (m, 2H), 2.07-1.99 (m, 1H), 1.90-1.78 (m, 1H), 1.56-1.44 (n, 1H); LCMS (ESI$^+$): m/z 503.3 $[M+H]^+$, Retention time: 3.162 min; SFC Retention time: 1.279 mi and 1.422 min.

Example 19

The following compounds were prepared according to similar procedure as described for compound 84 with corresponding starting materials of aldehydes, Grignard reagents and the following coupling steps (Example 18).

For compounds 86, 87, 88 and 89, the corresponding diastereomer intermediate of sulfonimide was separated by prep-HPLC or SFC before the following step.

TABLE 6

| | | |
|---|---|---|
| 86 | 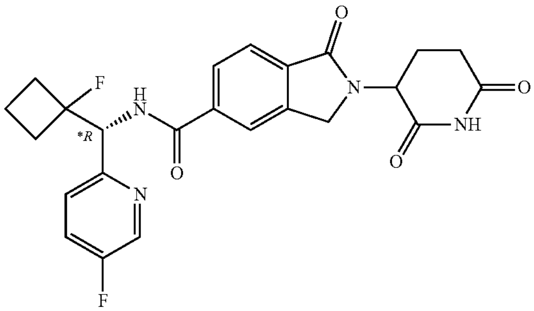 [SMILES: O=C1CCC(N2Cc3cc(C(=O)N[C@H](c4ccc(F)cn4)C4(F)CCC4)ccc3C2=O)C(=O)N1] | 2-(2,6-dioxopiperidin-3-yl)-N-((*R)-(1-fluorocyclobutyl)(5-fluoropyridin-2-yl)methyl)-1-oxoisoindoline-5-carboxamide $^1$HNMR (400 MHz, DMSO-$d_6$) 11.03 (s, 1H), 9.18 (d, J = 8.8 Hz, 1H), 8.56 (d, J = 2.4 Hz, 1H), 8.12 (s, 1H), 8.02 (d, J = 7.6 Hz, 1H), 7.83 (d, J = 7.6 Hz, 1H), 7.79-7.71 (m, 2H), 5.68-5.52 (m, 1H), 5.16 (dd, J = 5.2, 13.2 Hz, 1H), 4.58-4.35 (m, 2H), 2.99-2.86 (m, 1H), 2.71-2.58 (m, 1H), 2.46-2.42 (m, 1H), 2.40-2.22 (m, 3H), 2.18-2.00 (m, 2H), 1.90-1.75 (m, 1H), 1.62-1.48 (m, 1H); LCMS (ESI$^+$): m/z 469.3 $[M + H]^+$; Retention time: 3.483 min; SFC Retention time: 1.991 min and 2.121 min. |
| 87 | 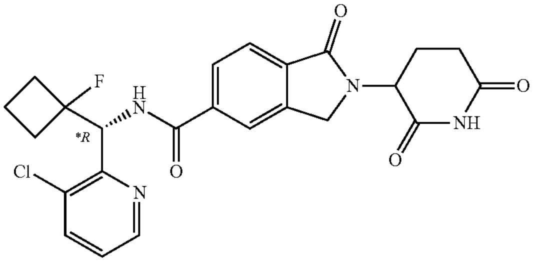 [SMILES: O=C1CCC(N2Cc3cc(C(=O)N[C@H](c4ncccc4Cl)C4(F)CCC4)ccc3C2=O)C(=O)N1] | N-[(*R)-(3-chloro-2-pyridyl)-(1-fluorocyclobutyl)methyl]-2-(2,6-dioxo-3-piperidyl)-1-oxo-isoindoline-5-carboxamide $^1$H NMR (400 MHz, DMSO-$d_6$) δ 10.96 (s, 1H), 8.97-8.85 (m, 1H), 8.58 (d, J = 4.4 Hz, 1H), 8.46-8.40 (m, 0.156H), 8.16-8.07 (m, 1H), 8.03-7.91 (m, 2H), 7.84-7.72 (m, 1H), 7.49-7.37 (m, 1H), 6.14-5.97 (m, 1H), 5.21-5.05 (m, 1H), 4.57-4.45 (m, 1H), 4.45-4.29 (m, 1H), 2.98-2.83 (m, 1H), 2.66-2.57 (m, 2H), 2.45-2.34 (m, 2H), 2.31-2.18 (m, 2H), 2.08-1.97 (m, 1H), 1.90-1.74 (m, 1H), 1.52-1.37 (m, 1H). LCMS (ESI+): m/z 485.3 $[M + H]^+$, Retention time: 1.778 min. SFC: Retention time: 1.367 min, 1.629 min. |
| 88 | 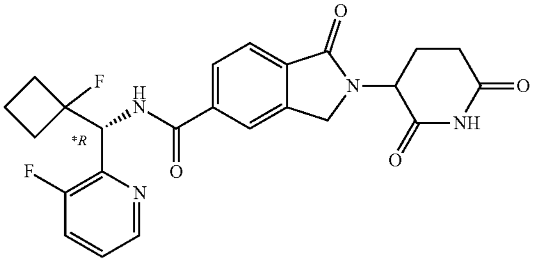 [SMILES: O=C1CCC(N2Cc3cc(C(=O)N[C@H](c4ncccc4F)C4(F)CCC4)ccc3C2=O)C(=O)N1] | 2-(2,6-dioxopiperidin-3-yl)-N-((*R)-(1-fluorocyclobutyl)(3-fluoropyridin-2-yl)methyl)-1-oxoisoindoline-5-carboxamide $^1$HNMR (400 MHz, DMSO-$d_6$) 11.02 (s, 1H), 9.16-8.90 (m, 1H), 8.51-8.43 (m, 1H), 8.16-8.06 (m, 1H), 8.03-7.96 (m, 1H), 7.85-7.73 (m, 2H), 7.53-7.44 (m, 1H), 5.92-5.77 (m, 1H), 5.20-5.03 (m, 1H), 4.57-4.33 (m, 2H), 3.02-2.85 (m, 1H), 2.64-2.57 (m, 1H), 2.49-2.35 (m, 3H), 2.30-2.16 (m, 2H), 2.06-1.98 (m, 1H), 1.89-1.75 (m, 1H), 1.53-1.41 (m, 1H); LCMS (ESI$^+$): m/z 469.3 $[M + H]^+$, Retention time: 2.033 min; SFC Retention time: 4.040 min and 5.320 min. |

TABLE 6-continued

| | | |
|---|---|---|
| 89 | 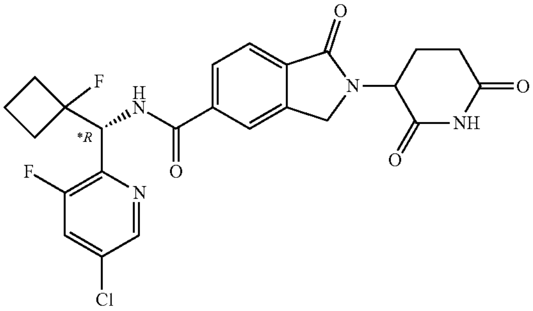 [SMILES: O=C1CCC(N2Cc3cc(C(=O)N[C@H](c4ncc(Cl)cc4F)C4(F)CCC4)ccc3C2=O)C(=O)N1] | N-((*R)-(5-chloro-3-fluoropyridin-2-yl)(1-fluorocyclobutyl)methyl)-2-(2,6-dioxopiperidin-3-yl)-1-oxoisoindoline-5-carboxamide<br>$^1$HNMR (400 MHz, DMSO-$d_6$) 11.03 (s 1H), 9.15 (d, J = 8.4 Hz, 1H), 8.64-8.52 (m, 1H), 8.16 (dd, J = 2.0, 9.6 Hz, 1H), 8.11 (s, 1H), 8.00 (dd, J = 2.4, 8.0 Hz, 1H), 7.81 (d, J = 8.0 Hz, 1H), 5.86-5.75 (m, 1H), 5.15 (dd, J = 5.2, 13.2 Hz, 1H), 4.56-4.36 (m, 2H), 2.98-2.87 (m, 1H), 2.63-2.59 (m, 1H), 2.47-2.35 (m, 3H), 2.30-2.19 (m, 2H), 2.07-2.00 (m, 1H), 1.89-1.80 (m, 1H), 1.58-1.49 (m, 1H);<br>LCMS (ESI+): m/z 503.2 [M + H]+, Retention time: 3.210 min;<br>SFC Retention time: 12.397 min and 12.704 min. |

Example 20

CK1α and GSPT1 Degradation Assay (HiBiT Assay)

The following is an example of an assay that can be used to determine the dose-dependent CK1α and GSPT1 degradation activities of test compounds in a human cell line such as HT-1080 (ATCC Cat #CRL-9591).

HT-1080 cells stably overexpressing wild-type CRBN, GSPT1A(1-138)/G575N mutant and HiBiT tagged CK1α or GSPT1 were seeded into 384-well plates (Cat #3764, Corning) pre-spotted with DMSO or test compounds. Increasing concentrations of test compounds (ranging from $3.162\times10^{-4}$ μM to 10 μM at a 3.16-fold increment) or DMSO were dispensed into an empty 384-well plate using an Echo Acoustic Liquid Handler (Beckman Coulter). About 10,000 cells in complete DMEM cell culture media were seeded per well. Assay plates were incubated at 37° C. with 5% $CO_2$ for 20 hours, followed by the assessment of CK1α or GSPT1 degradation using the Nano-Glo HiBiT Lytic Detection Reagent (Cat #N3050, Promega) according to the manufacturer's instruction. Luminescence was then measured with an EnVision plate reader (PerkinElmer) or a PHERAstar plate reader (BMG Labtech). All CK1α or GSPT1 degradation curves were processed using Collaborative Drug Discovery Vault softwares (Burlingame, CA., www.collaborativedrug.com).

CK1α or GSPT1 levels in compound-treated wells were normalized to that of DMSO control and expressed as Percent of Control (PoC, y). A four Parameter Logistic Model was used to determine the compound's $EC_{50}$ and $DC_{50}$, using the following equation:

$$y=(A+((B-A)/(1+((C/x)^A D))))$$

A lowest CK1α or GSPT1 level normalized to DMSO control in response to compound treatment, as determined by curve fit B=CK1α or GSPT1 level in DMSO control

C=$EC_{50}$

D=Hill Slope x=compound concentration $EC_{50}$=the concentration of compound when y=(B−A)/2

$DC_{50}$=the concentration of the compound when y=50% of DMSO control (50% CK1α or GSPT1 degradation)

y=CK1α or GSPT1 protein level normalized to DMSO control $$D_{max}=(1-A/B)*100\%$$

Dmax represents the maximum CK1α or GSPT1 protein degradation % that can be achieved by the compound treatment in the assay at the highest compound concentration.

Results:

Using the above assay $D_{max}$ and $DC_{50}$ data was determined for representative compounds in Table 7 below:

TABLE 7

| Compound No. | HiBiT CK1α: $DC_{50}$ (μM) | HiBiT CK1α: $D_{max}$ (%) | HiBiT GSPT1: $D_{max}$ (%) | Compound No. | HiBiT CK1α: $DC_{50}$ (μM) | HiBiT CK1α: $D_{max}$ (%) | HiBiT GSPT1: $D_{max}$(%) |
|---|---|---|---|---|---|---|---|
| 1 | 0.221 | 66.2 | 37 | 39 | 0.363 | 61 | 32.5 |
| 2 | 0.18 | 67 | 33.6 | 40 | 0.416 | 57.5 | 30.6 |
| 3 | 5.19 | 50.6 | 73.1 | 41 | 0.0824 | 70.5 | 24.9 |
| 4 | 0.183 | 63.4 | 31.1 | 42 | 1.15 | 57.7 | 40.8 |
| 5 | 0.243 | 75.9 | 30.3 | 43 | 0.0496 | 69.8 | 58.2 |
| 6 | 0.234 | 60.9 | 30.1 | 44 | NA | 49.5 | 22.5 |
| 7 | 0.0817 | 71.8 | 28.6 | 45 | 0.0578 | 73.8 | 42.4 |
| 8 | 0.16 | 72.9 | 23.4 | 46 | 1.3 | 54.6 | 32.4 |
| 9 | 0.116 | 71.6 | 22.6 | 47 | 2.96 | 56.1 | 29.7 |
| 10 | 0.706 | 60.8 | 36 | 48 | 0.13 | 66.2 | 26.2 |
| 11 | 0.308 | 64.7 | 23.4 | 49 | 0.112 | 68.6 | 28.6 |
| 12 | 0.14 | 64.7 | 36.8 | 50 | 0.237 | 63.1 | 42.7 |
| 13 | 0.293 | 65.9 | 37 | 51 | 0.142 | 62.3 | 46 |
| 14 | 0.284 | 67.1 | 45.5 | 52 | 0.095 | 73.9 | 28.5 |
| 15 | 0.0666 | 73.2 | 24.5 | 53 | 0.118 | 70.2 | 24.2 |
| 16 | 0.303 | 62.2 | 44.9 | 54 | 1.11 | 56.5 | 47.9 |
| 17 | 0.123 | 68.1 | 49.3 | 55 | 0.948 | 57.8 | 48 |
| 18 | 0.137 | 66 | 58.5 | 56 | 0.0937 | 63.6 | 15.3 |
| 19 | 0.0659 | 69.6 | 43 | 57 | 0.128 | 64.4 | 19.1 |

TABLE 7-continued

| Compound No. | HiBiT CK1α: $DC_{50}$ (μM) | HiBiT CK1α: $D_{max}$ (%) | HiBiT GSPT1: $D_{max}$ (%) | Compound No. | HiBiT CK1α: $DC_{50}$ (μM) | HiBiT CK1α: $D_{max}$ (%) | HiBiT GSPT1: $D_{max}$(%) |
|---|---|---|---|---|---|---|---|
| 20 | 0.0364 | 71.2 | 42 | 58 | NA | 49.7 | 16.5 |
| 21 | 0.132 | 60.6 | 20.6 | 59 | NA | 32.2 | 7.93 |
| 22 | 0.0797 | 70.7 | 48.3 | 60 | <0.0471 | 49 | 27.4 |
| 23 | 0.198 | 61.3 | 32 | 61 | NA | 49.5 | 29.3 |
| 24 | 0.363 | 63.2 | 63.1 | 62 | 0.0777 | 69.8 | 27.5 |
| 25 | 1.58 | 54.5 | 48.4 | 63 | 0.0535 | 72.2 | 29 |
| 26 | 0.417 | 58.4 | 30.7 | 64 | 0.162 | 66.7 | 27.9 |
| 27 | 0.345 | 59.3 | 40.3 | 65 | 0.721 | 59.6 | 23.1 |
| 28 | 1.15 | 60.1 | 70.8 | 66 | 0.118 | 67.9 | 55.3 |
| 29 | 0.553 | 58.8 | 22 | 67 | 0.04 | 76.4 | 31.7 |
| 30 | NA | 47.9 | 62.1 | 68 | 0.789 | 55.4 | 48.3 |
| 31 | NA | 48.1 | 60 | 69 | 0.0627 | 74 | 26 |
| 32 | 0.198 | 59.3 | 36.3 | 70 | 0.0503 | 73.9 | 58 |
| 33 | 1.3 | 56.3 | 66.3 | 71 | 0.455 | 61.7 | 19.1 |
| 34 | 0.446 | 59.5 | 25.8 | 72 | 0.132 | 65.5 | 45.2 |
| 35 | 0.0947 | 67 | 14.8 | 73 | 0.0735 | 71.4 | 30.4 |
| 36 | 0.0667 | 65.8 | 24.6 | 74 | 0.233 | 59.2 | 62.3 |
| 37 | 0.0727 | 70.8 | 36.2 | 75 | 3.88 | 50.4 | 24.1 |
| 38 | 0.218 | 64.1 | 19.9 | 76 | 0.219 | 64.4 | 23.5 |
| 77 | NA | 41.1 | 23.5 | 84 | 0.0741 | 72.4 | 15.2 |
| 78 | 0.198 | 67.2 | 14.4 | 85 | 0.0939 | 65.3 | 16.2 |
| 79 | 0.274 | 65.9 | 20.4 | 86 | 0.193 | 63 | 18.2 |
| 80 | 0.652 | 61.1 | 14.2 | 87 | 0.279 | 59.8 | 25 |
| 81 | 0.153 | 62.1 | 18.4 | 88 | 0.394 | 55.4 | 14.9 |
| 82 | 0.105 | 66.3 | 16.2 | 89 | 0.148 | 69 | 17.3 |
| 83 | 0.115 | 66 | 14.4 | CC-885 | 0.653 | 53.7 | 92.5 |

CC-885

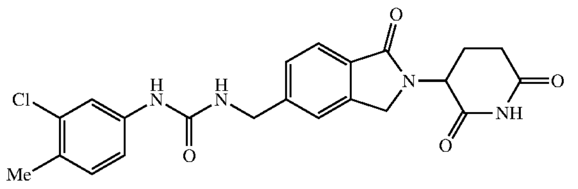

Reference compound CC-885 was synthesized according to published literature (Hanson et al., *J Med Chem* (2018) 61:492-503). CC-885 showed similar CK1α degradation activity in comparison with other test compounds (Table 7). However, CC-885 also effectively degraded GSPT1. It was known to those skilled in the art that the degradation of GSPT1 results in severe toxicities in human (Uy et al., *Blood* (2019) 134 (Supplement_1): 232).

NA: Not Available.

Example 21

MV4-11 Cell Proliferation Assay

The following is an example of an assay that can be used to determine the dose-dependent, anti-proliferative activity of CK1α degradating compounds in an AML cell line such as MV4-11 (ATCC Cat #CRL-9591).

MV4-11 cells were seeded into a 384-well plate (Cat #3764, Corning) pre-spotted with DMSO or test compounds. Increasing concentrations of test compounds (ranging from $1\times10^{-3}$ μM to 10 μM at a 3.162-fold increment in a 10-point dose response assay; ranging from $3.162\times10^{-4}$ μM to 10 μM at a 3.162-fold increment in a 11-point dose response assay) or DMSO were dispensed into an empty 384-well plate using an a D300e digital dispenser (Tecan) or an Echo Acoustic Liquid Handler (Beckman Coulter). About 2,000 cells in 50 μL of culture media (IMDM plus 10% heat-inactivated FBS) were seeded per well. Assay plates were incubated at 37° C. with 5% $CO_2$ for 120 hours. After that, 20 μL of the CellTiter-Glo Luminescent Cell Viability Assay Reagent (Cat #G7573, Promega) was added to each well and incubated at room temperature for 30 minutes. Luminescence was then measured with an EnVision plate reader (PerkinElmer) or a PHERAstar plate reader (BMG LABTECH). All cell growth inhibition curves were processed using Collaborative Drug Discovery Vault softwares (Burlingame, CA, www.collaborativedrug.com).

Cell viability reads in compound-treated wells were normalized to that of DMSO control and expressed as Percent of Control (PoC, y). A four Parameter Logistic Model was used to determine the compound's $EC_{50}$ and $DC_{50}$, using the following equation:

$$y = (A + ((B - A)/(1 + ((C/x)^{A}D))))$$

A==lowest cell viability read normalized to DMSO control in response to compound treatment, as determined by curve fit B=cell viability read in DMSO control $C=EC_{50}$ D=Hill Slope x=compound concentration $EC_{50}$=the concentration of compound when y=(B−A)/2

$IC_{50}$=the concentration of the compound when y=50% of DMSO control y=cell viability read normalized to DMSO control $$Y_{min}=(A/B)*100\%$$

$Y_{min}$ represents the lowest cell viability % that can be achieved by the compound treatment in the assay.

TABLE 8

| Compound No. | CTG cell viability assay_MV4-11: $IC_{50}$ (μM) | Compound No. | CTG cell viability assay_MV4-11: $IC_{50}$ (μM) |
|---|---|---|---|
| 7 | 0.112 | 76 | 0.071 |
| 8 | 0.205 | 78 | 0.176 |
| 9 | 0.172 | 79 | 0.176 |
| 4 | 0.262 | 82 | 0.060 |
| 5 | 0.363 | 83 | 0.027 |
| 6 | 0.691 | 84 | 0.024 |
| 35 | 0.198 | 85 | 0.102 |
| 41 | 0.115 | 86 | 0.142 |
| 42 | 0.42 | 87 | 0.133 |
| 36 | 0.128 | 89 | 0.198 |

KG-1a Cell Proliferation Assay

In keeping with the underlying mechanism of anti-tumor response to CK1α inactivation in AML (Jaras et al, *J Exp Med* (2014) 211(4): 605-612), we found that AML cell lines with loss of function in p53 were insensitive to CK1α ~ degradation. On the other hand, most AML cell lines were reported to be sensitive to GSPT1 degradation induced by CC-885 or CC-90009 regardless of their p53 mutational status (Matyskiela et al., *Nature* (2016) 535:252-257; Surka et al., *Blood* (2021) 137 (5): 661-677). Because the subtle to moderate degradation of GSPT1 induced by CK1α degraders with mild activity towards GSPT1 might still result in toxicity in human, a counter screen using an AML cell line harboring p53 mutation such as KG-1a (ATCC Cat #CCL-246.1), was performed to determine the GSPT1-mediated cytotoxicity in vitro.

The following is an example of an assay that can be used to determine the potential GSPT1-dependent cytotoxcity of test compounds that degrade GSPT1. KG-1a cells were seeded into a 384-well plate (Cat #3764, Corning) pre-spotted with DMSO or test compounds. Increasing concentrations of test compounds (ranging from $1\times10^{-3}$ M to 10 μM at a 3.162-fold increment in a 10-point dose response assay; ranging from $3.162\times10^{-4}$ M to 10 μM at a 3.162-fold increment in a 11-point dose response assay) or DMSO were dispensed into an empty 384-well plate using an a D300e digital dispenser (Tecan) or an Echo Acoustic Liquid Handler (Beckman Coulter). About 2,000 cells in 50 μL of culture media (IMDM plus 10% heat-inactivated FBS) were seeded per well. Assay plates were incubated at 37° C. with 5% $CO_2$ for 120 hours. After that, 20 μL of the CellTiter-Glo Luminescent Cell Viability Assay Reagent (Cat #G7573, Promega) was added to each well and incubated at room temperature for 30 minutes. Luminescence was then measured with EnVision Multimode Plate Reader (PerkinElmer) or a PHERAstar plate reader (BMG LABTECH). All cell growth inhibition curves were processed using Collaborative Drug Discovery Vault softwares (Burlingame, CA, www.collaborativedrug.com). Cell viability reads in compound-treated wells were normalized to that of DMSO control and expressed as Percent of Control (PoC, y). A four Parameter Logistic Model was used to determine the compound's $EC_{50}$ and $DC_{50}$, using the following equation:

$$y=\left(A+\left((B-A)/\left(1+\left((C/x)^{A}D\right)\right)\right)\right)$$

A=lowest cell viability read normalized to DMSO control in response to compound treatment, as determined by curve fit B:=cell viability read in DMSO control

C=$EC_{50}$

D=Hill Slope x=compound concentration $EC_{50}$=the concentration of compound when y=(B−A)/2

$IC_{50}$=the concentration of the compound when y=50% of DMSO control y=cell viability read normalized to DMSO control $$Y_{min}=(A/B)*100\%$$

$Y_{min}$ represents the lowest cell viability % that can be achieved by the compound treatment in the assay at the highest compound concentration.

TABLE 9

| No. | CTG cell viability assay KG1a: Ymin (%) |
|---|---|
| 7 | 91.7 |
| 4 | 90.9 |
| 35 | 92.1 |

Note: In KG-1a cell proliferation assay, the highest concentration used was 10 μM. All these compounds induced less than 10% of cell proliferation inhibition at 10 μM of the tested compounds.

Example 22

The pharmacokinetic study of single intravenous and oral administration in mouse Sample collection and preparation: After intravenous injection or oral administration of test compounds, blood samples were collected and the blood collection time was recorded. After the blood sample was collected, it was immediately transferred into a labeled centrifuge tube containing $K_2$-EDTA, followed by centrifugation and plasma collection. The plasma was then transferred into a pre-cooled centrifuge tube, quickly frozen on dry ice, and stored in an ultra-low temperature refrigerator at −70±10° C. until the LC-MS/MS analysis was performed.

Pharmacokinetic data analysis: The pharmacokinetic software was used to process the plasma drug concentration data of the compound in a non-compartmental model. The peak concentration ($C_{max}$), peak time ($T_{max}$) and quantifiable end time can be directly obtained from the plasma concentration-time diagram. The log-linear trapezoidal method was used to calculate the following pharmacokinetic parameters: half-life ($T_{1/2}$), apparent volume of distribution ($V_{dss}$) and clearance (Cl), and the area under the time-plasma concentration curve ($AUC_{0\text{-}inf}$) from the 0 point to the end point.

TABLE 10

| | Parameters | Compound 41 | Compound 82 | Compound 86 |
|---|---|---|---|---|
| Mouse (2 mg/kg, IV) | CL (mL/min/kg) | 23 | 10.5 | 7.85 |
| | $C_0$ (ng/mL) | 1856 | 6796 | 4912 |
| | $t_{1/2}$ (hr) | 2.84 | 1.34 | 3.62 |
| | $V_{ss}$ (L/kg) | 3.20 | 0.85 | 0.87 |
| Mouse (10 mg/kg, PO) | $C_{max}$ (ng/mL) | 1573 | 6080 | 5690 |
| | $T_{max}$ (hr) | 0.83 | 0.67 | 0.5 |
| | $T_{1/2}$ (hr) | 2.72 | 2.03 | 2.12 |
| | $AUC_{(0\text{-}inf)}$ (h*ng/mL) | 5867 | 13264 | 14940 |
| | F (%) | 76.8 | 85 | 70.4 |

Experimental conclusion: The compounds of the present invention showed low clearance rate, good oral exposure, and high oral bioavailability.

The invention claimed is:

1. A compound represented by structural formula (I):

(I)

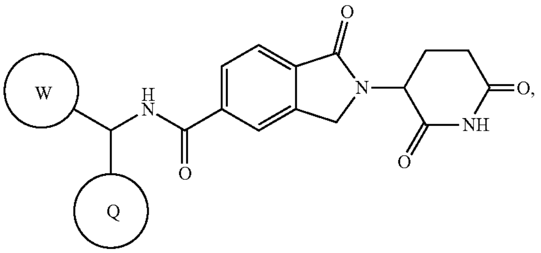

or a pharmaceutically acceptable salt thereof, wherein:

the moiety

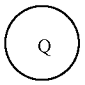

is $C_{3-8}$ cycloalkyl optionally substituted with 1 to 6 $R^a$, 4 to 10 membered monocyclic or bicyclic heterocyclyl optionally substituted with 1 to 6 $R^a$, having 1 to 3 heteroatoms selected from N, O, and S;

each $R^a$ is independently selected from hydrogen, halogen, hydroxyl, nitro, cyano, amino, mercapto, —COOH, $C_1$-$C_6$alkyl, $C_2$-$C_6$alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)O$R^{11}$, —$C_0$-$C_4$alkylN$R^{11}R^{12}$, —C(O)N$R^{11}R^{12}$, —$SO_2R^{11}$, —$SO_2NR^{11}R^{12}$, —OC(O)$R^{11}$, and —C(N$R^{11}$)N$R^{11}R^{12}$, wherein $R^{11}$ and $R^{12}$ are independently chosen from hydrogen, $C_1$-$C_6$alkyl, —$C_0$-$C_4$alkyl($C_3$-$C_7$cycloalkyl), and —O—$C_0$-$C_4$alkyl($C_3$-$C_7$cycloalkyl);

and wherein when moiety

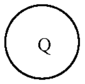

bears greater than or equal to two $R^a$, two $R^a$ are optionally taken together with atoms to which they are bound to form a carbocyclyl or heterocyclyl ring;

the moiety

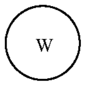

is 6 to 18 membered aryl optionally substituted with 1 to 6 $R^b$, 5 to 18 membered heteroaryl optionally substituted with 1 to 6 $R^b$, having 1 to 3 heteroatoms selected from N, O, and S, each $R^b$ is independently selected from hydrogen, halogen, hydroxyl, nitro, cyano, amino, mercapto, —COOH, $C_1$-$C_6$alkyl, $C_2$-$C_6$alkenyl, $C_2$-$C_6$alkynyl, $C_1$-$C_6$alkoxy, $C_2$-$C_6$alkenyloxy, $C_2$-$C_6$alkynyloxy, $C_2$-$C_6$alkanoyl, $C_2$-$C_6$alkylester, $C_1$-$C_6$thioalkyl, $C_1$-$C_6$ haloalkyl, $C_1$-$C_6$ haloalkoxy, hydroxy$C_1$-$C_6$alkyl, amino$C_1$-$C_6$alkyl, (mono- and di-$C_1$-$C_6$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), —$C_0$-$C_4$alkyl-(phenyl), —$C_0$-$C_4$alkylOC(O)O$C_1$-$C_6$alkyl, —$C_0$-$C_4$alkylOC(O)$C_1$-$C_6$alkyl, —$C_0$-$C_4$alkylC(O)O$C_1$-$C_6$alkyl, $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)O$R^{11}$, —$C_0$-$C_4$alkylN$R^{11}R^{12}$, —C(O)N$R^{11}R^{12}$, —$SO_2R^{11}$, —$SO_2NR^{11}R^{12}$, —OC(O)$R^{11}$, and —C(N$R^{11}$)N$R^{11}R^{12}$, wherein $R^{11}$ and $R^{12}$ are independently chosen from hydrogen, $C_1$-$C_6$alkyl, —$C_0$-$C_4$alkyl($C_3$-$C_7$cycloalkyl), and —O—$C_0$-$C_4$alkyl($C_3$-$C_7$cycloalkyl);

and wherein when moiety

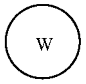

bears greater than or equal to two $R^b$, two $R^b$ are optionally taken together with atoms to which they are bound to form a carbocyclyl or heterocyclyl ring.

2. The compound of claim 1, wherein the compound is a compound represented by structural formula (I-1) or (I-2)

(I-1)

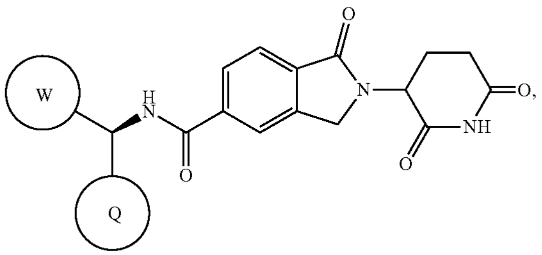

-continued (I-2)

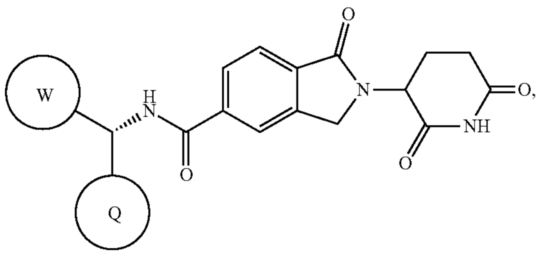

or a pharmaceutically acceptable salt thereof; wherein moiety

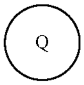

and moiety

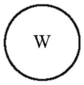

are as defined in claim 1.

3. The compound of claim 1, wherein the moiety

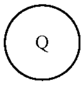

is selected from the group consisting of

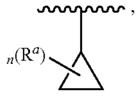, 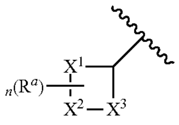, 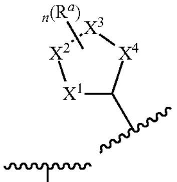, 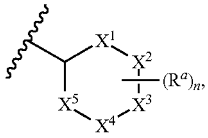 and 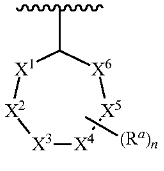, wherein:

n, for each occurrence, is independently 0, 1, 2, 3, 4, 5, or 6;

$X^1$, for each occurrence, is independently C, N, O, or S;

$X^2$, for each occurrence, is independently C, N, O, or S;

$X^3$, for each occurrence, is independently C, N, O, or S;

$X^4$, for each occurrence, is independently C, N, O, or S;

$X^5$, for each occurrence, is independently C, N, O, or S;

$X^6$, for each occurrence, is independently C, N, O, or S; and $R^a$ is as defined in claim 1.

4. The compound of claim 3, wherein the moiety

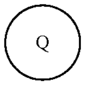

is

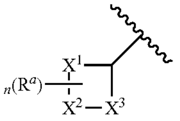

wherein:

n, for each occurrence, is independently 0, 1, 2, 3, 4, 5, or 6;

$X^1$, for each occurrence, is independently C, N, O, or S;

$X^2$, for each occurrence, is independently C, N, O, or S;

$X^3$, for each occurrence, is independently C, N, O, or S; and $R^a$, for each occurrence, is independently selected from H, F, Cl, Br, Me, CN, MeO, Et, $CF_3O$,

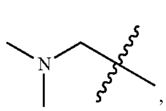, 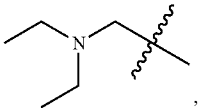, 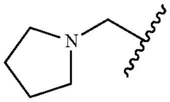, 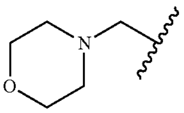, 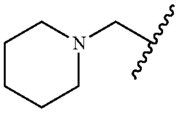, 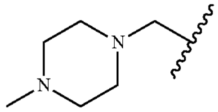, 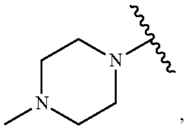, 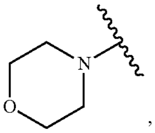, 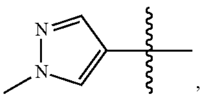, 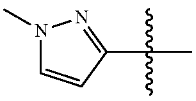, 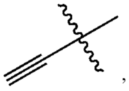, 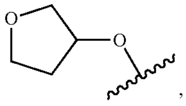, 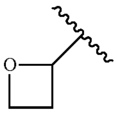, 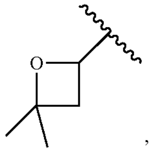, $CF_3$, and EtO—.

5. The compound of claim 3, wherein the moiety

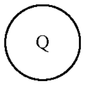

is selected from

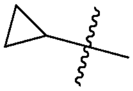, 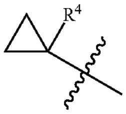, 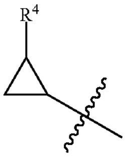,

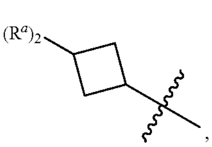, 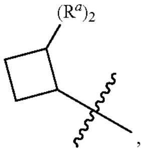, 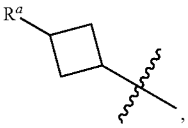,

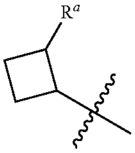, 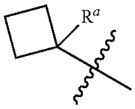, 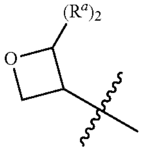,

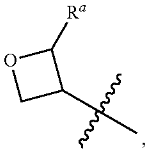, 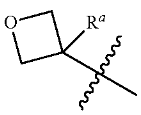, 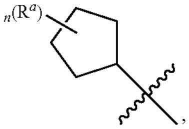,

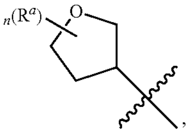, 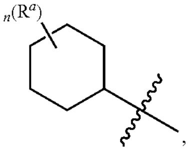, and

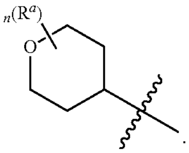.

wherein, n, for each occurrence, is independently 0, 1, 2, 3, 4, or 5; and $R^a$ is as defined in claim 3.

6. The compound of claim 1, wherein the moiety

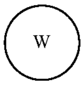 is 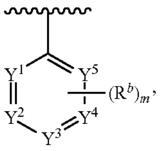, or 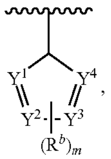, wherein m, for each occurrence, is independently 0, 1, 2, 3, 4, or 5;

$Y^1$, for each occurrence, is independently C, N, O, or S;

$Y^2$, for each occurrence, is independently C, N, O, or S;

$Y^3$, for each occurrence, is independently C, N, O, or S;

$Y^4$, for each occurrence, is independently C, N, O, or S;

$Y^5$, for each occurrence, is independently C, N, O, or S; and $R^b$ is as defined in claim 1.

7. The compound of claim 6, wherein the moiety

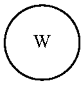

is

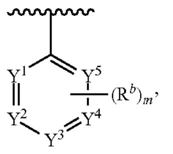, wherein m, for each occurrence, is independently 0, 1, 2, 3, 4, or 5;

$Y^1$, for each occurrence, is independently C, N, O, or S;

$Y^2$, for each occurrence, is independently C, N, O, or S;

$Y^3$, for each occurrence, is independently C, N, O, or S;

$Y^4$, for each occurrence, is independently C, N, O, or S;

$Y^5$, for each occurrence, is independently C, N, O, or S; and $R^b$ for each occurrence is selected from H, F, Cl, Br, Me, CN, MeO, Et, $CF_3O$,

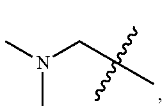, 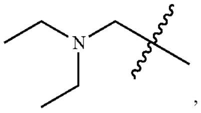, 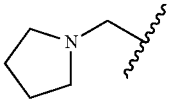,

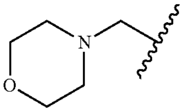, 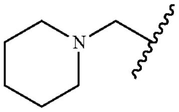,

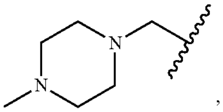, 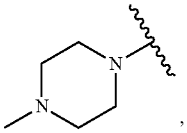,

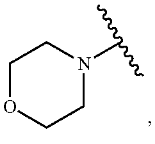, 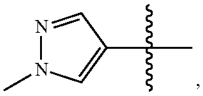,

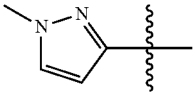, 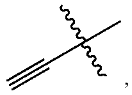, 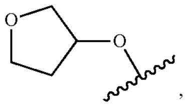,

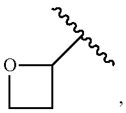, 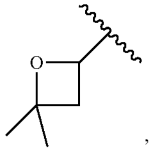, $CF_3$, and EtO—.

8. The compound of claim 6, wherein the moiety

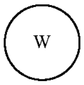

is selected from

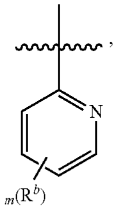,
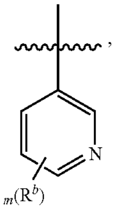,
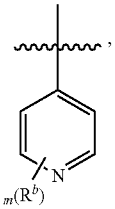,
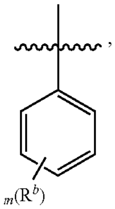,

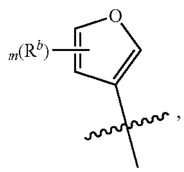, and 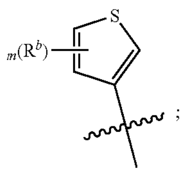;

wherein m, for each occurrence, is independently 0, 1, 2, 3, 4, or 5; and $R^b$ is as defined in claim 6.

9. The compound of claim 8, wherein the moiety

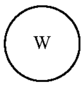

is selected from

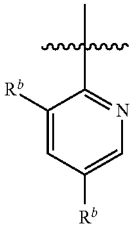,
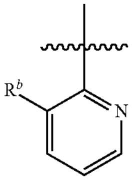,
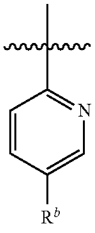,
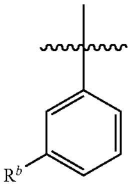,
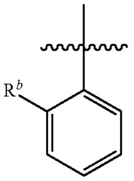,
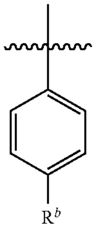,
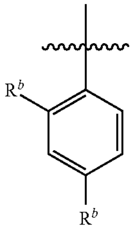,
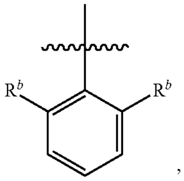,
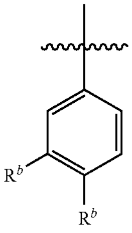, and -continued

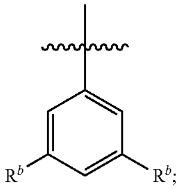

wherein $R^b$ is as defined in claim 8.

10. The compound of claim 1, wherein the compound is a compound represented by a structural formula selected from the following group: (II), (III), (IV), (V) and (VI)

(II)

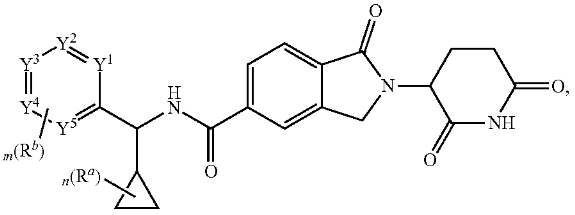

(III)

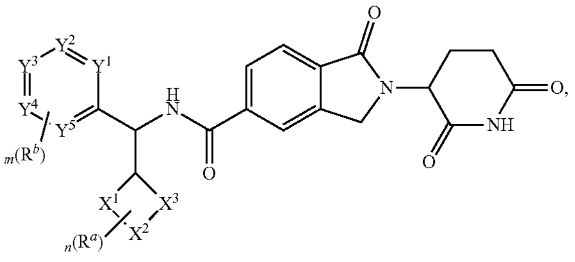

(IV)

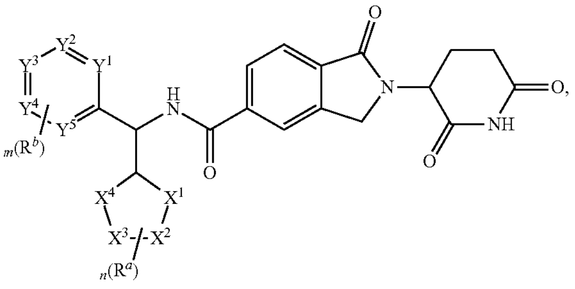

(V)

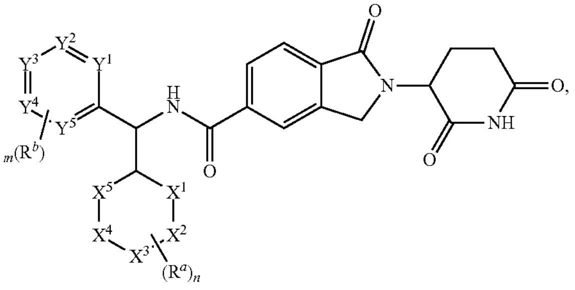

-continued (VI)

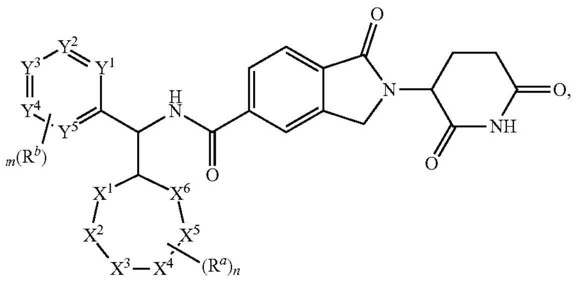

or a pharmaceutically acceptable salt thereof, wherein m, for each occurrence, is independently 0, 1, 2, 3, 4, or 5;

n, for each occurrence, is independently 0, 1, 2, 3, 4, 5, or 6;

$X^1$, for each occurrence, is independently C, N, O, or S;

$X^2$, for each occurrence, is independently C, N, O, or S;

$X^3$, for each occurrence, is independently C, N, O, or S;

$X^4$, for each occurrence, is independently C, N, O, or S;

$X^5$, for each occurrence, is independently C, N, O, or S;

$X^6$, for each occurrence, is independently C, N, O, or S $Y^1$, for each occurrence, is independently C, N, O, or S;

$Y^2$, for each occurrence, is independently C, N, O, or S;

$Y^3$, for each occurrence, is independently C, N, O, or S;

$Y^4$, for each occurrence, is independently C, N, O, or S;

$Y^5$, for each occurrence, is independently C, N, O, or S; and $R^a$ and $R^b$ are as defined in claim 1.

11. The compound of claim 10, wherein the compound is a compound represented by structural formula (I-7) or (I-8)

(I-7)

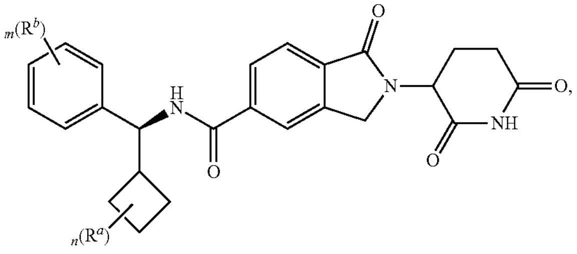

(I-8)

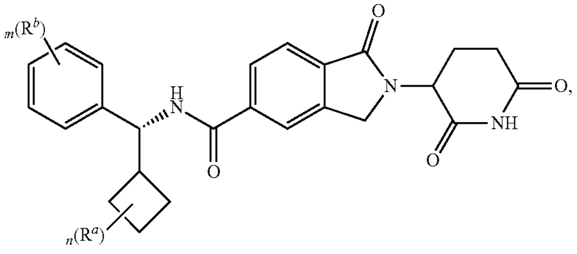

or a pharmaceutically acceptable salt thereof; wherein m, n, $R^a$ and $R^b$ are as defined in claim 10.

12. The compound of claim 10, wherein the compound is a compound represented by structural formula (I-9) or (I-10)

(I-9)

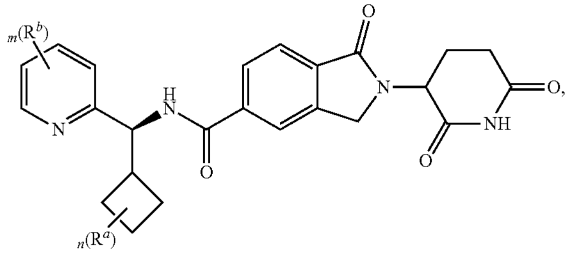

(I-10)

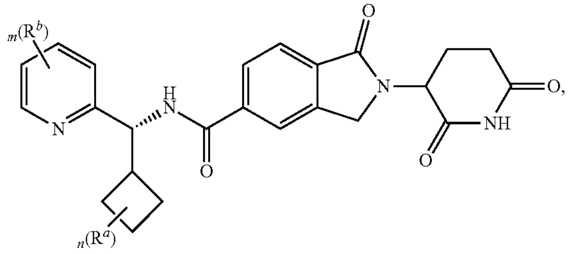

or a pharmaceutically acceptable salt thereof; wherein m, n, $R^a$ and $R^b$ are as defined in claim 10.

13. The compound of claim 1, wherein, each $R^a$ is independently selected from hydrogen, halogen, hydroxyl, nitro, cyano, trifluoromethyl, $C_1$-$C_6$alkyl, $C_1$-$C_6$alkoxy, $C_1$-$C_6$ haloalkyl, $C_1$-$C_6$ heterocycloalkyl, —N—($C_1$-$C_6$ alkyl)$_2$, $C_1$-$C_6$alkyl-$C_1$-$C_6$ heterocycloalkyl.

14. The compound of claim 1, wherein, each $R^b$ is independently selected from hydrogen, halogen, hydroxyl, nitro, cyano, amino, mercapto, $C_1$-$C_6$alkyl, $C_2$-$C_6$alkenyl, $C_2$-$C_6$alkynyl, $C_1$-$C_6$alkoxy, $C_1$-$C_6$ haloalkyl, $C_1$-$C_6$ haloalkoxy, amino$C_1$-$C_6$alkyl, (mono- and di-$C_1$-$C_6$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_0$-$C_4$alkyl-(4- to 7-membered heterocycloalkyl) having 1, 2, or 3 heteroatoms independently chosen from N, O, and S, and $C_0$-$C_4$alkyl-(5- or 6-membered unsaturated or aromatic heterocycle) having 1, 2, or 3 heteroatoms independently chosen from N, O, and S, —C(O)O$R^{11}$, —$C_0$-$C_4$alkylN$R^{11}R^{12}$, —C(O)N$R^{11}R^{12}$, —$SO_2R^{11}$, —$SO_2NR^{11}R^{12}$, —OC(O)$R^{11}$, and —C(N$R^{11}$)N$R^{11}R^{12}$, wherein $R^{11}$ and $R^{12}$ are independently chosen from hydrogen, $C_1$-$C_6$alkyl, —$C_0$-$C_4$alkyl($C_3$-$C_7$cycloalkyl), and —O—$C_0$-$C_4$alkyl($C_3$-$C_7$cycloalkyl).

15. The compound of claim 1, or a pharmaceutically acceptable salt thereof, which is:

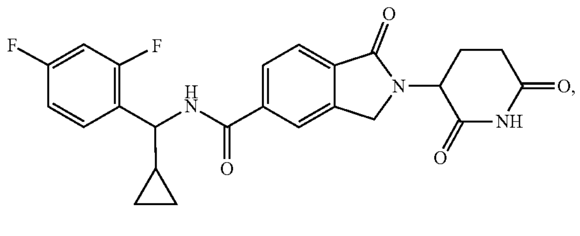

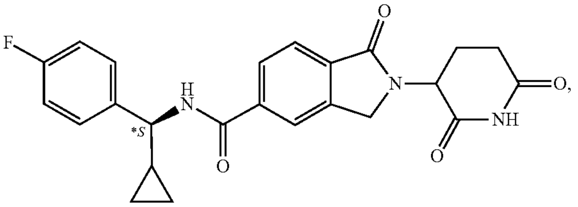,
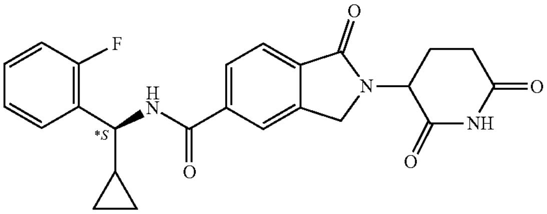
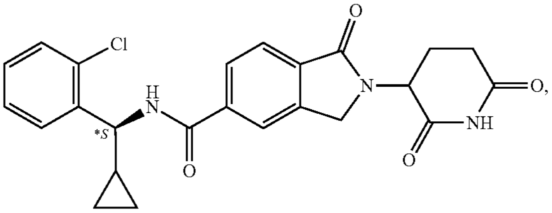,
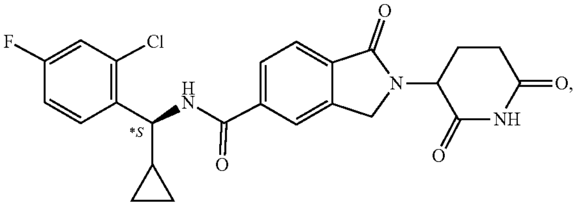,
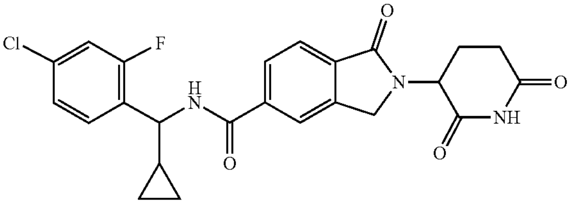
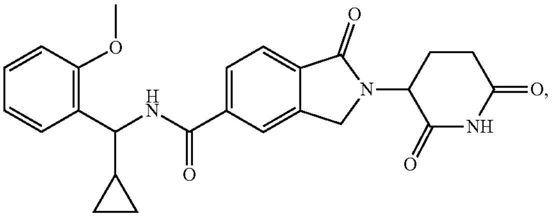,
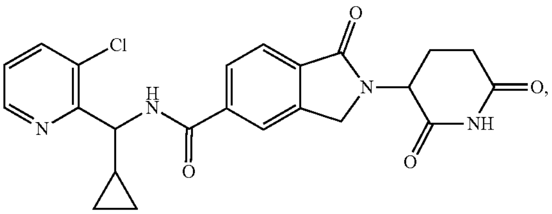,
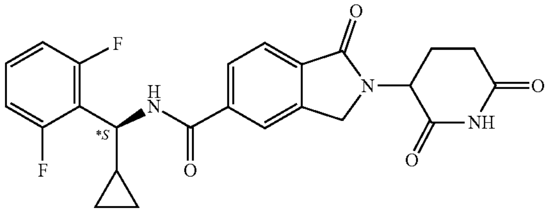
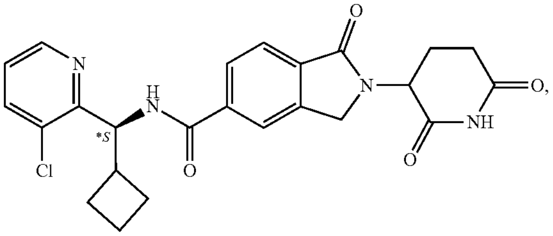,
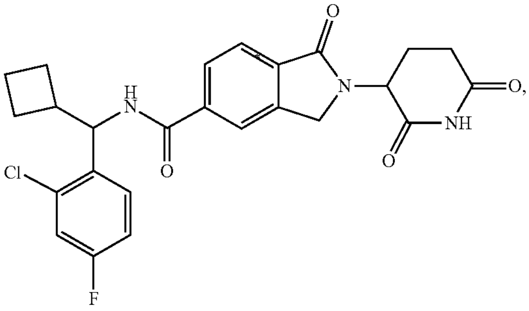,
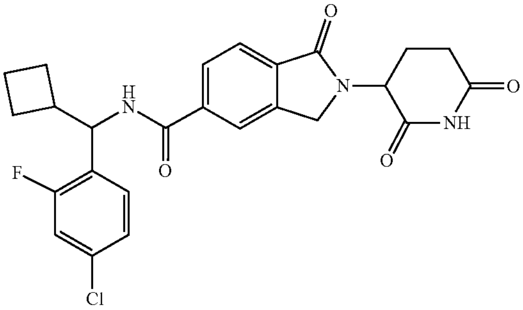
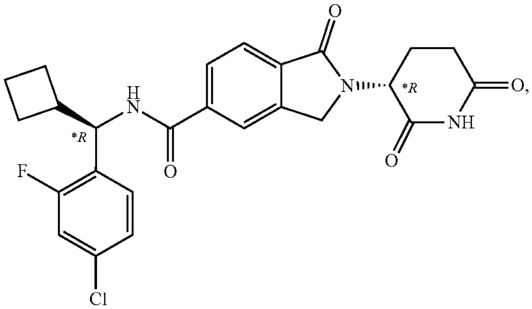,
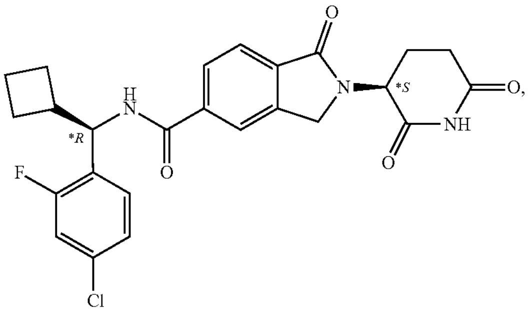, -continued
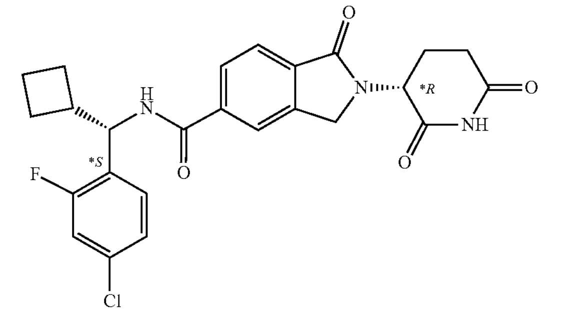
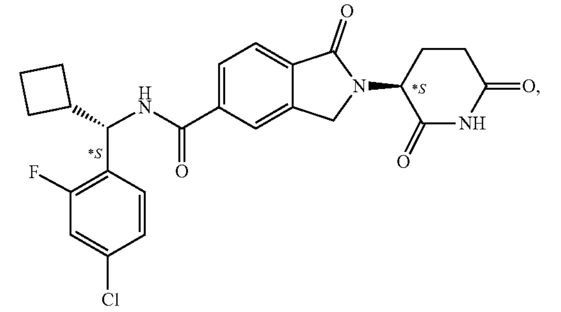
,
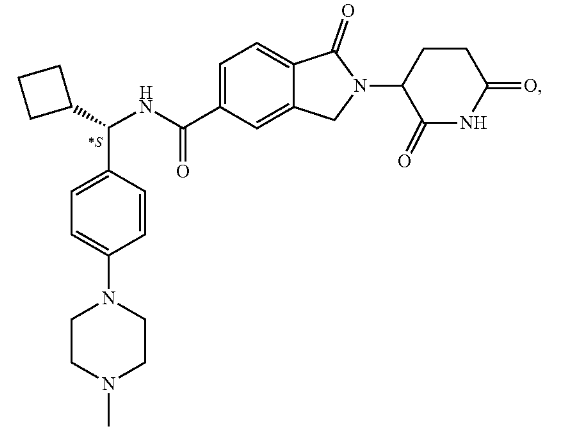
,
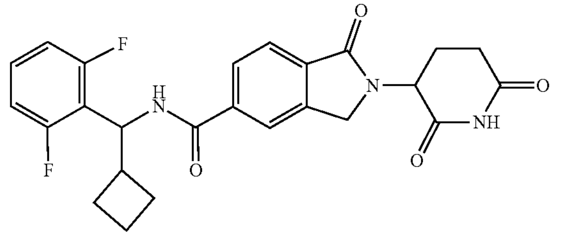
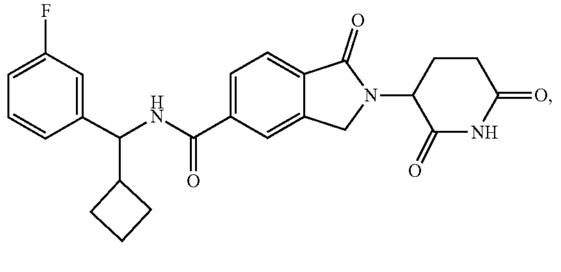
,
-continued
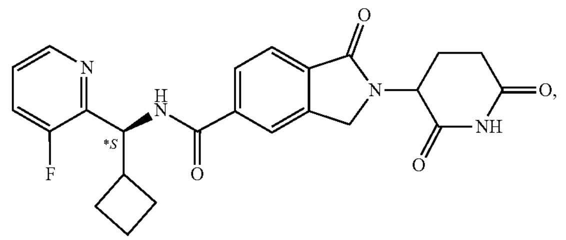
,
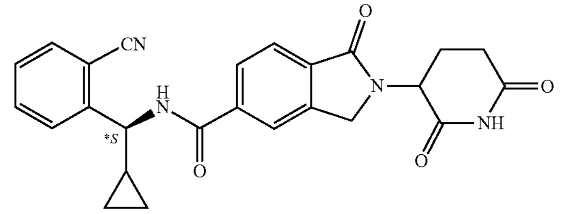
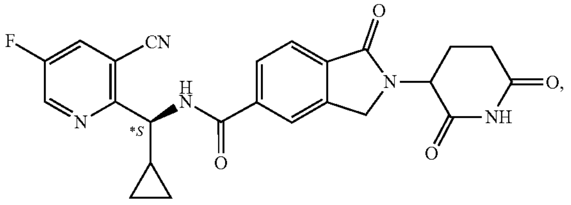
,
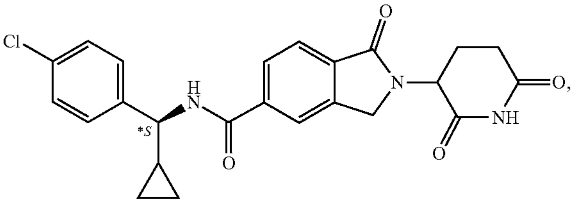
,
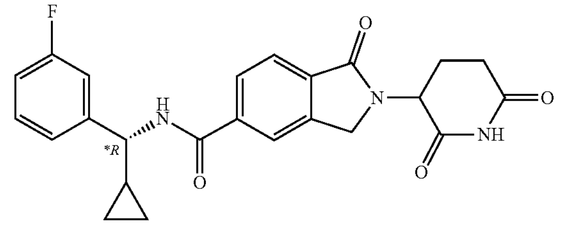
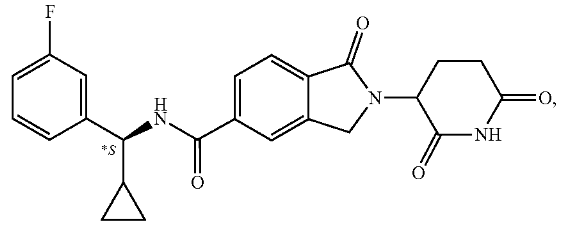
,
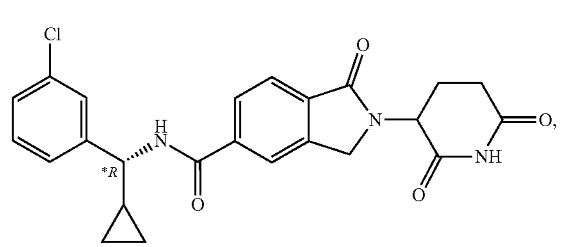
, -continued
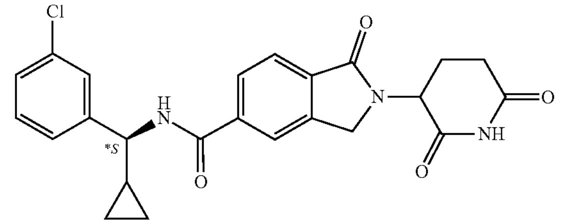
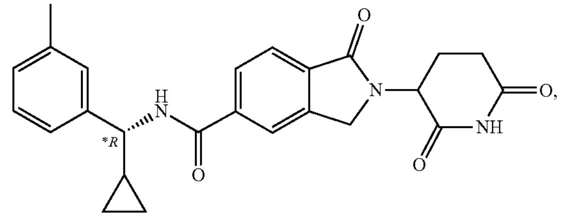,
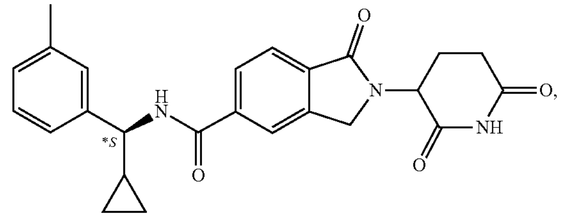,
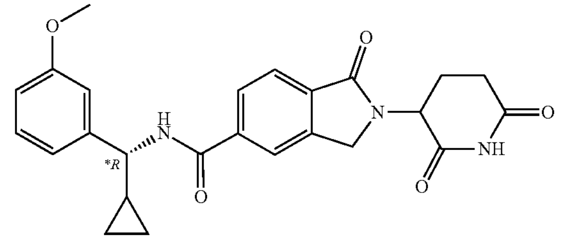
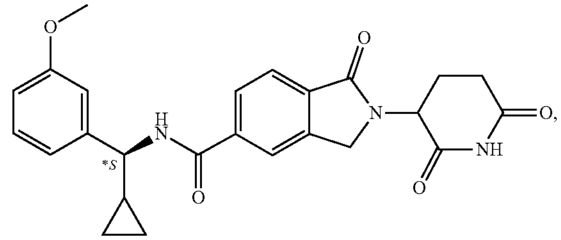,
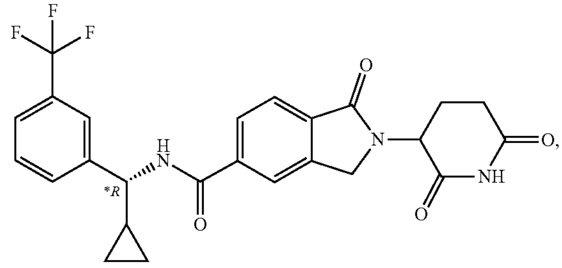,
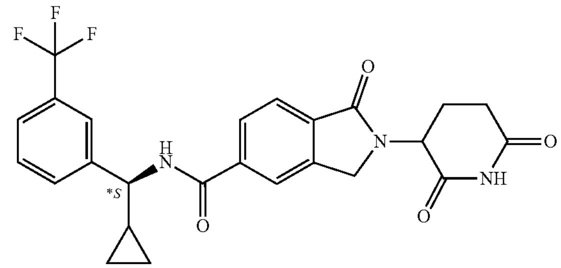
-continued
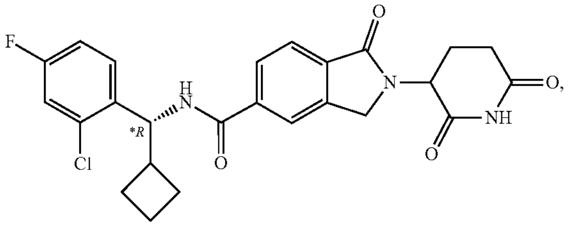,
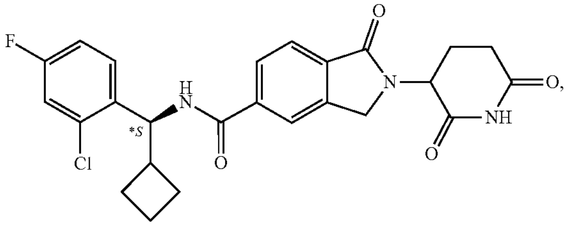,
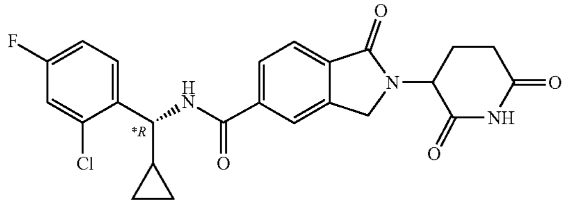
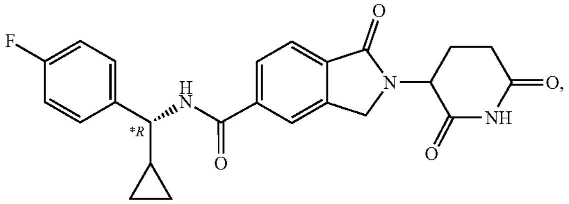,
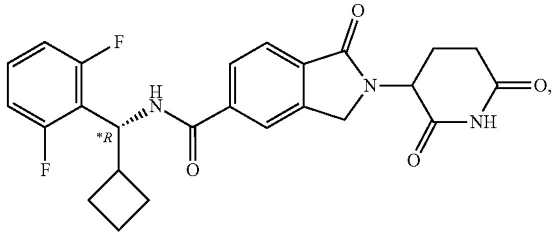,
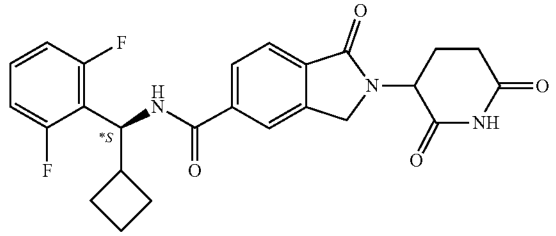
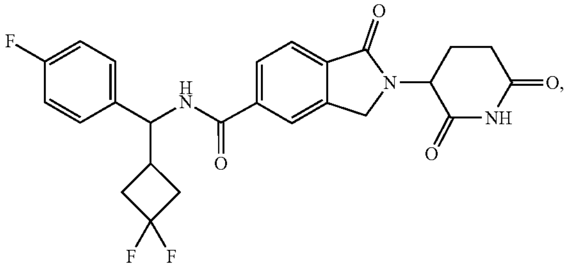, -continued
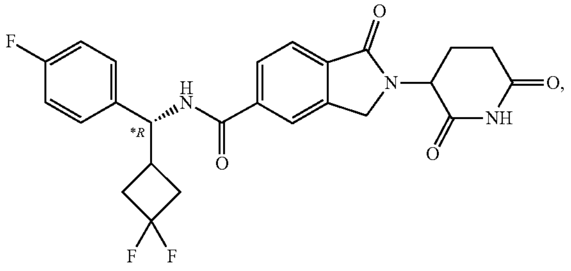
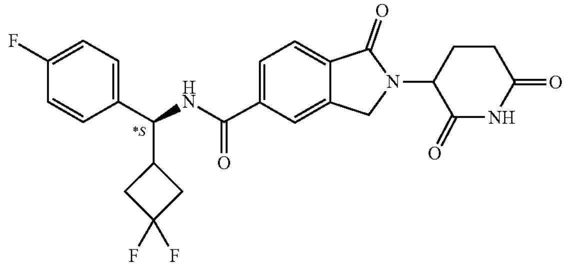
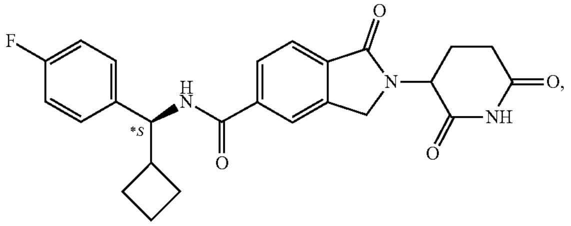
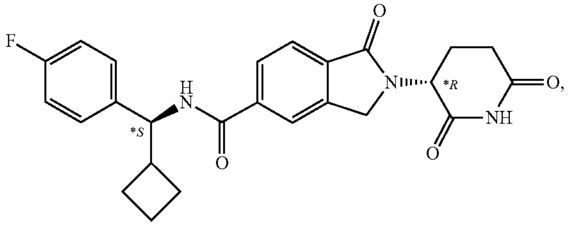
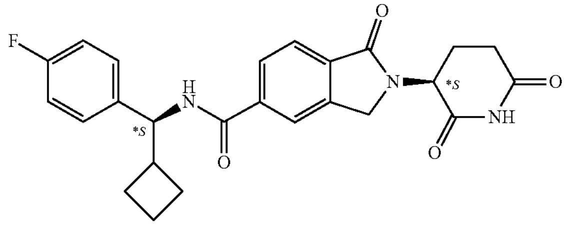
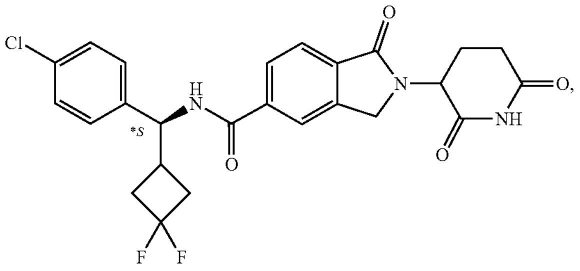
-continued
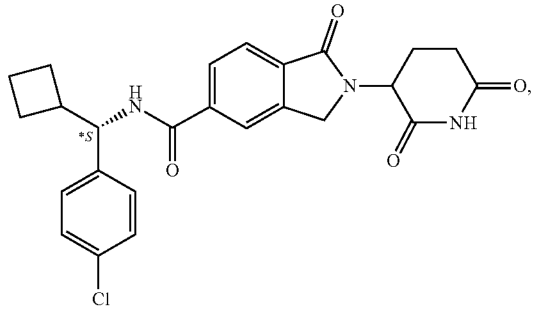
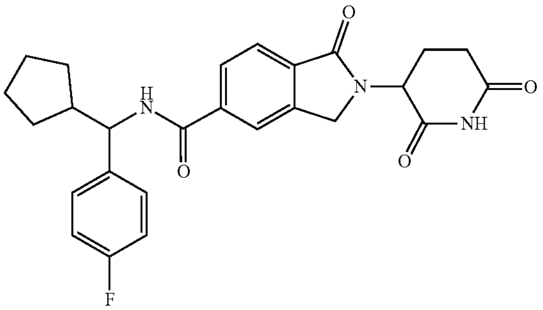
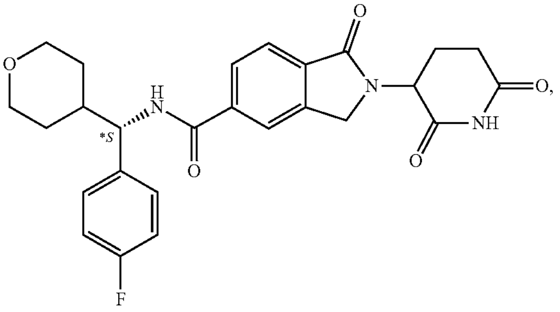
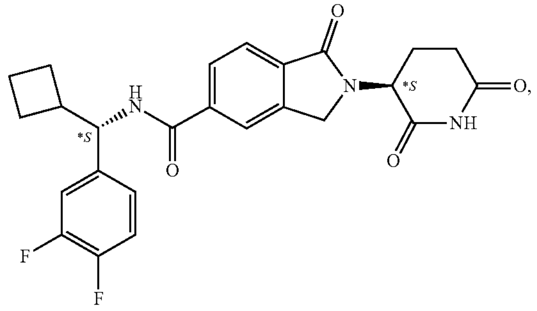
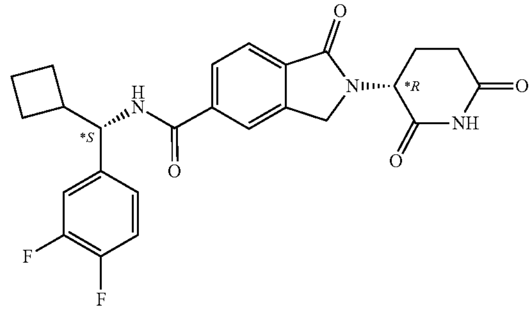

-continued
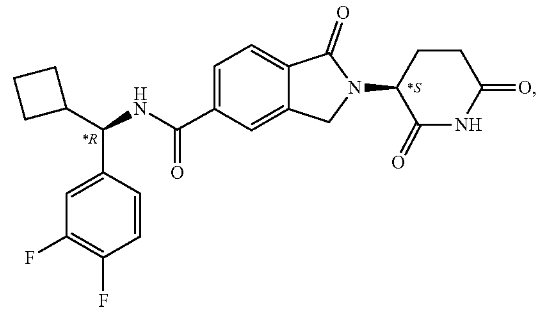
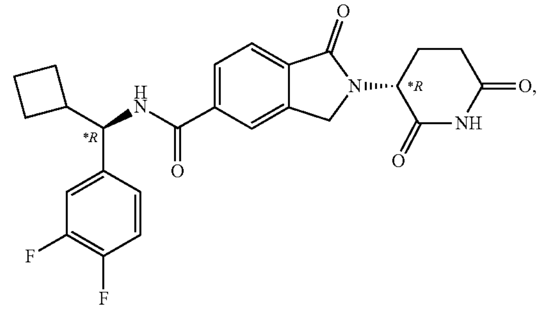
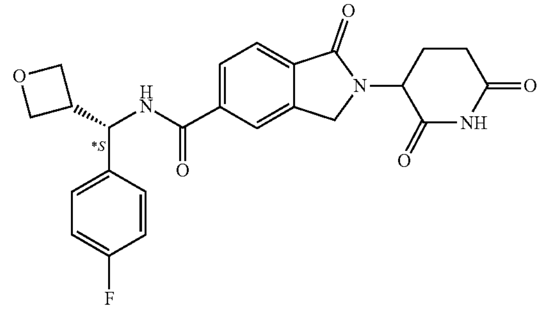
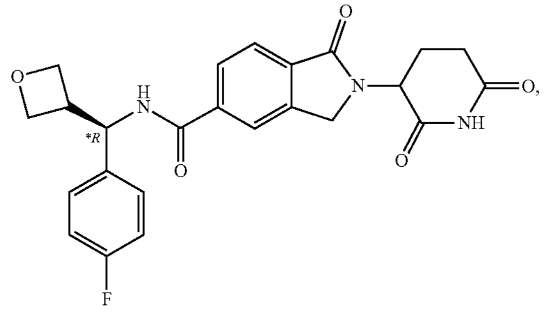
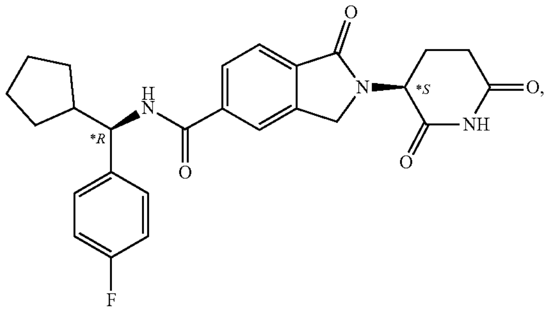
-continued
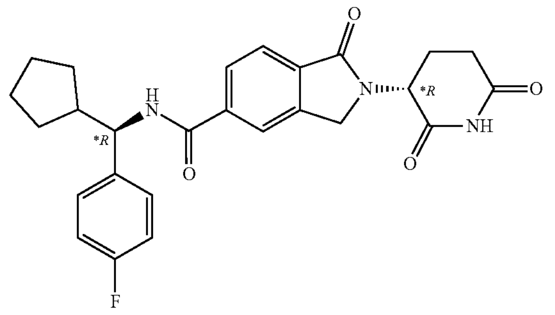
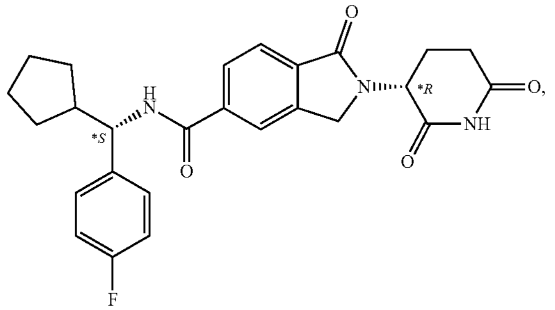
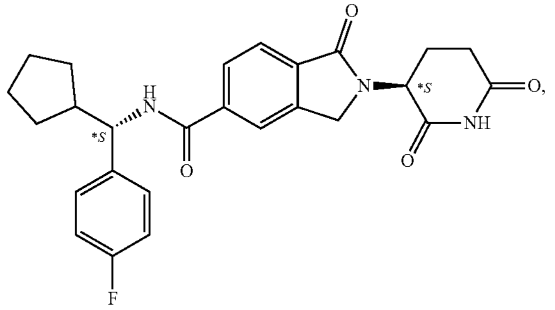
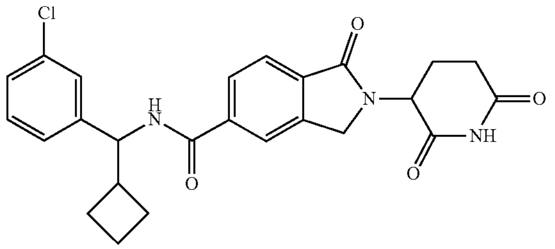
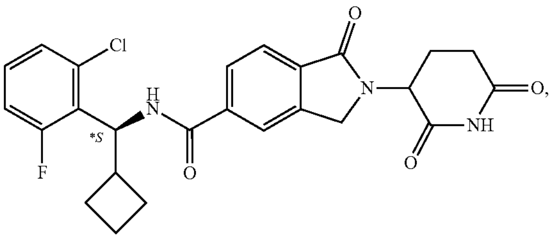
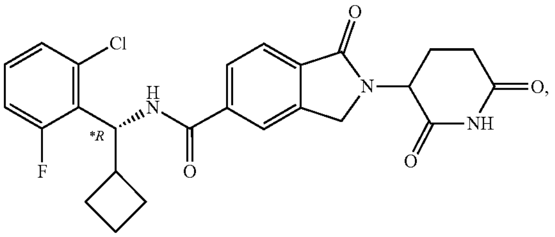

-continued
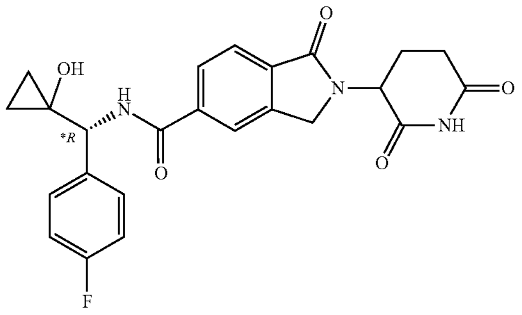
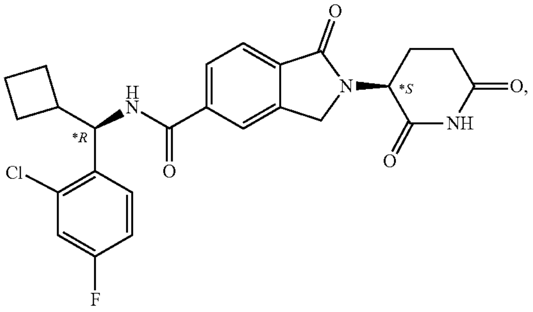
,
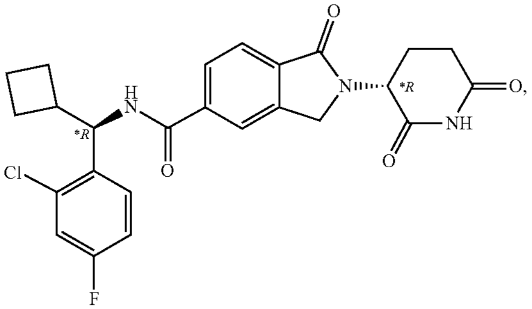
,
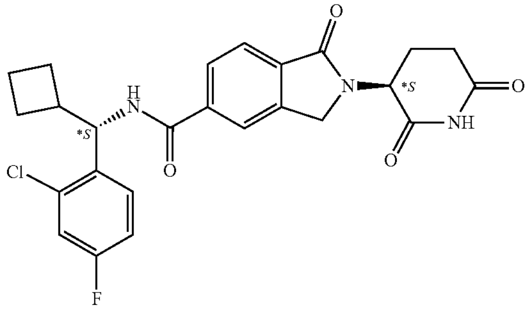
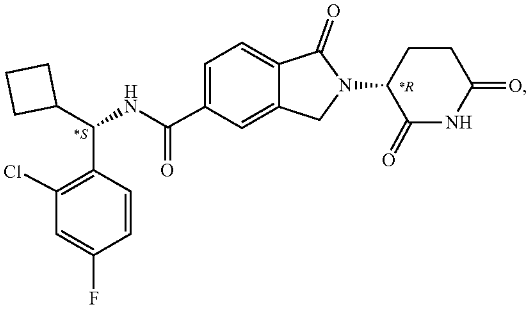
,
-continued
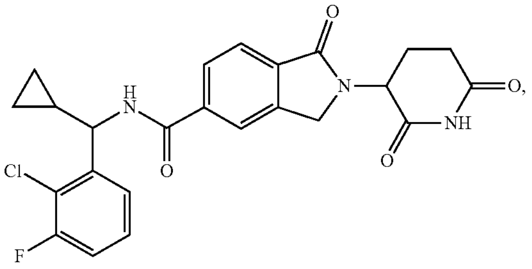
,
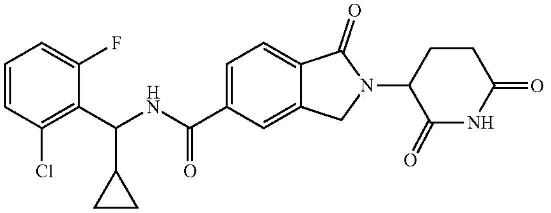
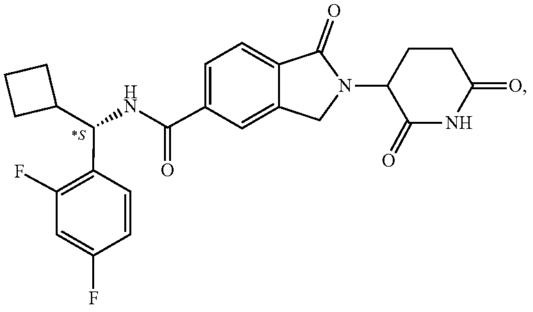
,
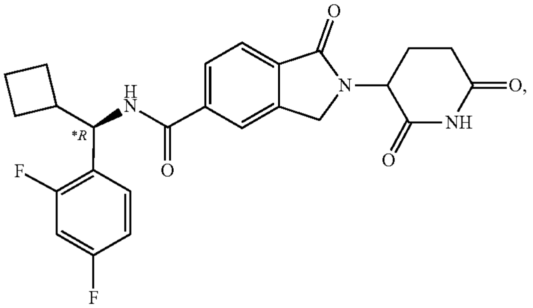
,
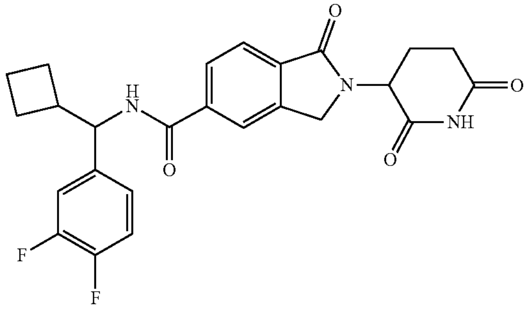
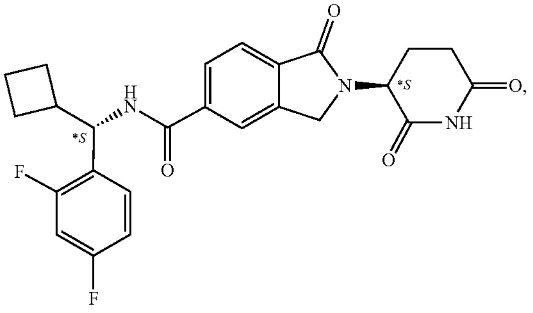
, -continued
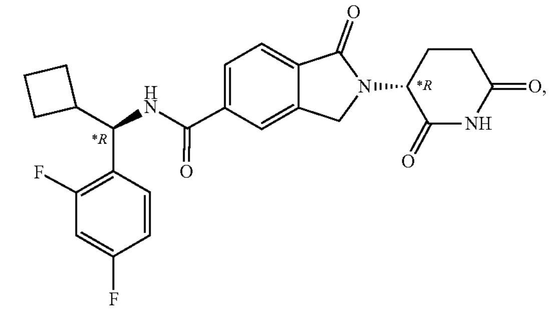
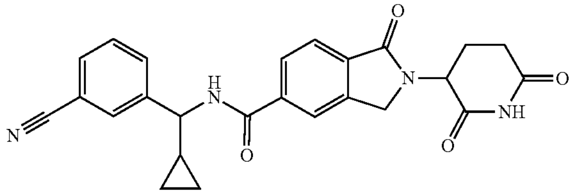
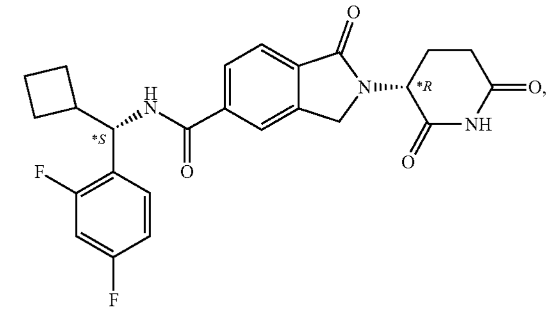
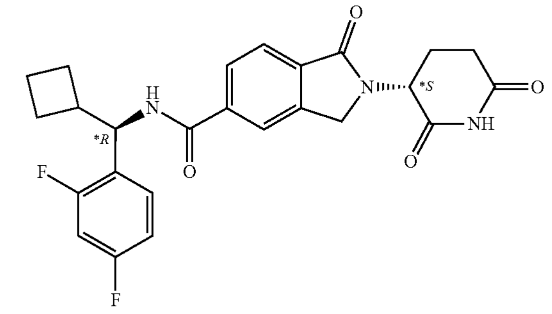
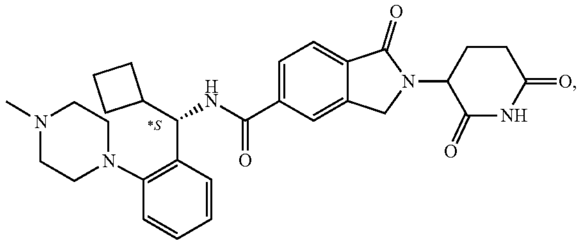
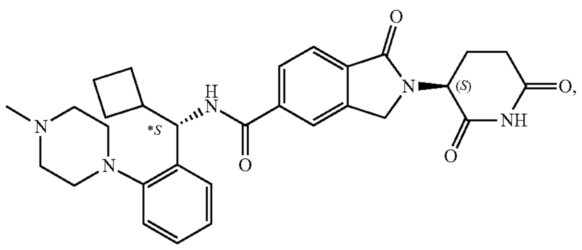
-continued
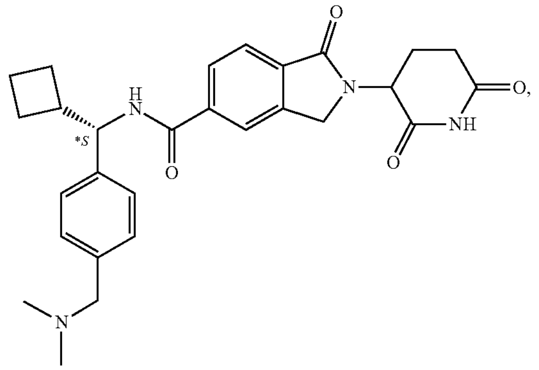
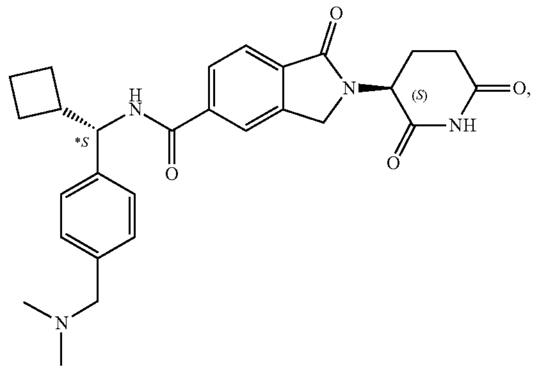
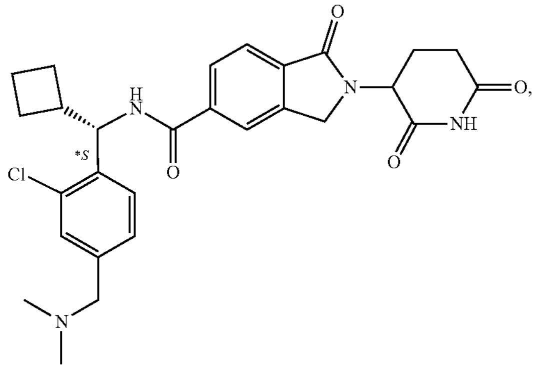
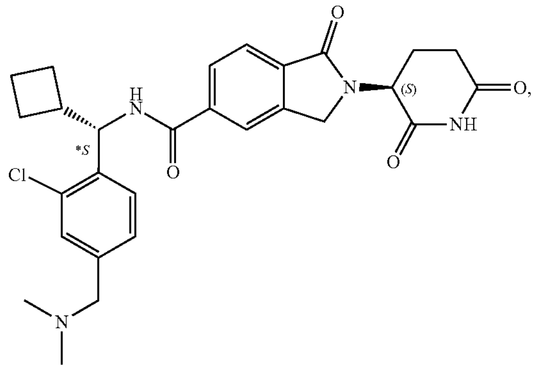

-continued
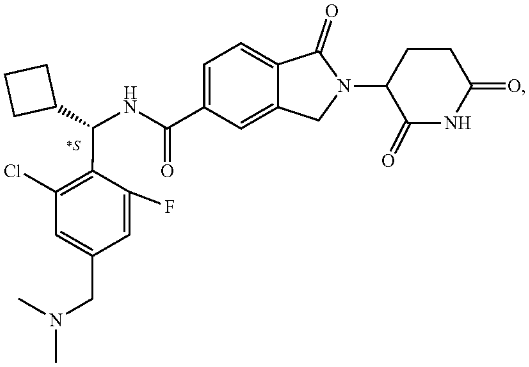,
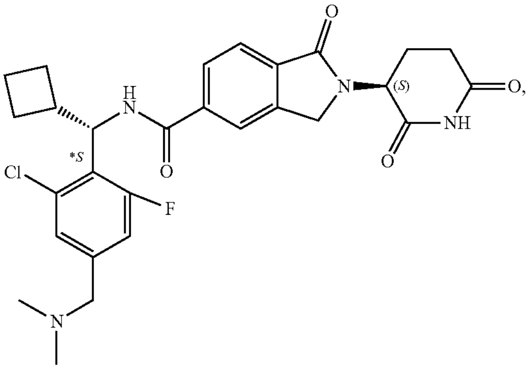,
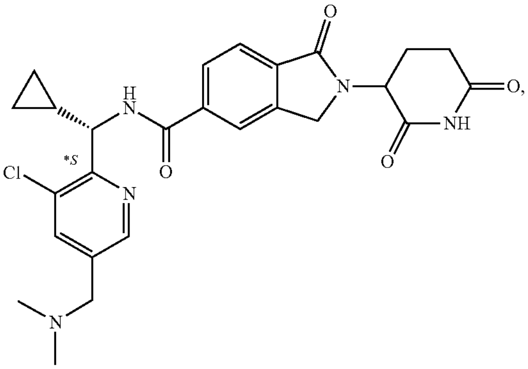,
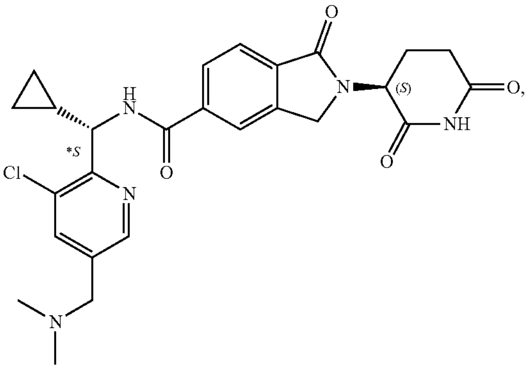,
-continued
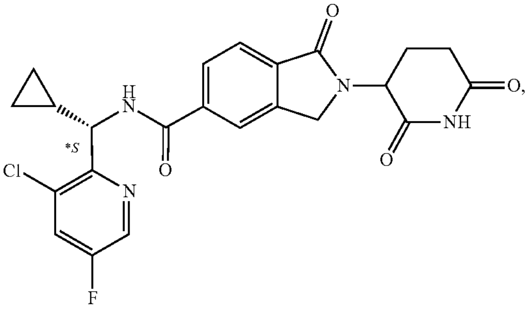,
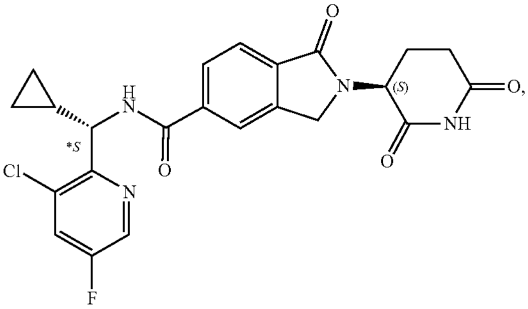,
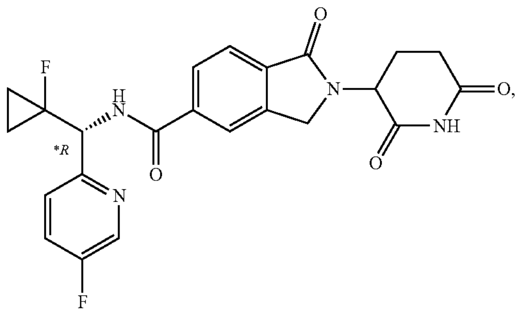,
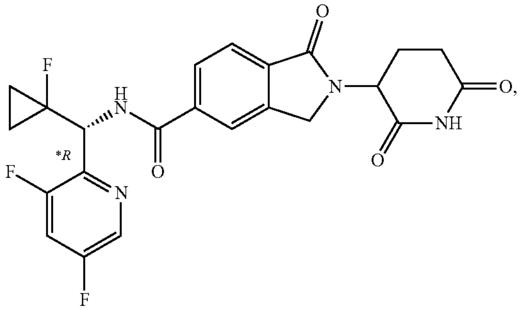,
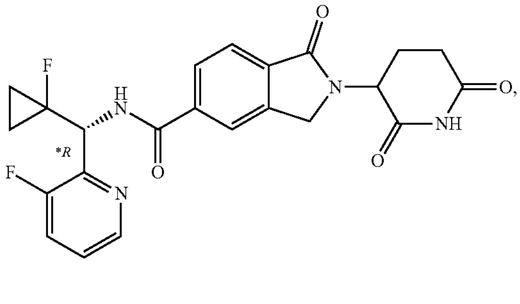, -continued
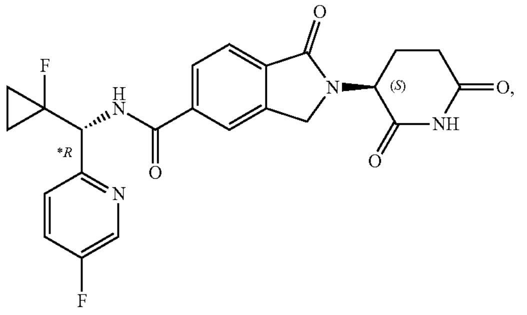
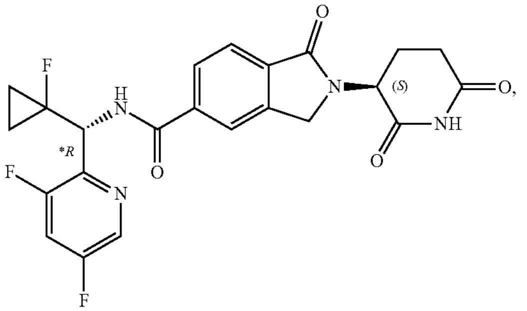
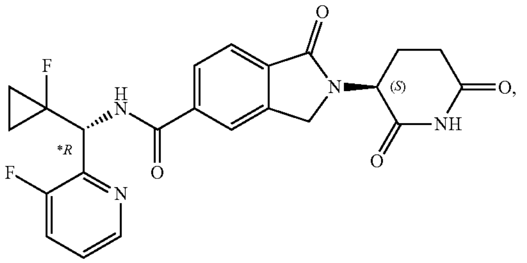
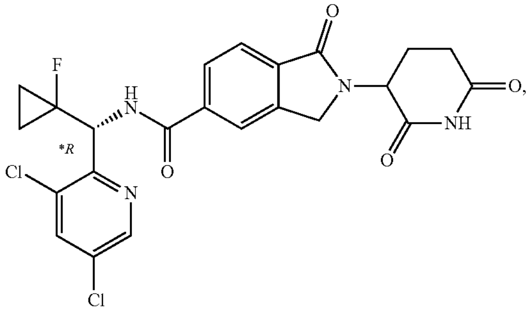
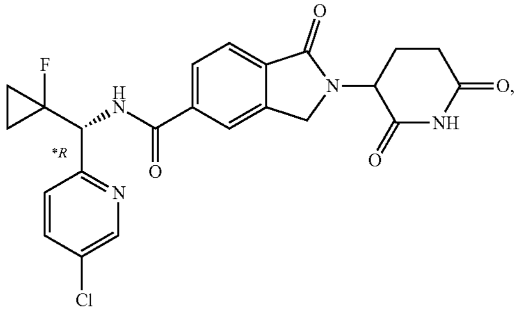
-continued
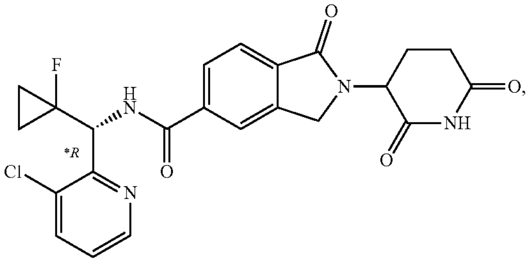
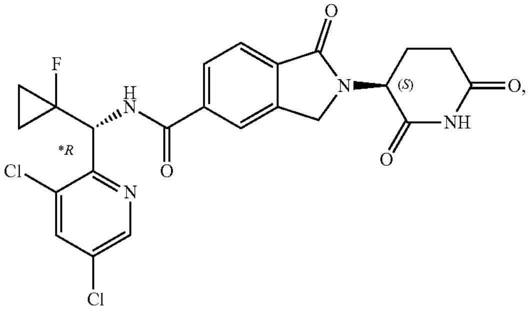
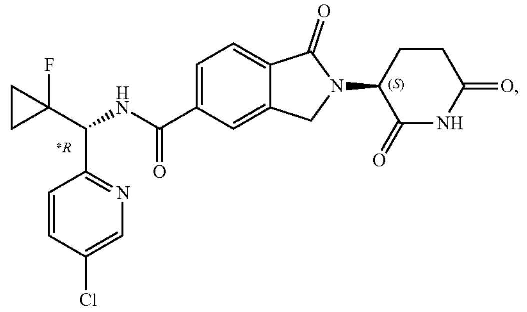
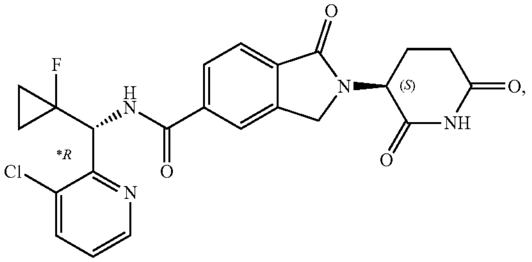
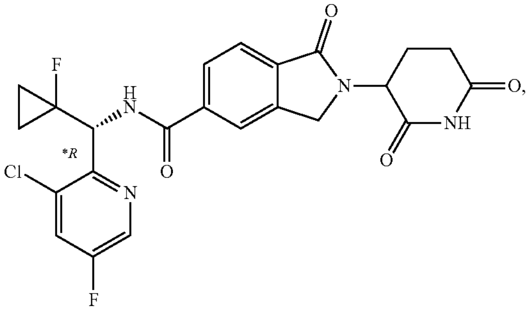

-continued
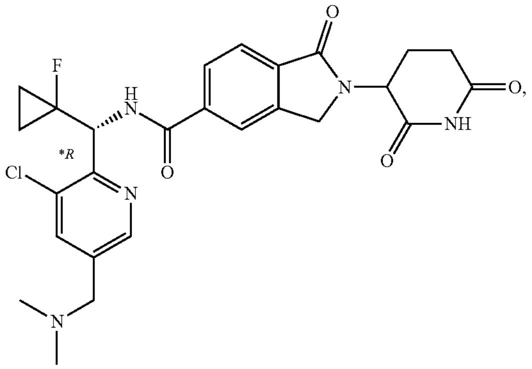
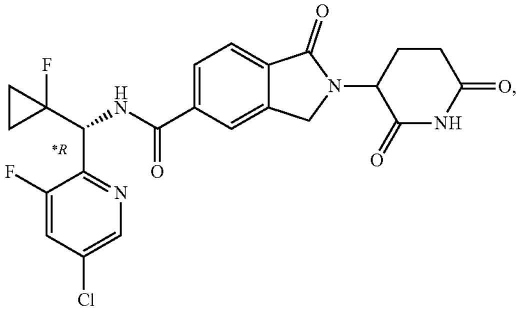
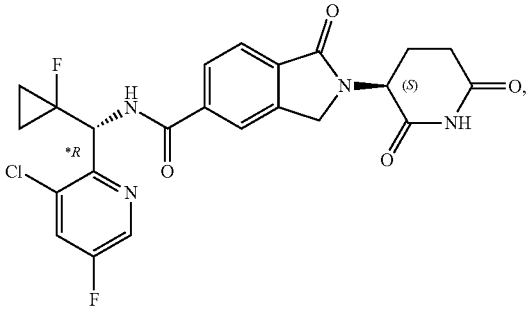
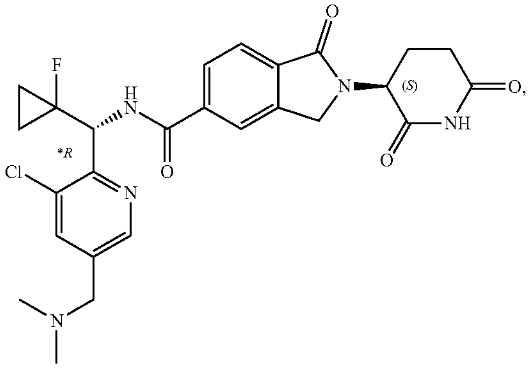
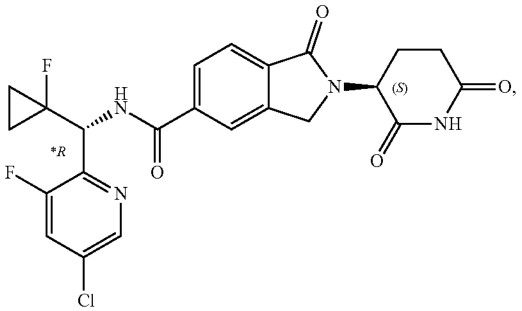
-continued
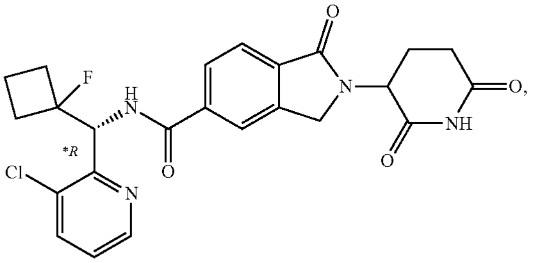
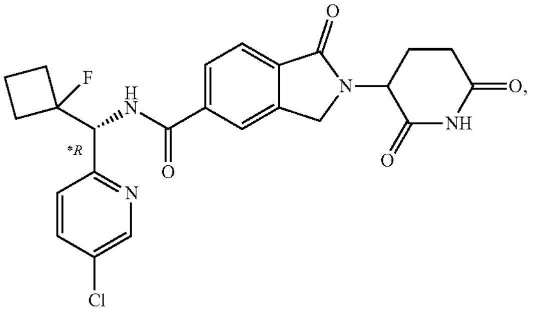
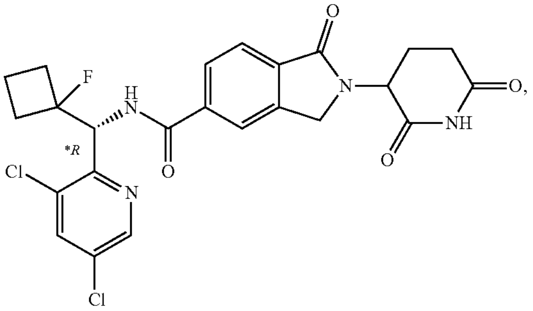
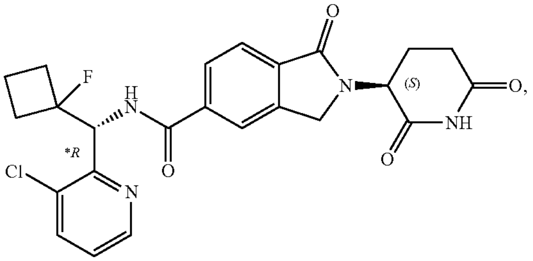
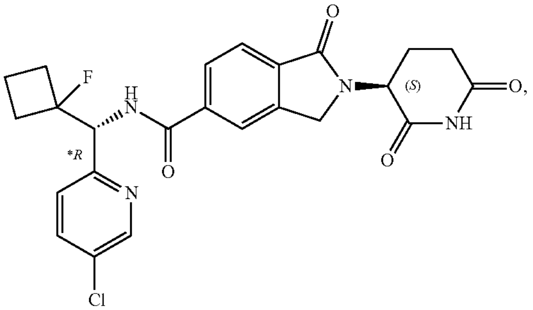

-continued
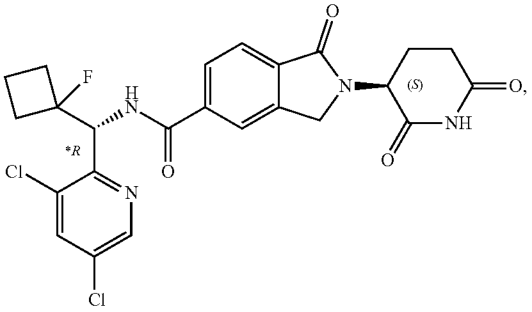
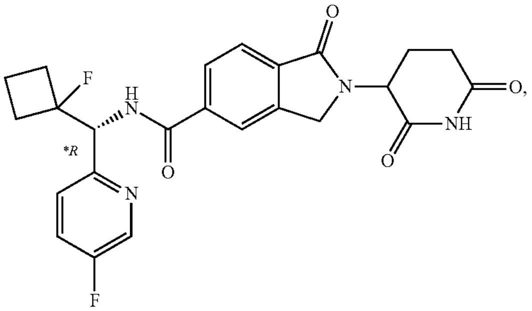
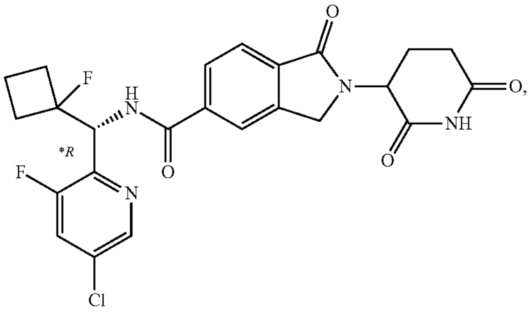
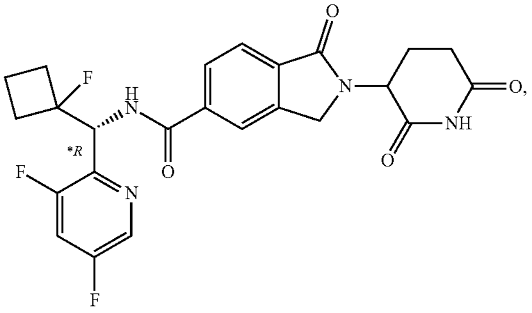
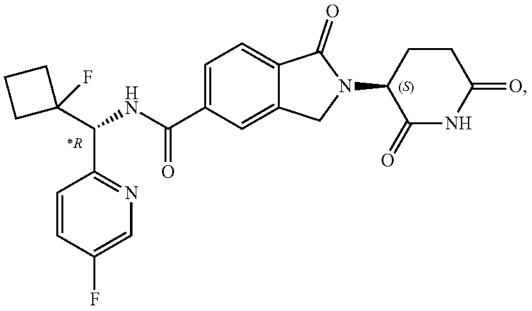
-continued
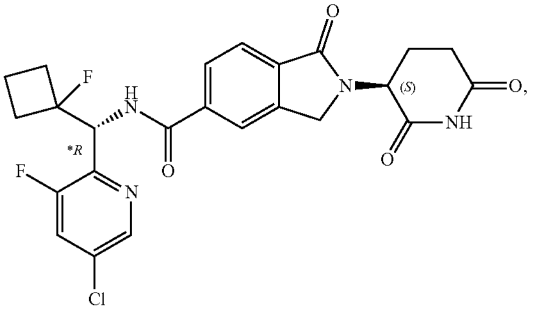
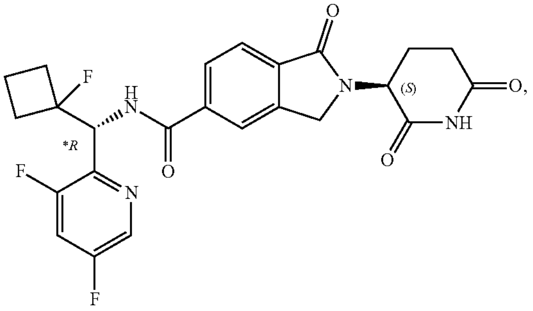
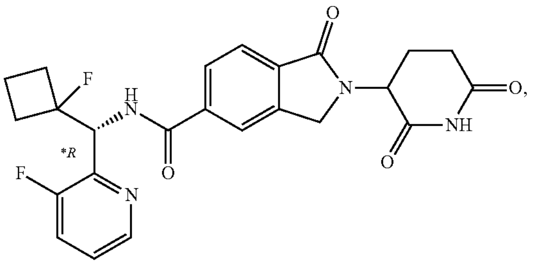
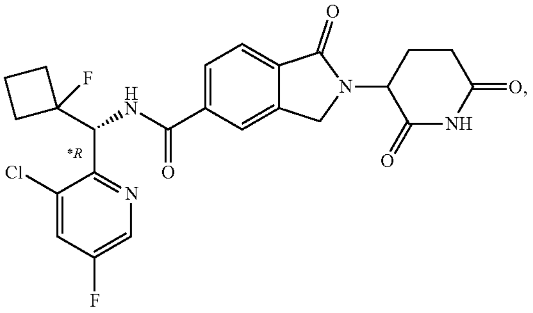
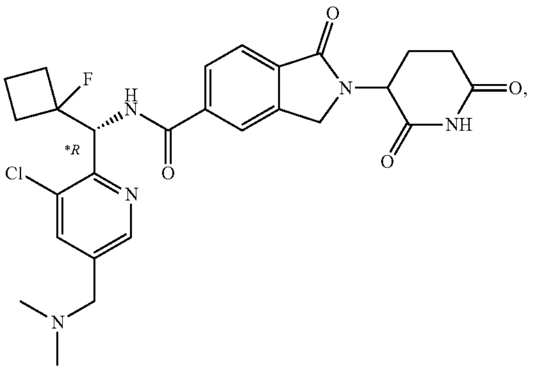

-continued
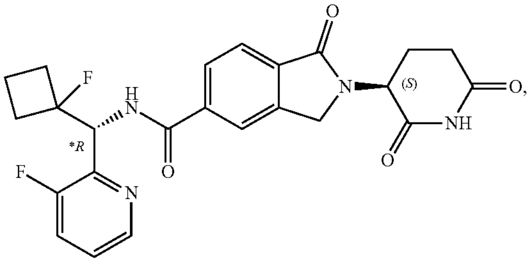,
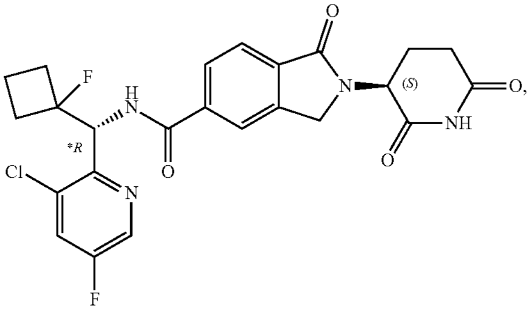,
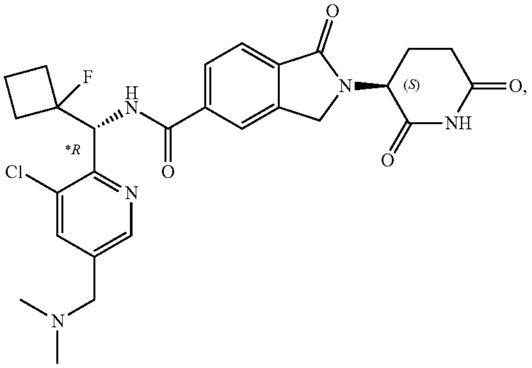,
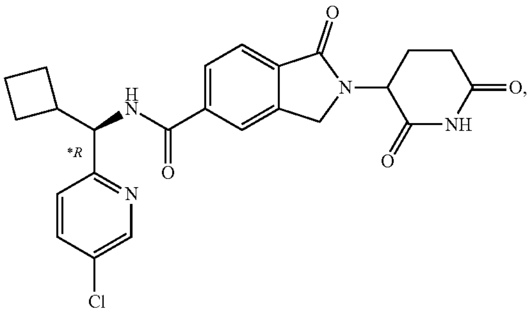,
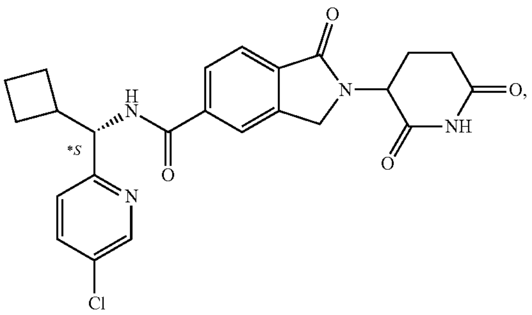,
-continued
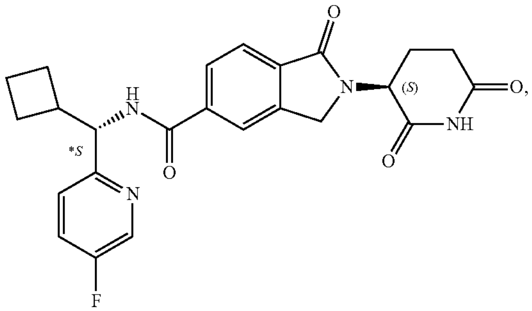,
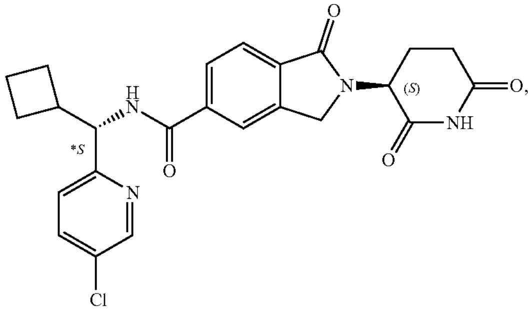,
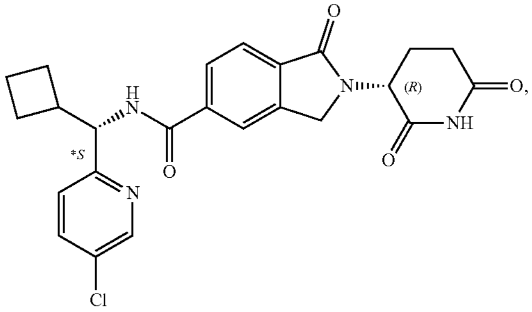,
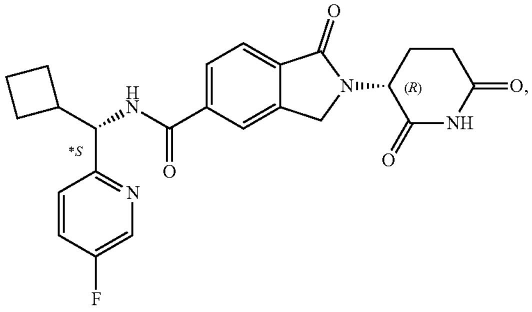,
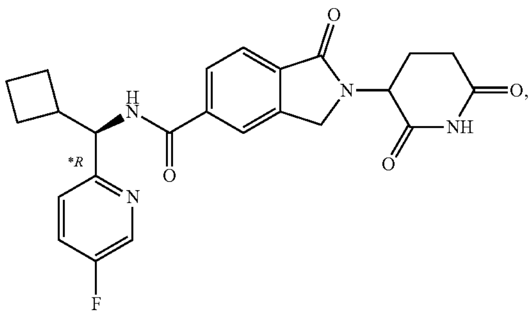, -continued
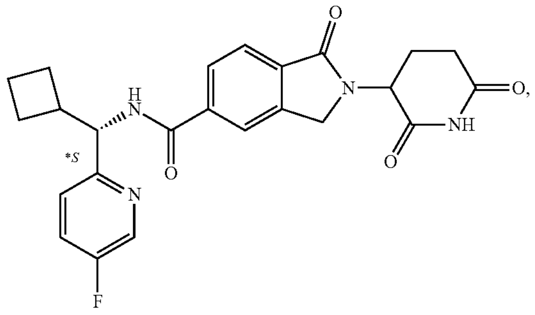,
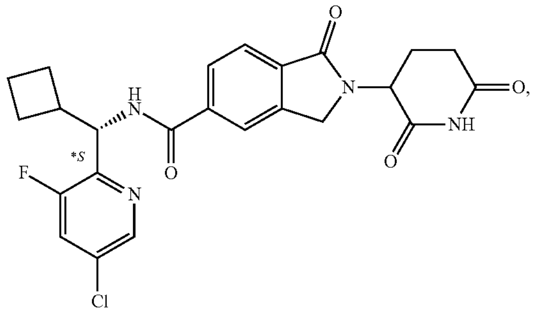,
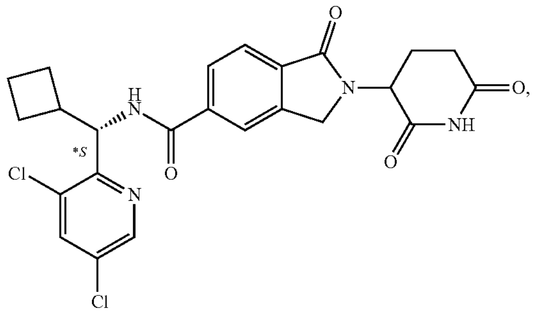,
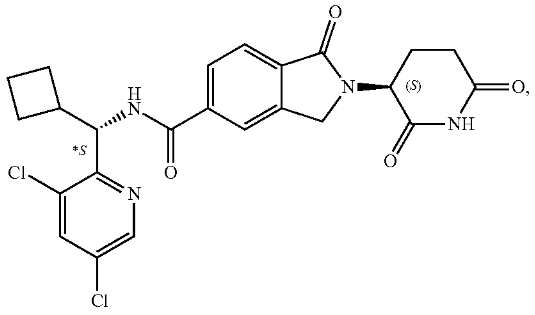,
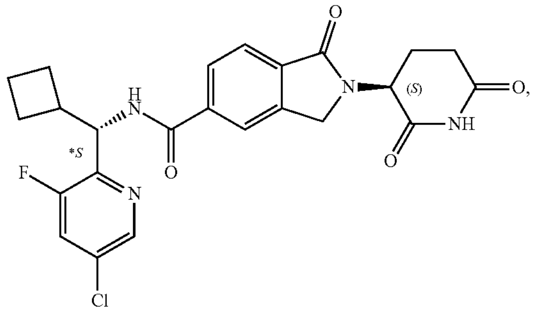,
-continued
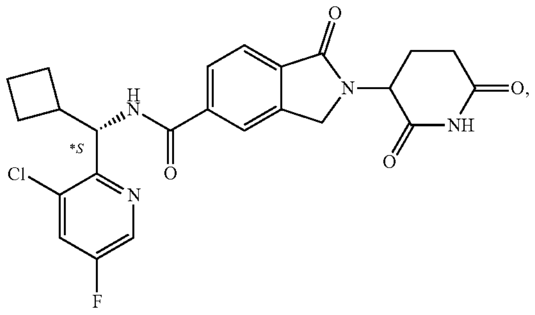,
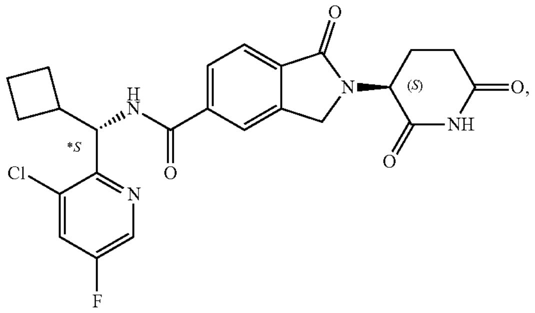,
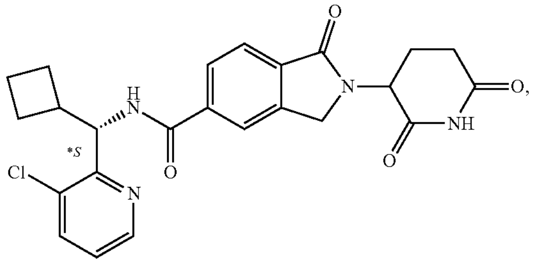,
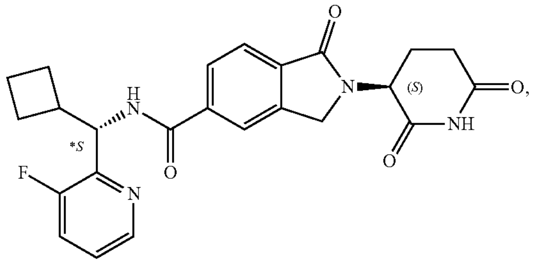,
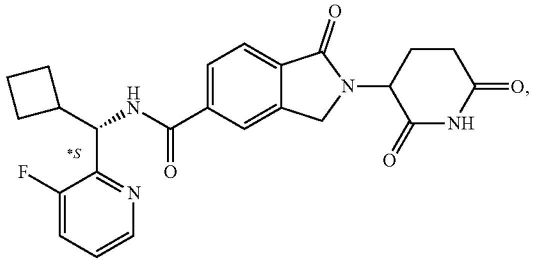,
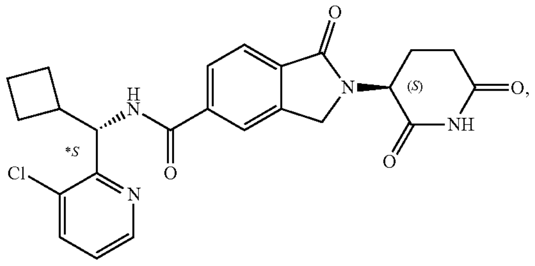, -continued
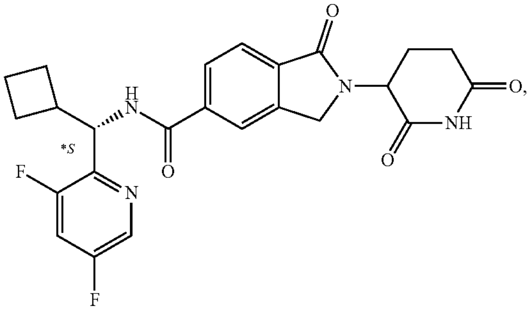
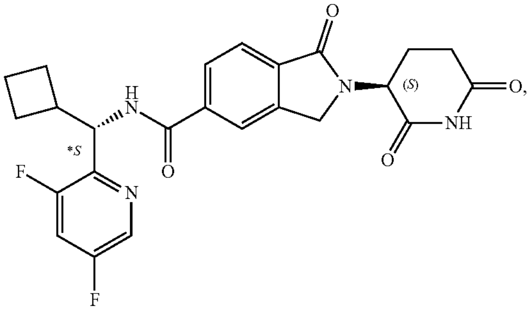
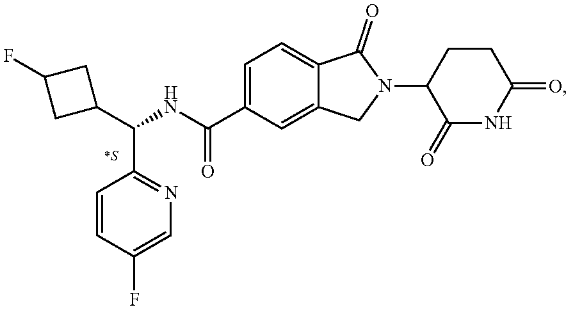
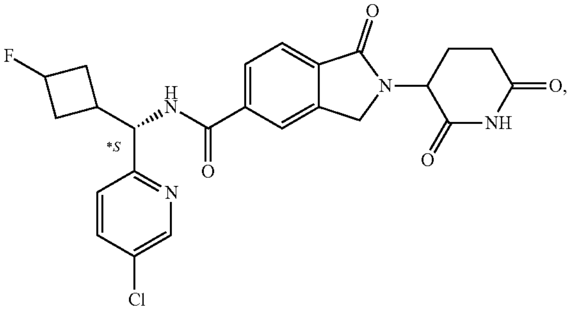
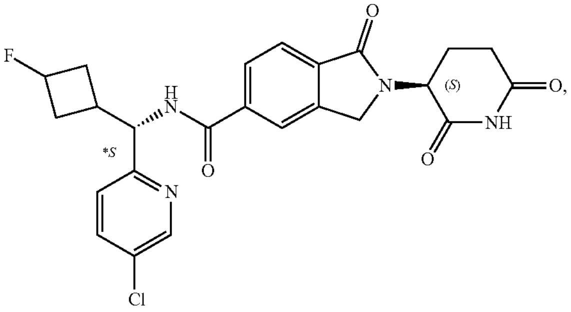
-continued
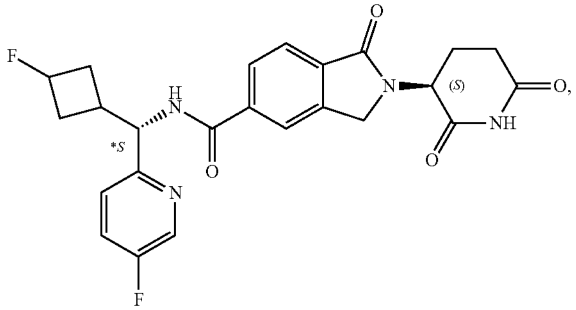
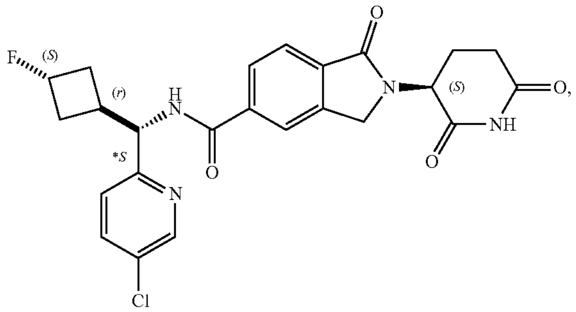
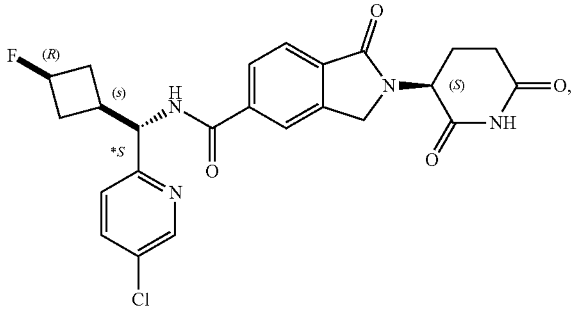
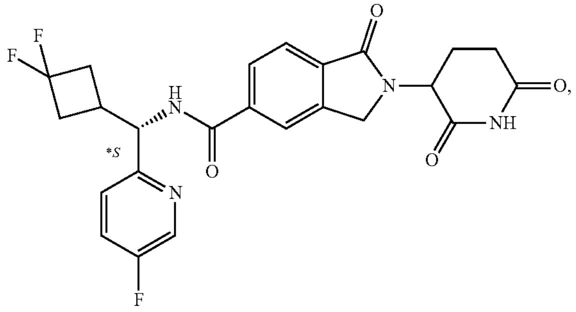
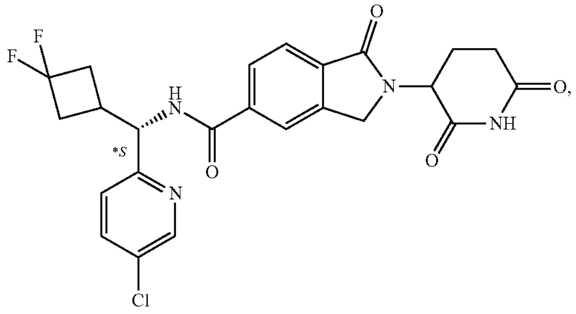

-continued
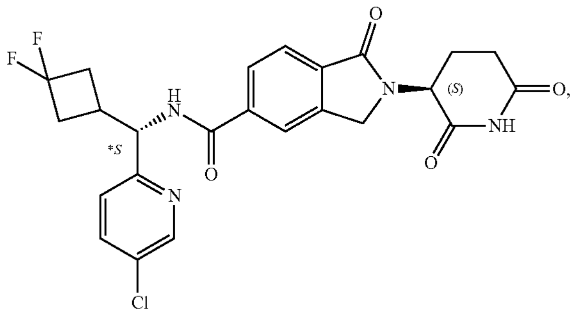
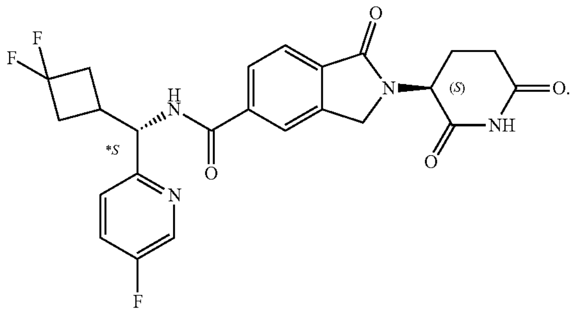
16. The compound of claim 1, wherein, the compound is selected from
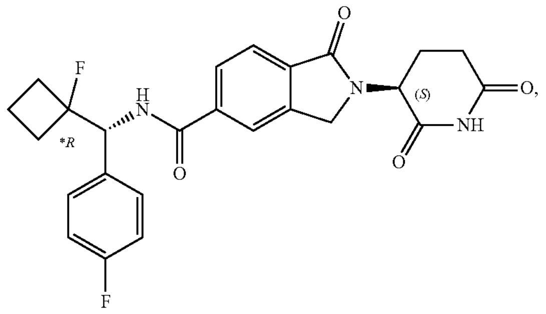
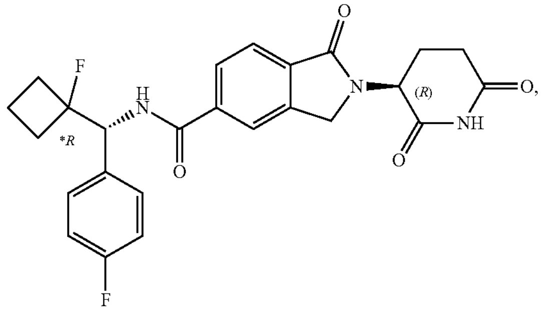
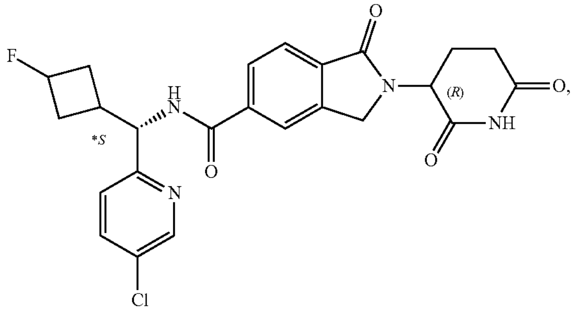
-continued
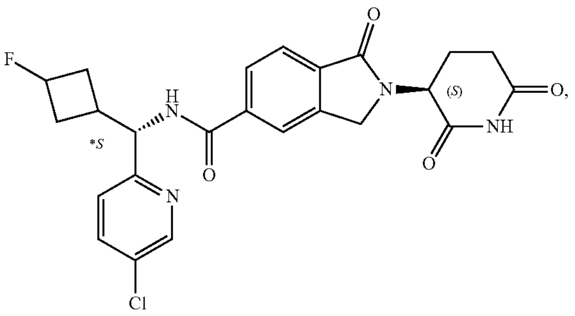
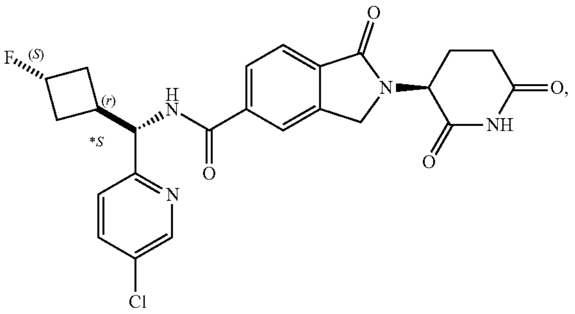
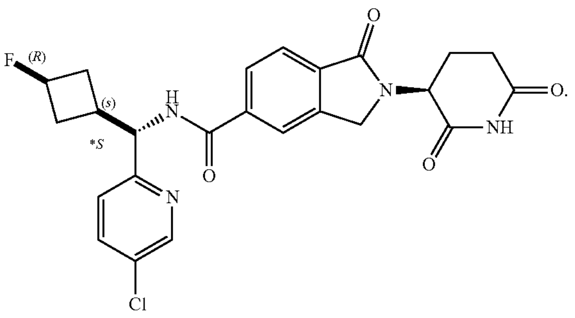
17. The compound of claim 1, wherein, the compound is selected from
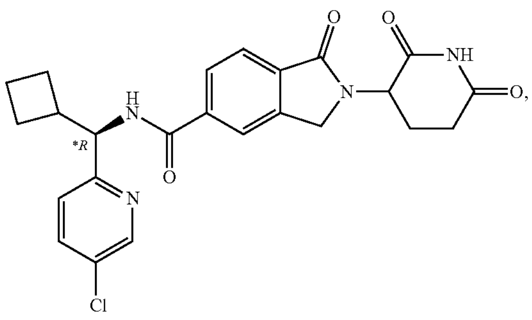

-continued

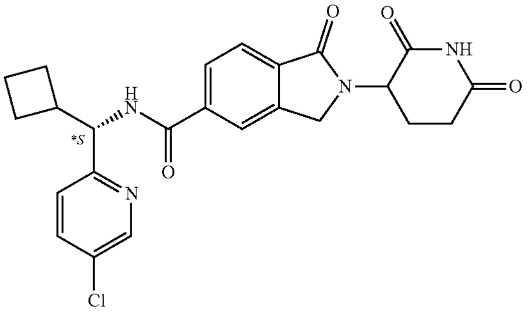

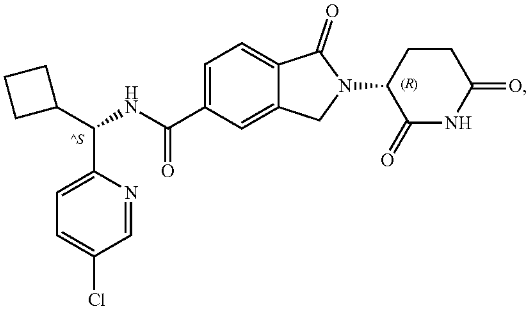

-continued

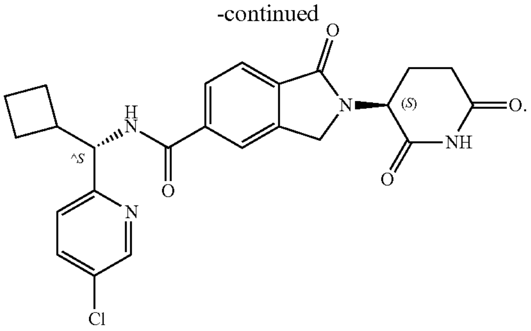

18. A pharmaceutical composition comprising a compound of claim 1 or a pharmaceutically acceptable salt thereof, and a pharmaceutically acceptable carrier.

19. A method of treating a disorder in a subject in need thereof, comprising administering to a subject in need thereof a therapeutically effective amount of the compound or a pharmaceutically acceptable salt thereof according to claim 1, wherein the disorder comprises Acute lymphoblastic leukemia (ALL), Acute myelogenous leukemia (AML), Chronic lymphocytic leukemia (CLL), Chronic myelogenous leukemia (CML), Acute monocytic leukemia (AMOL), Hairy cell leukemia (HCL), T-cell prolymphocytic leukemia (T-PLL), Large granular lymphocytic leukemia, Adult T-cell leukemia and Chronic lymphocytic leukemia.

* * * * *